(12) United States Patent
Ollier et al.

(10) Patent No.: US 11,773,166 B2
(45) Date of Patent: *Oct. 3, 2023

(54) CD3/CD38 T CELL RETARGETING HETERO-DIMERIC IMMUNOGLOBULINS AND METHODS OF THEIR PRODUCTION

(71) Applicant: Ichnos Sciences SA, La Chaux-de-Fonds (CH)

(72) Inventors: Romain Ollier, La Chaux-de-Fonds (CH); Samuel Hou, La Chaux-de-Fonds (CH); Rami Lissilaa, La Chaux-de-Fonds (CH); Darko Skegro, La Chaux-de-Fonds (CH); Jonathan Back, La Chaux-de-Fonds (CH)

(73) Assignee: Ichnos Sciences SA, La Chaux-de Fonds (CH)

( * ) Notice: Subject to any disclaimer, the term of this patent is extended or adjusted under 35 U.S.C. 154(b) by 384 days.

This patent is subject to a terminal disclaimer.

(21) Appl. No.: 16/159,231

(22) Filed: Oct. 12, 2018

(65) Prior Publication Data

US 2019/0135918 A1    May 9, 2019

Related U.S. Application Data

(63) Continuation of application No. 15/524,485, filed as application No. PCT/EP2015/075628 on Nov. 3, 2015, now abandoned.

(30) Foreign Application Priority Data

May 8, 2015 (EP) .................................. 15167034

(51) Int. Cl.
*A61P 35/00* (2006.01)
*C07K 16/28* (2006.01)
*A61K 38/00* (2006.01)

(52) U.S. Cl.
CPC .......... *C07K 16/2809* (2013.01); *A61P 35/00* (2018.01); *C07K 16/2896* (2013.01); *A61K 38/00* (2013.01); *C07K 2317/24* (2013.01); *C07K 2317/31* (2013.01); *C07K 2317/33* (2013.01); *C07K 2317/52* (2013.01); *C07K 2317/524* (2013.01); *C07K 2317/55* (2013.01); *C07K 2317/565* (2013.01); *C07K 2317/622* (2013.01); *C07K 2317/73* (2013.01); *C07K 2317/94* (2013.01)

(58) Field of Classification Search
CPC .................................................. C07K 16/2809
USPC ..................................................... 424/136.1
See application file for complete search history.

(56) References Cited

U.S. PATENT DOCUMENTS

| 5,807,706 A | 9/1998 | Carter et al. |
| 5,821,337 A | 10/1998 | Carter et al. |
| 6,329,509 B1 | 12/2001 | Jardieu et al. |
| 6,761,889 B2 | 7/2004 | Lowman et al. |
| 9,493,563 B2 | 11/2016 | Blein et al. |
| 9,683,052 B2 | 6/2017 | Blein et al. |
| 9,683,053 B2 | 6/2017 | Blein et al. |
| 2003/0194406 A1 | 10/2003 | Reinhard et al. |
| 2008/0003218 A1 | 1/2008 | Lowman et al. |
| 2012/0128586 A1* | 5/2012 | Calissano ............... A61P 35/02 424/9.1 |
| 2013/0178605 A1 | 7/2013 | Blein et al. |
| 2013/0209355 A1* | 8/2013 | De Weers ............... A61P 29/00 424/1.49 |
| 2014/0050660 A1* | 2/2014 | Chang ................ A61K 38/1709 424/85.5 |
| 2014/0066599 A2 | 3/2014 | Blein et al. |
| 2014/0187753 A1 | 7/2014 | Blein et al. |
| 2015/0133640 A1 | 5/2015 | Blein et al. |
| 2015/0239991 A1 | 8/2015 | Blein et al. |
| 2017/0145115 A1 | 5/2017 | Blein et al. |
| 2018/0094077 A1 | 4/2018 | Blein et al. |
| 2018/0112011 A1 | 4/2018 | Ollier et al. |
| 2018/0355064 A1 | 12/2018 | Blein et al. |
| 2019/0135918 A1 | 5/2019 | Ollier et al. |
| 2020/0024367 A1 | 1/2020 | Blein et al. |
| 2020/0102403 A1 | 4/2020 | Ollier |
| 2021/0171661 A1 | 6/2021 | Blein et al. |
| 2022/0213227 A1 | 7/2022 | Ollier |

FOREIGN PATENT DOCUMENTS

| CL | 2016000999 A1 | 11/2016 |
| CL | 2016002460 A1 | 5/2018 |
| CN | 101218256 A | 7/2008 |
| CN | 101287764 A | 10/2008 |
| EP | 1629011 A2 | 3/2006 |
| EP | 2522724 A1 | 11/2012 |

(Continued)

OTHER PUBLICATIONS

Rudikoff et al. (Proceedings of the National Academy of Sciences, 1982, 79:1979-1983.*
MacCallum et al. (Journal of Molecular Biology, 1996, 262:732-745).*
Casset et al. (Biochemical and Biophysical Research Communications, 2003, 307:198-205).*
Vajdos et al. (Journal of Molecular Biology, 2002, 320:415-428).*
Holm et al. (Molecular Immunology, 2007:1075-1084).*
Chen et al. (Journal of Molecular Biology, 1999, 293:865-881).*
Funaro et al (International Immunology, 1996, 8(11): 1643-1650).*
Ferrero et al (BMC Immunology, 2004, 5(21): 1-13).*
Almagro, J. C., & Fransson, J., "Humanization of antibodies," Front Biosci 13:1619-33, Frontiers inBioscience, United Sates (2008).

(Continued)

*Primary Examiner* — Sean E Aeder
(74) *Attorney, Agent, or Firm* — STERNE, KESSLER, GOLDSTEIN & FOX P.L.L.C.

(57) ABSTRACT

The present invention relates to hetero-dimeric immunoglobulins that target both a component of the human CD3 antigen and a component of the human CD38 antigen and methods of making the same. The present invention also relates to antibodies which bind to the human CD38 antigen and derivatives thereof for use as therapeutic or diagnostic reagents and methods of making the same.

12 Claims, 44 Drawing Sheets

Specification includes a Sequence Listing.

(56) References Cited

FOREIGN PATENT DOCUMENTS

| | | |
|---|---|---|
| WO | WO-9411026 A2 | 5/1994 |
| WO | WO-9533844 A1 | 12/1995 |
| WO | WO-1996027011 A1 | 9/1996 |
| WO | WO-9640210 A1 | 12/1996 |
| WO | WO-9850431 A2 | 11/1998 |
| WO | WO-2004003019 A2 | 1/2004 |
| WO | WO-2005103083 A2 | 11/2005 |
| WO | WO-2006099875 A1 | 9/2006 |
| WO | WO-2007110205 A2 | 10/2007 |
| WO | WO-2007147901 A1 | 12/2007 |
| WO | WO-2008047242 A2 | 4/2008 |
| WO | WO-2008119353 A1 | 10/2008 |
| WO | WO-2008119565 A2 | 10/2008 |
| WO | WO-2009089004 A1 | 7/2009 |
| WO | WO-2010033736 A1 | 3/2010 |
| WO | WO-2010075548 A2 | 7/2010 |
| WO | WO-2010095031 A2 | 8/2010 |
| WO | WO-2010108127 A1 | 9/2010 |
| WO | WO-2010151792 A1 | 12/2010 |
| WO | WO-2011131746 A2 | 10/2011 |
| WO | WO-2011154453 A1 | 12/2011 |
| WO | WO-2012058768 A1 | 5/2012 |
| WO | WO-2012092612 A1 | 7/2012 |
| WO | WO-2012131555 A2 | 10/2012 |
| WO | WO-2012138997 A1 | 10/2012 |
| WO | WO-2012143524 A2 | 10/2012 |
| WO | WO-2012158818 A2 | 11/2012 |
| WO | WO-2013008171 A1 | 1/2013 |
| WO | WO-2013060867 A2 | 5/2013 |
| WO | WO-2014049003 A1 | 4/2014 |
| WO | WO-2014068114 A1 | 5/2014 |
| WO | WO-2015016946 A1 | 2/2015 |
| WO | WO-2015063339 A1 | 5/2015 |
| WO | WO-2016020444 A1 | 2/2016 |
| WO | WO-2016071355 A1 | 5/2016 |

OTHER PUBLICATIONS

Bensmana, M., "The human immunoglobulin pseudo-gamma IGHGP gene shows no major structural defect," Nucleic Acids Res 16(7): 3108, IRL Press Limited, United Kingdom (1988).

Bird, R. E., et al., "Single-chain antigen-binding proteins," Science, 242(4877): 423-6, American Association for the Advancement of Science, United States (1988).

Binz, H. K., et al., "Engineering novel binding proteins from nonimmunoglobulin domains," Nat Biotechnol, 23(10):1257-1268, Nature Publishing Group, United Kingdom (2005).

Buhler, P., "A bispecific diabody directed against prostate-specific membrane antigen and CD3 induces T-cell mediated lysis of prostate cancer cells," Cancer Immunol Immunother, 57: 43-52, Springer Publishing, Germany (2008).

Deckert et al., "SAR650984, A Novel Humanized CD38-Targeting Antibody, Demonstrates Potent Antitumor Activity in Models of Multiple Myeloma and Other CD38p Hematologic Malignancies," Clin Cancer Res. 20: 4574, American Association for Cancer Research, United States (2014).

Ewert, S., et al., "Biophysical properties of human antibody variable domains," J Mol Biol, 325(3): 531-553, Elsevier, Netherlands (2003).

Frankel, S. R., & Baeuerle, P. A., "Targeting T cells to tumor cells using bispecific antibodies," Current Opinion in Chemical Biology, 17(3): 385-92, Elsevier Ltd., Netherlands (2013).

Friedrich et al. "Regression of Human Prostate Cancer Xenografts in Mice by AMG 212/BAY2010112, aNovel PSMA/CD3-Bispecific BiTE Antibody Cross-Reactive with Non-Human Primate Antigens," Molecular Cancer Therapeutics 11:2664-2673; American Association for Cancer Research, United States (2012).

Garber, E., & Demarest, S. J., "A broad range of Fab stabilities within a host of therapeutic IgGs," Biochemical and Biophysical Research Communications 355(3):751-7, Elsevier, Netherlands (2007).

Graille, M. et al., "Crystal structure of a *Staphylococcus aureus* protein A domain complexed with the Fab fragment of a human IgM antibody: Structural basis for recognition of B-cell receptors and superantigen activity," Proc Natl Acad Sci U S A 97(10):5399-5404, National Academy of Sciences, United States (2000).

Holliger, P., et al., "Diabodies: small bivalent and bispecific antibody fragments," Proc Natl Acad Sci USA, 90(14): 6444-8, United States National Academy of Sciences, United States (1993).

Holt, L. J., et al., "Domain antibodies: proteins for therapy," Trends Biotechnol, 21(11): 484-490, Elsevier, Netherlands (2003).

Hoshino, S., et al., "Mapping of the catalytic and epitopic sites of human CD38/NAD+ glycohydrolase to a functional domain in the carboxyl terminus," J Immunol, 158(2):741-7, The American Association of Immunologists, United States (1997).

Huston, J. S., et al., "Protein engineering of antibody binding sites: recovery of specific activity in an anti-digoxin single-chain Fv analogue produced in *Escherichia coli*," Proc Natl Acad Sci USA, 85(16): 5879-83, United States National Academy of Sciences, United States (1988).

Jackman, J., et al., "Development of a two-part strategy to identify a therapeutic human bispecific antibody that inhibits IgE receptor signaling," Journal of Biological Chemistry 285(27):20850-9, The American Society for Biochemistiy and Molecular Biology, Inc. (2010).

Jung, S., & Pliickthun, A., "Improving in vivo folding and stability of a single-chain Fv antibody fragment by loop grafting," Protein Eng, 10(8): 959-66, Biochemisches Institut der Universität, Switzerland (1997).

Kaas, Q., et al., "IG, TR and IgSF, MHC and MhcSF: what do we learn from the IMGT Colliers de Perles?" Briefings in Functional Genomics & Proteomics, 6(4): 253-64, Oxford Univeisity Press, United Kingdom (2007).

Klein, C., et al., "Progress in overcoming the chain association issue in bispecific heterodimeric IgG antibodies," MAbs, 4(6): 653-63, Taylor & Francis, United Kingdom (2012).

Kufer, P., et al., "A revival of bispecific antibodies," Trends Biotechnol., 22(5): 238-244, Elsevier, Netherlands (2004).

Labrijn, A. F., et al., "Efficient generation of stable bispecific IgG1 by conliolled Fab-arm exchange," Proc Natl Acad Sci USA, 110(13): 5145-50, United States National Academy of Sciences, United States (2013).

Lefranc, M. P., et al., "IMGT, the international ImMunoGeneTics database," Nucleic Acids Res, 27(1): 209-12, Oxford University Press, United Kingdom (1999).

Lefranc, M. P., "MGT, the international ImMunoGeneTics database," Nucleic Acids Res 29(1): 207-9; Oxford University Press, United Kingdom (2001).

Lefranc, M. P., "IMGT, the international ImMunoGeneTics information system," Nucleic Acids Res 31(1): 307-10, Oxford University Press, United Kingdom (2003).

Lefranc, M. P., et al., "IMGT unique numbering for immunoglobulin and T cell receptor constant domains and Ig superfamily C-like domains," Developmental & Comparative Immunology 29(3): 185-203; Elsevier, Netherlands (2005).

May, C., et al., "Advances in bispecific biotherapeutics for the treatment of cancer," Biochem Pharmacol 84(9): 1105-12, Elsevier, Netherlands (2012).

Marks, J. D., et al., "By-passing immunization. Human antibodies from V-gene libranies displayed on phage," J Mol Biol, 222(3): 581-97, Elsevier, Netherlands (1991).

Merchant, A. M., et al., "An efficient route to humanbispecific IgG," Nat Biotechnol, 16(7): 677-81, Nature Publishing Group, United Kingdom (1998).

Moore, P. A., et al., "Application of dual affinity lelargeting molecules to achieve optimal redirected T-cell killing of B-cell lymphoma," Blood, 117(17): 4542-51; American Society of Hematology, United States (2011).

Murali, R., & Greene, M. I., "Structure Based Antibody-Like Peptidomimetics" Pharmaceuticals 5(2): 209-235, Multidisciplinary Digital Publishing Institute, Switzerland (2012).

(56) References Cited

OTHER PUBLICATIONS

Polonelli, L., et al., "Antibody complementarity-determining regions (CDRs) can display differential antimicrobial, antiviral and antitumor activities," PLoS ONE 3(6): e237I, Public Library of Science, United States (2008).

Potter, K. N. et al., "Staphylococcal protein A binding to VH3 encoded immunoglobulins," International Reviews of Immunology 14(4):291-308, Harwood Academic Publishers, United Kingdom (1997).

Pessano, S., et al., The T3/T cell receptor complex: antigenic distinction between the two 20-kd T3 (T3-delta and T3-epsilon) subunits, EMBO J, 4(2):337-44, EMBO Press Heidelberg, Germany (1985).

Roben, P. W. et al., "VH3 family antibodies bind domain D of staphulococcal protein A," The Journal of Immunology 154(12):6437-6445, American Association of Immunologists, United States (1995).

Ruiz, M., et al., "IMGT, the international ImMunoGeneTics database," Nucleic Acids Res, 28(1): 219-21; Oxford University Press, United Kingdom (2000).

Schlereth, B., et al., "Eradication of Tumors from a Human Colon Cancer Cell Line and from Ovarian Cancer Metastases in Imumunodeficient Mice by a Single-Chain Ep-CAM-/CD3-Bispecific Antibody Construct," Cancer Res 65:2882-9, American Association for Cancer Research, United States (2005).

Schofield, D. J., et al., "Application of phage display to high throughput antibody generation and characterization," Genome Biol 8(11):R254, BioMed Central, United Kingdom (2007).

Tomlinson, I., & Bolliger, P., "Methods for generating multivalent and bispecific antibody fragments," Methods Enzymol 326:461-79, Elsevier, Netherlands (2000).

UniProt accession No. P09693, CD3G_Human, T-cell surface glycoprotein CD3 gamma chain, accessed at https://www.uniprot.org/uniprot/P09693.

UniProt accession No. P07766, CD3E Human, T-cell surface glycoprotein CD3 epsilon chain, accessed at https://www.uniprot.org/unipivt/P07766.

UniProt accession No. Q95LI5, CD3E_MACFA, T-cell surface glycoprotein CD3 epsilon chain, accessed at https://www.uniprot.org/uniprot/Q95LI5.

UniProt accession No. P28907, CD38_HUMAN, ADP-ribosyl cyclase/cyclic ADP-ribose hydrolase 1, accessed at https://www.uniprot.org/uniprot/P28907.

Van Der Merwe, P. A. & Dushek, O., "Mechanisms for T cell receptor triggering," Nat Rev Immunol, 11(1): 47-55, Nature Publishing Group, United Kingdom (2011).

Ward, E. S., et al., "Binding activities of a repertoire of single immunoglobulin variable domains secreted from *Escherichia coli*.," Nature 341(6242): 544-6, Nature Publishing Group, United Kingdom (1989).

Wucherpfennig, K. W., et al., "Structural Biology of the T-cell Receptor: Insights into Receptor Assembly, Ligand Recognition, and Initiation of Signaling," Cold Spring Harbor Perspectives in Biology 2(4): a005140, Cold Spring Harbor Laboratory Press, United States (2009).

Viti, F., et al., "Design and use of phage display libraries for the selection of antibodies and enzymes," Methods Enzymol, 326:480-505, Elsevier, Netherlands (2000).

Ellis, J. H., et al., "Engineered anti-CD38 monoclonal antibodies for immunotherapy of multiple myeloma," J of Immunology 155(2):925-37, American Association of Immunologists, United States (1995).

De Weeks, M., et al., "Daratumumab, a novel therapeutic human CD38 monoclonal antibody, induces killing of multiple myeloma and other hematological tumors," J of Immunology 186(3):1840-8, American Association of Immunologists, United States (2010).

Lum, L. G., et al., "Development and prospects for bispecific antibody-based therapeutics in cancer and other applications," Expert Opinion on Drug Discovery 3(9):1081-1097, Taylor and Francis, United Kingdom (2008).

International Search Report and Written Opinion for International Application No. PCT/EP2014/073738, European Patent Office, Netherlands, dated Feb. 20, 2015, 16 pages.

Co-pending U.S. Appl. No. 16/931,506, inventors Blein, S., et al., filed Jul. 17, 2020 (Not yet Published).

Anderson, K. C., et al., "Expression of human B cell-associated antigens on leukemias and lymphomas: a model of human B cell differentiation," Blood 63(6):1424-1433, Grune & Stratton, Inc., United States (1984).

Edelman, G. M., et al., "The Covalent Structure of an Entire γG Immunoglobulin Molecule," PNAS 63:78-85, National Academy of Sciences, United States (1969).

Grossbard, M. L., et al., "Anti-B4-blocked ricin: a phase II trial of 7 day continuous infusion inpatients with multiple myeloma," Br J Haematol 102(2):509-515, Blackwell Science Ltd., England (1998).

Hober, S., et al., "Protein A chromatography for antibody purification," Journal of Chromatography B 848(1):40-47, Elsevier B.V., Netherlands (2007).

Jansson, B., et al., "All individual domains of staphylococcal protein A show Fab binding," FEMS Immunol Med Microbiol 20(1):69-78, Elsevier Science B.V., Netherlands (1998).

Jendeberg, L., et al., "Engineering of $Fc_1$ and $Fc_3$ from human immunoglobulin G to analyse subclass specificity for staphylococcal protein A," J Immunol Methods 201(1):25-34, Elsevier Science B.V., Netherlands (1997).

Kabat, E. A., "The structural basis of antibody complementarity," Adv Protein Chem 32:1-75, Academic Press, United States (1978).

Lindhofer, H., et al., "Preferential species-restricted heavy/light chain pairing in rat/mouse quadromas: Implications for a single-step purification of bispecific antibodies," J Immunol 155(1):219-225, American Association of Immunologists, United States (1995).

Liu, H. F., et al., "Recovery and purification process development for monoclonal antibody production," mAbs 2(5):480-499, Landes Bioscience, United States (2010).

Loken, M. R., et al., "Flow cytometric analysis of human bone marrow. II. Normal B lymphocyte development," Blood 70(5)1316-1324, Grune & Stratton, Inc., United States (1987).

Nadler, L. M., et al., "B4, a Human B Lymphocyte-Associated Antigen Expressed on Normal Mitogen-Activated, and Malignant B Lymphocytes," J Immunol 131(1):244-250, The American Association of Immunologists, United States (1983).

Nagy, P., et al., "Decreased accessibility and lack of activation of ErbB2 in JIMT-1, a herceptin-resistant, MUC4-expressing breast cancer cell line," Cancer Res 65(2)473-482, American Association for Cancer Research, United States (2005).

Paterson, D. J., et al., "Antigens of Activated Rat T Lymphocytes Including a Molecule of 50,000 $M_r$. Detected Only on CD4 Positive T Blasts," Molecular Immunology 24(12):1281-1290, Pergamon Journals Ltd., United Kingdom (1987).

Presta, L. G., et al., "Humanization of an antibody directed against IgE," J Immunol 151(5):2623-2632, American Association of Immunologists, United States (1993).

Scheuermann, R. H. and Racila, E., "CD19 antigen in leukemia and lymphoma diagnosis and immunotherapy," Leuk Lymphoma 18:385-397, Harwood Academic Publishers GmbH, Singapore (1995).

Tashiro, M., and Montelione, G. T., "Structures of bacterial immunoglobulin-binding domains and their complexes with immunoglobulins," Curr Opin Struct Biol 5(4):471-481, Current Biology Ltd., England (1995).

Treon, S. P., et al., "Expression of serotherapy target antigens in Waldenstrom's macroglobulinemia: therapeutic applications and considerations," Semin Oncol 30(2):248-252, Elsevier Inc., United States (2003).

Uckun, F. M., et al., "Detailed studies on expression and function of CD 19 surface determinant by using B43 monoclonal antibody and the clinical potential of anti-CD19 immunotoxins," Blood 71(1)13-29, Grune & Stratton, Inc., United States (1988).

Vogel, M., et al., "A highly conserved interspecies $V_H$ in the human genome," J Mol Biol 341(2):477-489, Elsevier Ltd., United Kingdom (2004).

Blumenthal, G. M., et al., "First FDA Approval of Dual Anti-HER2 Regimen: Pertuzumab in Combination with Trastuzumab and Docetaxel

(56) References Cited

OTHER PUBLICATIONS for HER2-Positive Metastatic Breast Cancer," *Clin. Cancer Res.* 19(18):4911-4916, The American Association for Cancer Research, United States (Jun. 2013).

Tsang, R. Y. and Finn, R. S., "Beyond Trastuzumab: Novel Therapeutic Strategies in HER2-positive Metastatic Breast Cancer," *Br J Cancer* 106:6-13, Nature Publishing Group, United Kingdom (Jan. 2012).

Roopenian, D. C., et al., "FcRn: the neonatal Fc receptor comes of age," The Journal Of Immunology 7(9):715-725, Nature Publishing Group, United Kingdom (2007).

Office Action dated Dec. 22, 2015, in United States U.S. Appl. No. 14/532,923, Blein, S., et al., filed Nov. 4, 2014, 13 pages.

Co-pending U.S. Appl. No. 15/524,485, inventor Ollier, R., International Application, filed Nov. 3, 2015 (Not yet Published).

Conrad, M.L., et al., "TCR and CD3 antibody cross-reactivity in 44 species," *Cytometry Part A* 71A(11):925-933, Journal of the International Society for Advancement of Cytometry, United States (2007).

International Preliminary Report on Patentability and Written Opinion for International Application No. PCT/EP2015/060003, The International Bureau of WIPO, Switzerland, dated May 9, 2017, 9 pages.

International Search Report for International Application No. PCT/EP2015/060003, European Patent Office, Netherlands, dated Jul. 10, 2015, 6 pages.

Skegro, D., et al., "Immunoglobulin domain interface exchange as a platform technology for the generation of Fc heterodimers and bispecific antibodies," *J. Biol. Chem.* 292(23):9745-9759, The American Society for Biochemistry and Molecular Biology, Inc., United States (2017).

Office Action dated Jan. 22, 2019, in U.S. Appl. No. 15/524,482, Ollier, R et al., filed May 4, 2017, 9 pages.

Ollier, R., et al., "Single-step Protein A and Protein G avidity purification methods to support bispecific antibody discovery and development," mAbs. 11(8):1464-78, Taylor & Francis, United States (2019).

Moretti, P., Skegro, D., et al., "09: BEAT® the bispecific challenge: a novel and efficient platform for the expression of bispecific IgGs," *BMC Proceedings* 7(6_Suppl):O9, 23rd European Society for Animal Cell Technology (ESACT) Meeting: Better Cells for Better Health (Jun. 2013).

Potter, K. N. et al., "Staphylococcal protein A simultaneously interacts with framework region 1, complementarity-determining region 2, and framework region 3 on human VH3-encoded Igs," The Journal of Immunology 157(7): 2982-2988, American Association of Immunologists (1996).

Allison, T.J., et al., "Structure of a human γδ T-cell antigen receptor," *Nature* 411:820-824, Nature Publishing Group, United Kingdom (2001).

Arnold, K., et al., "The Swiss-Model workspace: a web-based environment for protein structure homology modelling," *Bioinformatics* 22(2)'. 195-201, Oxford University Press, United Kingdom (2006).

Baselga, J. and Swain, S.M., "Novel anticancer targets: revisiting ERBB2 and discovering ERBB3," *Nat Rev Cancer* 9(7):463-475, Macmillan Publishers Ltd., United Kingdom (2009).

Berman, H.M., et al., "The Protein Data Bank," *Nucleic Acids Res.* 28(1):235-242, Oxford University Press, United Kingdom (2000).

Bernstein, F.C., et al., "The Protein Data Bank: A Computer-Based Archival File for Macromolecular Structures," *Eur J Biochem* 80:319-324, Federation of European Biochemical Societies, United Kingdom (1977).

Carter, P., "Bispecific human IgG by design," *J Immunol Methods* 248:7-15, Elsevier Science B. V., Netherlands (2001).

Chacko, S., et al., "Structural Studies of Human Autoantibodies: crystal structure of a thyroid peroxidase autoantibody Fab," *J Biol Chem* 271(21):12191-12198, American Society for Biochemistry and Molecular Biology, United States (1996).

Chirino, A.J., et al., "Minimizing the immunogenicity of protein therapeutics," *Drug Discov Today* 9(2):82-90, Elsevier Ltd., United Kingdom (2004).

Emsley, P., and Cowtan, K., "Coot: model-building tools for molecular graphics," *Acta Crystallogr D Biol Crystallogr* 60(Pt 12 Pt 1):2126-2132, International Union of Crystallography, Denmark (2004).

Engelman, J.A. and Jänne, P.A., "Mechanisms of Acquired Resistance to Epidermal Growth Factor Receptor Tyrosine Kinase Inhibitors in Non-Small Cell Lung Cancer," *Clin Cancer Res* 14(10):2895-2899, American Association for Cancer Research, United States (2008).

Gadola, S.D., et al., "Structure and binding kinetics of three different human CD1d-α-galctosylceramide-specific T cell receptors," *J Exp Med* 203(3):699-710, The Rockefeller University Press, United States (2006).

Gunasekaran, K., et al., "Enhancing Antibody Fc Heterodimer Formation through Electrostatic Steering Effects: Applications to Bispecific Molecules and Monovalent IgG," *J Biol Chem* 285(25):19637-19646, American Society for Biochemistry and Molecular Biology, United States (2010).

Hennecke, J. and Wiley, D.C., "Structure of a Complex of the Human α/βT Cell Receptor (TCR) HA1.7, Influenza Hemagglutinin Peptide, and Major Histocompatibility Complex Class II Molecule, HLA-DR4 (DRA*0101 and DRB1*0401): Insight into TCR Cross-Restriction and Alloreactivity," *J Exp Med* 195(5):571-581, The Rockefeller University Press, United States (2002).

Herr, A.B., et al., "Insights into IgA-mediated immune responses from the crystal structures of human FcαRI and its complex with IgA1-Fc," *Nature* 423:614-620, Nature Publishing Group, United Kingdom (2003).

Hynes, N.E., and Lane, H.A., "ERBB Receptors and Cancer: The Complexity of Targeted Inhibitors," *Nat Rev Cancer* 5(5):341-354, Nature Publishing Group, United Kingdom (2005).

Jones, K.L. and Buzdar, A.U., "Evolving novel anti-HER2 strategies," *Lance Oncol* 10:1179-1187, Lancet Publishing Group, United Kingdom (2009).

Kjer-Nielsen, L., et al., "The 1.5 Å Crystal Structure of a Highly Selected Antiviral T cell Receptor Provides Evidence for a Structural Basis of Immunodominance," *Structure* 10(11):1521-1532, Elsevier Science Ltd., United Kingdom (2002).

Krapp, S., et al., "Structural Analysis of Human IgG-Fc Glycoforms Reveals a Correlation between Glycosylation and Structural Integrity," *J Mol Biol* 325(5):979-989, Elsevier Science Ltd.., United Kingdom (2003).

Liu, H., et al., "Effect of posttranslational modifications on the thermal stability of a recombinant monoclonal antibody," *Immunol Lett* 706(2):144-153, Elsevier B.V., Netherlands (2006).

Milstein, C., and Cuello, A.C., "Hybrid hybridomas and their use in immunohistochemistry," *Nature* 305(5934):537-540, Macmillan Publishing Ltd., United Kingdom (1983).

Nilson, B.H.K., et al., "Protein L from *Peptostreptococcus magnus* Binds to the κ Light Chain Variable Domain," *J Biol Chem* 267(4):2234-2239, The American Society for Biochemistry and Molecular Biology, Inc., United States (1992).

Pecorari, F., et al., "Folding, Heterodimeric Association and Specific Peptide Recognition of a Murine αβ T-cell Receptor Expressed in *Escherichia coli*," *J Mol Biol* 285:1831-1843, Academic Press, United Kingdom (1999).

Retter, I., et al., "VBASE2, an integrative V gene database," *Nucleic Acids Research* 33(Database issue):D671-D674, Oxford University Press, United Kingdom (2005).

Ridgway, J.B.B., et al., "'Knobs-into-holes' engineering of antibody $C_H3$ domains for heavy chain heterodimerization," *Protein Eng* 9(7):617-621, Oxford University Press, United Kingdom (1996).

Robert, C., et al., "Cutaneous side-effects of kinase inhibitors and blocking antibodies," *Lancet Oncol* 6(70):491-500, Lancet Publishing Group, United Kingdom (2005).

Rowinsky, E.K., "The erbB family: Targets for Therapeutic Development Against Cancer and Therapeutic Strategies using Monoclonal Antibodies and Tyrosine Kinase Inhibitors," *Annu Rev Med* 55:433-457, Annual Reviews, Inc., United States (2004).

(56) References Cited

OTHER PUBLICATIONS

Tina, K.G., et al., "PIC: Protein Interactions Calculator," *Nucleic Acids Res* 35(*Web Server Issue*):W473-W476, Oxford University Press, United Kingdom (2007).
Willcox, B.E., et al., "Production of soluble αβ T-cell receptor heterodimers suitable for biophysical analysis of ligand binding," *Protein Sci* 8:2418-2423, Cambridge University Press, United States (1999).
International Search Report for International Patent Application PCT/IB2012/051410, European Patent Office, Rijswijk, Netherlands, dated Nov. 6, 2012.
Written Opinion for International Patent Application PCT/IB2012/051410, European Patent Office, Rijswijk, Netherlands, dated Dec. 27, 2012.
Dall'Acqua, W., et al., "Contribution of domain interface residues to the stability of antibody $C_H3$ domain homodimers," *Biochemistry* 37(26):9266-9213, American Chemical Society, United States (1998).
Potapov, V., et al., "Protein-Protein Recognition: Juxtaposition of Domain and Interface Cores in Immunoglobulins and Other Sandwich-like Proteins," *J Mol Biol* 342:665-679, Elsevier Ltd., United Kingdom (2004).
International Preliminary Report on Patentability for International Patent Application No. PCT/IB2012/051410, European Patent Office, dated Oct. 1, 2013.
Office Action dated Aug. 8, 2014, in U.S. Appl. No. 13/695,773, inventors Blein, S., et al., filed Nov. 1, 2012.
Office Action dated Feb. 6, 2015, in U.S. Appl. No. 13/695,773, inventors Blein, S., et al., filed Nov. 1, 2012.
Office Action dated Sep. 1, 2015, in U.S. Appl. No. 13/695,773, inventors Blein, S., et al., filed Nov. 1, 2012.
Office Action dated Dec. 9, 2015, in United States U.S. Appl. No. 13/695,773, Blein, S., et al., filed Nov. 1, 2012.
Office Action dated Jul. 5, 2016, in U.S. Appl. No. 13/695,773, Blein, S., et al., filed Nov. 1, 2012.
Office Action dated Nov. 20, 2014, in U.S. Appl. No. 14/167,712, inventors Blein, S., et al., filed Jan. 29, 2014.
Office Action dated Apr. 3, 2015, in U.S. Appl. No. 14/167,712, inventors Blein, S., et al., filed Jan. 29, 2014.
Office Action dated Jul. 21, 2015, in U.S. Appl. No. 14/167,712, inventors Blein, S., et al., filed Jan. 29, 2014.
Office Action dated Oct. 27, 2015, in United States U.S. Appl. No. 14/167,712, inventors Blein, S., et al., filed Jan. 29, 2014.
Office Action dated May 23, 2016, in U.S. Appl. No. 14/167,712, inventors Blein, S., et al., filed Jan. 29, 2014.
Dall'Acqua, W.F., et al., "Modulation of the Effector Functions of a Human IgG1 through Engineering of its Hinge Region," *J. Immunol.* 117:1129-1138, American Association of Immunologists, United States (2006).
Ibragimova, G.T., et al., "Stability of the Beta-Sheet of the WW Domain: A Molecular Dynamics Simulation Study," *Biophysical J.* 77:2191-2198, Rockefeller University Press, United States (1999).
Kumar, S., et al., "Molecular Cloning and Expression of the Fabs of Human Autoantibodies in *Escherichia coli*," *J. Biol. Chem.* 275:35129-35136, American Society for Biochemistry and Molecular Biology, United States (2000).
Salfeld, J. G., "Isotype Selection in Antibody Engineering," *Nature Biotechnol.* 25(12):1369-1372, Nature America Publishing, United States (2007).
Song, M. K., et al., "Light Chain of Natural Antibody Plays a Dominant Role in Protein Antigen Binding," *Biochem. Biophys. Res. Commun.* 268:390-394, Academic Press, United States (2000).
Smith-Gill, S. J., et al., "Contributions of immunoglobulin heavy and light chains to antibody specificity for lysozyme and two haptens," *J. Immunol.* 139:4135-4144, American Association of Immunologists, United States (1987).
International Search Report and Written Opinion for International Application No. PCT/EP2015/075628, European Patent Office, Netherlands, dated Jan. 29, 2016, 19 pages.
Office Action dated May 20, 2021, in U.S. Appl. No. 16/288,980, Blein, S., et al., filed Feb. 28, 2019, 37 pages.
Office Action dated Jan. 12, 2022, in U.S. Appl. No. 16/288,980, Blein, S., et al., filed Feb. 28, 2019, 22 pages.
Office Action dated Aug. 19, 2022, in U.S. Appl. No. 16/288,980, Blein, S., et al., filed Feb. 28, 2019, 12 pages.
Office Action dated Apr. 5, 2023, in U.S. Appl. No. 16/288,980, Blein, S., et al., filed Feb. 28, 2019, 11 pages.
Office Action dated Mar. 23, 2020, in U.S. Appl. No. 15/984,822, Blein, S., et al., filed May 21, 2018, 16 pages.
Office Action dated Sep. 21, 2020, in U.S. Appl. No. 15/984,822, Blein, S., et al., filed May 21, 2018, 14 pages.
Office Action dated Apr. 22, 2021, in U.S. Appl. No. 15/984,822, Blein, S., et al., filed May 21, 2018, 14 pages.
Office Action dated Dec. 15, 2021, in U.S. Appl. No. 15/984,822, Blein, S., et al., filed May 21, 2018, 22 pages.
Office Action dated Jul. 7, 2022, in U.S. Appl. No. 15/984,822, Blein, S., et al., filed May 21, 2018, 13 pages.
Office Action dated Dec. 13, 2022, in U.S. Appl. No. 15/984,822, Blein, S., et al., filed May 21, 2018, 7 pages.
Office Action dated Nov. 15, 2022, in U.S. Appl. No. 16/931,506, Blein, S., et al., filed Jul. 17, 2020, 17 pages.

\* cited by examiner

FIG. 1A

| Antibody | Back-mutations VH / VL | SEQ ID NO H / L chains | Transient expression (mg/L) | FAB Tm (°C) | HPB-ALL staining relative to OKT3 chimera |
|---|---|---|---|---|---|
| Chimeric OKT3 | N.A. | 25/26 | 20 | 80.7 | +++ |
| VH/VL | - / - | 27/39 | 50 | 88.1 | - |
| VH/VL2 | - / M4L | 27/41 | 47 | 90.6 | - |
| VH/VL3 | - / M4L- F71Y | 27/42 | 43 | 89.8 | + |
| VH1/VL1 | A49G / F71Y | 28/40 | 22 | 90.1 | - |
| VH1/VL2 | A49G / M4L | 28/41 | 42 | 90.5 | - |
| VH1/VL3 | A49G / M4L-F71Y | 28/42 | 40 | 90.7 | + |
| VH2/VL1 | I34M-A49G / F71Y | 29/40 | 51 | 89.5 | - |
| VH2/VL2 | I34M-A49G / M4L | 29/41 | 43 | 90.1 | - |
| VH2/VL3 | I34M-A49G / M4L- F71Y | 29/42 | 42.5 | 89.5 | + |
| VH3/VL1 | A49G-A71T / F71Y | 30/40 | 33.5 | 89.7 | - |
| VH3/VL2 | A49G-A71T / M4L | 30/41 | 42 | 90.4 | - |
| VH3/VL3 | A49G-A71T / M4L- F71Y | 30/42 | 56.5 | 89.8 | + |

FIG. 1B

| Antibody | Back-mutations | SEQ ID NO H / L chains | Transient expression (mg/l) | FAB Tm (°C) | HPB-ALL staining relative to OKT3 chimera |
|---|---|---|---|---|---|
| VH4/VL2 | I34M-A49G-A71T / M4L | 31/41 | 20 | 88.4 | ++ |
| VH4/VL3 | I34M-A49G-A71T / M4L-F71Y | 31/42 | 34 | 88.7 | ++ |
| VH5/VL2 | I34M-A49G-I69L-A71T-T73K / M4L | 32/41 | 40 | 87 | ++ |
| VH5/VL3 | I34M-A49G-I69L-A71T-T73K / M4L-F71Y | 32/42 | 36 | 87.2 | ++ |
| VH5/VL4 | I34M-A49G-I69L-A71T-T73K / M4L-L46R-L47W-F71Y | 32/43 | 12 | 80.3 | +++ |
| VH5/VL6 | I34M-A49G-I69L-A71T-T73K / M4L-L46R-L47W-F71Y-P96F | 32/45 | 15.6 | 78.6 | +++ |
| VH5/VL7 | I34M-A49G-I69L-A71T-T73K / M4L-V33M-A34N-F71Y-P96F | 32/46 | 35.4 | 84.1 | ++ |
| VH6/VL3 | I34M-V48I-A49G-I69L-A71T-T73K / M4L-F71Y | 33/42 | 23 | 88.3 | ++ |
| VH6/VL4 | I34M-V48I-A49G-I69L-A71T-T73K / M4L-L46R-L47W-F71Y | 33/43 | 14 | 80.8 | +++ |
| VH6/VL5 | I34M-V48I-A49G-I69L-A71T-T73K / M4L-V33M-A34N-F71Y | 33/44 | 26 | 86.1 | ++ |
| VH6/VL6 | I34M-V48I-A49G-I69L-A71T-T73K / M4L-L46R-L47W-F71Y-P96F | 33/45 | 14.8 | 79.1 | +++ |
| VH6/VL7 | I34M-V48I-A49G-I69L-A71T-T73K / M4L-V33M-A34N-F71Y-P96F | 33/46 | 32 | 85.3 | ++ |

FIG. 1C

| Antibody | Back-mutations | SEQ ID NO H/L chains | Transient expression (mg/l) | FAB Tm (°C) | HPB-ALL staining relative to OKT3 chimera |
|---|---|---|---|---|---|
| VH6/VL8 | I34M-V48I-A49G-I69L-A71T-T73K / M4L-L46R-L47W-R66G-F71Y | 33/47 | 7 | 80.6 | +++ |
| VH7/VL3 | I34M-A49G-R58N-I69L-A71T-T73K / M4L-F71Y | 34/42 | 21 | 86.1 | ++ |
| VH7/VL4 | I34M-A49G-R58N-I69L-A71T-T73K / M4L-L46R-L47W-F71Y | 34/43 | 25 | 80.5 | +++ |
| VH7/VL5 | I34M-A49G-R58N-I69L-A71T-T73K / M4L-V33M-A34N-F71Y | 34/44 | 26 | 84.12 | ++ |
| VH8/VL4 | I34M-V48I-A49G-R58Y-I69L-A71T-T73K / M4L-L46R-L47W-F71Y | 35/43 | 7 | 80.9 | +++ |
| VH8/VL8 | I34M-V48I-A49G-R58Y-I69L-A71T-T73K / M4L-L46R-L47W-R66G-F71Y | 35/47 | 23 | 83.5 | +++ |
| VH9/VL8 | I34M-V48I-A49G-R58Y-G65S-I69L-A71T-T73K / M4L-L46R-L47W-R66G-F71Y | 36/47 | 13 | 82 | +++ |
| VH10/VL4 | I34M-V48I-A49G-R58Y-G65S-F67A-I69L-A71T-T73K / M4L-L46R-L47W-F71Y | 37/43 | 7 | 78.6 | +++ |
| VH10/VL8 | I34M-V48I-A49G-R58Y-G65S-F67A-I69L-A71T-T73K / M4L-L46R-L47W-R66G-F71Y | 37/47 | 10 | 80.4 | +++ |
| VH11/VL4 | I34M-V48I-A49G-R58Y-I69L-A71T-T73K-N82aS / M4L-L46R-L47W-F71Y | 38/43 | 8 | 80.3 | +++ |
| VH11/VL8 | I34M-V48I-A49G-R58Y-I69L-A71T-T73K-N82aS / M4L-L46R-L47W-R66G-F71Y | 38/47 | 15 | 82.3 | +++ |

FIG. 1D
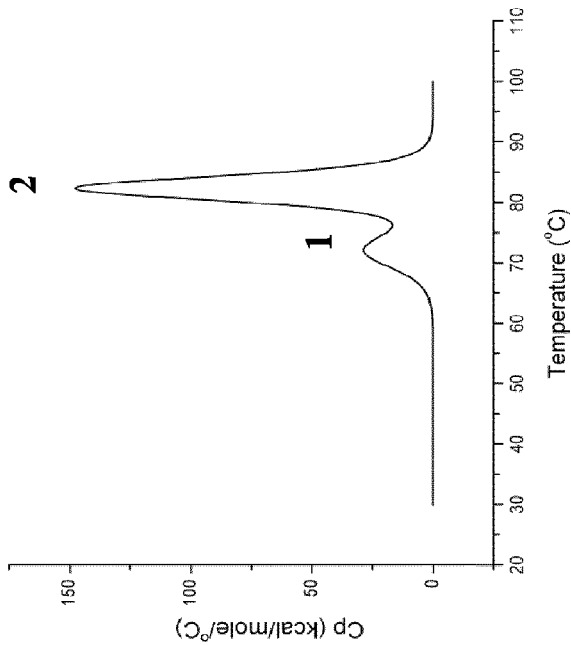
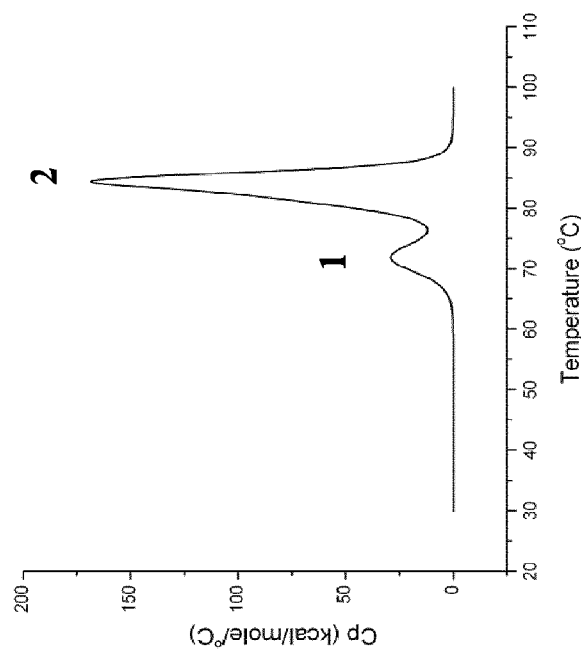

FIG. 1E

| scFv-Fc fusion | SEQ ID NO | Transient expression (mg/L) | scFv Tm (°C) | HPB-ALL staining relative to OKT3 chimera |
|---|---|---|---|---|
| Mouse OKT3 | 52 | 0.35 | - | ++ |
| VH5-VL3 | 53 | 21 | 71.2 | + |
| VH6-VL4 | 54 | 29 | 65.3 | ++ |
| VH6-VL5 | 55 | 27 | 71.2 | ++ |
| VH8-VL4 | 56 | 28 | 66.4 | +++ |
| VH8-VL8 | 57 | 28 | 69.2 | +++ |

FIG. 1F
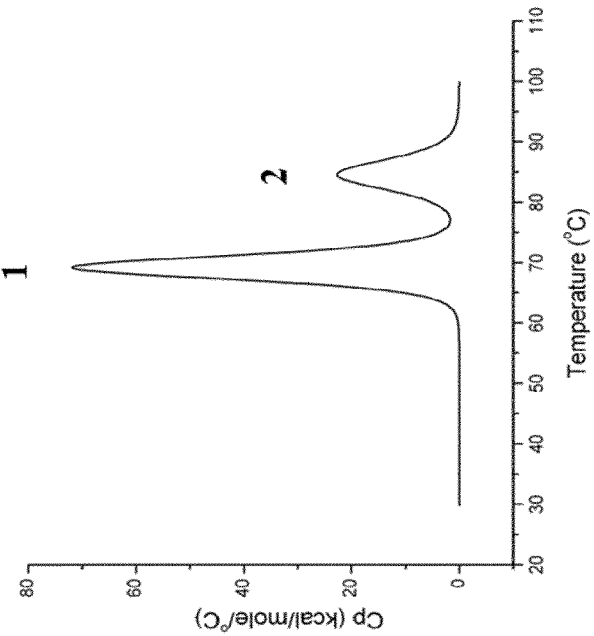
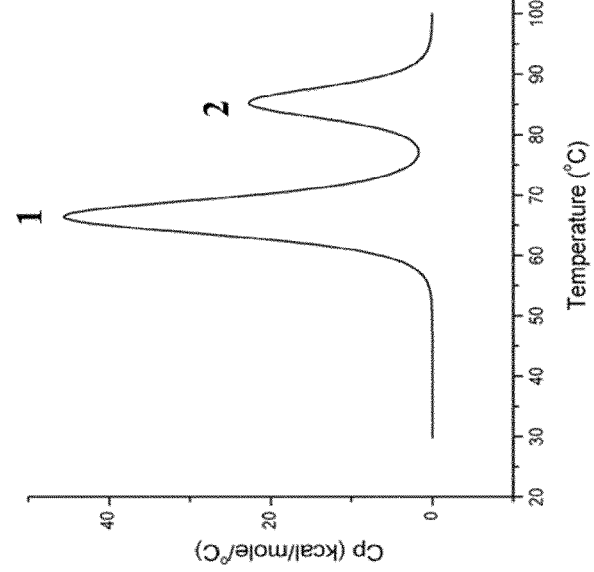

FIG. 2A

| Antibody | Back-mutations VH/VL | SEQ ID NO H/L chains | Format | Transient expression (mg/L) | SPR-Binding to human/cynomolgus monkey CD3 epsilon 1-26_Fc proteins |
|---|---|---|---|---|---|
| Chimeric SP34 | N.A. | 62/63 | IgG1 | 7 | ++++ |
| VH1/VL1 | -/- | 64/69 | IgG1 | 8 | + |
| VH1/VL2 | -/Q89A | 64/70 | IgG1 | 1 | ++++ |
| VH1/VL3 | -/deleted 8P | 64/71 | IgG1 | 0.5 | - |
| VH1/VL4 | -/deleted 8P-Q89A | 64/72 | IgG1 | 0.5 | ++++ |
| VH1/VL5 | -/A2I-Q89A | 64/73 | IgG1 | 2.6 | ++++ |
| VH1/VL6 | -/F44P-Q89A | 64/74 | IgG1 | 0.9 | ++++ |
| VH1/VL7 | -/A2I-F44P-Q89A | 64/75 | IgG1 | No expression | Not tested |
| VH1/VL8 | -/L66G-Q89A | 64/76 | IgG1 | 0.8 | + |
| VH1/VL9 | -/A2I-L66G-Q89A | 64/77 | IgG1 | No expression | Not tested |
| VH1/VL10 | -/F87Y-Q89A | 64/78 | IgG1 | 6 | ++++ |
| VH1/VL11 | -/L66G-D69T-Q89A | 64/79 | IgG1 | 0.8 | + |
| VH1/VL12 | -/D69T-Q89A | 64/80 | IgG1 | 1.5 | ++ |
| VH1/VL13 | -/S25A/Q89A | 64/81 | IgG1 | 1 | +++ |
| VH1/VL14 | -/G46L-Q89A | 64/82 | IgG1 | 3 | - |
| VH1/VL15 | -/E38Q-Q89A | 64/83 | IgG1 | 3 | ++++ |
| VH1/VL16 | -/A2I-D69T-Q89A | 64/84 | IgG1 | 0.5 | + |
| VH1/VL17 | -/A2I-S25A-Q89A | 64/85 | IgG1 | 1 | ++ |
| VH1/VL18 | -/A2I-Q89A-Q100G | 64/86 | IgG1 | 1 | ++ |
| VH1/VL19 | -/A2I-D69T-F87Y-Q89A | 64/87 | IgG1 | 0.2 | + |
| VH1/VL20 | -/A2I-E38Q-D69T-F87Y-Q89A | 64/88 | IgG1 | No expression | Not tested |
| VH1/VL21 | -/A2I-F87Y-Q89A | 64/89 | IgG1 | 8 | ++++ |
| VH1/VL22 | -/A2I-E38Q-F87Y-Q89A | 64/90 | IgG1 | 2 | +++ |

FIG. 2B

| ScFv-Fc fusion | Back-mutations VH/VL | SEQ ID NO H/L chains | Format | Transient expression (mg/L) | SPR-Binding to human/cynomolgus monkey CD3 epsilon 1-26_Fc proteins |
|---|---|---|---|---|---|
| VH2/VL21 | G65S /A2I-F87Y-Q89A | 91 | scFv-Fc | 5 | +++ |
| VH3/VL23 | G65S-W100eY /A2I-F87Y-Q89A-W91F | 92 | scFv-Fc | 10 | ++ |
| VH4/VL23 | G65S-W100eF /A2I-F87Y-Q89A-W91F | 93 | scFv-Fc | 5.5 | ++++ |
| VH5/VL23 | W100eY/A2I-F87Y-Q89A-W91F | 94 | scFv-Fc | 15 | ++++ |
| VH1/VL24 | -/A2I-T27A-G27aA- F87Y-Q89A | 349 | scFvFc | No expression | Not tested |
| VH1/VL25 | -/A2I-V27cA-T28A- F87Y-Q89A | 350 | scFvFc | 4 | - |
| VH1/VL26 | -/A2I-T29A-S30A- F87Y-Q89A | 351 | scFvFc | 12 | ++++ |
| VH1/VL27 | -/A2I-N31A-Y32A- F87Y-Q89A | 95 | scFv-Fc | 2 | - |
| VH1/VL28 | -/A2I-N52A-K53A- F87Y-Q89A | 96 | scFv-Fc | No expression | Not tested |
| VH1/VL29 | -/A2I-R54A-P56A- F87Y-Q89A | 97 | scFv-Fc | 4 | - |
| VH1/VL30 | -/A2I-Y92A-S93A- F87Y-Q89A | 98 | scFv-Fc | 2 | + |
| VH1/VL31 | -/A2I-N94A -F87Y-Q89A | 99 | scFv-Fc | 2 | ++ |
| VH5/VL32 | W100eY/A2I-T29A-S30A-T51A-F87Y-Q89A-W91F | 100 | scFv-Fc | 25 | ++++ |

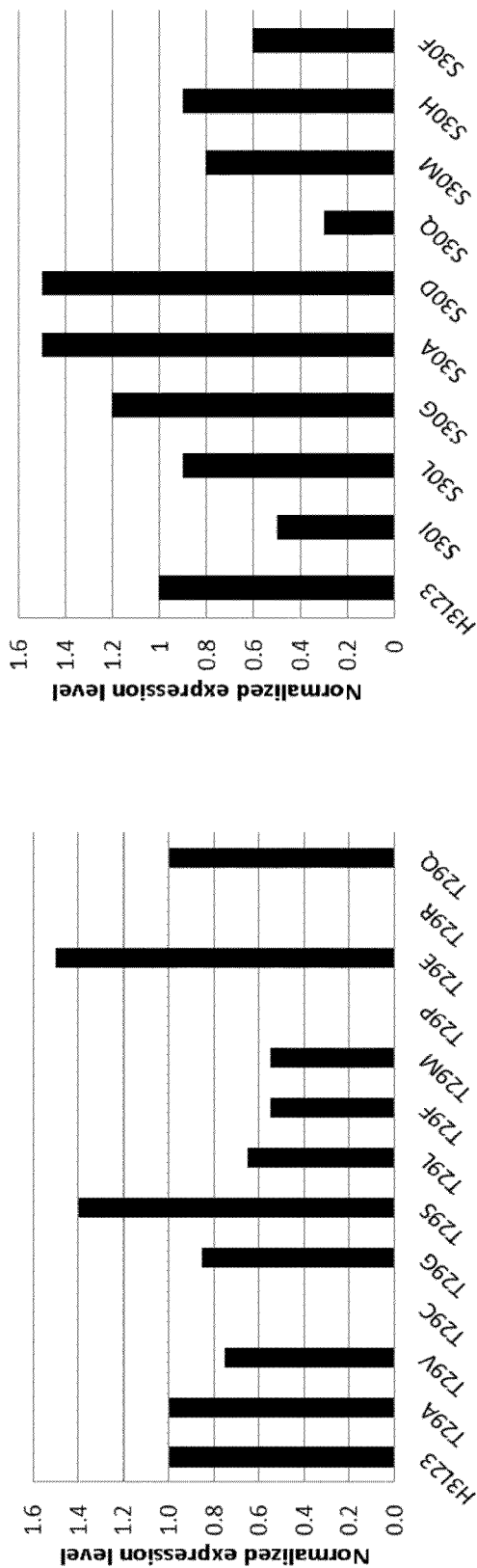
FIG. 5A
FIG. 5B
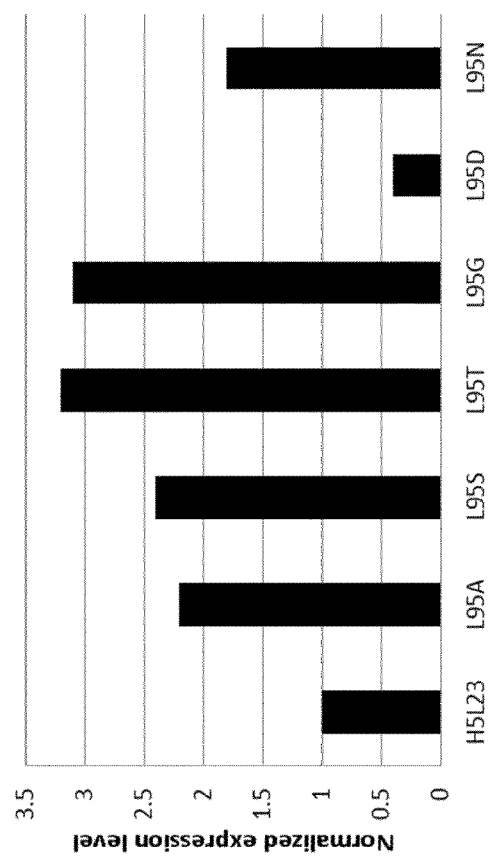
FIG. 5C

FIG. 7E
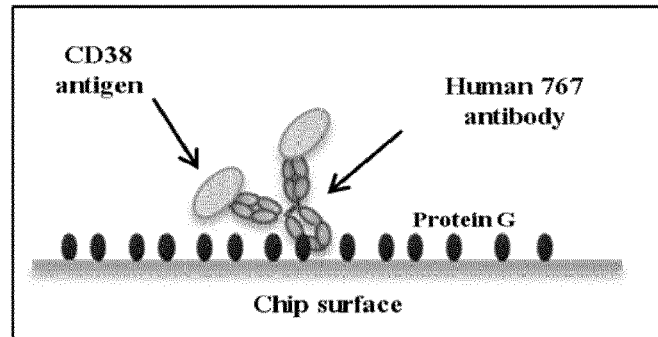
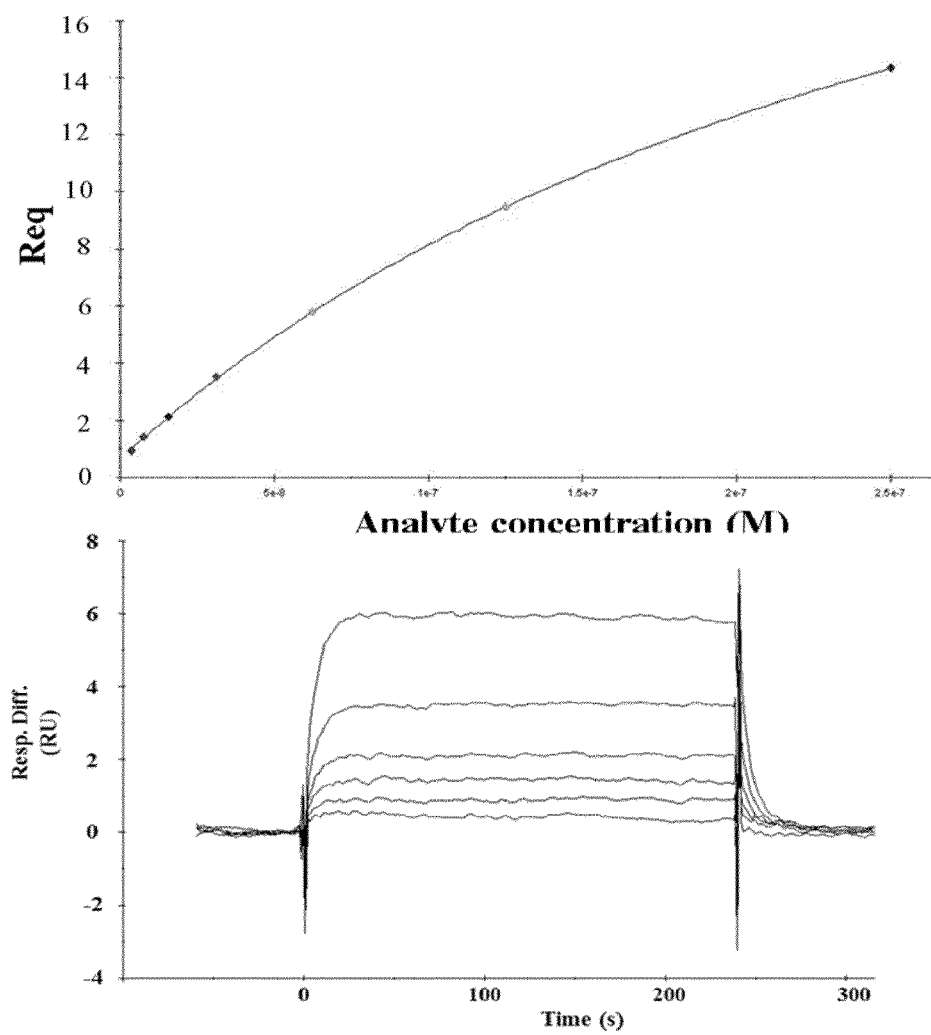

FIG. 7F
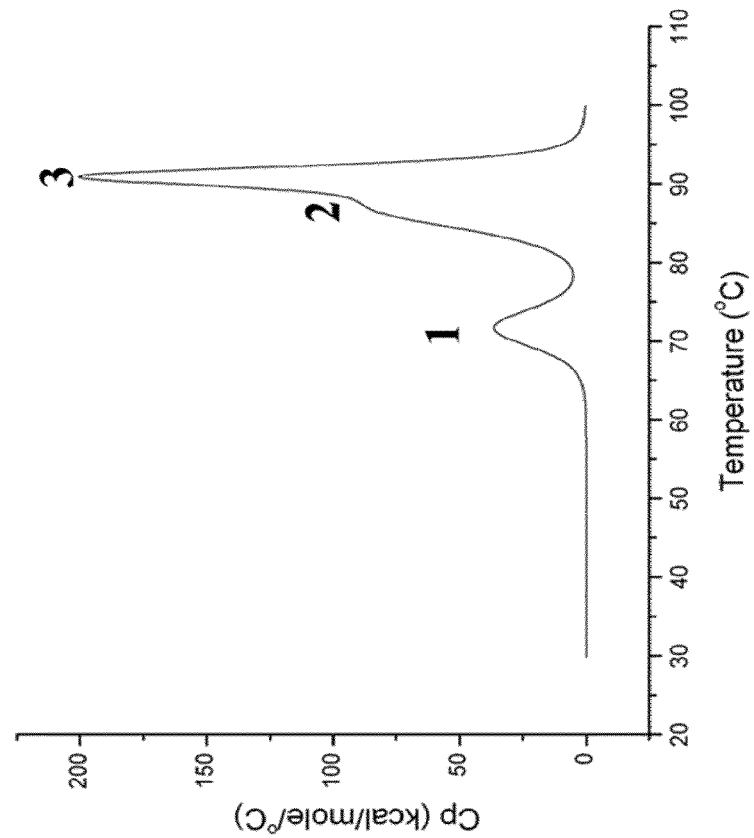
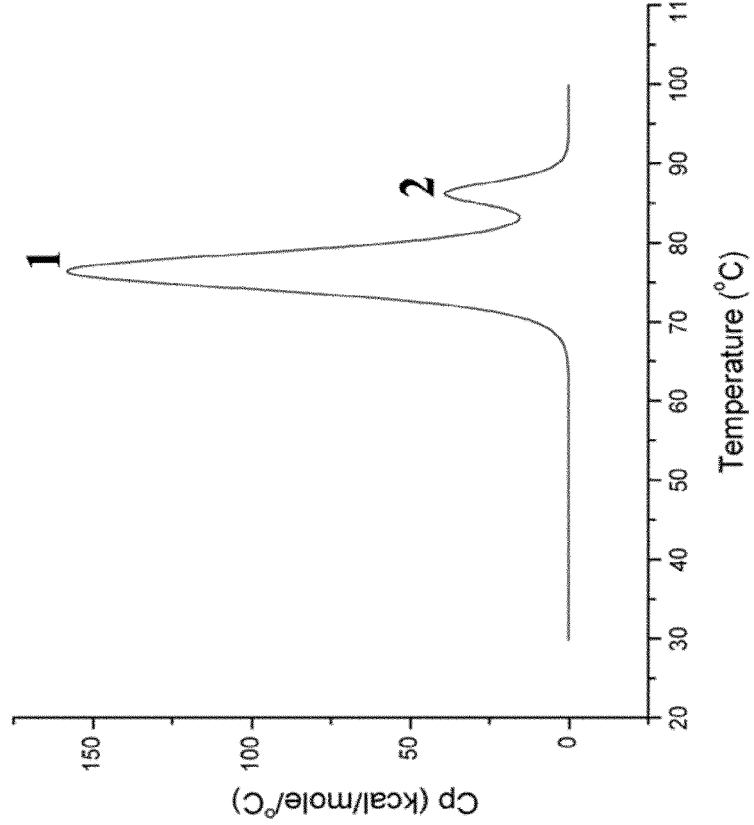

FIG. 7G
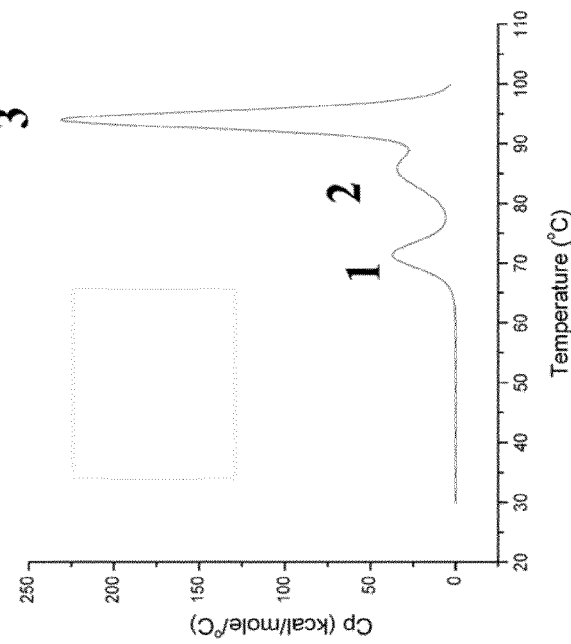
Humanized 9G7 best-fit antibody
Tm(1): 71.4°C; Tm(2): 85.8 °C; Tm(3): 94.0°C (FAB)
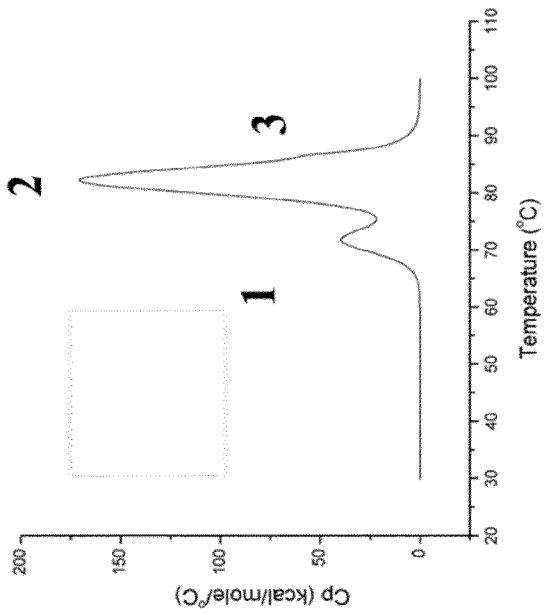
Chimeric 9G7 antibody
Tm(1): 71.70°C; Tm(2): 82.20°C (FAB); Tm(3): 86.6 °C

FIG. 7J

| | Chimeric 9G7 antibody | Humanized 9G7 best-fit antibody | Humanized 9G7 best-framework antibody |
|---|---|---|---|
| HC/LC SEQ ID NO | 126/127 | 124/128 | 131/132 |
| Transient expression levels (mg/l) | 20 | 11 | 17 |
| KD human CD38 (nM) | 0.4 | 0.5 | 0.4 |
| KD cynomolgus monkey CD38 (nM) | 1 | 3.2 | 1 |
| FAB Tm (°C) | 82.2 | 94 | 89.2 |

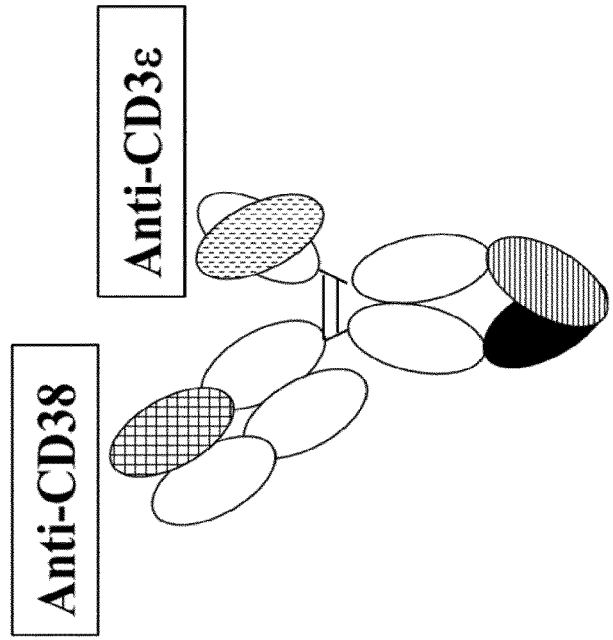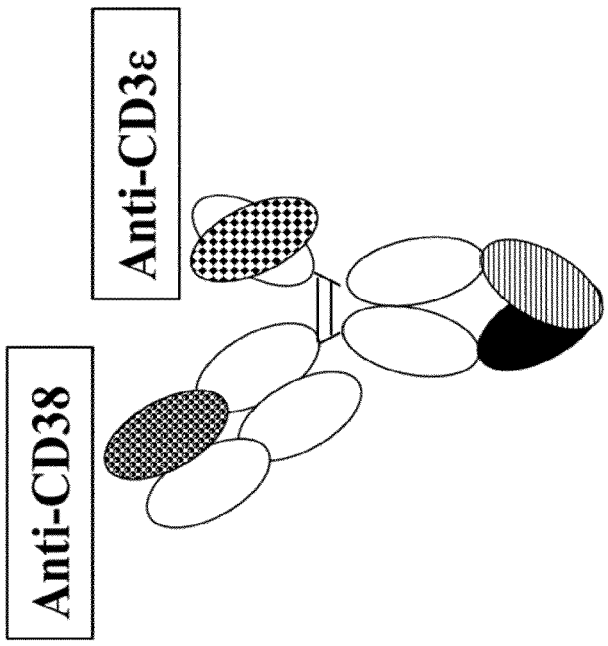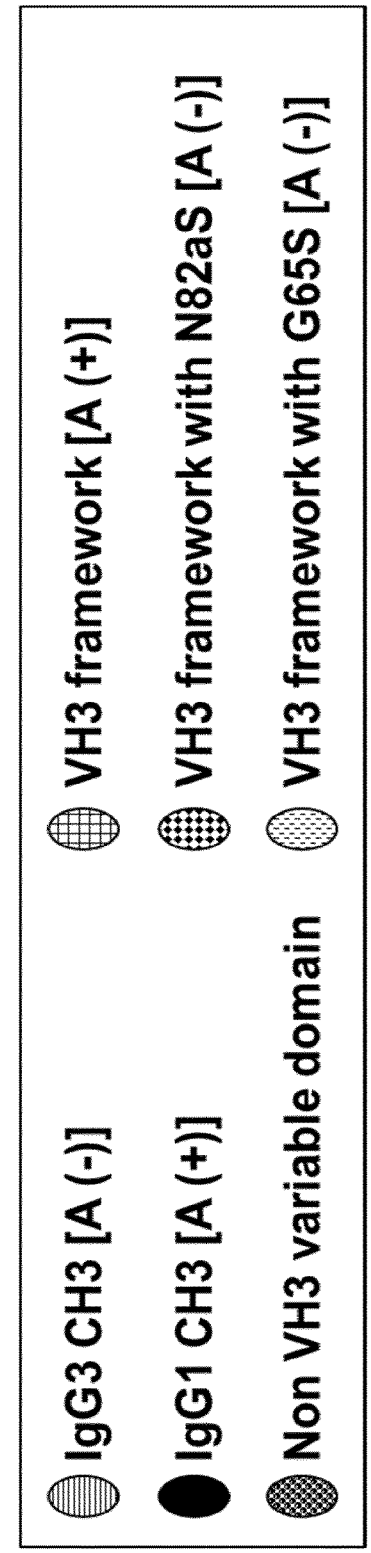

CD3/CD38 T CELL RETARGETING HETERO-DIMERIC IMMUNOGLOBULINS AND METHODS OF THEIR PRODUCTION

CROSS REFERENCE TO RELATED APPLICATIONS

This application is a continuation of U.S. application Ser. No. 15/524,485, which is the National Stage of International Patent Application No. PCT/EP2015/075628, filed Nov. 3, 2015, the disclosures of which are herein incorporated by reference in their entireties.

REFERENCE TO A SEQUENCE LISTING SUBMITTED ELECTRONICALLY VIA EFS-WEB

The content of the electronically submitted sequence listing (Name: 3305_0240003_ST25.txt; Size:425,461 bytes; and Date of Creation: Oct. 9, 2018) is herein incorporated by reference in its entirety.

FIELD OF THE INVENTION

The present invention relates to hetero-dimeric immunoglobulins that target both a component of the human CD3 antigen and a component of the human CD38 antigen and methods of making the same. The present invention also relates to antibodies which bind to the human CD38 antigen and derivatives thereof for use as therapeutic or diagnostic reagents and methods of making the same.

BACKGROUND OF THE INVENTION

The in vivo use of monoclonal antibodies (mAbs) has become a mainstay of routine clinical practice in the treatment of various human diseases and targeted immunotherapy with mAbs has become critical for the successful treatment of many forms of cancer. This is exemplified by rituximab, a chimeric CD20 Antibody, which has revolutionized the treatment of several B cell malignancies such as follicular lymphoma. B cells, however, lose CD20 expression upon terminal differentiation into plasma cells, and rituximab consequently has conveyed very limited benefit to the treatment of Multiple Myeloma amongst other cancers.

The CD38 molecule is an attractive target because of its pattern of expression and its twin role as receptor and ectoenzyme. The targeting of CD38 has been proposed particularly as a means of treating multiple myeloma and chronic lymphocytic leukemia (CLL).

T cell redirected killing is a desirable mode of action in many therapeutic areas. Various bispecific antibody formats have been shown to mediate T cell redirection both in pre-clinical and clinical investigations (May C et al., (2012) Biochem Pharmacol, 84(9): 1105-12; Frankel S R & Baeuerle P A, (2013) Curr Opin Chem Biol, 17(3): 385-92). All T cell retargeting bispecific antibodies or fragments thereof are engineered to have at least two antigen binding sites wherein one site binds a surface antigen on a target cell and the other site binds a T cell surface antigen. Amongst T cell surface antigens, the human CD3 epsilon subunit from the TCR protein complex has been the most targeted to redirect T cell killing.

Many bispecific antibody formats have been used to redirect T cell killing, these mainly include tandem of scFv fragments and diabody based formats with only few examples of Fc-based bispecific antibody formats reported (Moore P A et al., (2011) Blood, 117(17): 4542-51; May C et al., (2012) supra; Frankel S R & Baeuerle P A, (2013) supra). Bispecific formats that will encompass a human Fc region will have longer circulation half-lives which may result in enhanced efficacy and/or less frequent dosing regimens. Among possible Fc-based bispecific formats, one preferred format to redirect T cell killing is the so-called heavy chain hetero-dimer format. This format is of particular interest as it does not allows aggregation of multiple copies of human CD3 molecules at the T cell surface thereby preventing any T cell inactivation (Klein C et al., (2012) MAbs, 4(6): 653-63).

The first described method to engineer heavy chain hetero-dimers is a method known as the "knob-into-hole" method (PCT Publication No: WO199627011; Merchant A M et al., (1998) Nat Biotechnol, 16(7): 677-81). Recently a chemical method known as the FAB-arm exchange method wherein two antibodies are combined into one bispecific antibody via reduction and in vitro reshuffling of half-immunoglobulins has been reported (PCT Publication Nos: WO2008119353 (Schuurman J et al.) and WO2013060867 (Gramer M et al.); Labrijn A F et al., (2013) Proc Natl Acad Sci USA, 110(13): 5145-50).

SUMMARY OF THE INVENTION

The present invention provides an antibody or fragment thereof that binds to human CD38 comprising a heavy chain CDR1 comprising the amino acid sequence of SEQ ID NO: 25 or SEQ ID NO: 208, and/or a heavy chain CDR2 comprising the amino acid sequence of SEQ ID NO: 26 or SEQ ID NO: 209, and/or a heavy chain CDR3 comprising the amino acid sequence of SEQ ID NO: 27 or SEQ ID NO: 210; and/or comprising a light chain CDR1 comprising the amino acid sequence of SEQ ID NO: 28 or SEQ ID NO:211 or SEQ ID NO: 214, and/or a light chain CDR2 comprising the amino acid sequence of SEQ ID NO: 29 or SEQ ID NO: 212, and/or a light chain CDR3 comprising the amino acid sequence of SEQ ID NO: 30 or SEQ ID NO: 213; or wherein the epitope binding region that binds the CD38 protein complex comprises a heavy chain CDR1 comprising the amino acid sequence of SEQ ID NO: 31, a heavy chain CDR2 comprising the amino acid sequence of SEQ ID NO: 32 and a heavy chain CDR3 comprising the amino acid sequence of SEQ ID NO: 33, and a light chain CDR1 comprising the amino acid sequence of SEQ ID NO: 34, a light chain CDR2 comprising the amino acid sequence of SEQ ID NO: 35 and a light chain CDR3 comprising the amino acid sequences of SEQ ID NO: 36.

In accordance with this aspect of the present invention the anti CD38 antibody or fragment thereof, is a murine antibody, chimeric antibody, humanized antibody or a fully human antibody.

In particular the antibody or fragment thereof comprises a heavy chain variable region sequence comprising the amino acid sequence consisting of SEQ ID NO: 52, SEQ ID NO: 58, SEQ ID NO: 60 or a sequence at least 80% identical to the non-CDR region of either of said heavy chain variable region sequences and/or wherein the antibody or fragment thereof comprises a light chain variable region sequence comprising the amino acid sequence of SEQ ID NO: 55, SEQ ID NO: 59, SEQ ID NO: 61 or a sequence at least 80% identical to the non-CDR region of any one of said light chain variable region sequences.

In particular the antibody or fragment thereof comprises a heavy chain sequence comprising the amino acid sequence consisting of SEQ ID NO: 73, SEQ ID NO: 75, SEQ ID NO:

76, SEQ ID NO: 145, SEQ ID NO: 147, SEQ ID NO: 149 or a sequence at least 80% identical to the non-CDR region of either of said heavy chain variable region sequences and/or wherein the antibody or fragment thereof comprises a light chain sequence comprising the amino acid sequence of SEQ ID NO: 74, SEQ ID NO: 77, SEQ ID NO: 146, SEQ ID NO: 148, SEQ ID NO: 150 or a sequence at least 80% identical to the non-CDR region of any one of said light chain variable region sequences.

In particular the antibody or fragment comprises human heavy and/or light chain constant regions and wherein the human heavy constant region is selected from the group of human immunoglobulins consisting of IGHG1, non fucosylated IGHG1 and IGHG4.

The present invention also provides new anti-human CD3/CD38 bispecific antibodies.

In accordance with the present invention the target binding portion of the anti-human CD3 binding arm preferably comprises a single chain variable fragment (scFv) of SP34 or OKT3. In particular wherein the anti-human CD3 binding arm is SP34 it has a better expression profile in comparison to a scFv-Fc comprising the heavy and light variable regions encoded by SEQ ID NOs: 1 and 2, whilst maintaining its CD3 binding properties.

In particular when expressed as a scFv-Fc it has at least a twofold improvement in expression in comparison to a SP34 chimera formatted as a scFv-Fc comprising the heavy and light variable regions encoded by SEQ ID NOs: 1 and 2. Preferably the improved SP34 scFv has at least a sixfold improvement in expression in comparison to a SP34 chimera formatted as an scFv comprising the heavy and light variable regions encoded by SEQ ID NOs: 1 and 2 and most preferably a twelvefold improvement in expression in comparison to a SP34 chimera formatted as an scFv comprising the heavy and light variable regions encoded by SEQ ID NOs: 1 and 2.

In accordance with another aspect of the present invention when expressed as a scFv in a bispecific antibody comprising a FAB arm in the BEAT format, it has at least a twofold improvement in expression in comparison to a SP34 chimera formatted as an scFv comprising the heavy and light variable regions encoded by SEQ ID NOs: 1 and 2. Preferably the improved SP34 scFv as a component of a BEAT bispecific antibody has at least a fivefold improvement in expression in comparison to a SP34 chimera formatted as an scFv, comprising the heavy and light variable regions encoded by SEQ ID NOs: 1 and 2, as a component of a BEAT bispecific antibody.

In accordance with the present invention the two binding arms of the anti-human CD3 bispecific antibody each comprise an immunoglobulin constant region and wherein the first arm or polypeptide binds to protein A and the second arm or polypeptide does not bind to protein A.

According to a further aspect of the present invention the epitope binding region of the polypeptide which binds the CD3 protein complex comprises a heavy chain CDR1 comprising the amino acid sequence of SEQ ID NO: 3, a heavy chain CDR2 comprising the amino acid sequence of SEQ ID NO: 4 and a heavy chain CDR3 comprising the amino acid sequence of SEQ ID NO: 5 or SEQ ID NO: 9, and a light chain CDR1 comprising the amino acid sequence of SEQ ID NO: 6, a light chain CDR2 comprising the amino acid sequence of SEQ ID NO: 7 or SEQ ID NO: 11 and a light chain CDR3 comprising the amino acid sequences of: SEQ ID NO: 8, SEQ ID NO: 10 or SEQ ID NO: 12; or wherein the epitope binding region that binds the CD3 protein complex comprises a heavy chain CDR1 comprising the amino acid sequence of SEQ ID NO: 163, and a heavy chain CDR2 comprising the amino acid sequence of SEQ ID NO:164, and a heavy chain CDR3 comprising the amino acid sequence of SEQ ID NO: 165; and comprising a light chain CDR1 comprising the amino acid sequence of SEQ ID NO: 166, and a light chain CDR2 comprising the amino acid sequence of SEQ ID NO: 167, and a light chain CDR3 comprising the amino acid sequence of SEQ ID NO: 168.

According to a further aspect of the present invention the epitope binding region of the polypeptide binds the CD38 protein comprises a heavy chain CDR1 comprising the amino acid sequence of SEQ ID NO: 13, a heavy chain CDR2 comprising the amino acid sequence of SEQ ID NO: 14 and a heavy chain CDR3 comprising the amino acid sequence of SEQ ID NO: 15, and a light chain CDR1 comprising the amino acid sequence of SEQ ID NO: 16, a light chain CDR2 comprising the amino acid sequence of SEQ ID NO: 17 and a light chain CDR3 comprising the amino acid sequences of: SEQ ID NO: 18; or wherein the epitope binding region that binds the CD38 protein complex comprises a heavy chain CDR1 comprising the amino acid sequence of SEQ ID NO: 19, a heavy chain CDR2 comprising the amino acid sequence of SEQ ID NO: 20 and a heavy chain CDR3 comprising the amino acid sequence of SEQ ID NO: 21, and a light chain CDR1 comprising the amino acid sequence of SEQ ID NO: 22, a light chain CDR2 comprising the amino acid sequence of SEQ ID NO: 23 and a light chain CDR3 comprising the amino acid sequences of SEQ ID NO: 24; or the epitope binding region of the polypeptide binds the CD38 protein comprises a heavy chain CDR1 comprising the amino acid sequence of SEQ ID NO: 25, a heavy chain CDR2 comprising the amino acid sequence of SEQ ID NO: 26 and a heavy chain CDR3 comprising the amino acid sequence of SEQ ID NO: 27, and a light chain CDR1 comprising the amino acid sequence of SEQ ID NO: 28, a light chain CDR2 comprising the amino acid sequence of SEQ ID NO: 29 and a light chain CDR3 comprising the amino acid sequences of: SEQ ID NO: 30; or wherein the epitope binding region that binds the CD38 protein complex comprises a heavy chain CDR1 comprising the amino acid sequence of SEQ ID NO: 31, a heavy chain CDR2 comprising the amino acid sequence of SEQ ID NO: 32 and a heavy chain CDR3 comprising the amino acid sequence of SEQ ID NO: 33, and a light chain CDR1 comprising the amino acid sequence of SEQ ID NO: 34, a light chain CDR2 comprising the amino acid sequence of SEQ ID NO: 35 and a light chain CDR3 comprising the amino acid sequences of SEQ ID NO: 36.

Use of these new anti-human CD3/CD38 bispecific antibodies is not limited to but includes the treatments of various human cancers, autoimmune and inflammatory diseases. The specific destruction of cancer cells over healthy cells and tissues represents a primary objective in oncology. Therapeutics that could safely redirect T cell killing against tumour associated cell surface antigens may offer improved clinical efficacy. Known areas of clinical unmet needs in oncology include but are not limited to breast cancer, metastatic breast cancer, ovarian cancer, pancreatic cancer, lung cancer, lymphomas and multiple myeloma.

In accordance with a further aspect of the present invention the constant region of the second polypeptide of the hetero-dimeric immunoglobulin or fragment thereof, comprises an IgG3 CH3 region.

In accordance with a further aspect of the present invention the constant region of the second polypeptide of the hetero-dimeric immunoglobulin or fragment thereof, comprises a CH3 region other than that from IgG, and the non-IgG3 CH3 region comprises at least one substitution so as to decrease/abolish protein A binding.

According to a further aspect of the present invention the epitope binding region of second polypeptide of the hetero-dimeric immunoglobulin or fragment thereof comprises a VH3 region comprising at least one modification that reduces protein A binding.

The present invention also provides a method to produce anti-human CD3/CD38 bispecific heavy chain hetero-dimers having at least one VH3 based antigen binding site from a recombinant mammalian host cell line wherein the bispecific antibody product is readily isolated after a single Protein A chromatography step with a high degree of purity.

In particular the modified VH3 region comprises an amino acid substitution selected from the group consisting of: 57, 65, 81, 82a and combination 19/57/59 (Kabat numbering) and even more preferably wherein the modified VH3 region comprises an amino acid substitution selected from the group consisting of: 57A, 57E, 65S, 81E, 82aS and combination 19G/57A/59A (Kabat numbering).

According to a further aspect of the present invention the hetero-dimeric immunoglobulin or fragment thereof, may comprise further substitutions wherein the heavy chain variable framework region comprises an amino acid substitution selected from the group consisting of: I34M, V48I, A49G, R58N/Y, I69L, A71T and T73K (Kabat numbering) and the light chain variable framework region comprises an amino acid substitution selected from the group consisting of: M4L, V33M, A34N, L46R, L47W, T51A, R66G, F71Y and P96F (Kabat numbering); or wherein the heavy chain variable framework region comprises the amino acid substitutions I34M, A49G and A71T (Kabat numbering) and the light chain variable framework region comprises the amino acid substitutions M4L, L46R, L47W and F71Y (Kabat numbering).

In a further embodiment, the epitope binding region that binds to the CD3 protein complex comprises a heavy chain variable framework region that is the product of or derived from the human VH3 subclass. Preferably the heavy chain variable framework region is the product of or derived from human IGHV3-23. More preferably, the heavy chain variable framework region is the product of or derived from human IGHV3-23*04 (SEQ ID NO: 37). The heavy chain variable framework region comprises at least one amino acid modification from the corresponding framework region of the heavy chain variable region of the corresponding murine antibody comprising the amino acid sequence of SEQ ID NO: 38 or SEQ ID NO: 1.

In a preferred embodiment, the epitope binding region of the first polypeptide that binds to the CD3 protein complex comprises a light chain variable framework region that is the product of or derived from the human VK1 subclass or the human VK3 subclass. Preferably the light chain variable framework region is the product of or derived from human VK1-39 or VK3-20. More preferably the light chain variable framework region is the product of or derived from human IGKV1-39*01 (SEQ ID NO: 39) or IGKV3-20*01 (SEQ ID NO: 40). The light chain variable framework region comprises at least one amino acid modification from the corresponding framework region of the light chain variable region of the corresponding murine antibody comprising the amino acid sequence of SEQ ID NO: 41 or SEQ ID NO: 2.

In a preferred embodiment, the epitope binding region that binds to the CD3 protein complex comprises a humanized heavy chain variable domain having the back mutations selected from the group consisting of: I34M, V48I, A49G, R58N/Y, I69L, A71T and T73K (Kabat numbering) and a humanized light chain variable domain having the back mutations selected from the group consisting of: M4L, V33M, A34N, L46R, L47W, R66G, F71Y and P96F (Kabat numbering). More preferably, the epitope binding region that binds to the CD3 protein complex comprises a humanized heavy chain variable domain having the back mutations I34M, A49G and A71T (Kabat numbering) and a humanized light chain variable domain having the back mutations M4L, L46R, L47W and F71Y (Kabat numbering).

According to a further aspect of the present invention the epitope binding region that binds the CD3 protein complex of the hetero-dimeric immunoglobulin or fragment thereof, wherein the epitope binding region that binds the CD3 protein complex comprises a heavy chain variable region comprising the amino acid sequence of SEQ ID NO: 42, and a light chain variable region comprising the amino acid sequence of SEQ ID NO: 46; or
wherein the epitope binding region that binds the CD3 protein complex comprises a heavy chain variable region comprising the amino acid sequence of SEQ ID NO: 44, and a light chain variable region comprising the amino acid sequence of SEQ ID NO: 47; or
wherein the epitope binding region that binds the CD3 protein complex comprises a heavy chain variable region comprising the amino acid sequence of SEQ ID NO: 45, and a light chain variable region comprising the amino acid sequence of SEQ ID NO: 47; or
wherein the epitope binding region that binds the CD3 protein complex comprises a heavy chain variable region comprising the amino acid sequence of SEQ ID NO: 45, and a light chain variable region comprising the amino acid sequence of SEQ ID NO: 48; or
wherein the epitope binding region that binds the CD3 protein complex comprises a heavy chain variable region comprising the amino acid sequence of SEQ ID NO: 45, and a light chain variable region comprising the amino acid sequence of SEQ ID NO: 49.

The CD3 protein complex comprises a number of subunits, for example, delta, epsilon and gamma. In a preferred embodiment, the epitope binding region that binds to the CD3 protein complex binds to the CD3 epsilon subunit.

An epitope binding region as described herein includes the combination of one or more heavy chain variable domains and one or more complementary light chain variable domains which together form a binding site which permits the specific binding of the hetero-dimeric immunoglobulin or fragment thereof to one or more epitopes. In an embodiment of the present invention, the epitope binding region of the first poly peptide comprises a FAB and the epitope binding region of the second polypeptide comprises a scFv. Alternatively, the epitope binding region of the first poly peptide comprises a scFv and the epitope binding region of the second polypeptide comprises a FAB.

The epitope binding region that binds to CD38 comprises a heavy chain variable framework region that is the product of or derived from the human VH3 subclass, preferably human VH3-23, more preferably human IGHV3-23*04 (SEQ ID NO: 37). The heavy chain variable framework region comprises at least one amino acid modification from the corresponding framework region of the heavy chain variable region of the corresponding murine antibody comprising the amino acid sequence of SEQ ID NO: 50 or 51 or 52. The epitope binding region further comprises a light chain variable framework region that is the product of or derived from the human VK1 subclass, preferably human VK1-39, more preferably human IGKV1-39*01 (SEQ ID NO: 39). The light chain variable framework region comprises at least one amino acid modification from the corresponding framework region of the light chain variable region of the corresponding murine antibody comprising the amino acid sequence of SEQ ID NO: 53 or 54 or 55.

In particular the CD38 binding polypeptide comprises variable heavy chain domain and variable light chain domain pair encoded by SEQ ID NOs: 56/57, 58/59, 60/61 and 62/63.

Anti-CD3 antibodies have been found to trigger toxicity by both direct and indirect mechanisms. Indirect mechanisms are mediated by the Fc region of the CD3 antibody which acts with the Fc receptor expressing immune cells and lead to transient T cell activation and cytokine release. Therefore in order to improve the safety of the hetero-dimeric immunoglobulins or fragment thereof as described herein, the immunoglobulin constant region of the first and/or second polypeptide has reduced or no binding for effector immune cells and/or complement C1q. Preferably, the immunoglobulin constant region is engineered to abrogate Fc receptor binding in the lower hinge region. More preferably the immunoglobulin constant region of the first and/or second polypeptide comprises the substitution(s) L234A and/or L235A (EU numbering). Most preferably, the immunoglobulin constant region of the first and/or second polypeptide comprises the substitutions L234A and L235A (EU numbering).

In another aspect, the disclosure of the present invention also describes a hetero-dimeric immunoglobulin or fragment thereof wherein the epitope binding region binds to the CD3 epsilon subunit of the CD3 protein complex and comprises a FAB having a FAB thermo-stability superior to the FAB thermo-stability of the SP34 chimera comprising a heavy chain variable domain of amino acid sequence of SEQ ID NO: 1 and a light chain variable domain of amino acid sequence of SEQ ID NO: 2, as measured by Differential Scanning calorimetry (DSC) as in Table 1. This increased thermostability will mean that these improved SP34 binding arms will have increased in vivo and in vitro stability, meaning better performance as a therapeutic and also in terms of its stability/storage/shelf life.

In a preferred embodiment, the present invention provides hetero-dimeric immunoglobulin or fragment thereof binding to:
i) the CD3 protein complex and CD38, wherein the first polypeptide has an amino acid sequence of SEQ ID NO: 65 and is assembled with a cognate light chain of amino acid sequence of SEQ ID NO: 66 and binds CD38, and wherein the second polypeptide has an amino acid sequence of SEQ ID NO: 67, SEQ ID NO: 68, SEQ ID NO: 69 and SEQ ID NO: 70 and binds CD3 epsilon;
ii) the CD3 protein complex and CD38, wherein the first polypeptide has an amino acid sequence of SEQ ID NO: 71 and is assembled with a cognate light chain of amino acid sequence of SEQ ID NO: 72 and binds CD38, and wherein the second polypeptide has an amino acid sequence of SEQ ID NO: 67, SEQ ID NO: 68, SEQ ID NO: 69 and SEQ ID NO: 70 and binds CD3 epsilon;
iii) the CD3 protein complex and CD38, wherein the first polypeptide has an amino acid sequence of SEQ ID NO: 73 and is assembled with a cognate light chain of amino acid sequence of SEQ ID NO: 74 and binds CD38, and wherein the second polypeptide has an amino acid sequence of SEQ ID NO: 67, SEQ ID NO: 68, SEQ ID NO: 69 and SEQ ID NO: 70 and binds CD3 epsilon;

In a further embodiment, the present invention provides hetero-dimeric immunoglobulin or fragment thereof binding to:
the CD3 protein complex and CD38, wherein the first polypeptide has an amino acid sequence of SEQ ID NO: 75 or 76 and is assembled with a light chain of amino acid sequence of SEQ ID NO: 77 and binds CD38, and wherein the second polypeptide has an amino acid sequence selected from the group comprising of SEQ ID NO: 67, SEQ ID NO: 68, SEQ ID NO: 69 and SEQ ID NO: 70 and binds CD3 epsilon;
the CD3 protein complex and CD38, wherein the first polypeptide has an amino acid sequence of SEQ ID NO: 78 and is assembled with a light chain of amino acid sequence of SEQ ID NO: 66 and binds CD38, and wherein the second polypeptide has an amino acid sequence selected from the group comprising of SEQ ID NO: 67, SEQ ID NO: 68, SEQ ID NO: 69 and SEQ ID NO: 70 and binds CD3 epsilon;

In accordance with a further aspect of the present invention there is provided a hetero-dimeric immunoglobulin or fragment thereof, comprising (a) a first polypeptide comprising an immunoglobulin constant region with a CH2 domain and a first engineered CH3 domain;
(b) a second polypeptide comprising an immunoglobulin constant region with a CH2 domain and a second engineered CH3 domain, wherein the two polypeptide heterodimerize through their engineered CH3 domains; and wherein the first polypeptide does not bind protein A or protein G and the second polypeptide only binds protein A and/or protein G through its immunoglobulin constant region; wherein the first engineered CH3 domain has substitutions at one or more of the following residues 20, 22, 26, 79, 85.1, 86, 88, 90 and the second engineered CH3 domain has substitutions in at least one residue selected from the group 3, 5, 20, 22, 26, 27, 81, 84, 85.1, 86, 88 and wherein said second chain also comprises a substitution at residue 84.4 according to the IMGT numbering.

According to a further aspect of the present invention the substitution at position 84.4 is selected form the group 84.4Q, 84.4V, 84.4A, 84.4S, 84.4T, 84.4N, 84.4G, 84.4L, 84.4L, 84.4Y, 84.4F, 84.4M.

In accordance with a further aspect of the present invention the first engineered CH3 domain has substitutions at least at the following residues 22, 86, 88 and the second engineered CH3 domain has substitutions at least at the following residues 7, 84.4, 85.1, 86 according to the IMGT numbering.

In accordance with a further aspect of the present invention the first engineered CH3 domain has substitutions at least at the following residues 20, 22, 79, 86, 88 and the second engineered CH3 domain has substitutions at least at the following residues 7, 26, 84, 84.4, 85.1, 86 according to the IMGT numbering.

In accordance with a further aspect of the present invention the first engineered CH3 domain has substitutions at least at the following residues 20, 22, 26, 79, 85.1, 86, 88, 90 and the second engineered CH3 domain has substitutions at least at the following residues 3, 5, 7, 20, 22, 26, 81, 84, 84.2, 84.4, 85.1, 86, 88, 90.

In accordance with a further aspect of the present invention the first engineered CH3 domain has substitutions at least at the following residues 3, 20, 22, 26, 79, 85.1, 86, 88, 90 and the second engineered CH3 domain has substitutions at least at the following residues 3, 5, 7, 20, 22, 26, 81, 84, 84.2, 84.4, 85.1, 86, 88, 90

In accordance with a further aspect of the present invention there is provided a heterodimeric immunoglobulin has a first chain encompassing a Fc region of the IgG3 isotype that will include a BTA CH3 domain and a non-VH3 variable domain or a VH3 based variable domain abrogated for protein A binding (using the G65S or N82aS substitutions for example) or no variable domain and therefore has no binding to protein A, and a second chain that binds protein A encompassing a BTB D401Q CH3 domain (originating from a human IgG1 isotype for example) and either a non-VH3 variable domain or a VH3 variable domain abrogated for protein A binding (using the G65S or N82aS substitutions for example), or no variable domain.

BRIEF DESCRIPTION OF THE FIGURES

FIG. 1A-F: These figures all relate to OKT3 humanization on stable human frameworks. FIG. 1A-C: Summary of humanized candidates formatted as human IgG1 antibodies. HPB-ALL staining relative to the chimeric OKT3 antibody: (−) indicates no binding, (+) weaker binding, (++) moderate binding and (+++) similar binding. FIG. 1D: DSC profiles of selected antibodies of candidates. FIG. 1E: Summary of humanized candidates formatted as scFv-Fc fusions. HPB-ALL staining relative to the chimeric OKT3 antibody: (−) indicates no binding, (+) weaker binding, (++) moderate binding and (+++) similar binding. FIG. 1F: DSC profiles of selected scFv-Fc candidates.

FIG. 2A-B: These figures all relate to SP34 humanization on stable human frameworks. FIG. 2A: Summary of humanized candidates formatted as human IgG1 antibodies. FIG. 2B: Summary of humanized candidates formatted as scFv-Fc fusion proteins (Fc of human IgG1 isotype). SPR data relative to the chimeric SP34 antibody for human and cynomolgus monkey CD3 epsilon 1-26_Fc fusion proteins: (−) indicates no binding, (+) weaker binding, (++) moderate binding, strong but not similar binding (+++), and (++++) similar binding.

FIG. 5A Shows the effects on expression level of random mutation at position 29 of a SP34 H3L23 ScFv-Fc; FIG. 5B Shows the effects on expression level of random mutation at position 30 of a SP34 H3L23 ScFv-Fc; FIG. 5C Shows the effects on expression level of random mutation at position 95 of a SP34 H5L23 ScFv-Fc.

FIG. 7E: Antibody-antigen interaction measured by SPR between the human 767 antibody and the human CD38 antigen. A CM5 sensor chip was covalently coupled with protein G and 200 RUs of human 767 antibody were captured. Human CD38 protein (human CD38 extracellular domain with a poly-histidine tag) was injected at 500, 250, 125, 62.5, 31.25, and 15.6 nM at a flow rate of 30 µl/min in HBS-P. Affinity was obtained from a plot of the equilibrium response (Req) vs. analyte concentration (C) according to the following equation: Req=KA*C*Rmax/(KA*C*n+1), concentration at 50% saturation is KD. All SPR data are expressed as number of response units (abbreviated RU; Y axis) vs. time (X axis). FIG. 7F: DSC profiles of chimeric HB-7 and humanized HB-7 best-fit antibodies. FIG. 7G: DSC profiles of chimeric 9G7 and humanized 9G7 best-fit antibodies. FIG. 7J: summary table for the 9G7 humanized antibodies.

FIG. 8A-B: Schematic diagram of the BEAT CD38-HB7bestfit/CD3 (format 8A) and BEAT CD38-767/CD3 (format 8B) antibodies. [(A+)] means functional Protein A binding site. [(A−)] means nonfunctional Protein A binding site.

RDL-FACS method. Effector cells: Human PBMCs. Effector cells-to-targeted cells ratio of 10:1. Mean of three donors with 24 h incubation. Target cells: Daudi cells. Antibody concentration is shown in nM.

Figure 14:
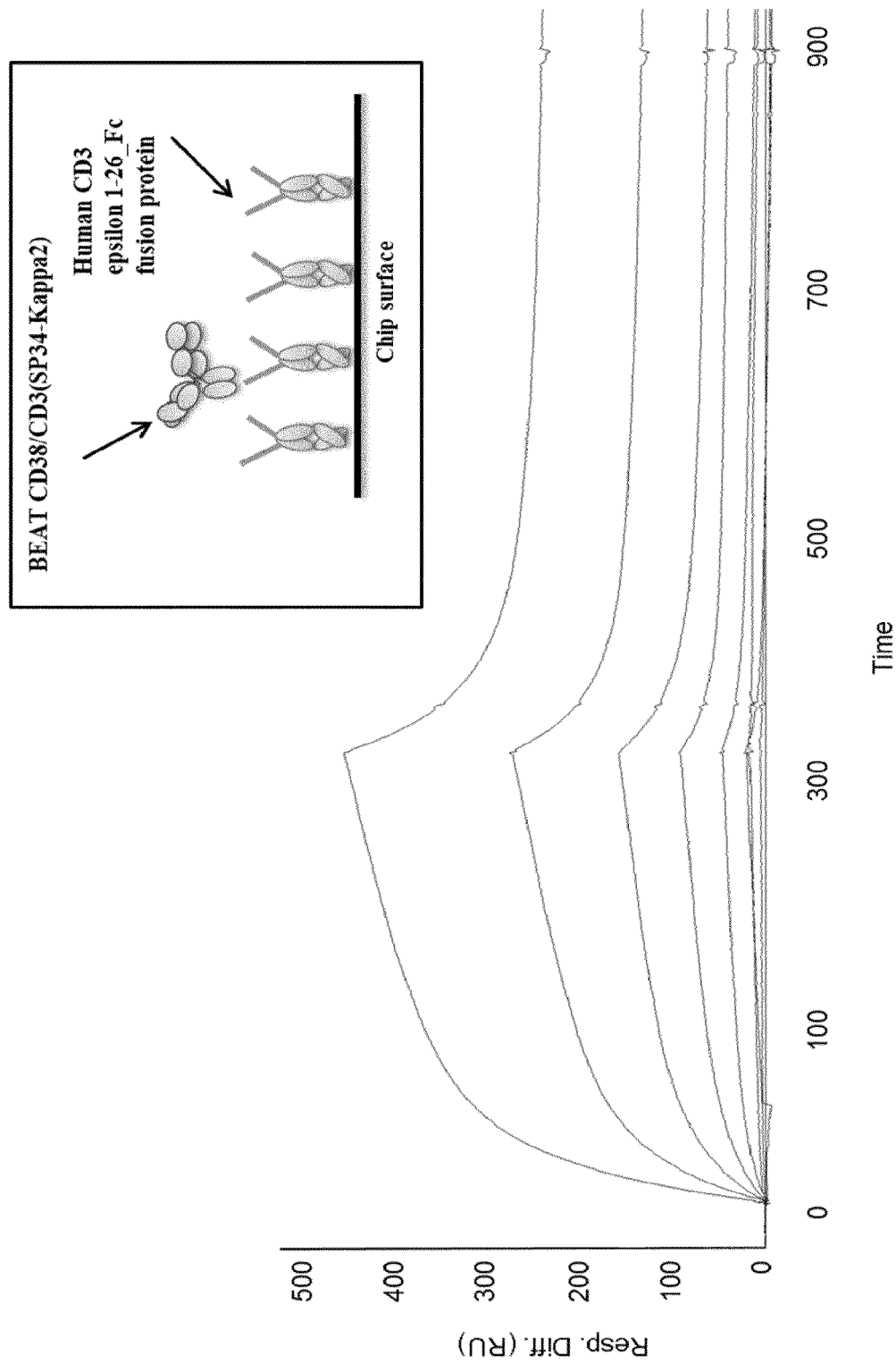

FIG. 14: Antibody-antigen interaction measured by SPR between the BEAT CD38-9G7bestfit/CD3(SP34-Kappa2) antibody and the human CD3 epsilon 1-26_Fc fusion protein. A CM5 sensor chip was covalently coupled with 500 RUs of the human CD3 epsilon 1-26_Fc fusion protein. BEAT CD38-9G7bestfit/CD3(SP34-Kappa2) antibody was injected at 50, 25, 12.5, 6.2, 3.1, 0.8 and 0.4 nM at a flow rate of 30 μl/min in HBS-P. Data are expressed as number of response units (abbreviated RU; Y axis) vs. time (X axis).

Figure 15:
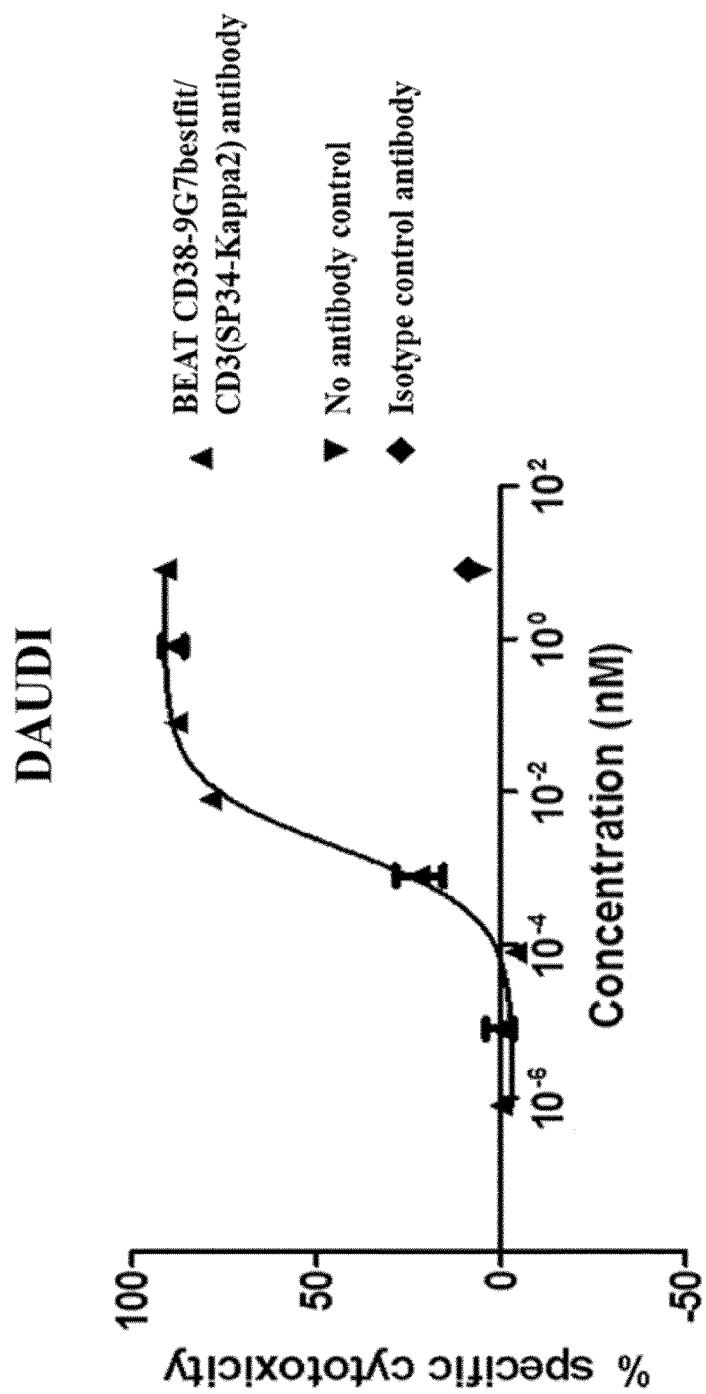

FIG. 15: Example of T cell redirected killing by the BEAT CD38/CD3(SP34-Kappa2) antibody. Readout: RDL-FACS method. Effector cells: Human PBMCs. Effector cells-to-targeted cells ratio of 10:1. Mean of three donors with 24 h incubation. Target cells: Daudi cells. Antibody concentration is shown in nM.

Figure 16:
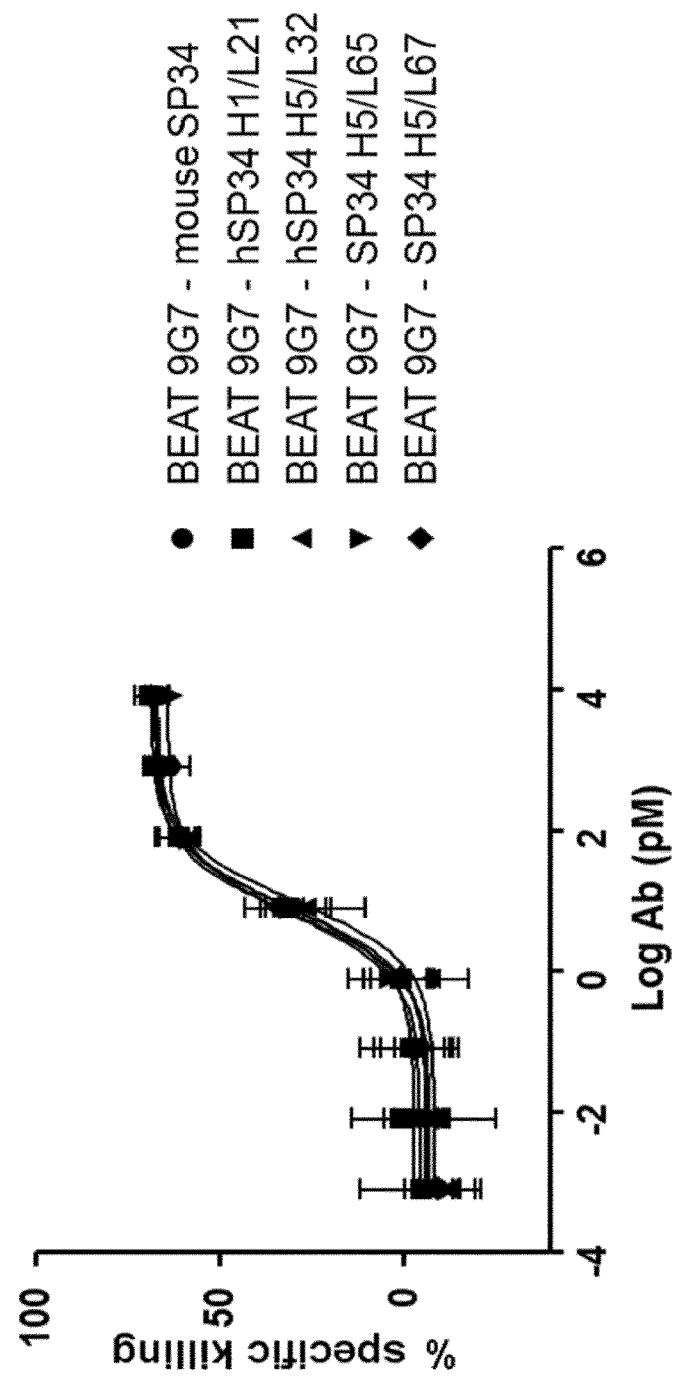

FIG. 16 shows the performance in an RDL assay of several CD38/CD3 bispecific antibodies, in which the CD3 binding arm comprises the original mouse SP34 reformatted as an scFv (SEQ ID NO: 137), or modified humanised SP34 scFv's comprising the heavy/light chain combinations H1/L21 (SEQ ID NO: 67), H5/L32 (SEQ ID NO: 68), H5/L65 (SEQ ID NO: 69) and H5/L67 (SEQ ID NO: 70).

Figure 17:
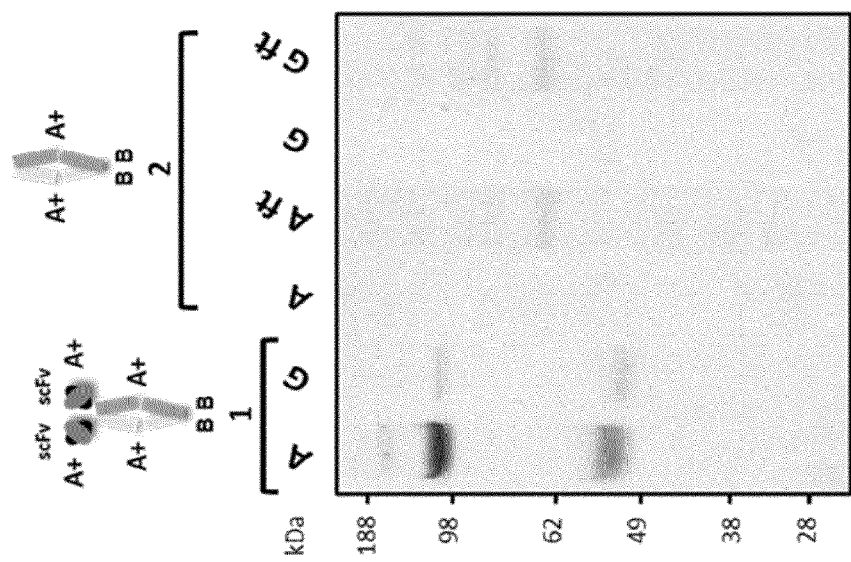

FIG. 17: Non reducing SDS-PAGE analysis of BTB homodimers with (lanes group 1) and without protein A binding scFv moiety (lanes group 2). Purification using affinity chromatography: eluted and neutralized fractions were analyzed after protein A chromatography (A) or protein G chromatography (G). For group 2, flow-through or unbound fractions were collected and showed no binding to protein A or G (abbreviated A ft and G ft, respectively). Elutions were performed at pH 3.0. [(A+)] means a Protein A binding site. Molecular weight markers as indicated (kDa).

Figure 18B:
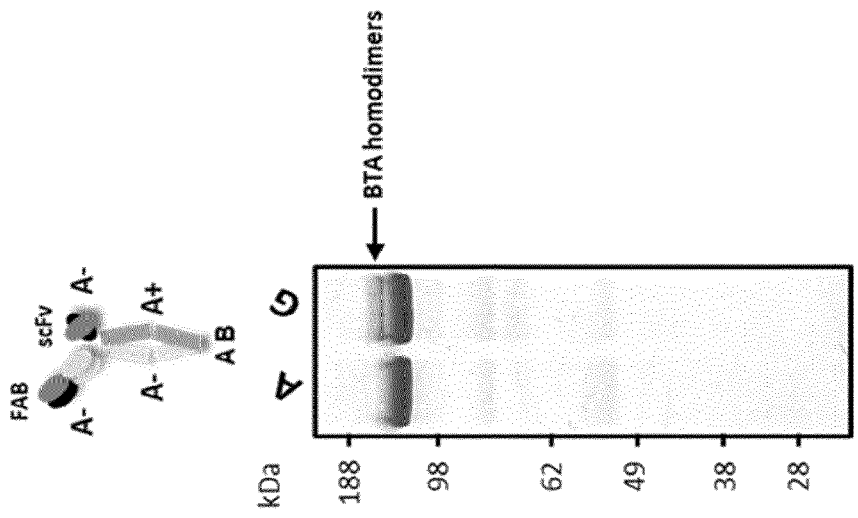
Figure 18A:
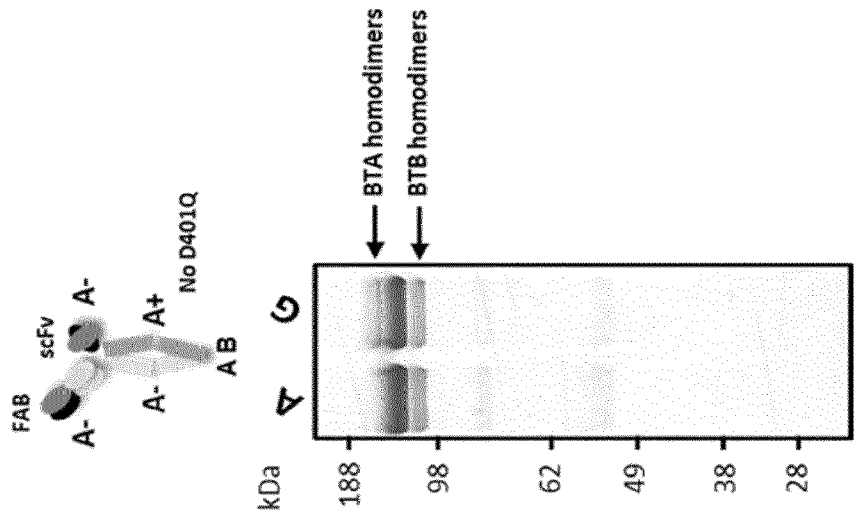

FIG. 18A: Non reducing SDS-PAGE analysis of the BEAT heterodimer containing only a single protein A site in the BTB chain carrying the D401Q substitution. Purification using affinity chromatography: eluted and neutralized fractions were analyzed after protein A chromatography (A) or protein G chromatography (G). Elutions were performed at pH 3.0. [(A+)] means a Protein A binding site. Molecular weight markers as indicated (kDa); 18B: SDS-PAGE analysis of the BEAT heterodimer containing a single protein A site in the BTB chain lacking the D401Q substitution. Purification using affinity chromatography: eluted and neutralized fractions were analyzed after protein A chromatography (A) or protein G chromatography (G). Elutions were performed at pH 3.0. [(A+)] means a Protein A binding site. Molecular weight markers as indicated (kDa).

Figure 19:
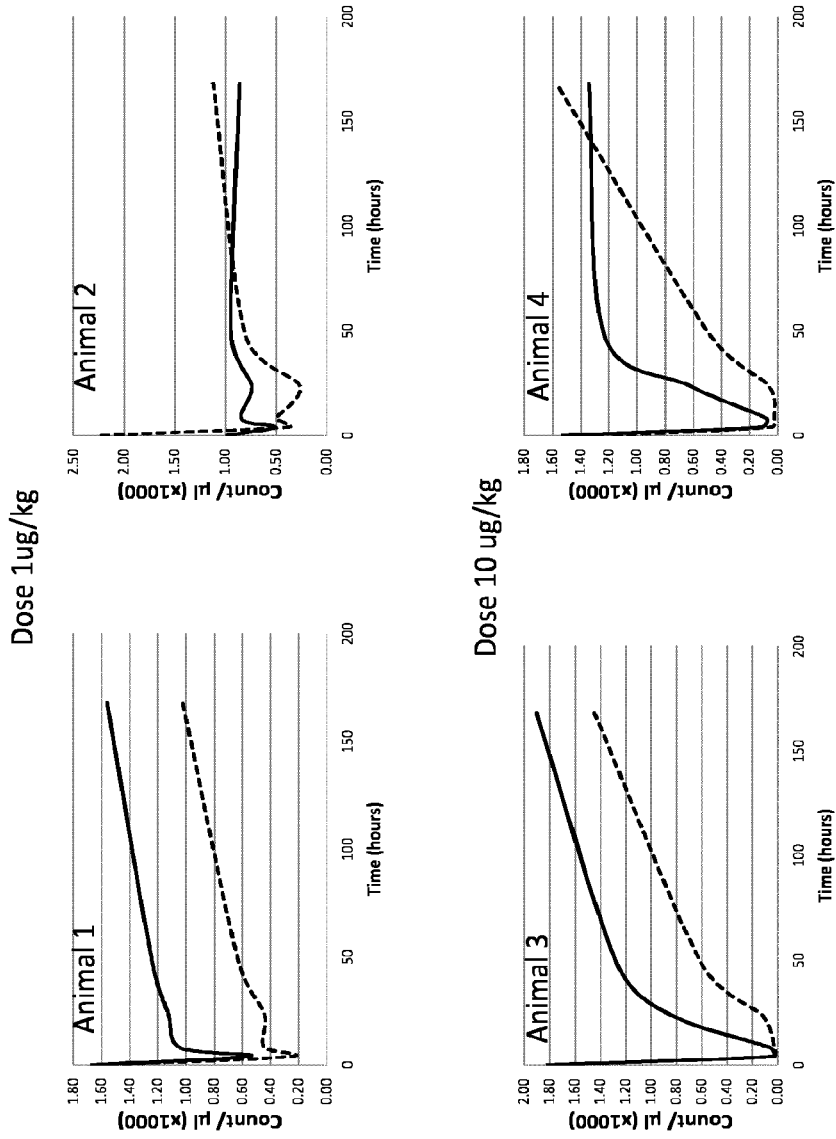

FIG. 19: The graphs show the count per μl of blood for the CD4+ population (plain line) and CD8+ population (dotted line), for both animals that were injected with CD3/CD38 BEAT. The upper graphs show the counts for the animals dosed with 1 μg/kg. The bottom graphs show the counts for the animals dosed with 10 μg/kg. The counts at time points zero correspond to samples harvested 1 day prior to dosing.

Figure 20:
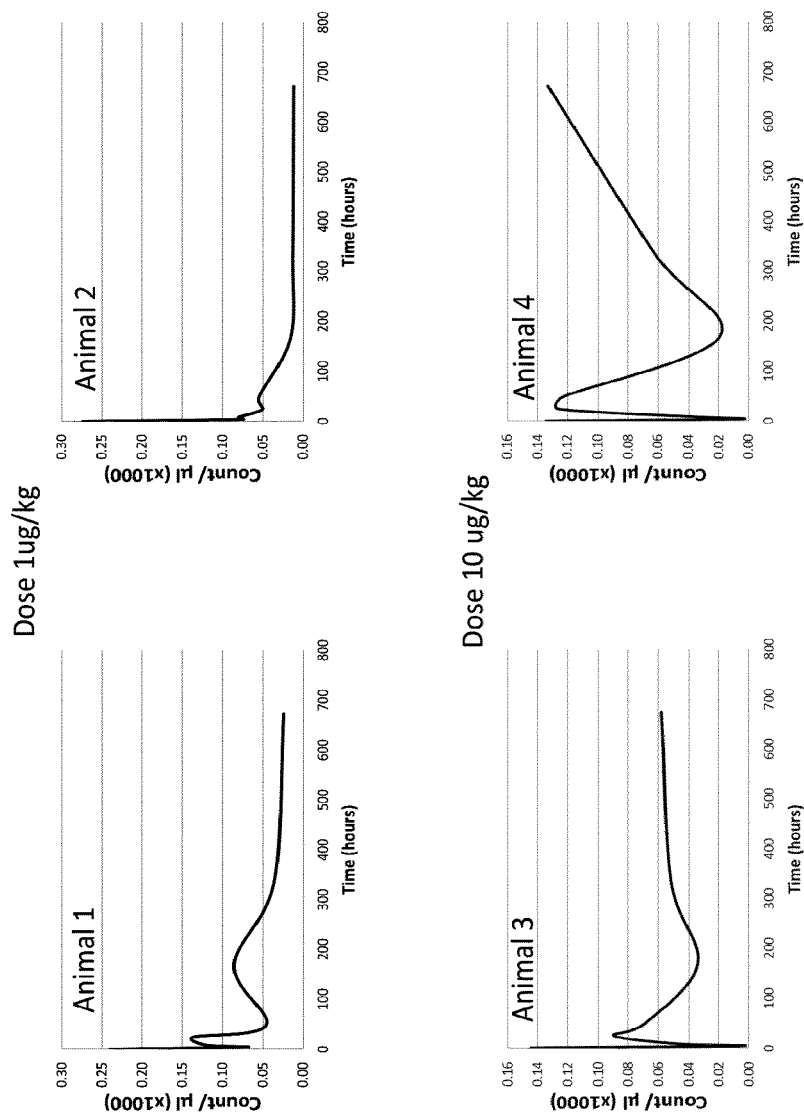

FIG. 20: The graphs show the count per μl of blood for the CD14+CD38+ monocyte population, for both animals that were injected with CD3/CD38 BEAT. The upper graphs show the counts for the animals dosed with 1 μg/kg. The bottom graph shows the counts for the animals dosed with 10 μg/kg. The counts at time points zero correspond to samples harvested 1 day prior to dosing.

Figure 21:
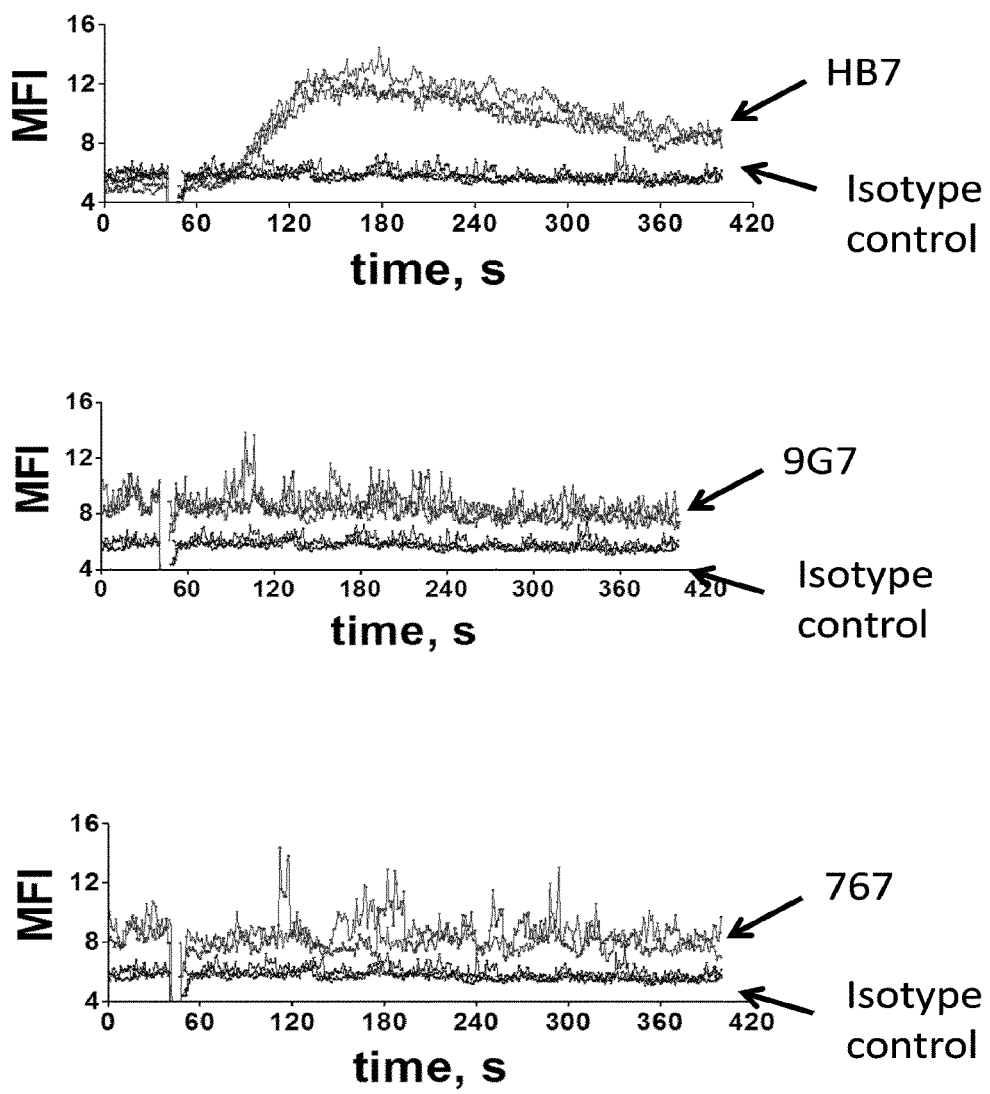

FIG. 21: The graphs show the mean fluorescence intensity (MFI) of the fluo-4 dye as a function of time in seconds. The isotype control condition is included in each graph. After the baseline acquisition during 40 s, the indicated antibodies were added into the samples and the acquisition was resumed. The isotype control was a human IgG1 antibody. Increase in MFI indicates a calcium mobilization into the cytoplasm of the cells.

Figure 22:
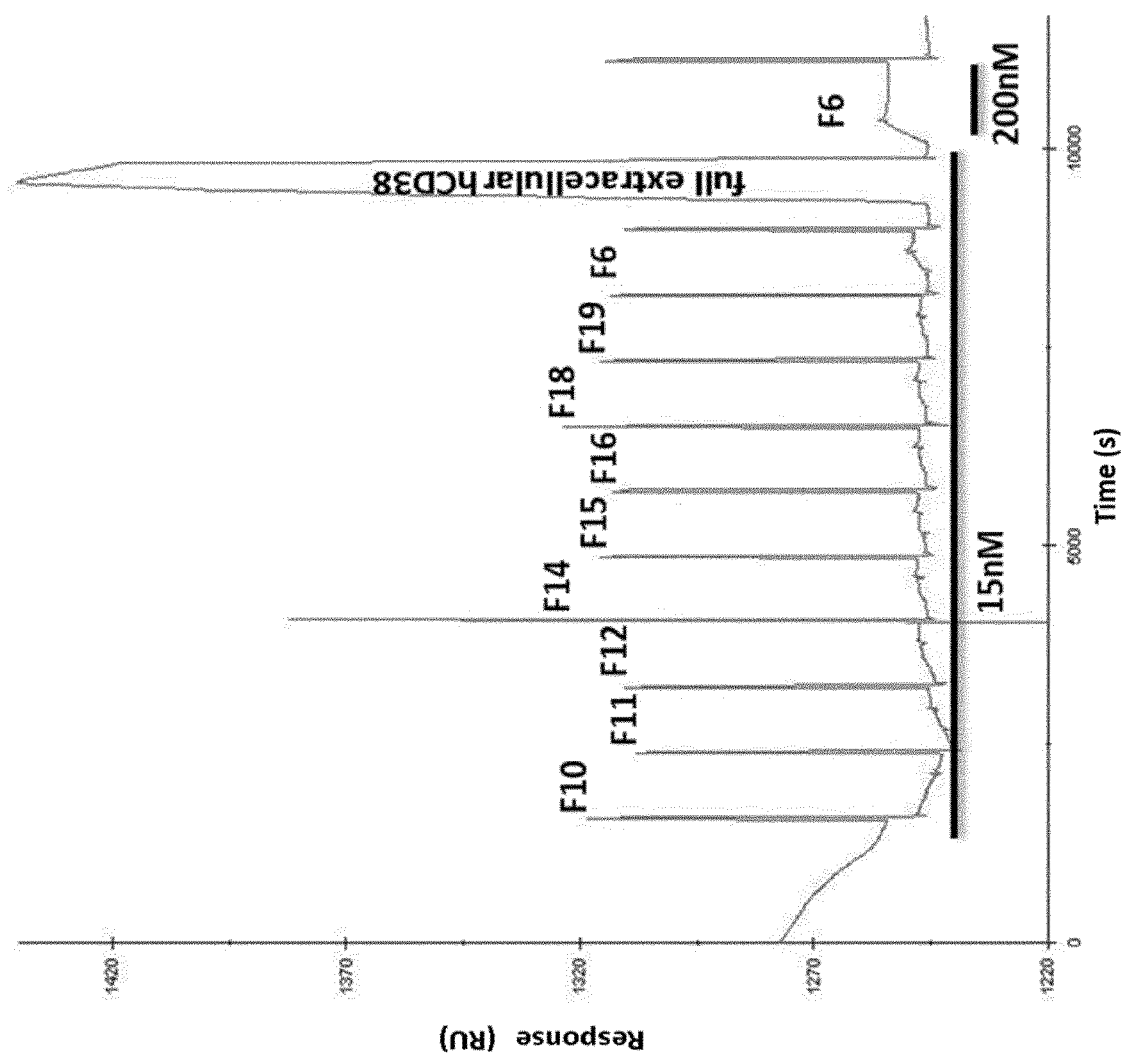

FIG. 22: Epitope mapping of the humanized 9G7 antibody by SPR using peptide-Fc fusions derived from the extracellular domain of human CD38. Data are expressed as number of response units (abbreviated RU; Y axis) vs. time (X axis).

Figure 23:
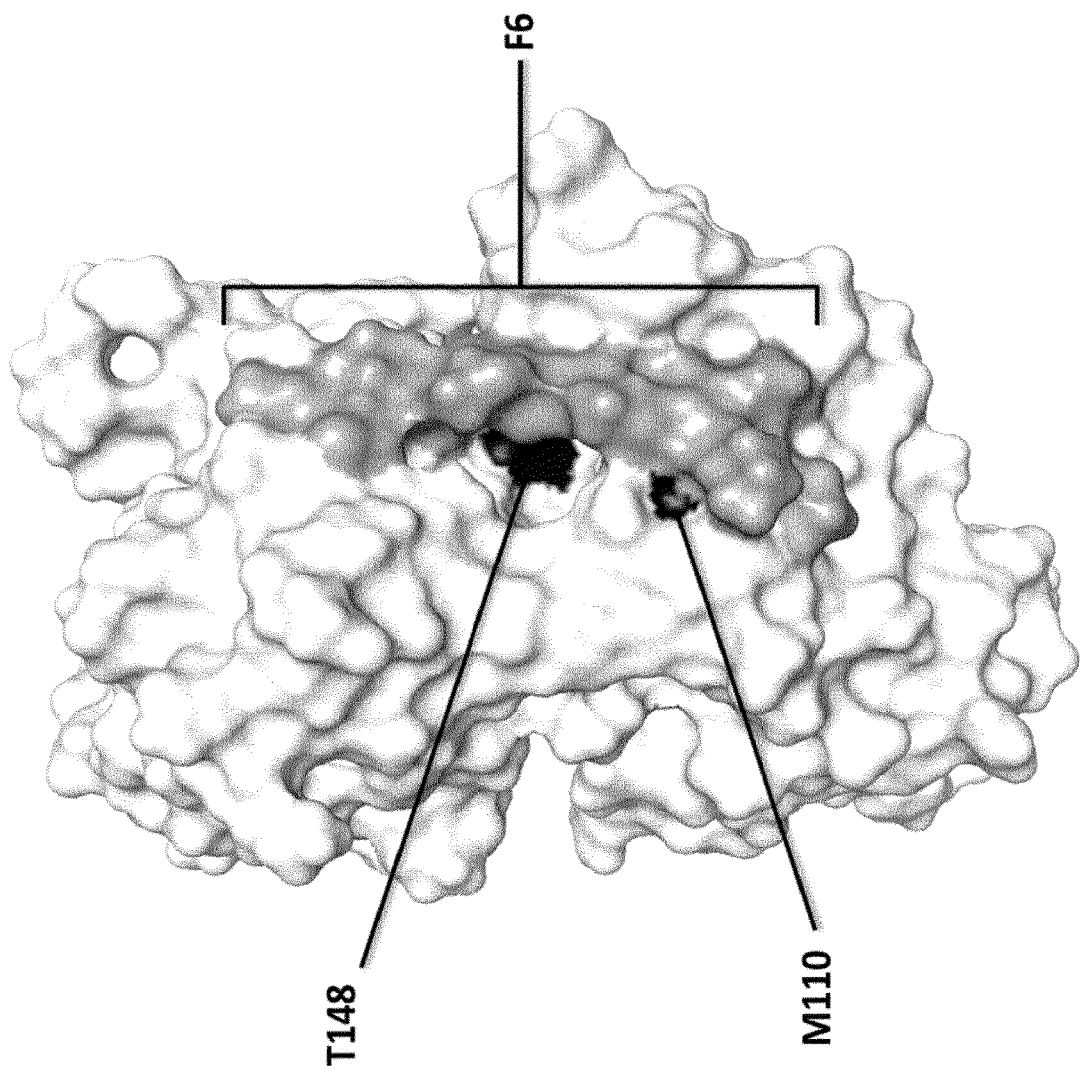

FIG. 23: 3D rendering of the extracellular domain of human CD38. The F6 peptide sequence is colored grey, positions M110 and T148 are colored black.

Figure 24:
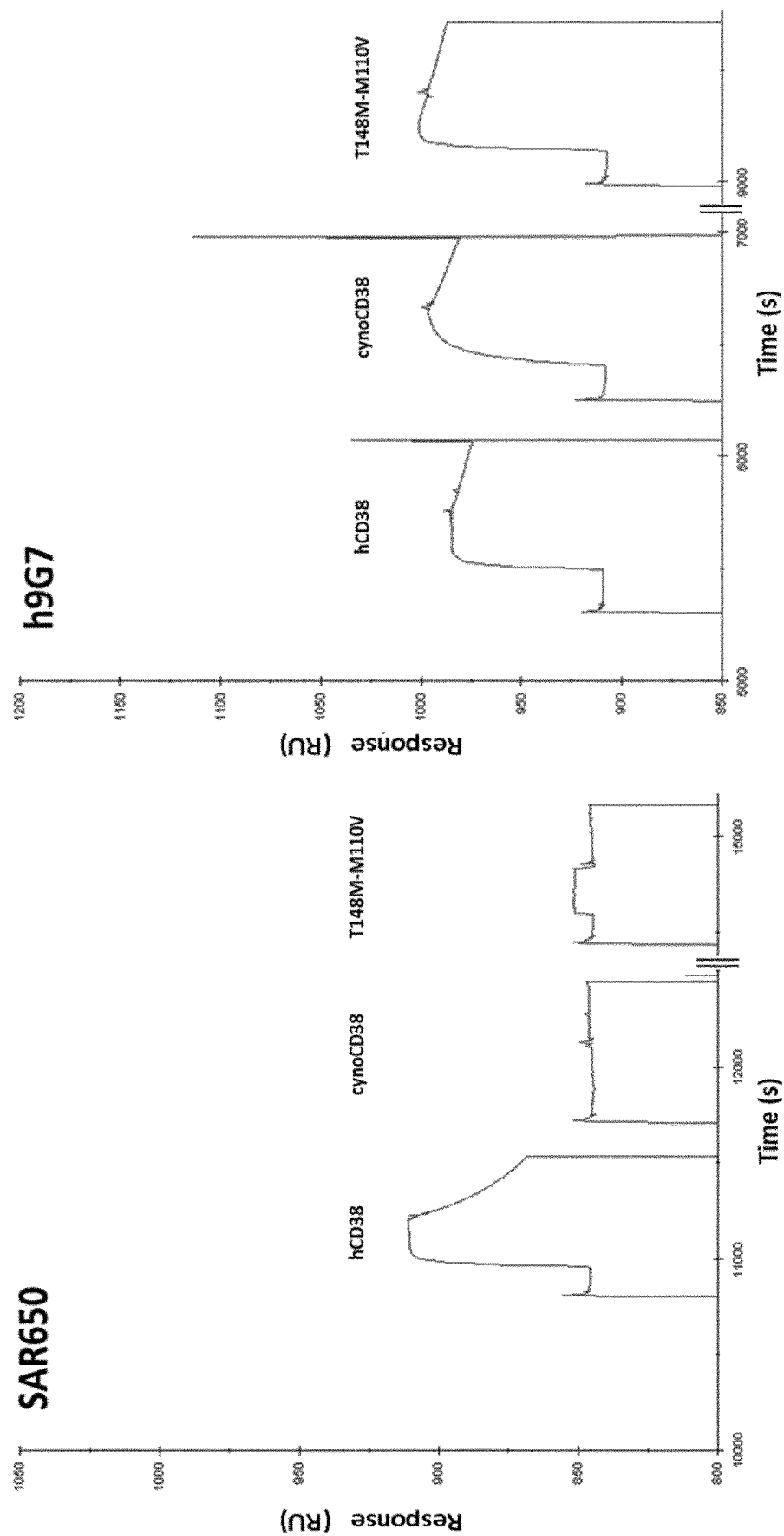

FIG. 24: Epitope mapping of the humanized 9G7 and SAR650984 antibodies by SPR using the extracellular domains of human and cynomolgus monkey CD38. Data are expressed as number of response units (abbreviated RU; Y axis) vs. time (X axis).

Figure 25:
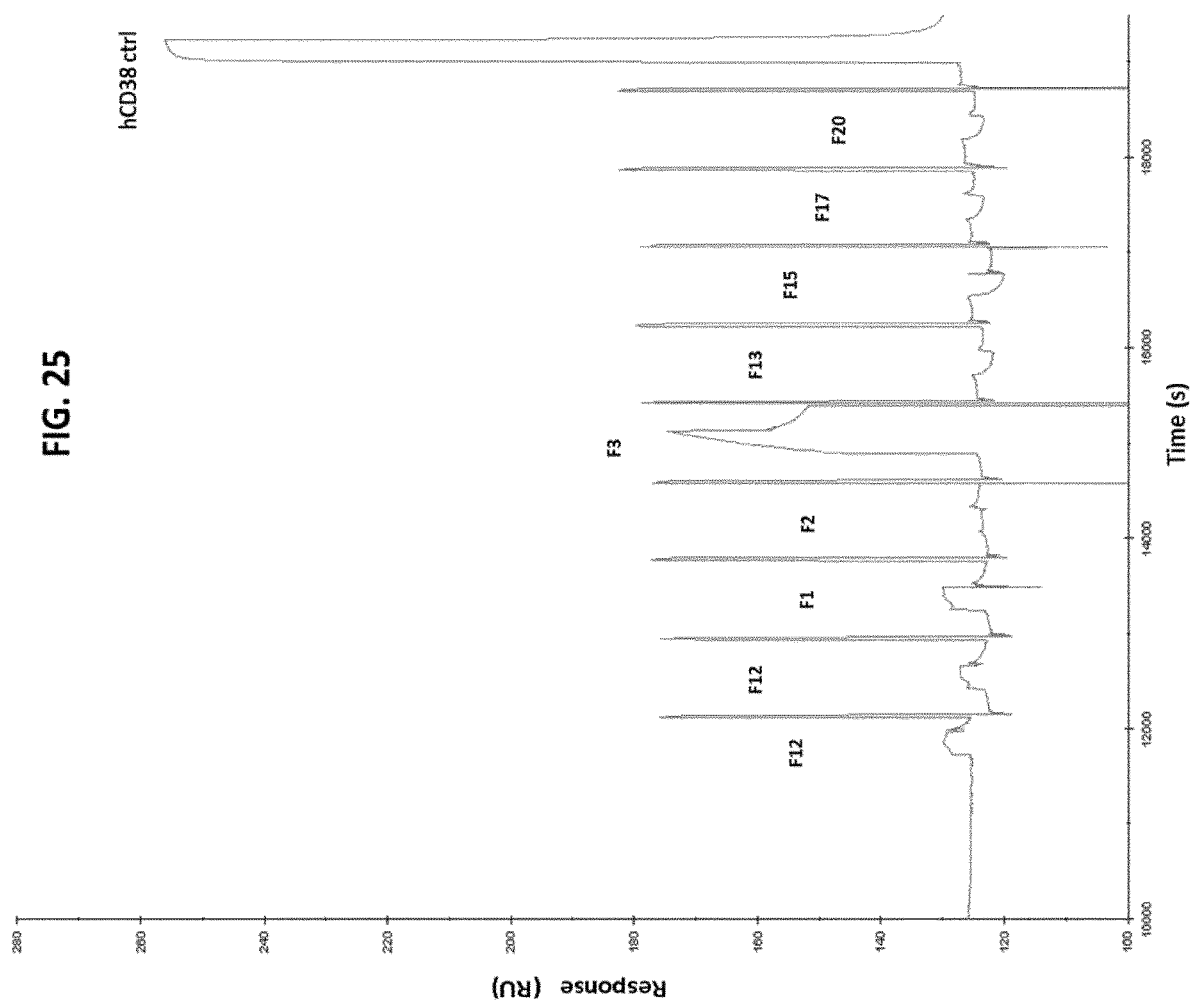

FIG. 25: Epitope mapping of the human 767 antibody by SPR using peptide-Fc fusions derived from the extracellular domain of human CD38. Data are expressed as number of response units (abbreviated RU; Y axis) vs. time (X axis).

Figure 26:
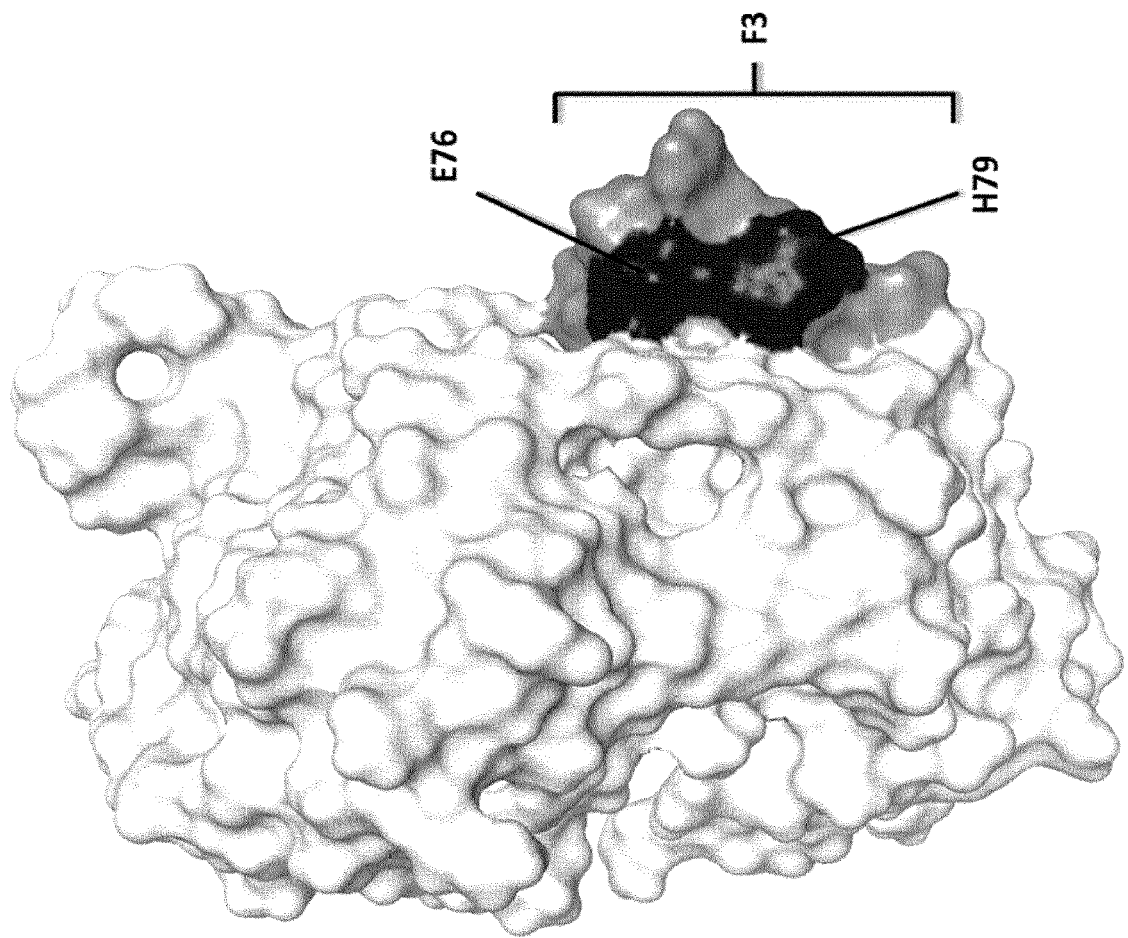

FIG. 26: 3D rendering of the extracellular domain of human CD38. The F3 peptide sequence is colored grey, positions E76 and H79 are colored black.

Figure 27:
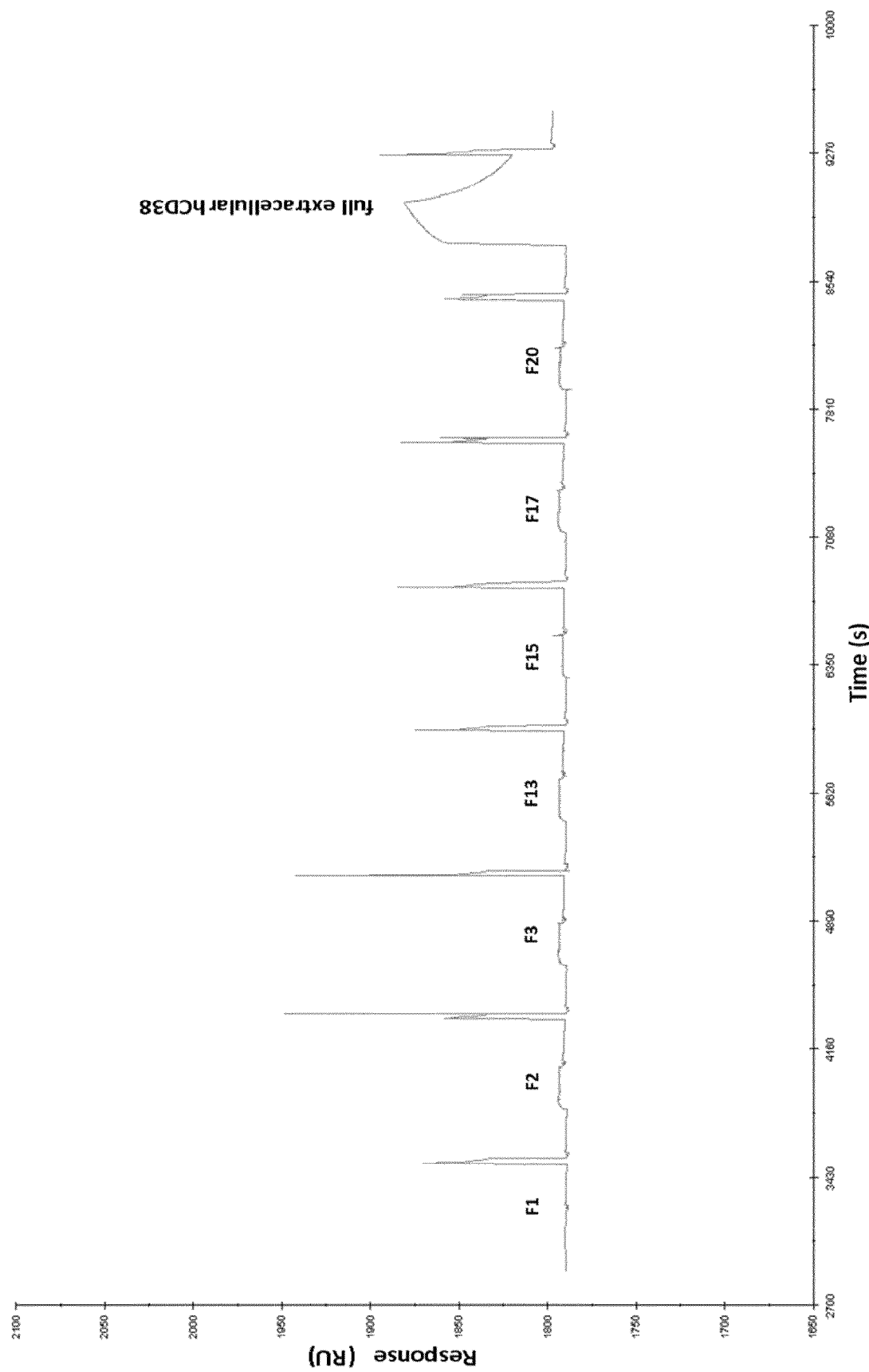

FIG. 27: Epitope mapping of the humanized SAR650984 antibody by SPR using peptide-Fc fusions derived from the extracellular domain of human CD38. Data are expressed as number of response units (abbreviated RU; Y axis) vs. time (X axis).

DETAILED DESCRIPTION OF THE INVENTION

The present invention relates generally to novel hetero-dimeric immunoglobulins that bind to the CD3 protein complex and a CD38 antigen.

Furthermore, these hetero-dimeric immunoglobulins have reduced or eliminated binding to protein A and therefore can be purified to a very high degree of purity using affinity chromatography.

For the purposes of interpreting this specification, the following definitions will apply and whenever appropriate, terms used in the singular will also include the plural and vice versa. It is to be understood that the terminology used herein is for the purpose of describing particular embodiments only and is not intended to be limiting.

The terms "polypeptide" and "protein" refer to a polymer of amino acid residues wherein amino acids are combined via peptide bonds to form a chain of amino acids that have been linked together via dehydration synthesis. Polypeptides and proteins can be synthesized through chemical synthesis or recombinant expression and are not limited to a minimum amino acid length.

In accordance with the invention, the group of polypeptides comprises "proteins" as long as the proteins consist of a single polypeptide chain. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or hetero-dimers, homo- or hetero-trimers etc. An example for a hetero-multimer is an antibody molecule, which, in its naturally occurring form, consists of two identical light polypeptide chains and two identical heavy polypeptide chains. The terms "polypeptide" and "protein" also refer to naturally modified polypeptides/proteins wherein the modification is effected e.g. by post-translational modifications like glycosylation, acetylation, phosphorylation and the like. Such modifications are well known in the art. Furthermore, for purposes of the present invention, a "polypeptide" refers to a protein which includes modifications, such as deletions, additions and substitutions (which can be conservative in nature) to the native sequence. These modifications may be deliberate, as through site-directed mutagenesis, or may be accidental, such as through mutations of hosts which produce the proteins or errors due to PCR amplification.

The term "CD3 complex" as used herein refers to the protein complex known as the CD3 (cluster of differentiation 3) T-cell co-receptor (Wucherpfennig K W et al., (2010) Cold Spring Harb Perspect Biol, 2(4): a005140). The CD3 protein complex is composed of four distinct chains. In mammals, the complex contains a CD3γ chain, a CD3δ chain, and two CD3ε chains. These chains associate with a molecule known as the T-cell receptor (TCR) and the ζ-chain to generate an activation signal in T lymphocytes (van der Merwe P A & Dushek O (2011) Nat Rev Immunol, 11(1): 47-55). The TCR, ζ-chain, and CD3 molecules together comprise the TCR complex. The CD3γ, CD3δ, and CD3ε chains are highly related cell-surface proteins of the immunoglobulin superfamily containing a single extracellular immunoglobulin domain. The intracellular tails of the CD3 molecules contain a single conserved motif known as an immunoreceptor tyrosine-based activation motif or ITAM for short, which is essential for the signalling capacity of the TCR. Since CD3 is required for T-cell activation, drugs (often monoclonal antibodies) that target CD3 have and are being investigated as immunosuppressant therapies.

The term "immunoglobulin" as referred to herein can be used interchangeably with the term "antibody". Immunoglobulin includes full-length antibodies and any antigen binding fragment or single chains thereof. Immunoglobulins can be homo-dimeric or hetero-dimeric. Immunoglobulins and specifically naturally occurring antibodies are glycoproteins which exist as one or more copies of a Y-shaped unit, composed of four polypeptide chains. Each "Y" shape contains two identical copies of a heavy (H) chain and two identical copies of a light (L) chain, named as such by their relative molecular weights. Each light chain pairs with a heavy chain and each heavy chain pairs with another heavy chain. Covalent interchain disulfide bonds and non-covalent interactions link the chains together. Immunoglobulins and specifically naturally occurring antibodies contain variable regions, which are the two copies of the antigen binding site. Papain, a proteolytic enzyme splits the "Y" shape into three separate molecules, two so called "Fab" or "FAB" fragments (Fab=fragment antigen binding) and one so called "Fc" fragment or "Fc region" (Fc=fragment crystallizable). A Fab fragment consists of the entire light chain and part of the heavy chain. The heavy chain contains one variable region (VH) and either three or four constant regions (CH1, CH2, CH3 and CH4, depending on the antibody class or isotype). The region between the CH1 and CH2 regions is called the hinge region and permits flexibility between the two Fab arms of the Y-shaped antibody molecule, allowing them to open and close to accommodate binding to two antigenic determinants separated by a fixed distance. The "hinge region" as referred to herein is a sequence region of 6-62 amino acids in length, only present in IgA, IgD and IgG, which encompasses the cysteine residues that bridge the two heavy chains. The heavy chains of IgA, IgD and IgG each have four regions, i.e. one variable region (VH) and three constant regions (CH1-3). IgE and IgM have one variable and four constant regions (CH1-4) on the heavy chain. The constant regions of the immunoglobulins may mediate the binding to host tissues or factors, including various cells of the immune system (e.g., effector cells) and the first component (C1q) of the complement system classical pathway. Each light chain is usually linked to a heavy chain by one covalent disulfide bond. Each light chain contains one variable region (VL) and one light chain constant region. The light chain constant region is a kappa light chain constant region designated herein as IGKC or is a lambda light chain constant region designated herein as IGLC. IGKC is used herein equivalently to Cκ or CK and has the same meaning. IGLC is used herein equivalently to Cλ or CL and has the same meaning. The term "an IGLC region" as used herein refer to all lambda light chain constant regions e.g. to all lambda light chain constant regions selected from the group consisting of IGLC1, IGLC2, IGLC3, IGLC6 and IGLC7. The VH and VL regions can be further subdivided into regions of hypervariability, termed complementarity determining regions (CDR), interspersed with regions that are more conserved, termed framework regions (FR or FW). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain an epitope-binding region that interacts with an antigen. Engineered immunoglobulins can encompass different epitope binding region formats such as scFv, FAB or dAb fragments. These fragments are usually assembled in an antibody-like structure by genetic fusion to a IgG Fc region. Engineered immunoglobulins can be constructed as homo or hetero-dimers with or without the use of hetero-dimerization enhancing techniques, and can have mono- or bispecific binding properties.

The term "full length antibody" as used herein includes the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin regions VL and a light chain constant region, and each heavy chain comprising immunoglobulin regions VH, CH1 (Cγ1), CH2 (Cγ2), CH3 (Cγ3) and CH4 (Cγ4), depending on the antibody class or isotype). In some mammals, for example in camels and llamas, IgG antibodies may consist of only two heavy chains, each heavy chain comprising a variable region attached to the Fc region.

Antibodies are grouped into classes, also referred to as isotypes, as determined genetically by the constant region. Human constant light chains are classified as kappa (CK) and lambda (Cλ) light chains. Heavy chains are classified as mu (μ), delta (δ), gamma (γ), alpha (α), or epsilon (ε) and define the antibody's isotype as IgM, IgD, IgG, IgA and IgE, respectively. Thus, "isotype" as used herein is meant any of the classes and/or subclasses of immunoglobulins defined by the chemical and antigenic characteristics of their constant regions. The known human immunoglobulin isotypes are IGHG1 (IgG1), IGHG2 (IgG2), IGHG3 (IgG3), IGHG4 (IgG4), IGHA1 (IgA1), IGHA2 (IgA2), IGHM (IgM), IGHD (IgD) and IGHE (IgE). The so-called human immunoglobulin pseudo-gamma IGHGP gene represents an additional human immunoglobulin heavy constant region gene which has been sequenced but does not encode a protein due to an altered switch region (Bensmana M et al., (1988) Nucleic Acids Res, 16(7): 3108). In spite of having an altered switch region, the human immunoglobulin pseudo-gamma IGHGP gene has open reading frames for all heavy constant regions (CH1-CH3) and hinge. All open reading frames for its heavy constant regions encode protein regions which align well with all human immunoglobulin constant regions with the predicted structural features. This additional pseudo-gamma isotype is referred herein as IgGP or IGHGP. Other pseudo immunoglobulin genes have been reported such as the human immunoglobulin heavy constant region epsilon P1 and P2 pseudo-genes (IGHEP1 and IGHEP2). The IgG class is the most commonly used for therapeutic purposes. In humans this class comprises subclasses IgG1, IgG2, IgG3 and IgG4. In mice this class comprises subclasses IgG1, IgG2a, IgG2b, IgG2c and IgG3.

The term "Immunoglobulin fragments" as used herein include, but is not limited to, (i) a region including for example a CH1, a CH2 or a CH3 region, (ii) the Fab fragment consisting of VL, VH, CL or CK and CH1 regions, including Fab' and Fab'-SH, (ii) the Fd fragment consisting of the VH and CH1 regions, (iii) the dAb fragment (Ward E S et al., (1989) Nature, 341(6242): 544-6) which consists of a single variable region (iv) F(ab')₂ fragments, a bivalent fragment comprising two linked Fab fragments (v) single chain Fv fragments (scFv), wherein a VH region and a VL region are linked by a peptide linker which allows the two regions to associate to form an antigen binding site (Bird R E et al., (1988) Science, 242(4877): 423-6; Huston J S et al., (1988) Proc Natl Acad Sci USA, 85(16): 5879-83), (vi) "diabodies" or "triabodies", multivalent or multispecific fragments constructed by gene fusion (Holliger P et al., (1993) Proc Natl Acad Sci USA, 90(14): 6444-8; Tomlinson I & Holliger P, (2000) Methods Enzymol, 326:461-79), (vii) scFv, diabody or region antibody fused to an Fc region and (viii) scFv fused to the same or a different antibody.

The term "variable region" refers to the regions or domains that mediates antigen-binding and defines specificity of a particular antibody for a particular antigen. In naturally occurring antibodies, the antigen-binding site consists of two variable regions that define specificity: one located in the heavy chain, referred herein as heavy chain variable region (VH) and the other located in the light chain, referred herein as light chain variable region (VL). In humans, the heavy chain variable region (VH) can be divided into seven subgroups or subclasses: VH1, VH2, VH3, VH4, VH5, VH6 and VH7. In some cases, specificity may exclusively reside in only one of the two regions as in single-domain antibodies from heavy-chain antibodies found in camelids. The V regions are usually about 110 amino acids long and consist of relatively invariant stretches of amino acid sequence called framework regions (FRs or "non-CDR regions") of 15-30 amino acids separated by shorter regions of extreme variability called "hypervariable regions" that are 7-17 amino acids long. The variable domains of native heavy and light chains comprise four FRs, largely adopting a beta-sheet configuration, connected by three hypervariable regions, which form loops. The hypervariable regions in each chain are held together in close proximity by FRs and, with the hypervariable regions from the other chain, contribute to the formation of the antigen binding site of antibodies (see Kabat E A et al., supra.). The term "hypervariable region" as used herein refers to the amino acid residues of an antibody which are responsible for antigen binding. The hypervariable region generally comprises amino acid residues from a "complementary determining region" or "CDR", the latter being of highest sequence variability and/or involved in antigen recognition. For all variable regions numbering is according to Kabat (Kabat E A et al., supra.).

A number of CDR definitions are in use and are encompassed herein. The Kabat definition is based on sequence variability and is the most commonly used (Kabat E A et al., supra.). Chothia refers instead to the location of the structural loops (Chothia & Lesk J. (1987) Mol Biol, 196: 901-917). The AbM definition is a compromise between the Kabat and the Chothia definitions and is used by Oxford Molecular's AbM antibody modelling software (Martin A C R et al., (1989) Proc Natl Acad Sci USA 86:9268-9272; Martin A C R et al., (1991) Methods Enzymol, 203: 121-153; Pedersen J T et al., (1992) Immunomethods, 1: 126-136; Rees A R et al., (1996) In Sternberg M. J. E. (ed.), Protein Structure Prediction. Oxford University Press, Oxford, 141-172). The contact definition has been recently introduced (MacCallum R M et al., (1996) J Mol Biol, 262: 732-745) and is based on an analysis of the available complex structures available in the Protein Databank. The definition of the CDR by IMGT®, the international ImMunoGeneTics information System® (http://www.imgt.org) is based on the IMGT numbering for all immunoglobulin and T cell receptor V-REGIONs of all species (IMGT®, the international ImMunoGeneTics information System®; Lefranc M P et al., (1999) Nucleic Acids Res, 27(1): 209-12; Ruiz M et al., (2000) Nucleic Acids Res, 28(1): 219-21; Lefranc M P (2001) Nucleic Acids Res, 29(1): 207-9; Lefranc M P (2003) Nucleic Acids Res, 31(1): 307-10; Lefranc M P et al., (2005) Dev Comp Immunol, 29(3): 185-203; Kaas Q et al., (2007) Briefings in Functional Genomics & Proteomics, 6(4): 253-64). All Complementarity Determining Regions (CDRs) as referred to in the present invention, are defined preferably as follows (numbering according to Kabat E A et al., supra): LCDR1: 24-34, LCDR2: 50-56, LCDR3: 89-98, HCDR1: 26-35, HCDR2: 50-65, HCDR3: 95-102.

The "non-CDR regions" of the variable domain are known as framework regions (FR). The "non-CDR regions" of the VL region as used herein comprise the amino acid sequences: 1-23 (FR1), 35-49 (FR2), 57-88 (FR3) and 99-107 (FR4). The "non-CDR regions" of the VH region as used herein comprise the amino acid sequences: 1-25 (FR1), 36-49 (FR2), 66-94 (FR3) and 103-113 (FR4).

The CDRs of the present invention may comprise "extended CDRs" which are based on the aforementioned definitions and have variable domain residues as follows: LCDR1: 24-36, LCDR2: 46-56, LCDR3:89-97, HCDR1: 26-35, HCDR2:47-65, HCDR3: 93-102. These extended CDRs are numbered as well according to Kabat et al., supra. The "non-extended CDR region" of the VL region as used herein comprise the amino acid sequences: 1-23 (FR1), 37-45 (FR2), 57-88 (FR3) and 98-approximately 107 (FR4). The "non-extended CDR region" of the VH region as used herein comprise the amino acid sequences: 1-25 (FR1), 37-46 (FR2), 66-92 (FR3) and 103-approximately 113 (FR4).

The term "Fab" or "FAB" or "Fab region" or "FAB region" as used herein includes the polypeptides that comprise the VH, CH1, VL and light chain constant immunoglobulin regions. Fab may refer to this region in isolation, or this region in the context of a full length antibody or antibody fragment.

The term "Fc" or "Fc region", as used herein includes the polypeptide comprising the constant region of an antibody heavy chain excluding the first constant region immunoglobulin region. Thus Fc refers to the last two constant region immunoglobulin regions of IgA, IgD and IgG or the last three constant region immunoglobulin regions of IgE and IgM, and the flexible hinge N-terminal to these regions. For IgA and IgM, Fc may include the J chain. For IgG, Fc comprises immunoglobulin regions Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index. Fc may refer to this region in isolation or this region in the context of an Fc polypeptide, for example an antibody.

The term "immunoglobulin constant region" as used herein refers to immunoglobulin or antibody heavy chain constant regions from human or animal species and encompasses all isotypes. Preferably, immunoglobulin constant regions are of human origin and are selected from the group consisting of, but not limited to: IGHG1 CH1, IGHG2 CH1, IGHG3 CH1, IGHG4 CH1, IGHA1 CH1, IGHA2 CH1, IGHE CH1, IGHEP1 CH1, IGHM CH1, IGHD CH1, IGHGP CH1, IGHG1 CH2, IGHG2 CH2, IGHG3 CH2, IGHG4 CH2, IGHA1 CH2, IGHA2 CH2, IGHE CH2, IGHEP1 CH2, IGHM CH2, IGHD CH2, IGHGP CH2, IGHG1 CH3, IGHG2 CH3, IGHG3 CH3, IGHG4 CH3, IGHA1 CH3, IGHA2 CH3, IGHE CH3, IGHEP1 CH3, IGHM CH3, IGHD CH3, IGHGP CH3, IGHE CH4 and IGHM CH4. Preferred "immunoglobulin constant regions" are selected from the group consisting of human IGHE CH2, IGHM CH2, IGHG1 CH3, IGHG2 CH3, IGHG3 CH3, IGHG4 CH3, IGHA1 CH3, IGHA2 CH3, IGHE CH3, IGHM CH3, IGHD CH3 and IGHGP CH3. More preferred "immunoglobulin constant regions" are selected from the group consisting of human IGHG1 CH3, IGHG2 CH3, IGHG3 CH3, IGHG4 CH3, IGHA1 CH3, IGHA2 CH3, IGHE CH3, IGHM CH3, IGHD CH3 and IGHGP CH3.

The term "epitope binding region" includes a polypeptide or a fragment thereof having minimal amino acid sequence to permit the specific binding of the immunoglobulin molecule to one or more epitopes. Naturally occurring antibodies have two epitope binding regions which are also known as antigen binding or combining sites or paratopes. Epitope binding regions in naturally occurring antibodies are confined within the CDR regions of the VH and/or VL domains wherein the amino acid mediating epitope binding are found. In addition to naturally occurring antibodies, artificial VH domains or VL domains or fragments thereof and combinations thereof can be engineered to provide epitope binding regions (Holt L J et al., (2003) Trends Biotechnol, 21(11): 484-490; Polonelli L et al., (2008) PLoS ONE, 3(6): e2371). Examples of non-immunoglobulin based epitope binding regions can be found in artificial protein domains used as "scaffold" for engineering epitope binding regions (Binz H K et al., (2005) Nat Biotechnol, 23(10): 1257-1268) or peptide mimetics (Murali R & Greene M I (2012) Pharmaceuticals, 5(2): 209-235). Preferably the term 'epitope binding region' includes the combination of one or more heavy chain variable domains and one or more complementary light chain variable domains which together forms a binding site which permits the specific binding of the immunoglobulin molecule to one or more epitopes. Examples of an epitope binding region as exemplified in the present invention include scFv and FAB.

As used herein, the term "epitope" includes a fragment of a polypeptide or protein or a non-protein molecule having antigenic or immunogenic activity in an animal, preferably in a mammal and most preferably in a human. An epitope having immunogenic activity is a fragment of a polypeptide or protein that elicits an antibody response in an animal. An epitope having antigenic activity is a fragment of a polypeptide or protein to which an antibody or polypeptide specifically binds as determined by any method well-known to one of skill in the art, for example by immunoassays. Antigenic epitopes need not necessarily be immunogenic. Preferably, the term "epitope" as used herein refers to a polypeptide sequence of at least about 3 to 5, preferably about 5 to 10 or 15 and not more than about 1,000 amino acids (or any integer there between), which define a sequence that by itself or as part of a larger sequence, binds to an antibody generated in response to such sequence. There is no critical upper limit to the length of the fragment, which may comprise nearly the full-length of the protein sequence, or even a fusion protein comprising one or more epitopes. An epitope for use in the subject invention is not limited to a polypeptide having the exact sequence of the portion of the parent protein from which it is derived. Thus the term "epitope" encompasses sequences identical to the native sequence, as well as modifications to the native sequence, such as deletions, additions and substitutions (generally conservative in nature). The epitopes of protein antigens are divided into two categories, conformational epitopes and linear epitopes, based on their structure and interaction with the epitope binding site (Goldsby R et al., (2003) "Antigens (Chapter 3)" Immunology (Fifth edition ed.), New York: W. H. Freeman and Company. pp. 57-75, ISBN 0-7167-4947-5). A conformational epitope is composed of discontinuous sections of the antigen's amino acid sequence. These epitopes interact with the paratope based on the 3-D surface features and shape or tertiary structure of the antigen. Most epitopes are conformational. By contrast, linear epitopes interact with the paratope based on their primary structure. A linear epitope is formed by a continuous sequence of amino acids from the antigen.

The term "hetero-dimeric immunoglobulin" or "hetero-dimeric fragment" or "hetero-dimer" or "hetero-dimer of heavy chains" as used herein includes an immunoglobulin molecule or part of comprising at least a first and a second polypeptide, like a first and a second region, wherein the second polypeptide differs in amino acid sequence from the first polypeptide. Preferably, a hetero-dimeric immunoglobulin comprises two polypeptide chains, wherein the first chain has at least one non-identical region to the second chain, and wherein both chains assemble, i.e. interact through their non-identical regions. More preferably the hetero-dimeric immunoglobulin, has binding specificity for at least two different ligands, antigens or binding sites, i.e. is bispecific. Hetero-dimeric immunoglobulin as used herein includes but is not limited to full length bispecific antibodies, bispecifc Fab, bispecifc F(ab')$_2$, bispecific scFv fused to an Fc region, diabody fused to an Fc region and domain antibody fused to an Fc region.

The term "homo-dimeric immunoglobulin" or "homo-dimeric fragment" or "homo-dimer" or "homo-dimer of heavy chains" as used herein includes an immunoglobulin molecule or part of comprising at least a first and a second polypeptide, like a first and a second region, wherein the second polypeptide is identical in amino acid sequence to the first polypeptide. Preferably, a homo-dimeric immunoglobulin comprises two polypeptide chains, wherein the first chain has at least one identical region to the second chain, and wherein both chains assemble, i.e. interact through their identical regions. Preferably, a homo-dimeric immunoglobulin fragment comprises at least two regions, wherein the first region is identical to the second region, and wherein both regions assemble, i.e. interact through their protein-protein interfaces.

For all immunoglobulin constant regions included in the present invention, numbering can be according to the IMGT® (IMGT®; supra).

For all human CH1, CH2, CH3 immunoglobulin heavy chain constant regions selected from the group consisting of IGHG1, IGHG2, IGHG3 and IGHG4, numbering can be according to the "EU numbering system" (Edelman G M et al., (1969) Proc Natl Acad Sci USA, 63(1): 78-85). A complete correspondence for the human CH1, hinge, CH2 and CH3 constant regions of IGHG1 can be found at the IMGT database (IMGT®; supra).

For the human kappa immunoglobulin light chain constant region (IGKC), numbering can be according to the "EU numbering system" (Edelman G M et al., supra). A complete correspondence for the human CK region can be found at IMGT database (IMGT®; supra).

For the human lambda immunoglobulin light chain constant regions (IGLC1, IGLC2, IGLC3, IGLC6 and IGLC7), numbering can be according to the "Kabat numbering system" (Kabat E A et al., supra). A complete correspondence for human IGLC regions can be found at the IMGT database (IMGT®; supra).

The human IGHG1 immunoglobulin heavy chain constant regions as referred to herein have the following region boundaries: CH1 region (EU numbering: 118-215), Hinge γ1 region (EU numbering: 216-230), CH2 region (EU numbering: 231-340) and CH3 region (EU numbering: 341-447). The human CK region referred herein spans residues 108 to 214 (EU numbering). The human IGLC1, IGLC2, IGLC3, IGLC6 and IGLC7 regions referred herein span residues 108-215 (Kabat numbering).

The terms "amino acid" or "amino acid residue" as used herein includes natural amino acids as well as non-natural amino acids. Preferably natural amino acids are included.

The term "modification" or "amino acid modification" herein includes an amino acid substitution, insertion and/or deletion in a polypeptide sequence. The terms "substitution" or "amino acid substitution" or "amino acid residue substitution" as used herein refers to a substitution of a first amino acid residue in an amino acid sequence with a second amino acid residue, whereas the first amino acid residue is different from the second amino acid residue i.e. the substituted amino acid residue is different from the amino acid which has been substituted. For example, the substitution R94K refers to a variant polypeptide, in which the arginine at position 94 is replaced with a lysine. For example 94K indicates the substitution of position 94 with a lysine. For the purposes herein, multiple substitutions are typically separated by a slash or a comma. For example, "R94K/L78V" or "R94K, L78V" refers to a double variant comprising the substitutions R94K and L78V. By "amino acid insertion" or "insertion" as used herein is meant the addition of an amino acid at a particular position in a parent polypeptide sequence. For example, insert –94 designates an insertion at position 94. By "amino acid deletion" or "deletion" as used herein is meant the removal of an amino acid at a particular position in a parent polypeptide sequence. For example, R94– designates the deletion of arginine at position 94.

In certain embodiments, the terms "decrease", "reduce", or "reduction" in binding to Protein A refers to an overall decrease of at least 25%, 30%, 40%, 50%, 60%, 70%, 80%, 85%, 90%, 95%, 97%, or 99% up to 100% (elimination) in the binding of a modified immunoglobulin or fragment thereof to Protein A detected by standard art known methods such as those described herein, as compared to a parental i.e. unmodified immunoglobulin or wild-type IgG or an IgG having the wild-type human IgG Fc region. In certain embodiments these terms alternatively may refer to an overall decrease of 10-fold (i.e. 1 log), 100-fold (2 logs), 1,000-fold (or 3 logs), 10,000-fold (or 4 logs), or 100,000-fold (or 5 logs).

The terms "eliminate", "abrogate", "elimination" or "abrogation" of binding to Protein A refers to an overall decrease of 100% in the binding of a modified immunoglobulin or fragment thereof to Protein A i.e. a complete loss of the binding of a modified immunoglobulin or fragment thereof to Protein A, detected by standard art known methods such as those described herein, as compared to a parental i.e. unmodified immunoglobulin or wild-type IgG or an IgG having the wild-type human IgG Fc region.

Similarly, the terms "decrease", "reduce", or "reduction" in binding to an affinity reagent refers to an overall decrease of at least 25%, 30%, 40%, 50%, 60%, 70%, 80%, 85%, 90%, 95%, 97%, or 99% up to 100% (elimination) in the binding of a modified immunoglobulin or fragment thereof to the affinity reagent detected by standard art known methods such as those described herein, as compared to a parental, i.e. unmodified immunoglobulin or wild-type IgG or an IgG having the wild-type human IgG Fc region. In certain embodiments these terms alternatively may refer to an overall decrease of 10-fold (i.e. 1 log), 100-fold (2 logs), 1,000-fold (or 3 logs), 10,000-fold (or 4 logs), or 100,000-fold (or 5 logs).

The terms "eliminate", "abrogate", "elimination" or "abrogation" of binding to an affinity reagent refers to an overall decrease of 100% in the binding of a modified immunoglobulin or fragment thereof to the affinity reagent i.e. a complete loss of the binding of a modified immunoglobulin or fragment thereof to the affinity reagent detected by standard art known methods such as those described herein, as compared to a parental, i.e. unmodified immunoglobulin or wild-type IgG or an IgG having the wild-type human IgG Fc region.

"Bispecific antibodies" are monoclonal antibodies that have binding specificities for at least two different antigens. In certain embodiments, the bispecific antibodies are bispecific antibodies with one or more amino acid modifications in the VH region relative to the parental antibody. In certain embodiments, bispecific antibodies may be human or humanized antibodies. Bispecific antibodies may also be used to localize cytotoxic agents to cells which express a target antigen. These antibodies possess a target-antigen-binding arm and an arm which binds a cytotoxic agent, such as, e.g., saporin, anti-interferon-α, vinca alkaloid, ricin A chain, methotrexate or radioactive isotope hapten. Bispecific antibodies can be prepared as full length antibodies or antibody fragments. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, (1983) Nature, 305: 537-40). Because of the random assortment of immunoglobulin heavy and light chains, these hybridomas (quadromas) produce a potential mixture of different antibody molecules, of which only one has the correct bispecific structure. The purification of the correct molecule, which is usually done by affinity chromatography steps, is rather cumbersome and the product yields are low. Similar procedures are disclosed in WO1993/08829 and in Traunecker et al., (1991) EMBO J, 10: 3655-9. According to a different approach, antibody variable regions with the desired binding specificities (antibody-antigen combining sites) are fused to immunoglobulin constant region sequences. The fusion, for example, is with an immunoglobulin heavy chain constant region, comprising at least part of the hinge, CH2 and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980) and for treatment of HIV infection (WO1991/00360, WO1992/00373 and EP03089). Heteroconjugate antibodies may be made using any convenient cross-linking method. Suitable cross-linking agents are well known in the art (see U.S. Pat. No. 4,676,980), along with a number of cross-linking techniques. Antibodies with more than two valencies are also contemplated. For example, trispecific antibodies can be prepared (see Tutt A et al. (1991) J. Immunol. 147: 60-9).

Protein A:

Protein A is a cell wall component produced by several strains of *Staphylococcus aureus* which consists of a single polypeptide chain. The Protein A gene product consists of five homologous repeats attached in a tandem fashion to the pathogen's cell wall. The five domains are approximately 58 amino acids in length and denoted EDABC, each exhibiting immunoglobulin binding activity (Tashiro M & Montelione G T (1995) Curr. Opin. Struct. Biol., 5(4): 471-481). The five homologous immunoglobulin binding domains fold into a three-helix bundle. Each domain is able to bind proteins from many mammalian species, most notably IgGs (Hober S et al., (2007) J. Chromatogr. B Analyt. Technol. Biomed. Life Sci., 848(1): 40-47). Protein A binds the heavy chain of most immunoglobulins within the Fc region but also within the Fab region in the case of the human VH3 family (Jansson B et al, (1998) FEMS Immunol. Med. Microbiol., 20(1): 69-78). Protein A binds IgG from various species including human, mouse, rabbit and guinea pig but does not bind human IgG3 (Hober S et al., (2007) supra). The inability of human IgG3 to bind Protein A can be explained by the H435R and Y436F substitutions in the human IgG3 Fc region (EU numbering, Jendeberg et al., (1997) J. Immunol. Methods, 201(1): 25-34). Besides IgG, Protein A also interacts with IgM and IgA.

Amongst human VH subclasses, VH3 is the only subclass to bind Protein A (Graille M et al., (2000) Proc. Natl. Acad. Sci. USA 97(10): 5399-5404), and all five variable domains of Protein A are known to bind this variable domain subclass (Jansson B et al, (1998) FEMS Immunol. Med. Microbiol., 20(1): 69-78. VH3 based immunoglobulins or fragments thereof are of major importance to the biotechnology industry. VH3 based molecules have been extensively developed since their ability to bind Protein A facilitates their functional pre-screening, and as such many synthetic or donor based phage display libraries or transgenic animal technologies used for antibody discovery are based on the VH3 subclass. In addition VH3 based molecules are often selected for their good expression and stability over other known heavy chain variable domain subclasses.

The capacity of Protein A to bind antibodies with such high affinity is the driving motivation for its industrial scale use in biologic pharmaceuticals. Protein A used for production of antibodies in bio-pharmaceuticals is usually produced recombinantly in *E. coli* and functions essentially the same as native Protein A (Liu H F et al., (2010) MAbs, 2(5): 480-499).

Most commonly, recombinant Protein A is bound to a stationary phase chromatography resin for purification of antibodies. Optimal binding occurs at pH8.2, although binding is also good at neutral or physiological conditions (pH 7.0-7.6). Elution is usually achieved through pH shift towards acidic pH (glycine-HCl, pH2.5-3.0). This effectively dissociates most protein-protein and antibody-antigen binding interactions without permanently affecting protein structure. Nevertheless, some antibodies and proteins are damaged by low pH and it is best to neutralize immediately after recovery by addition of $\frac{1}{10}$th volume of alkaline buffer such as 1 M Tris-HCl, pH 8.0 to minimize the duration of time in the low-pH condition.

There are various commercially available Protein A chromatography resins. The main differences between these media are the support matrix type, Protein A ligand modification, pore size and particle size. The differences in these factors give rise to differences in compressibility, chemical and physical robustness, diffusion resistance and binding capacity of the adsorbents (Hober S et al., (2007), supra). Examples of Protein A chromatography resins include but are not limited to the MabSelect SuRe™ Protein A resin and MabSelect™ Protein A resin from GE Healthcare as used in examples.

The term "chromatography" refers to protein liquid chromatography and includes fast protein liquid chromatography (FPLC) which is a form of liquid chromatography that is often used to analyze or purify mixtures of proteins. As in other forms of chromatography, separation is possible because the different components of a mixture have different affinities for two materials, a moving fluid (the mobile phase) which passes through a porous solid (the stationary phase). In FPLC, the mobile phase is an aqueous solution, or "buffer". The buffer flow rate can be operated under gravity flow or controlled by a positive-displacement pump which is normally kept at a constant rate, while the composition of the buffer can be varied by drawing fluids in different proportions from two or more external reservoirs. The stationary phase is a resin composed of beads, usually of cross-linked agarose, packed into a cylindrical glass or plastic column. FPLC resins are available in a wide range of bead sizes and surface ligands depending on the application.

The process of "affinity chromatography" involves the use of an affinity reagent as ligands which are cross-linked to the stationary phase and that have binding affinity to specific molecules or a class of molecules. Ligands can be biomolecules, like protein ligands or can be synthetic molecules. Both types of ligand tend to have good specificity. The most commonly used protein ligand in production is the affinity reagent Protein A. In affinity chromatography when the solution (for example a crude cell supernatant containing a protein of interest) is loaded onto to the column the target protein is usually adsorbed while allowing contaminants (other proteins, lipids, carbohydrates, DNA, pigments, etc.) to pass through the column. The adsorbent itself is normally packed in a chromatography column; though the adsorption stage can be performed by using the adsorbent as a stirred slurry in batch binding mode. The next stage after adsorption is the wash stage, in which the adsorbent is washed to remove residual contaminants. The bound protein is then eluted in a semi-pure or pure form. Elution is normally achieved by changing the buffer or salt composition so that the protein can no longer interact with the immobilized ligand and is released. In some instances the protein of interest may not bind the affinity resin and affinity chromatography is directed at binding unwanted contaminants and the unbound fraction is therefore collected to isolate the protein of interest. Affinity chromatography can be performed in a fixed bed or a fluidised bed.

The term "gradient mode chromatography" refers to a chromatography method wherein the proportion of the "elution" buffer (buffer B) is increased from 0% to 100% in a gradual or stepwise manner.

The terms "capture-elution mode chromatography" or "capture-elution purification mode" or "capture-elution purification" refers to a chromatography method wherein the proportion of the "elution" buffer (buffer B) is not increased from 0% to 100% in a gradual or stepwise manner but rather directly applied at a 100% after capture and optionally a wash step with running buffer (buffer A).

Development of Hetero-Dimeric Immunoglobulins Targeting CD3 and CD38

The present invention provides an epitope binding region that binds the CD3 protein complex comprising the heavy and light chain CDRs as described supra and further comprising a heavy chain variable framework region that is the product of or derived from human gene IGHV3-23*04 (SEQ ID NO: 37). The heavy chain variable framework region comprises at least one amino acid modification from the corresponding framework region of the heavy chain variable region of the corresponding murine antibody OKT3 comprising the amino acid sequence of SEQ ID NO: 38. Preferably the amino acid modification is an amino acid substitution. Typically, no more than seven, preferably no more than six, preferably no more than five, preferably no more than four, more preferably no more than three, even more preferably no more than two, most preferably no more than one amino acid modifications are performed within a framework region. In some embodiments the present disclosure provides an epitope binding region that binds to the CD3 protein complex, wherein the amino acid modification of the framework regions of the heavy chain variable region comprise an amino acid substitution at amino acid position selected from the group consisting of: 34, 48, 49, 58, 69, 71 and 73 and wherein the amino acid position of each group member is indicated according to the Kabat numbering. Preferably, amino acid substitutions of the framework regions of the heavy chain variable region are selected from the group consisting of: I34M, V48I, A49G, R58N, R58Y, I69L, A71T and T73K. Preferred amino acid substitution of the framework regions of the heavy chain variable region are at amino acid positions selected from the group consisting of 34, 49 and 71. More preferred amino acid substitutions of the framework regions of the heavy chain variable region are selected from the group consisting of I34M, A49G and A71T.

In a further aspect, the epitope binding region of the first polypeptide that binds the CD3 protein complex comprises a light chain variable framework region that is the product of or derived from a human gene selected from the group consisting of: IGKV1-39*01 (SEQ ID NO: 39) and IGKV3-20*01 (SEQ ID NO: 40). The light chain variable framework region comprises at least one amino acid modification from the corresponding framework region of the light chain variable region of the corresponding murine antibody OKT3 comprising the amino acid sequence of SEQ ID NO: 41. Preferably the amino acid modification is an amino acid substitution. Typically, no more than eight, preferably no more than seven, preferably no more than six, preferably no more than five, preferably no more than four, more preferably no more than three, even more preferably no more than two, most preferably no more than one amino acid modifications are performed within a framework region. In some embodiments the present disclosure provides an epitope binding region that binds to the CD3 protein complex, wherein the amino acid modification of the framework regions of the light chain variable region sequence comprises an amino acid substitution at amino acid position selected from the group consisting of: 4, 33, 34, 46, 47, 66, 71 and 96. Preferably, amino acid substitutions of the framework regions of the light chain variable region are selected from the group consisting of: M4L, V33M, A34N, L46R, L47W, R66G, F71Y and P96F. Preferred amino acid substitution of the framework regions of the light chain variable region are at amino acid positions selected from the group consisting of 4, 46 and 47. More preferred amino acid substitutions of the framework regions of the light chain variable region are selected from the group consisting of M4L, L46R, L47W and F71Y. In some embodiments the epitope binding region of the first polypeptide that binds to the CD3 protein complex may comprise amino acid modifications of the framework regions of the heavy chain variable region sequence as set out above and amino acid modifications of the framework regions of the light chain variable region sequence as set out above.

The present disclosure also provides an antibody or fragment thereof that binds to the CD3 protein complex that comprises a heavy chain sequence selected from the group consisting of SEQ ID NOs: 79 to 90, 91-95 and 64, preferably selected consisting of SEQ ID NO: 64. The present disclosure also provides an antibody or fragment thereof that binds to the CD3 protein complex that comprises a light chain sequence selected from the group consisting of SEQ ID NOs: 96 to 104, 105 to 126, 127, 128 and 129 preferably consisting of SEQ ID NO: 127.

Given that each of these heavy and light chain variable region sequences can bind to the CD3 protein complex, the heavy and light chain variable region sequences can be "mixed and matched" to create anti-CD3 binding molecules of the invention. CD3 binding of such "mixed and matched" antibodies can be tested using the binding assays described e.g. in the Examples.

Engineering of the Immunoglobulin Constant Region to Promote Hetero-Dimer Formation Over Homo-Dimer Formation Methods to produce hetero-dimeric immunoglobulins are known in the art and one of the simplest methods relies on expressing the two distinct immunoglobulin chains in a single cell (WO95/33844, Lindhofer H & Thierfelder S). Without engineering, this straightforward method is limited by the formation of homo-dimeric species over the hetero-dimer of interest (Kufer P et al., (2004) Trends Biotechnol., 22(5): 238-244). When using complementary technologies that will enhance heavy chain hetero-dimerization (Merchant A M et al., (1998) Nat. Biotechnol., 16(7): 677-681), greater hetero-dimer production can be achieved but still results in the production of a significant amount of undesirable homo-dimers (Jackman J et al., (2010) J Biol Chem., 285(27):20850-9, Klein C et al., (2012) MAbs, 4(6):653-63). The present invention therefore utilises the BEAT® technology described method (PCT publication No: WO2012/131555), which is based on a unique concept of bio-mimicry that exhibit superior hetero-dimerisation over prior art methods. The BEAT technology is based on an interface exchange between naturally occurring homo or hetero-dimeric immunoglobulin domain pairs to create new hetero-dimers which can be used as building blocks for Fc-based bispecific antibodies.

In one aspect, the present invention provides a hetero-dimeric immunoglobulin or fragment thereof comprising first and second polypeptides comprising an engineered immunoglobulin constant region with a modified CH3 domain having a protein-protein interface, wherein the protein-protein interface of the first polypeptide comprises an amino acid substitution at a position selected from the group consisting of: 3, 5, 7, 20, 22, 26, 27, 79, 81, 84, 84.2, 85.1, 86, 88 and 90 (IMGT® numbering), and wherein the protein-protein interface of the second polypeptide comprises an amino acid substitution at position 84.4 and at a position selected from the group consisting of 3, 5, 7, 20, 22, 26, 27, 79, 81, 84, 84.2, 85.1, 86, 88 and 90 (IMGT® numbering).

In a further embodiment, the present invention provides a hetero-dimeric immunoglobulin or fragment thereof, wherein the first and second polypeptides comprise an engineered immunoglobulin constant region with a modified CH3 domain having a protein-protein interface, wherein the protein-protein interface of the first polypeptide comprises an amino acid substitution at position 88 and at a position selected from the group consisting of: 3, 5, 7, 20, 22, 26, 27, 79, 81, 84, 84.2, 85.1, 86 and 90 (IMGT® numbering), and wherein the protein-protein interface of the second polypeptide comprises an amino acid substitution at position 85.1 and/or 86 and at a position selected from the group consisting of 3, 5, 7, 20, 22, 26, 27, 79, 81, 84, 84.2, 84.4, 88 and 90 (IMGT® numbering), wherein the amino acid residue substituted at position 88 in the first engineered immunoglobulin constant region is interacting with the amino acid residue substituted at position 85.1 and/or 86 in the second engineered immunoglobulin constant region, wherein the amino acid position of each group member is indicated according to the IMGT® numbering.

Preferably the amino acid residue which is substituted in the protein-protein interface of the first engineered immunoglobulin constant region at position 88 is 88W and conservative amino acid substitutions thereof, wherein the amino acid position is indicated according to IMGT® numbering. More preferably, the amino acid residue which is substituted in the protein-protein interface of the first engineered immunoglobulin constant region at position 88 is 88W and wherein the further amino acid residue substituted in the protein-protein interface of the first engineered immunoglobulin constant region is selected from the group consisting of: 3A, 20V, 20T, 20A, 20N, 20Q, 20E, 20S, 20K, 20W, 22A, 22G, 22T, 22L, 22I, 22V, 26R, 26Q, 26T, 26K, 26V, 26S, 26N, 26E, 79Y, 85.1T, 85.1M, 85.1A, 85.1S, 85.1R, 85.1H, 85.1K, 85.1F, 85.1C, 85.1N, 85.1W, 86S, 86I, 86T, 86H, 86Q, 86V, 86W, 86Y, 86F and 90N, wherein the amino acid position is indicated according to the IMGT® numbering.

Preferably the amino acid residue which is substituted at position 85 and 86 in the protein-protein interface of the second engineered immunoglobulin constant region is selected from the group consisting of: 85.1A, 85.1S, 85.1C and 86S and conservative amino acid substitutions thereof (IMGT® numbering). More preferably the amino acid residue which is substituted in the protein-protein interface of the second engineered immunoglobulin constant region is selected from the group consisting of: 85.1A, 85.1S, 85.1C and 86S and wherein the further amino acid residue substituted in the protein-protein interface of the second engineered immunoglobulin constant region is selected from the group consisting of: 3E, 5A, 7F, 20T, 22V, 26T, 81D, 84L, 84.2E, 88R and 90R and conservative amino acid substitutions thereof (IMGT® numbering).

In a preferred embodiment the amino acid residue which is substituted in the protein-protein interface of the first engineered immunoglobulin constant region at position 88 is 88W and wherein the further amino acid residue substituted in the protein-protein interface of the first engineered immunoglobulin constant region is: 3A, 20K, 22V, 26T, 79Y, 85.1S, 86V and 90N and, wherein the amino acid residues which are substituted in the protein-protein interface of the second engineered immunoglobulin constant region at positions 85.1 and 86 are 85.1A, 85.1S or 85.1A and 86S and wherein the further amino acid residue substituted in the protein-protein interface of the second engineered immunoglobulin constant region is: 3E, 5A, 7F, 20T, 22V, 26T, 81D, 84L, 84.2E, 84.4Q, 88R and 90R (IMGT® numbering).

In an alternative embodiment, the present invention provides a hetero-dimeric immunoglobulin or fragment thereof, wherein the first and second polypeptides comprise an engineered immunoglobulin constant region with a modified CH3 domain having a protein-protein interface, wherein the protein-protein interface of the first polypeptide comprises an amino acid substitution at position 20, and at a position selected from the group consisting of: 3, 5, 7, 22, 26, 27, 79, 81, 84, 84.2, 85.1, 86, 88 and 90 and, wherein the protein-protein interface of the second polypeptide comprises an amino acid substitution at position 26 and at a position selected from the group consisting of: 3, 22, 27, 79, 81, 84, 85.1, 86, and 88, wherein the amino acid residue substituted at position 20 in the first engineered immunoglobulin constant region is interacting with the amino acid residue substituted at position 26 in the second engineered immunoglobulin constant region, wherein the amino acid position of each group member is indicated according to the IMGT® numbering.

Preferably the amino acid residues which are substituted in the protein-protein interface of the first engineered immunoglobulin chain comprise the amino acid residues at positions 20 and 22, and optionally a further amino acid residue at a position selected from the group consisting of: 3, 5, 7, 26, 27, 79, 81, 84, 84.2, 84.4, 85.1, 86, 88 and 90 and, wherein the amino acid residues which are substituted in the protein-protein interface of the second engineered immunoglobulin chain comprise the amino acid residues at positions 26 and at a further position selected from the group consisting of: 3, 5, 7, 20, 22, 27, 79, 81, 84, 84.2, 84.4, 85.1, 86, 88 and 90, wherein the amino acid position of each group member is indicated according to the IMGT® numbering. Preferably the amino acid residues which are substituted in the protein-protein interface of the first engineered immunoglobulin chain comprise the amino acid residues at positions 20 and 22, and optionally a further amino acid residue at a position selected from the group consisting of: 3, 5, 7, 26, 27, 79, 81, 84, 84.2, 84.4, 85.1, 86, 88 and 90 and, wherein the amino acid residues which are substituted in the protein-protein interface of the second engineered immunoglobulin chain comprise the amino acid residues at positions 26 and 86 and optionally at a further position selected from the group consisting of 3, 5, 7, 20, 22, 27, 79, 81, 84, 84.2, 84.4, 85.1, 88 and 90, wherein the amino acid position of each group member is indicated according to the IMGT® numbering.

More preferably the amino acid residue which is substituted at position 20 in the protein-protein interface of the first engineered immunoglobulin constant region is selected from the group consisting of 20V, 20T, 20A, 20N, 20Q, 20K, 20S, 20W and 20E and wherein the further amino acid residue substituted in the protein-protein interface of the first engineered immunoglobulin constant region is selected from the group consisting of 3A, 22A, 22G, 22L, 22I, 22V, 22T, 26K, 26R, 26Q, 26T, 26V, 26S, 26N, 26E, 79Y, 85.1W, 85.1F, 85.1T, 85.1M, 85.1A, 85.1S, 85.1R, 85.1H, 85.1K, 85.1C, 85.1N, 86W, 86Y, 86S, 86I, 86H, 86Q, 86V, 86T, 86F, 88Q, 88L, 88V, 88R, 88E, 88T, 88I, 88Y, 88K, 88W and 90N, and wherein the amino acid residue which is substituted at position 26 in the protein-protein interface of the second engineered immunoglobulin constant region is selected from the group consisting of 26T and 26E and conservative amino acid substitutions thereof, wherein the amino acid position is indicated according to the IMGT® numbering.

In a most preferred embodiment the amino acid residue which is substituted in the protein-protein interface of the first engineered immunoglobulin constant region at position 20 is 20K and wherein the further amino acid residue substituted in the protein-protein interface of the first engineered immunoglobulin constant region is 3A, 22V, 26T, 79Y, 85.1S, 86V, 88W and 90N and, wherein the amino acid residues which are substituted in the protein-protein interface of the second engineered immunoglobulin constant region at position 26 is 26T and wherein the further amino acid residue substituted in the protein-protein interface of the second engineered immunoglobulin constant region is 3E, 5A, 7F, 20T, 22V, 81D, 84L, 84.2E, 84.4Q, 85.1C/S/A, 86S, 88R and 90R (IMGT® numbering).

EXAMPLES

Example 1. Materials and Methods

Construction of Expression Vectors for Transient Mammalian Cell Expression cDNAs encoding the different polypeptide chains in part or in full were first gene synthetized by GENEART AG (Regensburg, Germany) and modified using standard molecular biology techniques. PCR products were digested with appropriate DNA restriction enzymes, purified and ligated in a modified pcDNA3.1 plasmid (Invitrogen AG, Zug, Switzerland) carrying a CMV promoter and a bovine hormone poly-adenylation (poly(A)) previously digested with the same DNA restriction enzymes. All polypeptide chains were independently ligated in this expression vector where secretion was driven by the murine VJ2C leader peptide.

Expression of Recombinant Proteins

Antibodies, ScFv-Fc fusion proteins, BEAT antibodies and antigens were expressed as described below unless otherwise indicated. For transient expression, equal quantities of each engineered chains vectors were co-transfected into suspension-adapted HEK293-EBNA cells (ATCC-LGL standards, Teddington, UK; Cat. No: CRL-10852) using Polyethyleneimine (PEI; Sigma, Buchs, Switzerland). Typically, 100 ml of cells in suspension at a density of 0.8-1.2 million cells per ml is transfected with a DNA-PEI mixture. When recombinant expression vectors encoding each engineered chain genes are introduced into the host cells, the immunoglobulin construct is produced by further culturing the cells for a period of 4 to 5 days to allow for secretion into the culture medium (EX-CELL 293, HEK293-serum-free medium (Sigma), supplemented with 0.1% pluronic acid, 4 mM glutamine and 0.25 µg/ml geneticin). Cell-free culture supernatants containing the secreted immunoglobulins were prepared by centrifugation followed by sterile filtration and used for further analysis.

Differential Protein a Affinity Chromatography

Post production, cell-free supernatants were loaded onto a 1 ml HiTrap™ MabSelect SuRe™ Protein A column pre-equilibrated in 0.2M phosphate citrate buffer pH 6.0 and operated on an ÄKTApurifier™ chromatography system (both from GE Healthcare Europe GmbH; column Cat. No: 11-0034-93) at a flow rate of 1 ml/min. Running buffer was 0.2 M phosphate citrate buffer pH 6. Elution of the heterodimer of interest was performed using 20 mM sodium citrate buffer pH 4 whilst homo-dimeric species were eluted with 0.1 M glycine, pH3.0.

Elution was followed by OD reading at 280 nm; fraction containing the hetero-dimer of interest were pooled and neutralized with 0.1 volume of 1M Tris pH 8.0 (Sigma).

Supernatant, flow through and elution fractions were analysed under non-reduced conditions by SDS-PAGE (Nu-PAGE Bis-Tris 4-12% acrylamide, Invitrogen AG, Basel, Switzerland).

Differential Scanning Calorimetry (DSC)

The thermal stabilities of antibodies were compared using calorimetric measurements. Calorimetric measurements were carried out on a VP-DSC differential scanning microcalorimeter (MicroCal-GE Healthcare Europe GmbH, Glattbrugg, Switzerland). The cell volume was 0.128 ml, the heating rate was 1° C./min and the excess pressure was kept at 64 p.s.i. All protein fragments were used at a concentration of 1-0.5 mg/ml in PBS (pH 7.4). The molar heat capacity of each protein was estimated by comparison with duplicate samples containing identical buffer from which the protein had been omitted. The partial molar heat capacities and melting curves were analysed using standard procedures. Thermograms were baseline corrected and concentration normalized before being further analysed using a Non-Two State model in the software Origin v7.0.

The expected melting profiles for the human IgG subclasses are known (Garber E & Demarest S J (2007) Biochem Biophys Res Commun, 355(3): 751-7) and all profiles have been shown to contain three unfolding transitions corresponding to the independent unfolding of the CH2, CH3 and FAB domains. Of the four human IgG subclasses, IGHG1 has the most stable CH3 domain (~85° C.); while other subclasses CH3 domains are less stable, although none are known to melt below 70° C. Similarly, all subclasses are known to have a melting temperature of ~70° C. for the CH2 domain.

Purity Assessment by Capillary Gel Electrophoresis

Non-Reduced Sample Preparation

40 µg of desalted protein sample was buffered in SDS sample buffer (Beckman Coulter International S.A., Nyon, Switzerland; IgG Purity Kit, Cat. No: A10663) containing 5 mM Iodoacetamide (Sigma). A 10-kDa internal standard was added to the samples. The sample-mixtures were heated at 70° C. for 10 min.

Capillary Gel Electrophoresis

Following sample preparation, samples were run on a ProteomeLab PA 800 (Beckman Coulter International S.A., Nyon, Switzerland) fitted with a photodiode array detector (DAD) set at 220 nm. Bare-fused silica capillaries of 50 µm ID×30.2 cm (20.2 cm effective length to detector) were used as separation medium. Sample injection and separation were performed at constant voltages of 5 and 15 kV, respectively, with reverse polarity in SDS-molecular weight gel buffer. The data were recorded at a rate of 2 Hz and current was stable during separation. Capillary and samples were thermo-stated at 25° C.

Affinity Measurements by SPR

SPR analysis was used to measure the association and dissociation rate constants for the binding kinetics of the different antibodies (murine and humanized antibodies). The binding kinetics of antibodies were measured on a BIAcore 2000 instrument (BIAcore-GE Healthcare Europe GmbH, Glattbrugg, Switzerland) at room temperature and analysed with the BiaEvaluation software (version 4.1, BIAcore-GE Healthcare Europe GmbH).

Measurements were performed on CM5 sensor chips (GE Healthcare Europe GmbH, Cat. No: BR-1000-14) individually coupled with the ligand of interest using a commercial amine coupling kit (GE Healthcare Europe GmbH, Cat. No: BR-1000-50). Protein G ligand was from Pierce (Thermo Fisher Scientific-Perbio Science S.A., Lausanne, Switzerland, Cat. No: 21193).

Data (sensorgram: fc2-fc1) were fitted with a 1:1 Langmuir model with or without mass transfer as indicated. In capture experiments, to account for the experimental variations in at the beginning of each measurement, the Rmax value was set to local in all fits. Dissociation times were of at least 350 seconds. Measurements were performed in triplicate and included zero-concentration samples for referencing. Both Chi2 and residual values were used to evaluate the quality of a fit between the experimental data and individual binding models.

Affinity Measurements on HPB-ALL Cells by FACS

HPB-ALL cells (DSMZ, Braunschweig, Germany, Cat. No: ACC483) were used as CD3 positive cell line for FACS staining. HPB-ALL were maintained in RPMI 1640 supplemented with 10% FCS and 100 U/ml Penicillin and 100 ug/ml streptomycin. 100 μl dilution series of the chimeric OKT3 antibody and humanized variants were incubated with 4×10$^5$ HPB-all cells in PBS supplemented with 1% BSA and 0.1% Sodium Azide (referred as FACS buffer) for 45 min on ice. An irrelevant human IgG1 was used as isotype control and the chimeric OKT3 antibody as positive control. After washing, cells were incubated with a 1/200 dilution of anti-Human Fc-PE (EBioscience, Vienna, Austria) for 45 min on ice. Cells were then washed again and resuspended in 200 ul FACS buffer. The relative mean fluorescence of each sample was measured on FACSCalibur (BD Biosciences, Allschwil, Switzerland) Results are summarized in FIG. 9 as the relative staining of HBP-ALL compared to the chimeric OKT3 antibody.

Cell-Lines for In Vitro Assays

Human CD38 Positive Cell Lines

Human cells expressing CD38 antigen have been described in PCT Publication Nos: WO2005103083, WO2008047242, WO2011154453 and WO2012092612. CD38 positive human cell lines as used herein were as follows:

Stable Recombinant CHO[CD38] Cells

A gene coding for human CD38 was ordered at Source Biosciences (Berlin, Germany, Cat.-No.: IRAU37D11, 4309086). Human CD38 was amplified using primers adding a kozak sequence, a start codon followed by a signal peptide (murine V leader) to the 5' end and a NheI restriction site to the 3' end. The amplicon was cut using NheI and HindIII and cloned into the expression cassette of pT1, a pcDNA3.1 (Invitrogen AG) derived vector developed in-house. The expression cassette of pT1 links the expression of the gene of interest with expression of GFP and PAC (the gene for puromycin resistance) using two IRES (internal ribosome entry sites) on a polycistronic mRNA. A midiprep of the plasmid was prepared and the cloned CD38 open reading frame was confirmed by DNA sequencing. Suspension CHO-S cells (Invitrogen AG) were transfected using polyethyleneimine (JetPEI®, Polyplus-transfection, Illkirch, France) in 50 ml bioreactor format (TubeSpin 50 bioreactors, TPP, Trasadingen, Switzerland). For this purpose, exponential growing cells were seeded in OptiMEM medium (Invitrogen AG, Cat. No.: 31985-047). A JetPEI®:DNA complex was added to the cells. After 5 h incubation of the cells with the JetPEI®:DNA complex at 37° C. under shaking (200 RPM) for endocytosis, one volume of culture medium PowerCHO2 (Lonza, distributor RUWAG Lifescience, Bettlach, Switzerland, Cat. No: BE12-771Q) supplemented with 4 mM Gln was added to the cell suspension. The cells were then incubated on a shaken platform at 37° C., 5% CO2 and 80% humidity. One day after transfection the cells were seeded in 96 well plates at different concentrations in selective medium containing puromycin (Sigma, Cat. No: P8833-25 mg). After approximately 14 days of selection under static conditions, 46 high GFP expressing cell pools were expanded as suspension cultures using TubeSpin 50 bioreactors. Once successfully adapted to suspension, the cells were analysed for CD38 by FACS. Stable CHO[CD38] clones with a homogenous CD38 staining profile were selected and used herein.

Other CD38 Positive Cell Lines Included:

NCI-H929 (ATCC-LGL standards; Cat. No: CRL-9068).
Namalwa (ATCC-LGL standards; Cat. No: CRL-1432)
U266 (ATCC-LGL standards; Cat. No: TIB-196)
RPMI 8226 (ATCC-LGL standards; Cat. No: CCL-155)
Culture conditions: RPMI 1640 medium supplemented with 10% heat-inactivated FBS, 1% penicillin-streptomycin (Invitrogen AG) and 1% GlutaMAX-1 (Invitrogen AG)
Raji (ATCC-LGL standards; Cat. No: CCL-86)
Daudi (ATCC-LGL standards; Cat. No: CCL-213)

Recombinant Target Antigens

Human CD3 Gamma-Epsilon-Fc Fusion Protein

A cDNA encoding the human CD3 gamma extracellular region (UniProt accession No: P09693 residues 23-103 (SEQ ID NO: 184); UniProt Consortium (2013) Nucleic Acids Res., 41(Database issue): D43-7; http://www.uniprot.org/) fused to the human CD3 epsilon extracellular region (UniProt accession No: P07766, residues 22-118 (SEQ ID NO: 185)) by a 26-residue peptide linker (sequence: GSADDAKKDAAKKDDAKKDDAKKDGS; SEQ ID NO: 169) was first synthetized by GENEART AG (Regensburg, Germany). This synthetic gene was fused to a human IgG1 Fc portion using standard overlap PCR techniques and a human IgG1 Fc cDNA template also obtain from Geneart AG. The resulting cDNA was cloned in the modified pcDNA3.1 plasmid mentioned above.

For transient expression of the CD3 gamma-epsilon-Fc protein (SEQ ID NO: 170), the recombinant vector was transfected into suspension-adapted HEK-EBNA cells (ATCC-CRL-10852) using Polyethyleneimine (PEI) as described above. The CD3 gamma-epsilon-Fc construct was then purified from cell-free supernatant using recombinant Streamline rProtein A media (GE Healthcare Europe GmbH, Glattbrugg, Switzerland) and used for further analysis.

Human and Cynomolgus Monkey CD3 Epsilon 1-26_Fc Fusion Proteins

A cDNA encoding the human CD3 epsilon peptide 1-26 (UniProt accession No: P07766, amino acids 23-48, SEQ ID NO: 171) and a cDNA encoding the cynomolgus CD3 epsilon peptide 1-26 (UniProt accession No: Q95LI5, amino acids 22-47, SEQ ID NO: 172) were PCR amplified from synthetic cDNAs obtained from GENEART A.G. for the human and cynomolgus monkey CD3 epsilon extracellular regions, respectively. The amplified products were subsequently fused to a human IgG1 Fc portion using standard overlap PCR techniques. The human IgG1 Fc cDNA template was obtained from Geneart AG. The resulting cDNA were cloned in the modified pcDNA3.1 plasmid mentioned above.

For transient expression of human and cynomolgus CD3 epsilon constructs (SEQ ID NO: 173 and 174, respectively), the recombinant vectors were transfected into suspension-adapted HEK-EBNA cells (ATCC-CRL-10852) using Polyethyleneimine (PEI) as described above. The CD3 epsilon fusion constructs were then purified from cell-free supernatant using recombinant Streamline rProtein A media (GE Healthcare Europe GmbH, Glattbrugg, Switzerland) and used for further analysis. These two fusion proteins are referred herein as the human and cynomolgus monkey CD3 epsilon 1-26_Fc fusion proteins.

Human and Cynomolgus Monkey CD38 Extracellular Regions

A cDNA for human CD38 was obtained from Source Biosciences (Erwin-Negelein-Haus, Germany, Cat. No.: IRAU37D11, 4309086), its extracellular region (UniProt accession No: P28907 residues 43-300) was PCR amplified and cloned into an in-house expression vector derived from pcDNA3.1 (Invitrogen AG). This expression vector encompassed a kozak sequence and a start codon followed by the murine VJ2C leader peptide to the 5' end and a 6-His-tag to the 3' end of its multiple cloning site. The soluble extracellular region of human CD38 fused to a 6-His-tag (SEQ ID NO: 175) was expressed and purified as follows: one volume of RPMI 1640 medium (PAA Laboratories, Cat. No: E15-039) containing HEK cells, 0.1% pluronic acid (Invitrogen AG), expression vector and polyethylenimine (JetPEI®, Polyplus-transfection, Illkirch, France) was incubated in a shaker flask at 37° C., 5% $CO_2$ and 80% humidity. One volume of ExCell293 medium supplemented with 6 mM glutamine was added to the mixture after 4 hours and incubation continued further for a total of 5 days. Post production, cell-free supernatant was prepared by centrifugation and filtrated using 0.2 µm filters, pH was adjusted at 7.4 (4° C.) using Tris 1 M pH 8.7. Ni-Sepharose Excell beads (GE Healthcare, Cat. No: 17-3712-03) were added to the solution and incubated overnight at 4° C. under agitation. The solution was loaded on an Econo-Column (Bio-Rad Laboratories AG, Reinach, Switzerland, Cat. No: 737-4252) for gravity-flow purification. The beads were washed in PBS (2×), 20 mM imidazole and the protein was eluted in PBS, 500 mM Imidazole. Eluted fractions were pooled and buffer exchanged for PBS with two dialysis steps at 4° C. The purified human CD38 extracellular region was filtrated using 0.22 µm syringe filters.

Using the methods as described above the soluble extracellular region of cynomolgus monkey CD38 antigen fused to a 6-His-tag (SEQ ID NO: 176) was cloned, expressed and purified.

In Vitro T Cell Redirection Killing Assay
Preparation of Peripheral Blood Mononuclear Cells To produce peripheral blood mononuclear cells (PBMCs), blood filters containing human leukocytes were collected from the Blood Collection Centre in La Chaux-de-Fonds, Switzerland (Centre de Transfusion Sanguine et Laboratoire de Sérologie, rue Sophie-Mairet 29, CH-2300). Cells were removed from the filters by back-flushing with 60 ml of PBS containing 10 U/ml of liquemin (Drossapharm AG, Lucern, Switzerland). PBMCs were then purified with 50 mL Blood-Sep-Filter Tubes (Brunschwig, Basel, Switzerland) following manufacturer's instructions. Tubes were centrifuged for 20 min at 800 g at room temperature (without brake) and the cells were collected from the interface. Cells were washed 3× with Roswell Park Memorial Institute (RPMI, PAA Laboratories, Pasching, Austria) medium without FBS or phosphate buffered Saline (PBS). PBMCs were resuspended at 10e6 cells/mL in RDL medium (RPMI supplemented with 10% heat inactivated Fetal bovine serum (FBS) and penicillin/streptomycin) and were cultured overnight at 37° C. in a 5% $CO_2$ incubator prior to the assay.

T Cell Preparations

T cell purification was performed directly after the PBMC isolation using pan-T cell isolation kit II (Myltenyi Biotec GmbH, Bergisch Gladbach, Germany, Cat. No: 130-091-156) following manufacturer's instructions. After purification, T cells were resuspended at 10e6 cells/mL in RDL medium and cultured overnight at 37° C. in a 5% $CO_2$ incubator prior assay.

Assay Readouts

Two different readouts which gave highly comparable results were used to quantify the redirected killing.

A flow cytometry method, referred herein as RDL-FACS method, based on fluorescence-cytometry as described in Schlereth B et al. ((2005) Cancer Res, 65: 2882-2889), Moore P A et al. ((2011) Blood, 117(17): 4542-51) and Friedrich M et al. ((2012) Mol Cancer Ther, 11: 2664-2673). Target cells were harvested, counted, washed once and resuspended at 5×10e6 cells/mL in PBS+1 µM Carboxyfluorescein succinimidyl ester (CFSE, Sigma). Cells were incubated 15 min at 37° C. with gentle agitation every 5 min. CFSE loaded cells were washed 3× with RDL medium and resuspended at 2×10e5 cells/mL in RDL medium. PBMCs were harvested, counted and resuspended at 2×10e6 cells/mL in RDL medium. Antibodies serial dilutions (3× solutions) were prepared in RDL medium. Target cells (50 T cells (50 µl/well) and 3× antibody solutions (50 µl/well) were distributed in flat-bottom 96-well plate (TPP, Trasadingen, Switzerland). The effector: target ratio was 10:1. The plates were incubated for 48 h in a 5% $CO_2$ incubator at 37° C. After incubation the plates were centrifuged for 3 min at 300 g, the supernatants were discarded by flicking the plates. The plates were washed once with 200 µl of PBS, centrifuged again and the PBS was discarded. A pre-warmed solution of accutase (Invitrogen AG) was added and the plates were incubated 10 min at 37° C. The detached adherent cells were resuspended by pipetting up and down after addition of 100 µl of RDL medium. The solution was transferred into a U-bottom 96-well plate (TPP). The U-bottom plates were centrifuged for 3 min at 300 g, the supernatants were discarded and the cells were resuspended in 200 µl of cold FACS buffer (PBS+2% FBS+10% Versene) supplemented with 7-AAD (Becton Dickinson AG, Allschwil, Switzerland) at a 1/40 dilution. The plates were immediately acquired on a Guava easyCyte™ Flow Cytometer (Millipore AG, Zug, Switzerland). For each well, the absolute number of living target cells was determined by gating on CFSE positive 7ADD negative population using Flowjo® software (Miltenyi Biotec GmbH, Bergisch Gladbach, Germany). The percentage of specific cytotoxicity for each sample was determined using the condition in which only target cells were incubated as baseline. The $EC_{50}$ values were determined using nonlinear variable slope regression method with Prism software (GraphPad software, La Jolla, Calif., USA). The percentage of specific re-directed lysis (RDL) was calculated by subtracting the percentage of specific cytotoxicity of the condition without antibody to the conditions where a test antibody was added.

A cell viability method, referred herein as RDL-MTS method based on a colorimetric method to assess cell viability as described in in Bühler P et al. ((2008) Cancer Immunol Immunother, 57: 43-52, Labrijn A F et al. ((2013) Proc Natl Acad Sci USA, 110(13): 5145-50) and PCT Publication No: WO2012143524. Target cells were harvested, counted, washed once and resuspended at 2×10e5 cells/ml in RDL medium. PBMCs were harvested, counted and resuspended at 2×10e6 cells/mL in RDL medium. Antibodies serial dilutions (3× solutions) were prepared in RDL medium. Target cells (50 T cells (50 µl/well) and 3× antibody solutions (50 µl/well) were distributed in flat-bottom 96-well plate (TPP). The effector: target ratio was 10:1. The plates were incubated for 48 h in a 5% $CO_2$ incubator at 37° C. After incubation the supernatants were discarded and the plates were washed 3 times with 200 µl of PBS to remove the PBMCs and 100 µl of RDL medium was then added to each well. The readout was done using CellTiter 96® kit (Promega AG, Dübendorf, Switzerland) according to manufacturer's instructions. Briefly, 10-20 µl of MTS reagent was added to each well and the plates were incubated 2-6 h in a 5% $CO_2$ incubator at 37° C. The 490 nm absorbance was then read on a BioTek synergy plate reader (BioTek AG, Luzern, Switzerland). The percentage of specific killing was calculated using this formula: Specific killing=100×[(SD−Sp)/(SD−MD)]. SD is the absorbance measured in spontaneous death condition where target cells were incubated alone. Sp is the absorbance measured in each test condition (target cells+PBMCs+antibody). MD is the absorbance measured in the maximum death condition in which target cells were lysed by 3 freeze and thaw cycles. The percentage of specific redirected lysis (RDL) was calculated by subtracting the percentage specific cytotoxicity of the condition without antibody to the conditions where a test antibody was added. The $EC_{50}$ values were determined using nonlinear variable slope regression method with Prism software (GraphPad software).

Example 2: Antigen Binding Sites that Target the Human CD3 Antigen, and the CD38 Antigen 2.1 Antigen Binding Sites Against the Human CD3 Antigen The human CD3 epsilon subunit was selected to drive T cell redirect killing via bispecific engagement.

2.1A Humanized Variants of the Mouse OKT3 Antibody

The anti-human CD3 epsilon antigen binding site used herein was derived from the mouse OKT3 antibody (Muromonab-CD3, trade name Orthoclone OKT3, marketed by Janssen-Cilag and subsequently discontinued; murine variable heavy chain and light chain domains with SEQ ID NO: 38 and 41, respectively). OKT3 murine variable domains were humanized and formatted as scFv and FAB fragments.

Humanization followed the method described by Jung S & Plückthun A (1997, Protein Eng, 10(8): 959-66) to produce a highly stable humanized variant that would be suitable for both FAB and scFv formatting. The method makes use of the highly stable pair of VH/VL domains found in the Herceptin® antibody (rhuMAbHER2, huMAB4D5-8, trastuzumab or trade name Herceptin®; U.S. Pat. No. 5,821,337; variable heavy chain and light chain domains with SEQ ID NO: 20 and 21, respectively) and follows the workflow of a humanization process onto fixed frameworks (Almagro J C & Fransson J (2008), Front Biosci, 13: 1619-33). Since the Herceptin® antibody is originally derived from the highly stable human families of germline framework VH3 and VK1, germline frameworks from these two families can be equally used as a source of fixed frameworks. Alternatively, the human VK3 germline light chain framework family can be used instead of VK1 as it also has good stability properties (Ewert S et al., (2003) J Mol Biol, 325: 531-553). In addition to mouse antibodies, human antibodies can be engineered using this fixed framework method to improve stability. Preferred is the use of the human germline framework IGHV3-23*04, IGKV1-39*01 and IGKV3-20*01 having SEQ ID NO: 37, 39 and 40, respectively (referenced according to IMGT® (the international ImMunoGeneTics information system (Lefranc M P et al. (1999) Nucleic Acids Res, 27(1): 209-12; Ruiz M et al. (2000) Nucleic Acids Res, 28(1): 219-21; Lefranc M P (2001) Nucleic Acids Res, 29(1): 207-9; Lefranc M P (2003) Nucleic Acids Res, 31(1): 307-10; Lefranc M P et al., (2005) Dev Comp Immunol, 29(3): 185-203; Kaas Q et al., (2007) Briefings in Functional Genomics & Proteomics, 6(4): 253-64; http://www.imgt.org).

To this aim a first humanized antibody was constructed wherein the CDRs in the variable domains of the Herceptin® antibody were respectively replaced with the CDRs from the mouse OKT3 antibody and benchmarked against a chimera of the mouse OKT3 antibody (variable heavy chain and light chain with SEQ ID NO: 130 and 131, and referred herein as the chimeric OKT3 antibody).

The prototype antibody (variable heavy chain and light chain with SEQ ID NO: 79 and 96, and abbreviated VH/VL) had increased production levels in transient expression tests and increased FAB stability as measured by differential scanning calorimetry but had no binding to HPB-ALL cells (assessed by median fluorescence intensity in FACS experiments, see Materials and Methods section), a human CD3 epsilon positive T cell tumour line (FIG. 1A).

Based on a 3D model of the first prototype pair of variable domains, a subset of back mutations (from CDR grafted Herceptin® prototype to mouse OKT3 sequence) were selected and tested: I34M, V48I, A49G, R58N, R58Y, I69L, A71T and T73K in the variable heavy chain domain and M4L, V33M, A34N, L46R, L47W, R66G, F71Y and P96F in the variable light chain (Kabat numbering). Note that the R58N substitution corresponds to a CDR grafted Herceptin® prototype-to-mouse OKT3 mutation while the R58Y substitution corresponds to a CDR grafted Herceptin® prototype-to-human IGHV3-23*04 germline substitution. The engineering strategy with regard to the combination of substitutions was based on the complementarity of the different substitutions in terms of their putative influence on CDR regions and/or variable domain packing and/or immunogenicity.

In a first approach, all candidates were formatted as human IgG1 antibodies. Best variants were selected according to expression levels, FAB fragment thermo-stability and ability to bind HPB-ALL cells by FACS. Best humanized variants had the Protein A binding site present within their VH domain abrogated using the G65S or N82aS substitution. This engineering step was needed to further produce safe T cell retargeting BEAT antibodies free of anti-CD3 homo-dimers.

Back mutations in the VH of: I34M, A49G and A71T along with back mutations in the VL of: M4L, L46R, L47W and F71Y restored affinity. Best combinations of variable domains were VH8/VL4, VH8/VL8, VH11/VL4 and VH11/VL8 as these retained most of parental cell binding (FIG. 1A-C). In addition, combinations VH8/VL8 (variable domains with SEQ ID NO: 131 and 132, respectively) and VH11/VL8 (variable domains with SEQ ID NO: 133 and 132, respectively) had enhanced FAB stability and (+2.8° C. and +1.6° C., respectively, FIG. 1D).

Finally, best humanized variants were also reformatted as scFv-Fc fusions and transiently expressed. Variants were ranked in terms of their relative affinity, stability, expression levels in transient transfection in this format (FIG. 1E). Best combinations of variable domains in a scFv-Fc fusion format were similar to the combinations identified in an antibody format: VH8-VL4 (scFv fragment with SEQ ID NO: 135) and VH8-VL8 (scFv fragment with SEQ ID NO: 136). Both scFv fragments had good thermal stability with the scFv-Fc fusion format (FIG. 1F).

2.1B Humanized Variants of the Mouse SP34 Antibody

The mouse antibody SP34 was first described in 1985 (Pessano S et al., (1985) EMBO J, 4(2):337-44). It was produced by a hybridoma obtained from mice immunised with denatured protein extracts from HPB-ALL cells, the antibody has human specificity and cross-reactivity to cynomolgus monkey.

Following the methods and work flow described in this example supra, humanized VH and VL domains for the murine SP34 antibody having a VH domain with SEQ ID NO: 1 and a VL domain with SEQ ID NO: 2 were engineered via CDR grafting onto the VH3-23 and VK3 germline frameworks, respectively. The resulting VH3 based variable domains can be further abrogated for Protein A binding using the G65S or N82aS substitutions (Kabat numbering) depending on their usage in a BEAT antibody format.

To this aim a first humanized antibody was constructed wherein the CDRs in the variable domains of a human antibody having a germline VH3 heavy chain domain and a germline VK3 light chain domain were respectively replaced with the CDRs from the mouse SP34 antibody. The resulting humanized antibody was used a starting point for further affinity improvement and benchmarked against a chimera of the SP34 antibody (heavy chain and light chain with SEQ ID NO: 137 and 138, respectively, and referred herein as the chimeric SP34 antibody).

The prototype antibody (variable heavy chain and light chain with SEQ ID NO: 91 and 105, and abbreviated VH1/VL1) had a low binding to human CD3 epsilon 1-26_Fc fusion protein (assessed by SPR, see Materials and Methods section and FIG. 2A).

Based on a 3D model of the first prototype pair of variable domains, a subset of substitutions that corresponded to either back mutations between the CDR grafted human germline VH3/VK3 prototype and mouse SP34 sequence (human-to-mouse or mouse-to-human substitutions) or rationally designed amino acid changes was selected. The following changes were made and tested in various combinations: W100eF, and W100eY in the variable heavy chain domain and A21, S25A, T27A, G27aA, V27cA, T28A, T29A, S30A, N31A, Y32A, E38Q, F44P, G46L, T51A, N52A, K53A, R54A, P56A, L66G, D69T, F87Y, Q89A, W91F, Y92A, S93A, N94A, and Q100G in the variable light chain (Kabat numbering; see FIG. 2A). The engineering strategy with regard to the combination of substitutions was based on the complementarity of the different substitutions in terms of their putative influence on CDR regions and/or variable domain packing and/or immunogenicity and/or impact on transient expression in mammalian cells.

In a first approach, all candidates were formatted as human IgG1 antibodies and later further tested in a scFv-Fc fusion protein format (FIG. 2B) with some variants having the Protein A binding site present within their VH domain abrogated using the G65S. Best humanized candidates were selected according to expression levels and ability to bind the human and cynomolgus monkey CD3 epsilon 1-26_Fc fusion proteins by SPR.

Figure 3:
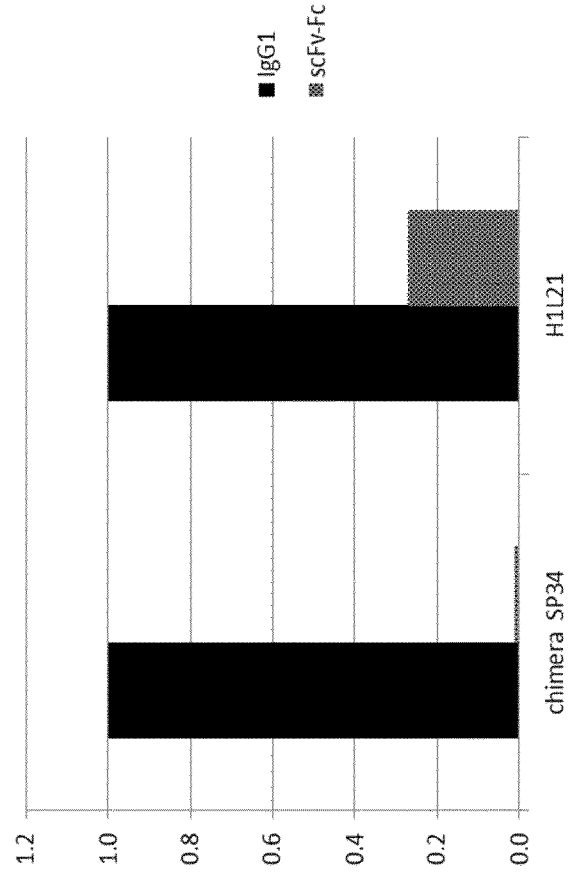
FIG. 3 Shows the relative expression levels after reformatting from IgG1 to scFv-Fc for the SP34 chimera as well as SP34 H1L21, wherein a dramatic loss of expression was observed.

Surprisingly, when reformatted as scFv, SP34 chimera and H1L21 lead to a dramatic loss of expression compare to the IgG1 format, (FIG. 3). However, scFv-Fc expression was enhanced by the combination of substitutions W100eY in the VH and W91F in the VL (FIG. 2B).

Figure 4:
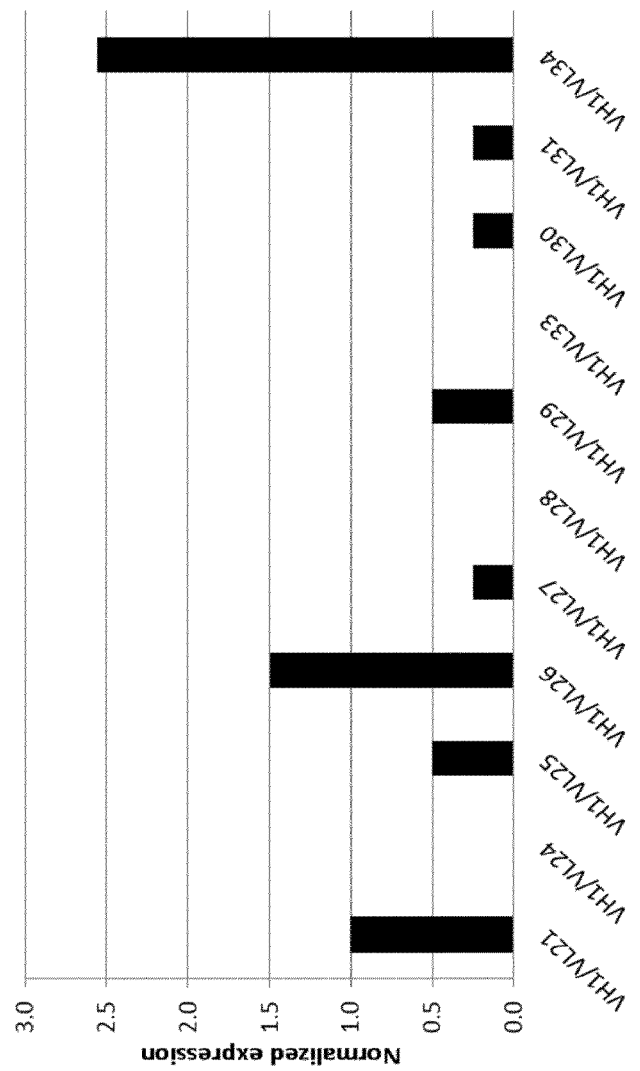
FIG. 4 Shows the effects on expression level of an SP34 H1L21 ScFv-Fc by Alanine scan in positions: T27, G27a, V27c, T28, T29, S30, N31, Y32, N52, K53, R54, P56, L90, Y92, S93, N94, and L95.

To further improve the manufacturability of CD3 based bispecifics, humanized SP34 scFv was therefore further engineered. To identify key positions impacting SP34 scFv-Fc expression, an Alanine scan was performed in VL21 CDR. The following changes were made: T27A, G27aA, V27cA, T28A, T29A, S30A, N31A, Y32A, N52A, K53A, R54A, P56A, L90A, Y92A, S93A, N94A, and L95A. Interestingly, only substitutions at position 29, 30 (VH1/VL26 SEQ NO: 139) and 95 (VH1/VL34 SEQ NO: 140) lead to significant increase in scFv-Fc expression (FIG. 4), moreover these mutants were the only ones to retain full binding to human and Cynomologus monkey CD3 epsilon.

Based on these results, more substitutions were tested at position 29, 30 and 95 in the light chain.

As position 29 and 30 display hyper variability in all the different variable light chain families, these two positions were randomly mutated by site directed PCR. From all the mutants produced, only substitutions T29A, T29E, T29S, S30A and S30D improved significantly transient expression level FIGS. 5a and 5b while maintaining binding to human CD3 epsilon.

In a different approach, L95, which is known in the art as a canonical structure residue, was substituted with residues most frequently found at this very same position in the variable lambda families. The following changes were made L95A, L95G, L95T, L95S, L95D, and L95N. Unexpectedly, only L95G and L95T significantly improved expression while maintaining binding to the target (FIG. 5c).

Figure 6:
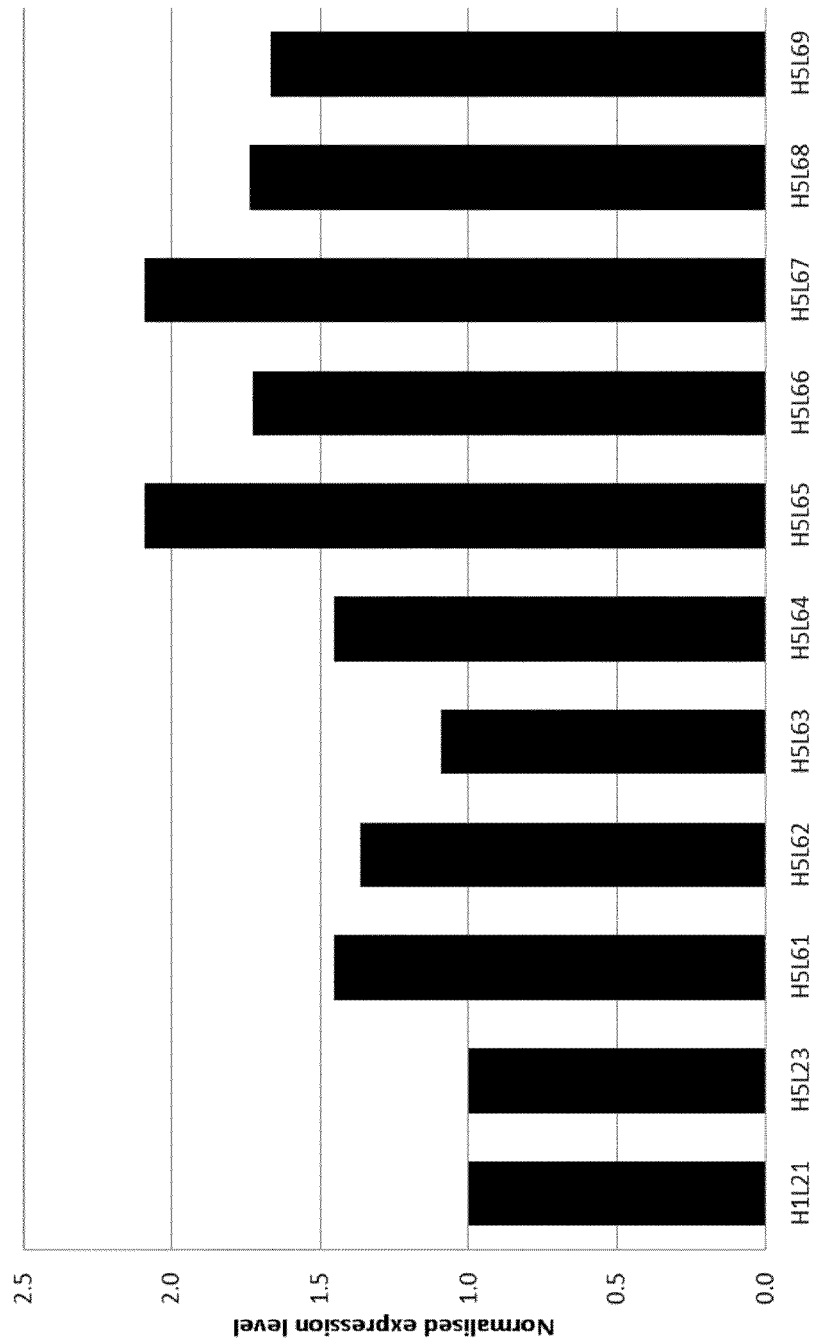
FIG. 6 shows the normalised expression level for several humanized SP34.

From this work, several humanized SP34 based BEAT were designed and tested for expression and binding to CD3 epsilon. Among all these constructs, bispecific containing H5L65 (SEQ ID NO: 69) and H5L67 (SEQ ID NO: 70) scFv, showed a 2 fold increase in expression over the H5L32 scFv based BEAT control, FIG. 6.

H5L65 and H5L67 were further characterized by DSC either as IgG1 or scFv-Fc and compare to H5L32, H1L21 and SP34 chimera. H5L65 showed superior thermostability as IgG1 but more interestingly an increase of 5 to 2° C. compared to other humanized variants in a scFv-Fc format. (Table 1) The in vivo stability of the improved antibodies is therefore increased as it also is in vitro.

TABLE 1

| SP34 Versions | Fab Tm (° C.) | IgG (Fab) Tm (° C.) | scFvFc Tm (° C.) |
| --- | --- | --- | --- |
| SP34 chimera | 66.9 | 66.7 | N/A |
| hSP34 H1/L21 | 75.1 | 73.1 | 56.7 |

TABLE 1-continued

| SP34 Versions | Fab Tm (° C.) | IgG (Fab) Tm (° C.) | scFvFc Tm (° C.) |
|---|---|---|---|
| hSP34 H5/L32 | 77.5 | 75.9 | 59.7 |
| hSP34 H5/L65 | 78.1 | 77.3 | 61.6 |
| hSP34 H5/L67 | 77.4 | 76.5 | 59.9 |

Preferred combinations of heavy chain and light chain variable domains with regard to antigen binding and recombinant expression were as follows: VH1 (SEQ ID NO: 42) or VH2 (SEQ ID NO: 43) or VH3 (SEQ ID NO: 44) or VH5 (SEQ ID NO: 45) paired with light chains domains VL21 (SEQ ID NO: 46), VL32 (SEQ ID NO: 47), VL65 (SEQ ID NO: 48) and VL67 (SEQ ID NO: 49).

2.2 Antigen Binding Sites Against the Human CD38 Antigen

CD38 is a type II transmembrane glycoprotein which is normally found on hemopoietic cells and in solid tissues. CD38 is also expressed in a variety of malignant hematological diseases. Bispecific antibodies that would redirect T cells to kill CD38 positive cancer cells will be useful to treat a variety of malignant hematological diseases, including multiple myeloma, B-cell chronic lymphocytic leukaemia, B-cell acute lymphocytic leukaemia, Waldenstrom's macroglobulinemia, primary systemic amyloidosis, mantle-cell lymphoma, pro-lymphocytic/myelocytic leukaemia, acute myeloid leukaemia, chronic myeloid leukaemia, follicular lymphoma, NK-cell leukaemia and plasma-cell leukaemia. Several anti-CD38 antibodies have been described as research reagents or therapeutic candidates (PCT Publication No: WO2006099875). Amongst the best characterized anti-human CD38 antibodies are OKT-10 and HB-7 mouse hybridomas (Hoshino S et al., (1997) J Immunol, 158(2): 741-7).

In a first approach, anti-human CD38 antigen binding sites can be derived from mouse hybridomas OKT10 (variable heavy chain and light chain with SEQ ID NO: 50 and 53, respectively) or HB-7 (variable heavy chain and light chain with SEQ ID NO: 51 and 54, respectively) and humanized versions thereof which can be further formatted as a FAB or scFv fragments. Following the methods and work flow described in Example 2.1, humanized VH and VL domains for the HB-7 hybridoma are can engineered via CDR grafting onto the VH3-23 and VK1 germline frameworks, respectively.

In a second approach, following the so-called best-fit humanization method described by Almagro J C & Fransson J (Front Biosci, (2008) 13: 1619-33), best-fit humanized VH and VL domains for the HB-7 hybridoma were engineered via CDR grafting onto the human IGHV4-59*03 and IGKV1-NL1*01 germline frameworks, respectively (referenced according to IMGT® supra). Humanized VH and VL variants with different degree of back mutations were investigated in silico and one preferred selection of humanized VH and VL was transiently expressed as a human IgG1 format and referred herein as humanized HB-7 best-fit VH (SEQ ID NO: 56) and VL (SEQ ID NO: 57) domains. The following mouse back mutations were introduced: (VH) S35H, I37V, I48L, V67L, V71K, T73N, F78V, Y91F and (VL): M4L, L48I, Y49S, T69K (Kabat numbering).

Figure 7A:
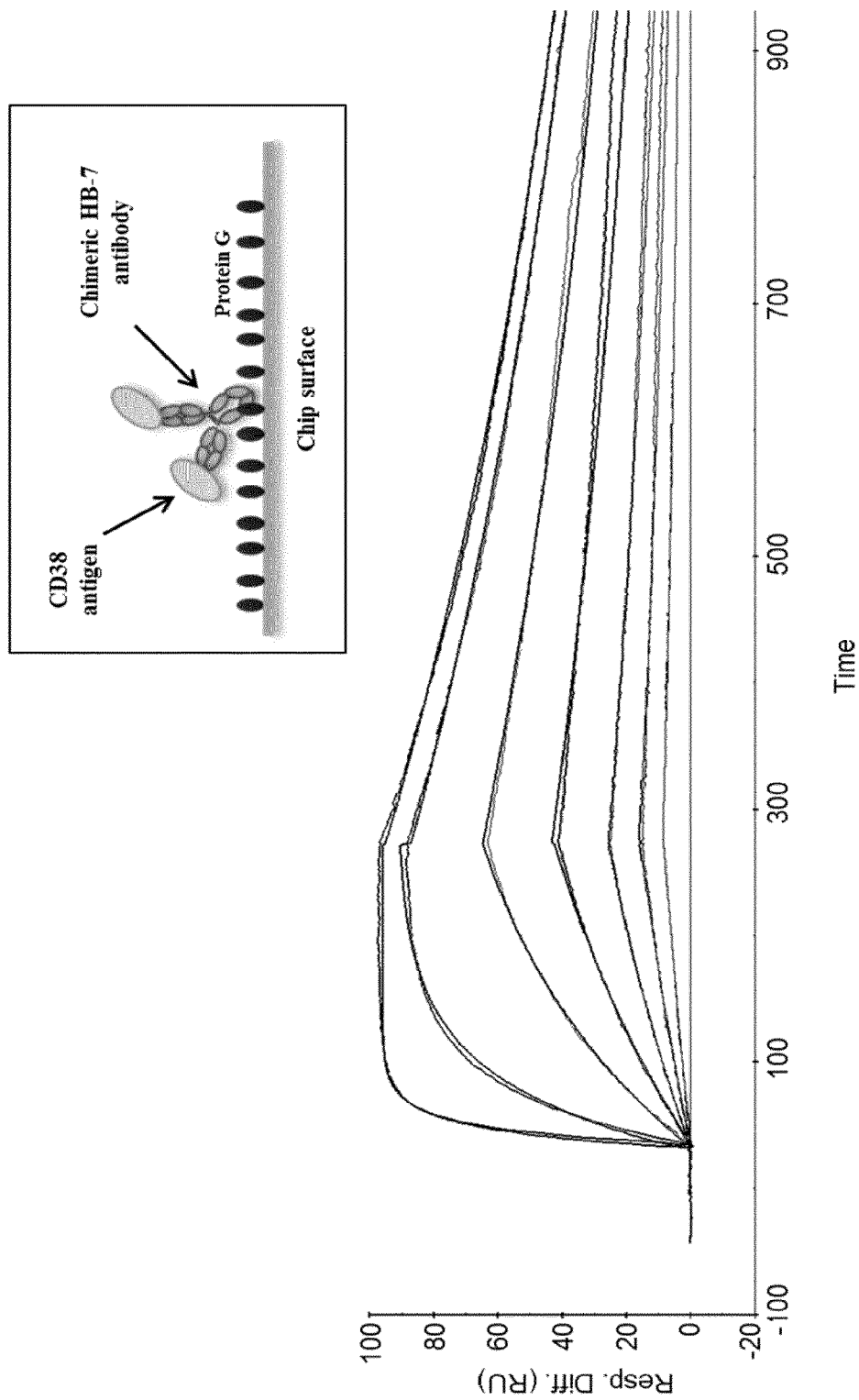
FIG. 7A: Antibody-antigen interaction measured by SPR between the chimeric HB-7 antibody and the human CD38 antigen. A CM5 sensor chip was covalently coupled with protein G and 200 RUs of chimeric HB-7 antibody were captured. Human CD38 protein (human CD38 extracellular domain with a poly-histidine tag) was injected at 125, 31, 7.8, 3.9, 1.9, 1 and 0.5 nM at a flow rate of 30 µl/min in HBS-P.
Figure 7B:
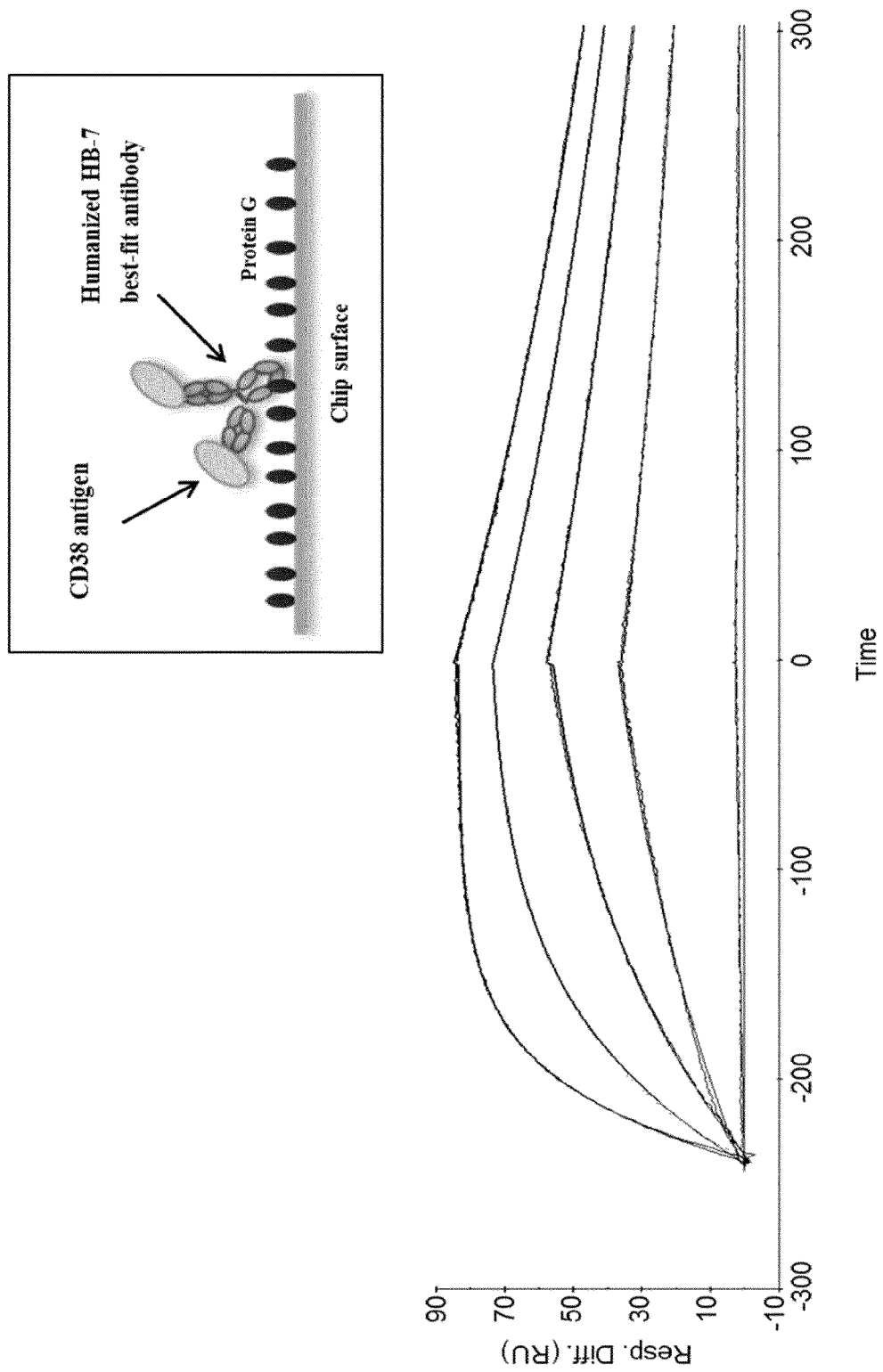
FIG. 7B: Antibody-antigen interaction measured by SPR between the humanized HB-7 best-fit antibody and the human CD38 antigen. A CM5 sensor chip was covalently coupled with protein G and 200 RUs of humanized HB-7 best-fit antibody were captured. Human CD38 protein (human CD38 extracellular domain with a poly-histidine tag) was injected at 50, 25, 12.5, 6.25 and 0.39 nM at a flow rate of 30 µl/min in HBS-P.

The humanized HB-7 best-fit antibody (heavy chain with SEQ ID NO: 141 and light chain with SEQ ID NO: 142) stained CHO[CD38] recombinant cells by FACS (data not shown). The humanized HB-7 best-fit antibody had a binding affinity for the CD38 extracellular region similar to that of the chimeric HB-7 antibody (heavy chain with SEQ ID NO: 143 and light chain with SEQ ID NO: 144) when assayed by SPR (KDs of 3.6 and 2.5 nM, respectively; FIG. 7A (chimeric) and FIG. 7B (humanized)). Surprisingly, the humanized HB-7 best-fit antibody displayed a significant enhancement (+14.6° C.) in FAB fragment stability compared to the chimeric HB-7 antibody as judged from calorimetry profiles (76.4° C. (chimeric) vs 91.0° C. (humanized), FIG. 7F).

Figure 7C:
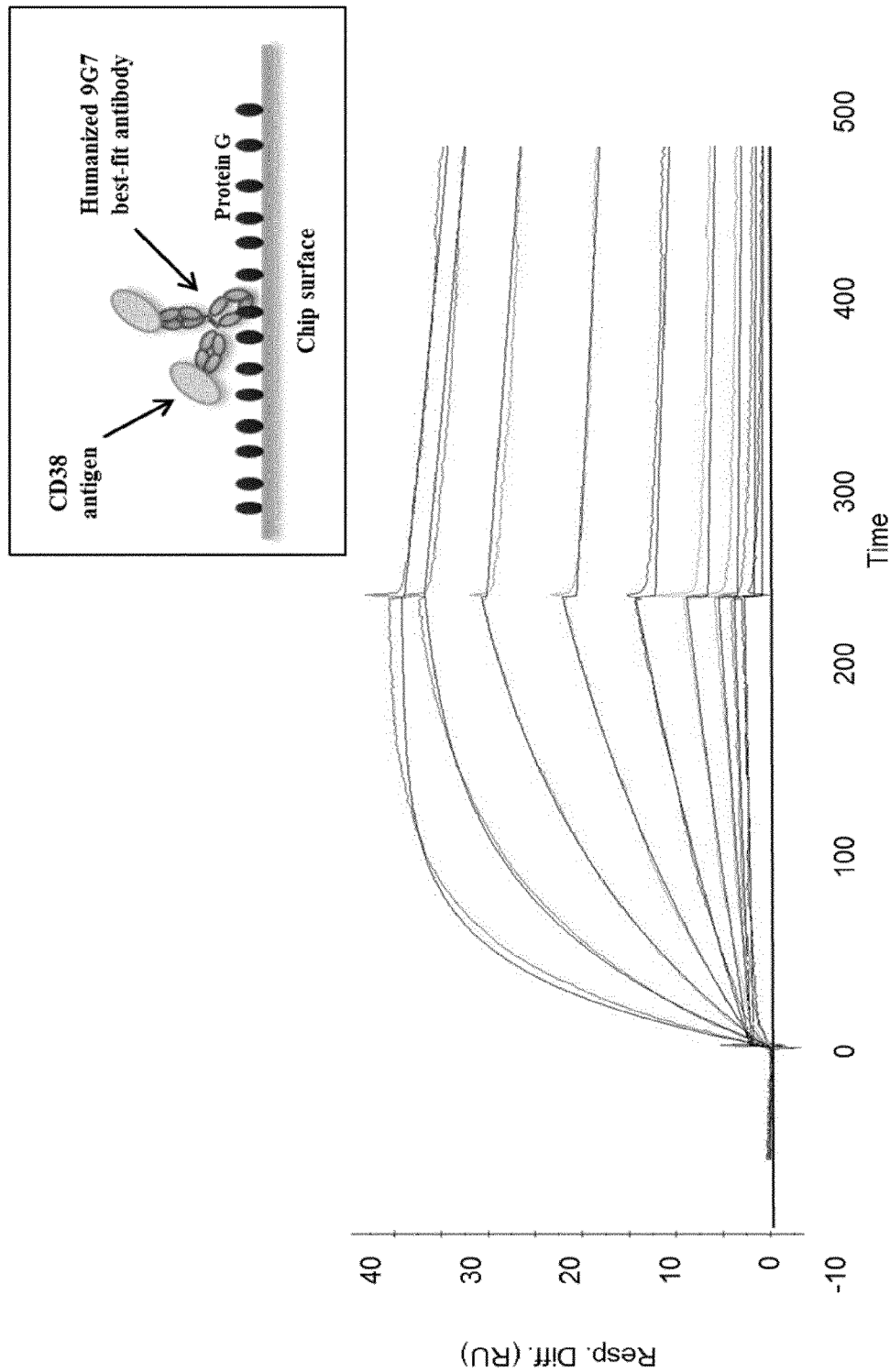
FIG. 7C: Antibody-antigen interaction measured by SPR between the humanized 9G7 best-fit antibody and the human CD38 antigen. A CM5 sensor chip was covalently coupled with protein G and 200 RUs of humanized 9G7 best-fit antibody were captured. Human CD38 protein (human CD38 extracellular domain with a poly-histidine tag) was injected at 25, 12.5, 6.25, 3.12, 1.56, 0.78, 0.39, 0.19, and 0.1 nM at a flow rate of 30 µl/min in HBS-P.

In a third approach, mice immunized with the human CD38 extracellular domain and human CD38+ cells were used to generate novel hybridoma candidates against human CD38. Methods to generate hybridomas are known and the methods used herein were similar to methods disclosed in PCT Publication No: WO2013008171. The 9G7 mouse antibody candidate had a high affinity for both human and cynomolgus monkey CD38 (variable heavy chain and light chain with SEQ ID NO: 52 and 55, respectively). This mouse antibody was first humanized according the methods described in this example supra. Using the best-fit approach, the germline VH framework IGHV2-5*09 and VK framework IGKV1-33*01 (referenced according to IMGT® supra) were selected as a starting point for the humanization process. Post CDR grafting, the first antibody prototype (formatted as a human IgG1 isotype, heavy chain SEQ ID NO: 145 and light chain with SEQ ID NO: 146) exhibited a strong binding to human CD38 only three fold lower than the mouse parental antibody as judged by SPR (chimeric 9G7 antibody with heavy chain SEQ ID NO: 147 and light chain with SEQ ID NO: 148; KD of 0.3 nM and 1 nM for the chimeric 9G7 antibody (data not shown) and first humanized prototype (data not shown), respectively). Affinity improved by two fold upon introduction of the F36Y back mutation in the variable light chain of the antibody (Kabat numbering) (the resulting antibody is referred herein as the humanized 9G7 best-fit antibody with heavy chain SEQ ID NO: 145 and light chain with SEQ ID NO: 74; KD of 0.5 nM for human CD38, FIG. 7C). The humanized 9G7 best-fit antibody also exhibited a high affinity for the cynomolgus monkey CD38 antigen (KD of 3.2 nM, data not shown), and an enhanced FAB thermo-stability (FAB Tm from DSC scans) over the chimeric 9G7 antibody (94° C. vs. 82.2° C. for the humanized 9G7 best-fit antibody and the chimeric 9G7 antibody, respectively; see FIG. 7G). The humanized 9G7 best-fit antibody has heavy chain variable domain with SEQ ID NO: 58 and light chain variable domain with SEQ ID NO: 59.

Figure 7D:
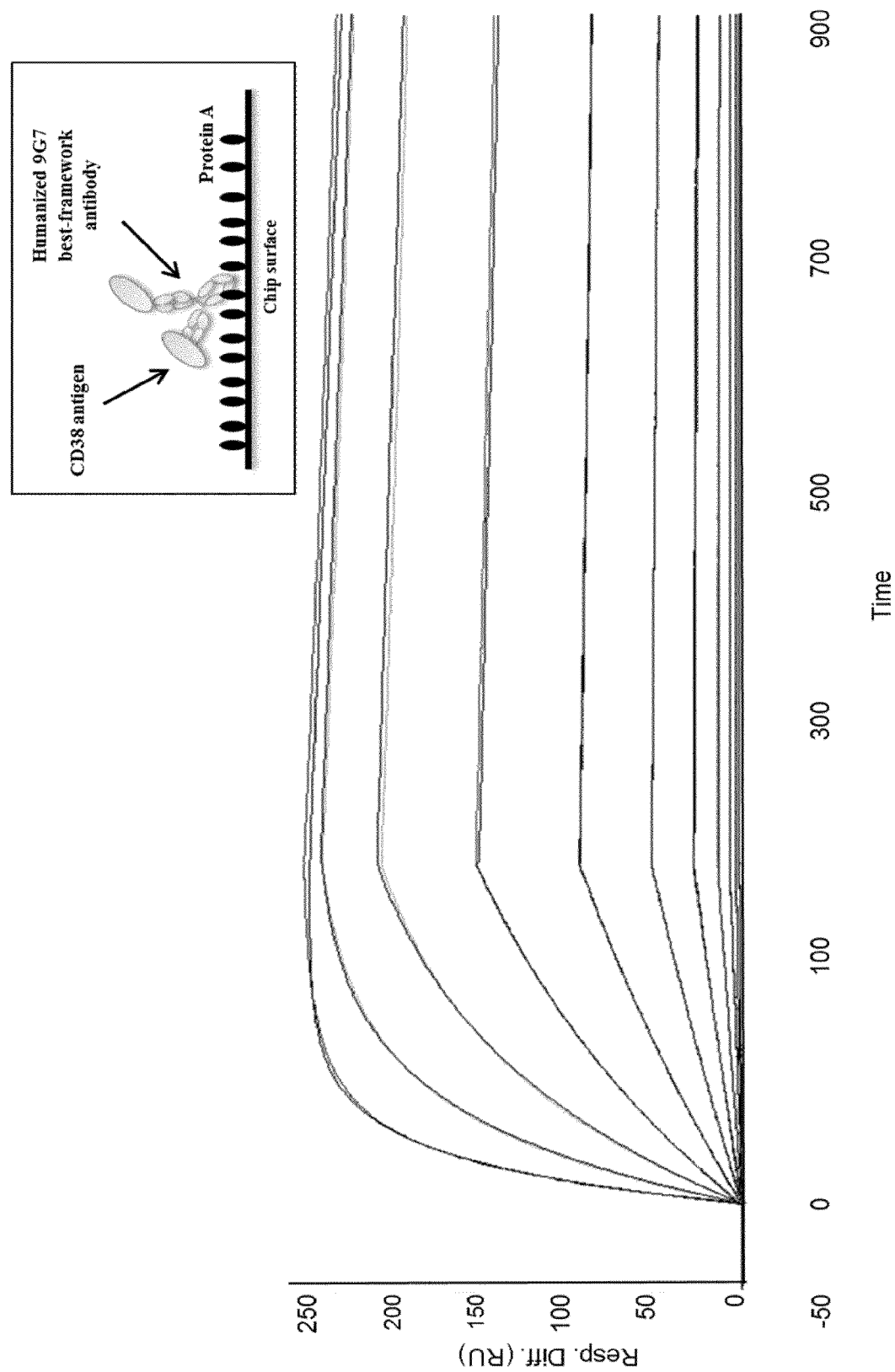
FIG. 7D: Antibody-antigen interaction measured by SPR between the humanized 9G7 best-framework antibody and the human CD38 antigen. A CM5 sensor chip was covalently coupled with protein G and 200 RUs of humanized 9G7 best-framework antibody were captured. Human CD38 protein (human CD38 extracellular domain with a poly-histidine tag) was injected at 50, 25, 12.5, 6.25, 3.12, 1.56, 0.78, 0.39, 0.19, and 0.1 nM at a flow rate of 30 µl/min in HBS-P.
Figure 7H:
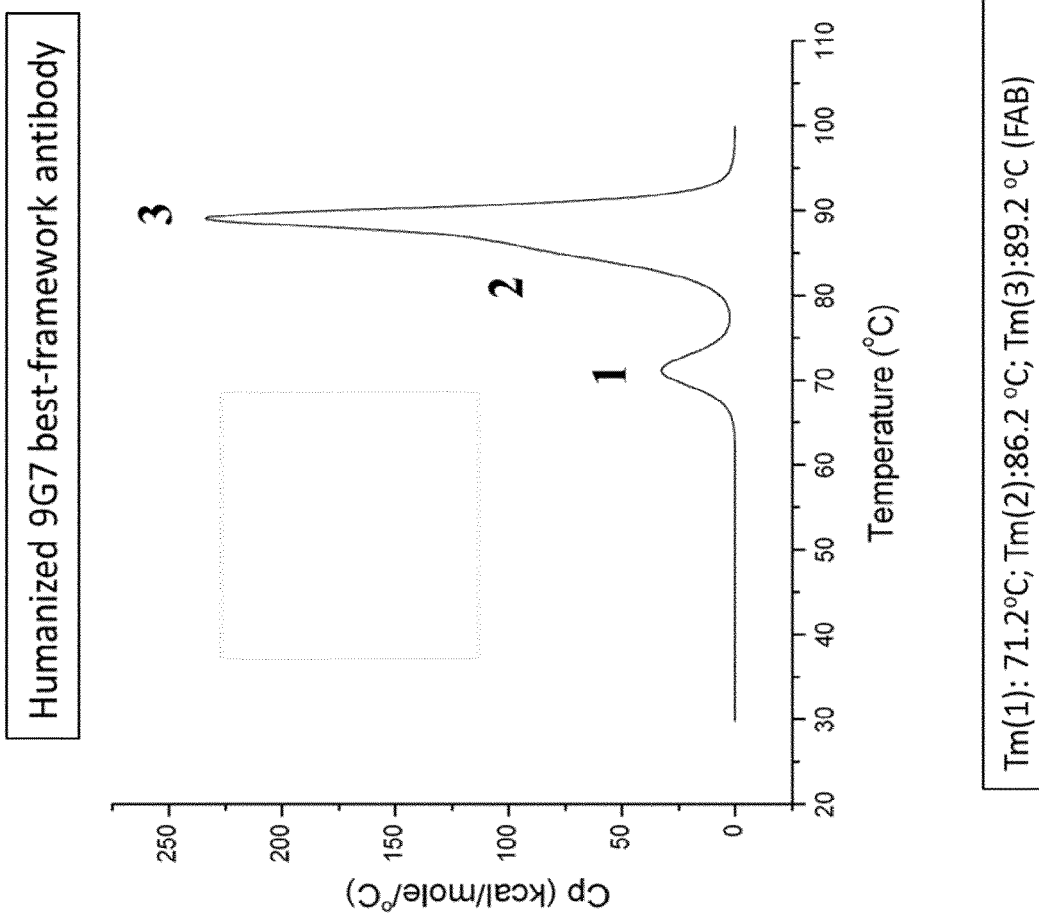
FIG. 7H: DSC profiles of humanized 9G7 best-framework antibody.

In addition, the 9G7 mouse antibody was humanized following the best-framework approach via CDR grafting onto the VH3-23 and VK1 germline frameworks. Humanized VH and VL variants with different degree of back mutations were investigated in silico and one preferred selection of humanized VH and VL combination was transiently expressed as a human IgG1 antibody (the resulting antibody is referred herein as the humanized 9G7 best-framework antibody with heavy chain SEQ ID NO: 149 and light chain with SEQ ID NO: 150). The following mouse back mutations were introduced: (VH) A24F, V37I, V48L, S49A, F67L, R71K, N73T, L78V, and K94R, and (VL) F36Y (Kabat numbering). This antibody exhibited a strong binding to human CD38 and cynomolgus monkey CD38 with affinity constants similar to that of the humanized 9G7 best-fit antibody (KD of 0.4 and 1 nM for human and cynomolgus monkey CD38, respectively; FIG. 7D). FAB thermo-stability (FAB Tm from DSC scans) was also very similar to that of the 9G7 best-fit F36Y humanized variant (89.2° C., see FIG. 7H). FIG. 7J summarizes the different humanized 9G7 antibodies described above. The humanized 9G7 best-framework antibody has heavy chain variable domain with SEQ ID NO: 60 and light chain variable domain with SEQ ID NO: 61.

Figure 7I:
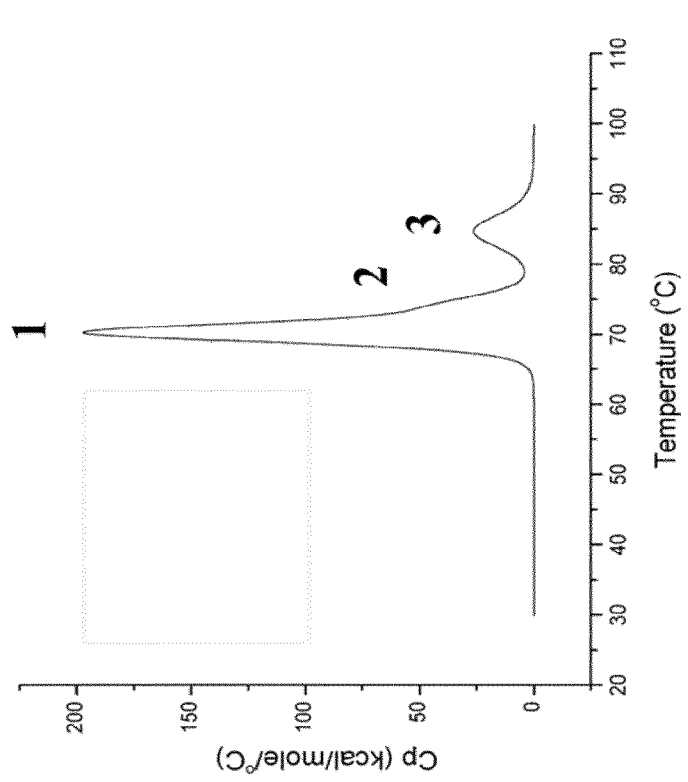
FIG. 7I: DSC profiles of human clone 767 antibody.

In a fourth approach, an antibody phage library was screened to generate additional scFv fragments against human CD38. The library had a diversity based on the naturally occurring human V genes. This donor derived antibody phage display library used cDNAs amplified from blood lymphocytes originating from 48 human donors of which 70% had an autoimmune disease (vasculitis, systemic lupus erythematosus, spondiloarthropathy, rheumatoid arthritis and scleroderma). Library construction followed the protocol described by Schofield et al. (2007, Genome Biol., 8(11): R254) with a total diversity of 2.53×10e10 clones. ScFv fragments recognizing human and/or cynomolgus monkey CD38 were isolated from this donor derived phage display library as follows. ScFv fragments were isolated in a series of repeated selection cycles on recombinantly derived human and/or cynomolgus monkey CD38 antigens (see Materials and Methods section). Methods to screen antibody phage display libraries are known (Viti F et al., (2000) Methods Enzymol, 326: 480-505). Briefly, following incubation with the library, the immobilised antigen which had been previously coated on a plastic immunotube (overnight in PBS at a concentration of 20 µg/ml) or captured on streptavidin beads (when using a biotin labelled form of the antigen, antigen captured at a concentration of 50 nM throughout the selection process), bound phages were recovered whist unbound phages were washed away. Bound phages were rescued as described by Marks et al (Marks J D et al., (1991) J Mol Biol, 222(3): 581-97) and the selection process repeated three times. Over one thousand clones from the second and third round of panning were expressed and analysed by ELISA against the human and cynomolgus monkey CD38 antigens. Positive clones were subjected to DNA sequencing and some of the unique clones were further analysed for their ability to bind cell lines expressing human CD38. Following a first round of panning on a biotin labelled version of the human CD38 antigen immobilized on streptavidin beads and a second round of panning on a biotin labelled version of the cynomolgus monkey CD38 antigen immobilized on streptavidin beads, one preferred scFv fragment (clone No 767) having a variable heavy chain sequence with SEQ ID NO: 62 and a variable light chain with SEQ ID NO: 63 was selected for its ability to bind both human and cynomolgus monkey CD38. When formatted as a human IgG1 antibody, clone 767 had a KD of about 300 nM for human CD38 (FIG. 7E) and about 1.2 µM for cynomolgus monkey CD38 (data not shown) (clone 767 IgG1 antibody is referred herein as human 767 antibody with heavy chain SEQ ID NO: 151 and light chain with SEQ ID NO: 152). FAB thermo-stability (FAB Tm from DSC scans) was 70.2° C. (FIG. 7I). Clone 767 VH domain belongs to the VH3 domain subclass.

Example 3: CD38/CD3 Targeting BEAT Antibodies

Anti-CD38 and anti-CD3 epsilon arms can be formatted either as a scFv-Fc type of heavy chains consisting of a scFv fragment fused to a BEAT chain or as a heavy chain consisting of a FAB fragment fused to a BEAT chain similar to that of a naturally occurring antibody. The FAB based heavy chain requires its association with its cognate light chain to assemble into a functional antigen binding site.

L234A and L235A substitutions were introduced in CH2 regions and residual Protein A binding was abrogated within using the G65S or N82aS substitutions (Kabat numbering) when appropriate. Examples of BEAT antibodies targeting both human CD38 antigen and human CD3 epsilon were formatted as follows:

A first example of BEAT antibodies targeting both human CD38 antigen and human CD3 epsilon using the humanized HB7 bestfit VH and VL sequences was formatted as follows:

A BEAT CD38/CD3 antibody was engineered using a combination of antigen binding sites described in Example 2.1 and 2.2 for the anti-human CD3 epsilon and the anti-human CD38 arms, respectively. The anti-human CD38 arm of the hetero-dimeric immunoglobulin consisted of a BEAT heavy chain (SEQ ID NO: 153) encompassing a variable heavy chain region, a CH1 γ1 region, a γ1 hinge region, a γ1 CH2 region with L234A and L235A substitutions (EU numbering), and a γ1 based BEAT CH3 domain assembled with its cognate light chain (SEQ ID NO: 72). The anti-human CD3 epsilon arm of the hetero-dimeric immunoglobulin consisted of a BEAT heavy chain (SEQ ID NO: 154) encompassing a scFv fragment, a CH1 γ1 region, a γ1 hinge region, a γ3 CH2 region with L234A and L235A substitutions (EU numbering), and a γ3 based BEAT CH3 domain. This heavy chain encompassed part of a human IgG3 Fc region and therefore had no binding to Protein A but since the heavy chain used herein had its heavy chain variable domain originating from a VH3 framework, the VH domain was mutated to include the N82aS substitution thereby removing any additional Protein A binding sites within the heavy chain. The bispecific antibody is referred herein as BEAT CD38-HB7bestfit/CD3 antibody (FIG. 8 format A).

Figure 9A:
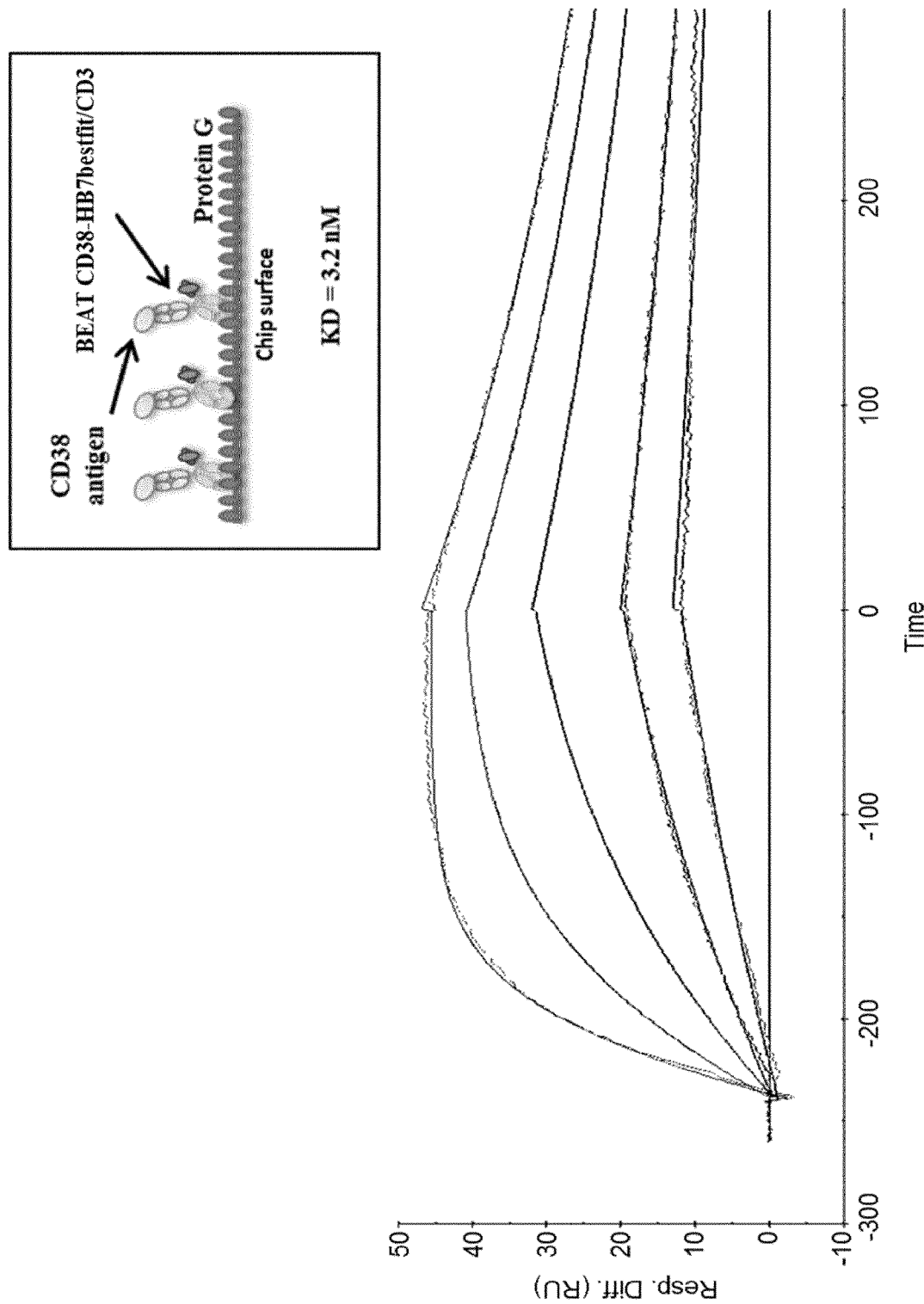
FIG. 9A: Antibody-antigen interaction measured by SPR between the BEAT CD38-HB7bestfit/CD3 antibody and the human CD38 antigen. A CM5 sensor chip was covalently coupled with protein G and 200 RUs of BEAT CD38-HB7bestfit/CD3 antibody were captured. Human CD38 protein (poly-histidine tagged protein) was injected at 50, 25, 12.5, 6.25 and 0.39 nM at a flow rate of 30 µl/min in HBS-P. Data are expressed as number of response units (abbreviated RU; Y axis) vs. time (X axis).
Figure 9B:
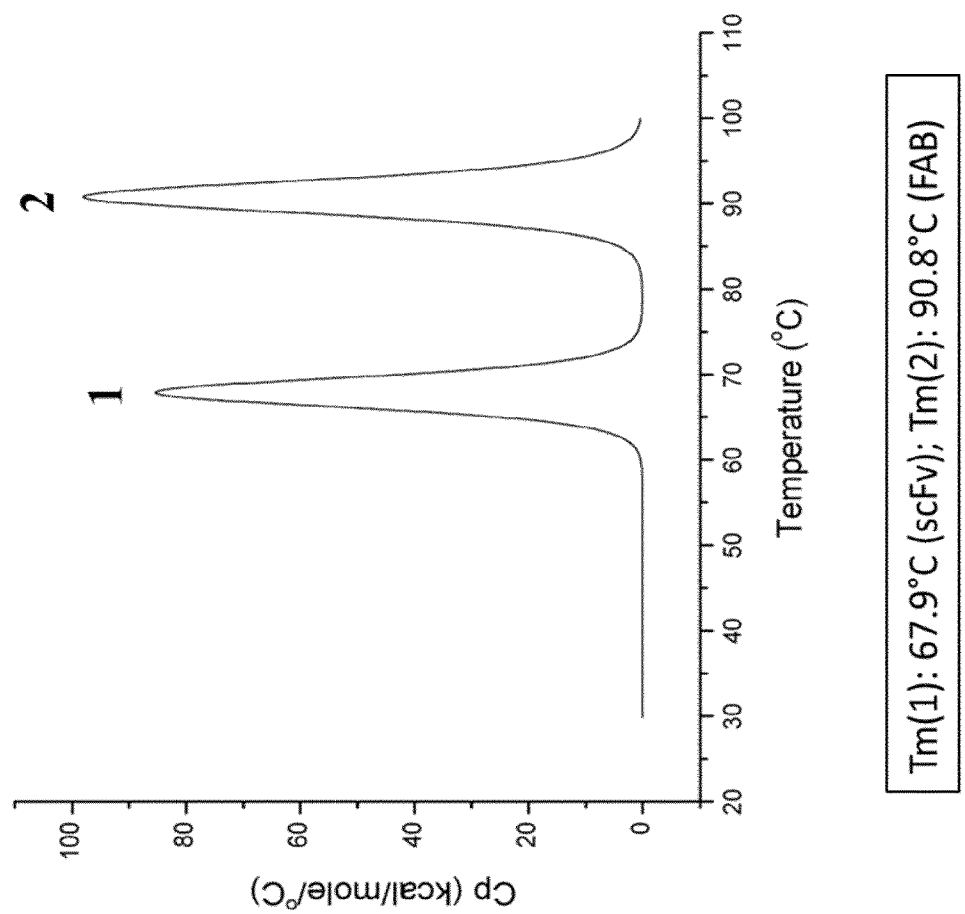
FIG. 9B: BEAT CD38-HB7bestfit/CD3 antibody DSC profile.

The BEAT CD38-HB7bestfit/CD3 antibody was expressed transiently, purified and tested in vitro for its affinity towards the CD38 and CD3 epsilon antigens, its stability and its ability to redirect T cell killing. The KD value was 3.2 nM for the human CD38 antigen (measured by SPR; FIG. 9A). DSC profiles for the bispecific antibody showed good thermo-stability profiles with a Tm of approximately 68° C. for the scFv portion. The FAB portion had a Tm of approximately 91° C. (FIG. 9B).

Figure 10:
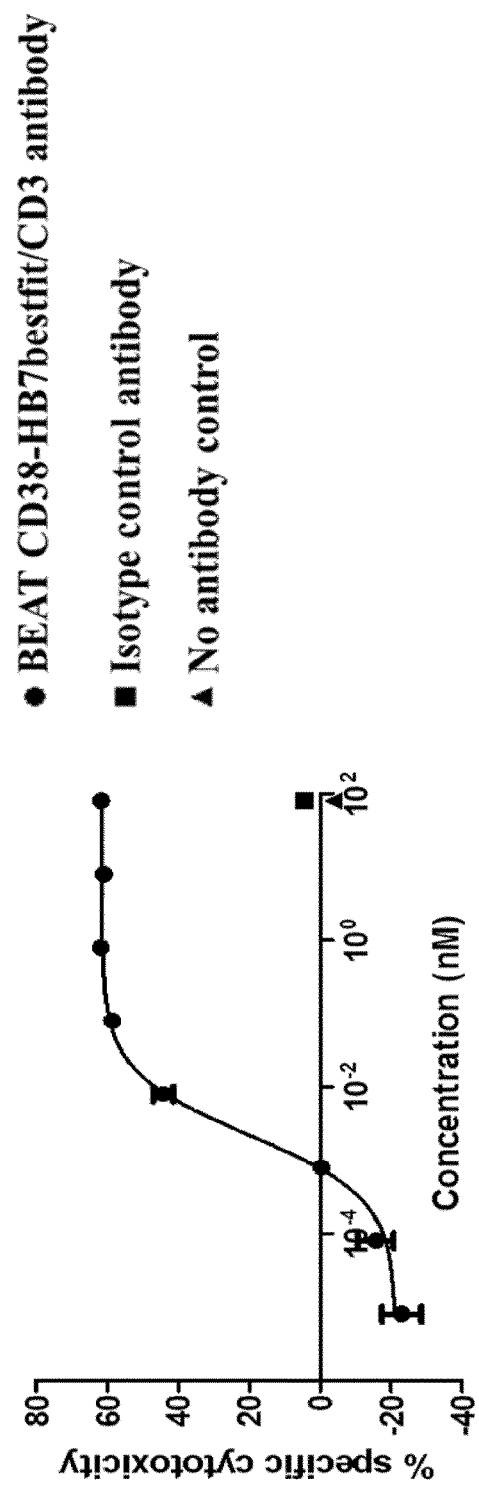
FIG. 10: Example of T cell redirected killing by the BEAT CD38-HB7bestfit/CD3 antibody. Readout: RDL-FACS method. Effector cells: purified human T cells. Effector cells-to-targeted cells ratio of 10:1. Mean of two donors with 48 h incubation. Target cells: RPMI 8226. Antibody concentration is shown in nM.

CD38 expressing cell lines (see Materials and Methods section) were used to assess redirected T cell killing in assays. FIG. 10 shows T cell redirected killing of RPMI 8226 myeloma cells using the BEAT CD38-HB7bestfit/CD3 antibody. Note that the assay used purified T cells as effector cells with an effector cells to target cells ratio of 10 to 1. When measured with the RDL-FACS method, the BEAT CD38-HB7bestfit/CD3 antibody had an $EC_{50}$ of 2.2 pM (mean of 2 donors, 48 h incubation).

A second example of BEAT antibodies targeting both human CD38 antigen and human CD3 epsilon using the human clone 767 VH and VL sequences was formatted as follows: a BEAT CD38/CD3 antibody was engineered using a combination of antigen binding sites described in Example 2.1 and 2.2 for the anti-human CD3 epsilon and the anti-human CD38 arms, respectively. The anti-human CD38 arm of the hetero-dimeric immunoglobulin consisted of a BEAT heavy chain (SEQ ID NO: 65) encompassing a variable heavy chain region, a CH1 γ1 region, a γ1 hinge region, a γ1 CH2 region with L234A and L235A substitutions (EU numbering), and a γ1 based BEAT CH3 domain assembled with its cognate light chain (SEQ ID NO: 138). The anti-human CD3 epsilon arm of the hetero-dimeric immunoglobulin consisted of a BEAT heavy chain (SEQ ID NO: 155) encompassing a scFv fragment, a CH1 γ1 region, a γ1 hinge region, a γ3 CH2 region with L234A and L235A substitutions (EU numbering), and a γ3 based BEAT CH3 domain. This heavy chain encompassed part of a human IgG3 Fc region and therefore had no binding to Protein A but since the heavy chain used herein had its heavy chain variable domain originating from a VH3 framework, the VH domain was mutated to include the G65S substitution thereby removing any additional Protein A binding sites within the heavy chain. This bispecific antibody is referred herein as BEAT CD38-767/CD3 antibody (FIG. 8 format B).

Figure 11:
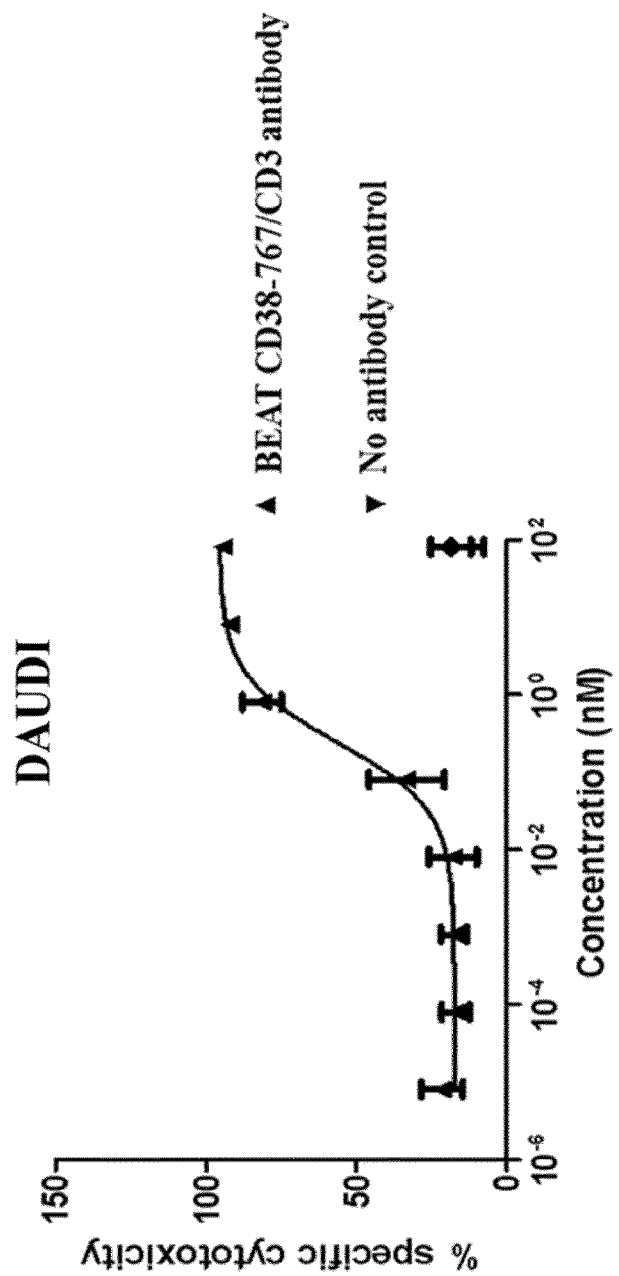
FIG. 11: Example of T cell redirected killing by the BEAT CD38-767/CD3(SP34) antibody. Readout: RDL-FACS method. Effector cells: human PBMCs. Effector cells-to-targeted cells ratio of 10:1. Mean of three donors with 24 h incubation. Target cells: Daudi. Antibody concentration is shown in nM.

The BEAT CD38-767/CD3 antibody was expressed transiently, purified and tested in vitro for its affinity towards the CD38 and CD3 epsilon antigens, its stability and its ability to redirect T cell killing. CD38 expressing cell lines (see Materials and Methods section) were used to assess redirected T cell killing in assays similar to that of described in Example 3.2.1. FIG. 11 shows T cell redirected killing of Daudi cells using the BEAT CD38-767/CD3 antibody. Note that the assay used human PBMCs as effector cells with an effector cells to target cells ratio of 10:1. When measured with the RDL-FACS method, the BEAT CD38-767/CD3 antibody had an $EC_{50}$ of 244 pM (mean of 3 donors, 24 h incubation).

Another example of BEAT antibodies targeting both human CD38 antigen and human CD3 epsilon using the humanized 9G7 best-framework VH and VL sequences is formatted as follows: a BEAT CD38/CD3 is engineered using a combination of antigen binding sites described in Example 2.1 and 2.2 for the anti-human CD3 epsilon and the anti-human CD38 antigen binding sites, respectively.

The anti-human CD38 arm of the hetero-dimeric immunoglobulin consists of a BEAT heavy chain (SEQ ID NO: 75 or 155) encompassing a variable heavy chain region, a CH1 γ1 region, a γ1 hinge region, a γ3 CH2 region with L234A and L235A substitutions (EU numbering), and a γ3 based BEAT CH3 domain assembled with its cognate light chain (SEQ ID NO: 77). This heavy chain encompasses part of a human IgG3 Fc region and therefore has no binding to Protein A but since the heavy chain used herein has its heavy chain variable domain originating from a VH3 framework, the VH domain is mutated to include the G65S substitution thereby removing any additional Protein A binding sites within the heavy chain. The anti-human CD3 epsilon arm of the hetero-dimeric immunoglobulin consists of a BEAT heavy chain (SEQ ID NO: 68) encompassing a scFv fragment, a CH1 γ1 region, a γ1 hinge region, a γ1 CH2 region with L234A and L235A substitutions (EU numbering), and a γ1 based BEAT CH3 domain. This bispecific antibody is referred herein as BEAT CD38-9G7bestframework/CD3 (SP34-Kappa2) antibody.

Another example of BEAT antibodies targeting both human CD38 antigen and human CD3 epsilon using the human clone 767 VH and VL sequences is formatted as follows: a BEAT CD38/CD3 is engineered using a combination of antigen binding sites described in Example 2.1 and 2.2 for the anti-human CD3 epsilon and the anti-human CD38 antigen binding sites, respectively.

The anti-human CD38 arm of the hetero-dimeric immunoglobulin consists of a BEAT heavy chain (SEQ ID NO: 78) encompassing a variable heavy chain region, a CH1 γ1 region, a γ1 hinge region, a γ3 CH2 region with L234A and L235A substitutions (EU numbering), and a γ3 based BEAT CH3 domain assembled with its cognate light chain (SEQ ID NO: 66). This heavy chain encompasses part of a human IgG3 Fc region and therefore has no binding to Protein A but since the heavy chain used herein has its heavy chain variable domain originating from a VH3 framework, the VH domain is mutated to include the G65S substitution thereby removing any additional Protein A binding sites within the heavy chain. The anti-human CD3 epsilon arm of the hetero-dimeric immunoglobulin consists of a BEAT heavy chain (SEQ ID NO: 68) encompassing a scFv fragment, a CH1 γ1 region, a γ1 hinge region, a γ1 CH2 region with L234A and L235A substitutions (EU numbering), and a γ1 based BEAT CH3 domain. This bispecific antibody is referred herein as BEAT CD38-767/CD3(SP34-Kappa2) antibody.

In a first set of experiments BEAT 9G7/SP34 showed the activation of T cells when in combination with PBMCs but not when isolated.

Example 4:CD3/CD38 BEAT Antibodies Encompassing Only One VH3 Domain

Figure 12A:
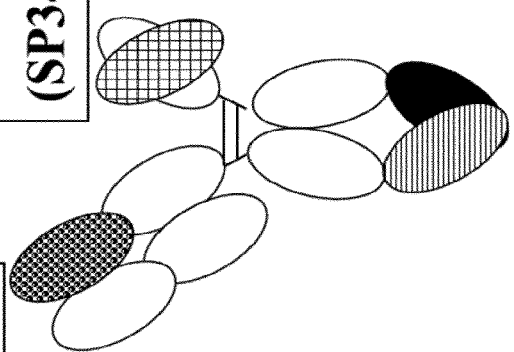
FIG. 12A-B: Schematic diagram of the BEAT CD38-HB7bestfit/CD3(SP34) (format 12A) and BEAT CD38-9G7bestfit/CD3(SP34-Kappa2) (format 12B) antibodies. [(A+)] means functional Protein A binding site.
Figure 12B:
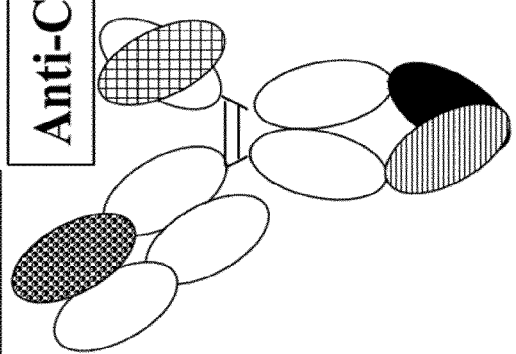

An example of BEAT antibodies targeting both human CD38 antigen and human CD3 epsilon using the humanized HB7/bestfit VH and VL sequences was formatted as follows: a BEAT CD38/CD3 was engineered using a combination of antigen binding sites described in Example 2.1 and 2.2 for the anti-human CD3 epsilon and the anti-human CD38 arms, respectively. The anti-human CD38 arm of the hetero-dimeric immunoglobulin consisted of a BEAT heavy chain (SEQ ID NO: 71) encompassing a variable heavy chain domain, a CH1 γ1 region, a γ1 hinge region, a γ3 CH2 region with L234A and L235A substitutions (EU numbering), and a γ3 based BEAT CH3 domain assembled with its cognate light chain (SEQ ID NO: 72). This heavy chain had no binding to Protein A as it encompassed part of a human IgG3 Fc region and had its heavy chain variable domain originating from a non-VH3 domain subclass. The anti-human CD3 epsilon arm of the hetero-dimeric immunoglobulin consisted of a BEAT heavy chain (SEQ ID NO: 157) encompassing a scFv fragment, a CH1 γ1 region, a γ1 hinge region, a γ1 CH2 region with L234A and L235A substitutions (EU numbering), and a γ1 based BEAT CH3 domain. This heavy chain and light assembly encompassed a humanized version of the anti-human CD3 epsilon antibody (SP34) as described in PCT Publication No: WO2008119565. This BEAT antibody format is referred herein as BEAT CD38-HB7bestfit/CD3 (SP34) antibody (FIG. 12 format A).

Figure 13A:
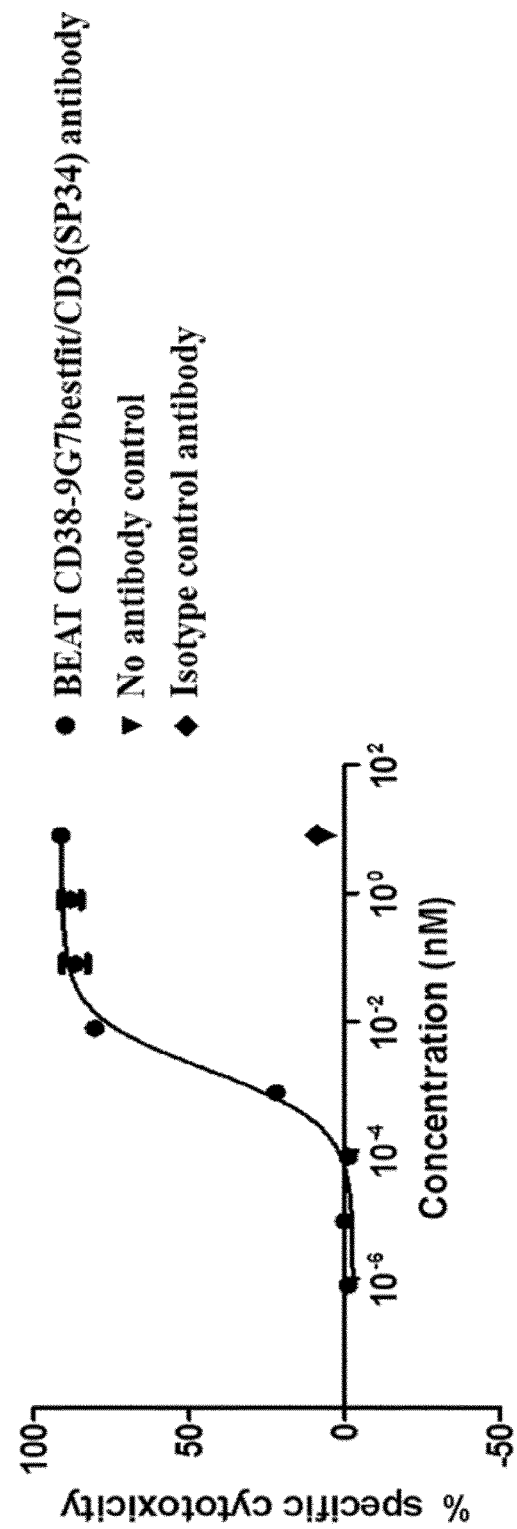
FIG. 13A-B: Example of T cell redirected killing by the BEAT CD38-HB7bestfit/CD3(SP34) antibody. Readout.
Figure 13B:
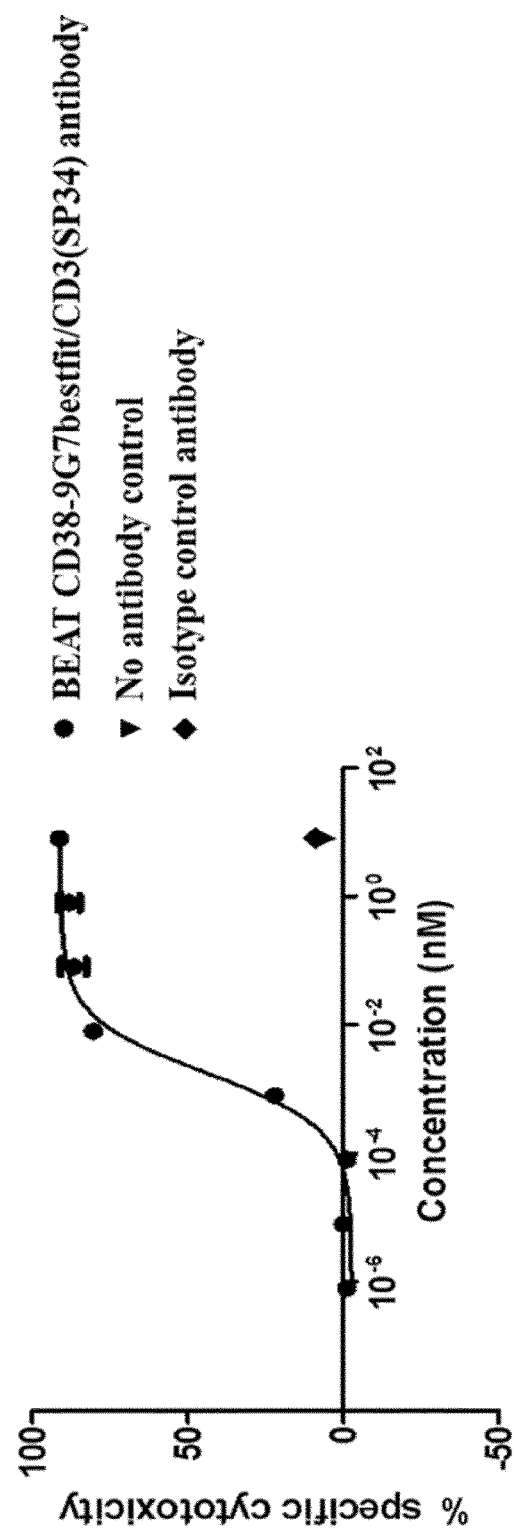

The ability of the BEAT CD38-HB7bestfit/CD3(SP34) antibody to redirect T cell killing towards CD38+ cells was investigated in-vitro. The CD38+B lymphoblast cell line Daudi was used in killing assays. FIG. 13 show T cell redirected killing of Daudi cells by the BEAT CD38-HB7bestfit/CD3(SP34) antibody. The assays used human PBMCs as effector cells with an effector cells to target cells ratio of 10 to 1, and the RDL-FACS readout method after a 24 h incubation period (see Materials and Methods section). The results show that the BEAT CD38-HB7bestfit/CD3 (SP34) antibody was highly potent at redirecting T cell killing against the Daudi CD38+ cell line with an $EC_{50}$ of 1.8 pM (mean of 3 donors).

A second example of BEAT antibodies targeting both human CD38 antigen and human CD3 epsilon using the humanized 9G7 best-fit VH and VL sequences (SEQ ID NO: 58 and 59, respectively) was formatted as follows: a BEAT CD38/CD3 was engineered using a combination of antigen binding sites described in Example 2.1 and 2.2 for the anti-human CD3 epsilon and the anti-human CD38 arms, respectively. The anti-human CD38 arm of the hetero-dimeric immunoglobulin consisted of a BEAT heavy chain (SEQ ID NO: 73) encompassing a variable heavy chain domain, a CH1 γ1 region, a γ1 hinge region, a γ3 CH2 region with L234A and L235A substitutions (EU numbering), and a γ3 based BEAT CH3 domain assembled with its cognate light chain (SEQ ID NO: 74). This heavy chain had no binding to Protein A as it encompassed part of a human IgG3 Fc region and had its heavy chain variable domain originating from a non-VH3 domain subclass. The anti-human CD3 epsilon arm of the hetero-dimeric immunoglobulin consisted of a BEAT heavy chain (SEQ ID NO: 158) encompassing a scFv fragment, a CH1 γ1 region, a γ1 hinge region, a γ1 CH2 region with L234A and L235A substitutions (EU numbering), and a γ1 based BEAT CH3 domain. This arm of the bispecific antibody encompassed the variable domains of the humanized SP34 VH5/VL32 antibody described in Example 2.1. This BEAT antibody format is referred herein as BEAT CD38-9G7best-fit/CD3(SP34-Kappa2) antibody (FIG. 12 format B). CD38-9G7best-fit/CD3(SP34-Kappa2) antibody had a KD value of 18 nM for the human CD3 1-26_Fc fusion protein (FIG. 14).

The ability of the BEAT CD38-9G7best-fit/CD3(SP34-Kappa2) antibody to redirect T cell killing towards CD38+ cells was investigated in vitro. The CD38+ B lymphoblast cell line Daudi was used in killing assays. FIG. 15 show T cell redirected killing of Daudi cells by the BEAT CD38-9G7best-fit/CD3(SP34-Kappa2) antibody. The assays used human PBMCs as effector cells with an effector cells to target cells ratio of 10 to 1, and the RDL-FACS readout method after a 24 h incubation period (see Materials and Methods section). The results show that the BEAT CD38-9G7best-fit/CD3(SP34-Kappa2) antibody was highly potent at redirecting T cell killing against the Daudi CD38+ cell line with an $EC_{50}$ of 2 pM (mean of 3 donors).

Example 5: Functional Equivalence of Improved SP34 in scFv Format

In order to determine whether of the modifications made to the various SP34 scFv so as to improve their expression also affected the functional properties, namely the binding of CD3, they were tested in the context of a CD38×CD3 bispecific. The CD38 binding arm present as a FAB, comprises the heavy chain variable region encoded by SEQ ID NO: 60 and the light chain variable region encoded by SEQ ID NO: 61. The CD3 binding arm comprises the original mouse SP34 reformatted as an scFv (SEQ ID NO: 207), or modified humanised SP34 scFv's comprising the heavy/light chain combinations H1/L21 (SEQ ID NO: 67), H5/L32 (SEQ ID NO: 68), H5/L65 (SEQ ID NO: 69) and H5/L67 (SEQ ID NO: 70).

Each of the CD3/CD38 BEAT using the different version of SP34 were transiently expressed and purified. They were tested in vitro to compare their ability to redirect T cell killing. Raji CD38 expressing cell line (see Materials and Methods section) was used to assess redirected T cell killing. The assay used human PBMCs as effector cells with an effector cells to target cells ratio of 10:1.

When measured with the RDL-FACS method, all BEAT showed comparable EC50 between 6 and 10 pM (the mean of 2 donors, 24 h incubation) FIG. 16.

Example 6: D401Q Substitution Abrogates Protein A and G Binding in One of the Two Homodimer Species For analytical purposes, we produced the BTA and BTB homodimers of a FABxscFv BEAT antibody wherein the FAB arm (BTA homodimer) had no binding to protein A since it encompassed a non-VH3 variable domain and part of a human IgG3 Fc region similarly to that described above, and the scFv arm (BTB homodimer) bound protein A using both its VH3 based variable domain and its human IgG1 Fc region. Upon expression and purification (as described above), we found that while the BTA homodimer could readily be purified by protein G (heavy chain SEQ ID NO: 156 and light chain SEQ ID NO: 74), the BTB homodimer could only be isolated by protein A and did not bind protein G, suggesting, for example, misfolding or conformational changes in the protein G binding site in the Fc region carrying the BTB CH3 domain (SEQ ID NO: 159). Considering that protein G binds to almost the same part of the Fc region as protein A does (at the CH2-CH3 interface), it is surprising that the BTB homodimers bound protein A but not protein G. It was then hypothesized that protein A binding by the BTB homodimer was solely mediated by the protein A binding site located in the scFv moiety which as mentioned above encompassed a VH3 based variable domain. To assess the contribution of the scFv binding to protein A, a construct lacking the VH3 based scFv was produced and found to no longer bind protein A (SEQ ID NO: 160, see FIG. 17). It was concluded that in a BTB homodimer, the protein A and G binding sites in the Fc region are both non-functional.

This later result suggested that the BTB homodimer was indeed misfolded or structurally altered in the protein A/G binding region. However, previous data wherein the BTB CH3 domain was used in the context of a heterodimeric immunoglobulin suggested otherwise. To further investigate the functionality of the BTB CH3 domain in a heterodimeric context with regard to protein A binding, we produced a FABxscFv BEAT antibody consisting of a FAB arm (BTA arm) with no binding to protein A since it encompassed a non-VH3 variable domain, a human IgG1 hinge, a human IgG3 CH2 domain and an engineered BTA CH3 domain originating from a human IgG3 isotype (FAB arm heavy chain with SEQ ID NO: 156 and light chain SEQ ID NO: 74), and a scFv arm (BTB arm) encompassing a VH3 based scFv fragment abrogated for protein A binding, a human IgG1 hinge, a human IgG1 CH2 domain and an engineered BTB CH3 domain originating from a human IgG1 isotype (scFv arm heavy chain with SEQ ID NO: 161)—therefore a heterodimer that was solely expected to bind protein A in the Fc region of the scFv arm. Upon expression and purification (as described above), it was found that indeed this molecule bound protein A and G (FIG. 18A) and had no trace of BTB homodimers. Thus it was concluded that the protein A and G sites are intact in the context of a heterodimeric immunoglobulin and that only when the BTA and BTB chains are associated is a functional protein A/G binding site formed.

To understand the molecular basis of the protein A/G abrogation within the BTB homodimer, previously engineered BTB CH3 domains originating from a human IgG1 isotype were investigated. Substitution D401Q, EU numbering, a comparison between EU and IMGT numbering is provided at http://www.imgt.org/IMGTScientificChart/Numbering/Hu_IGH Gnber.html, in the BTB CH3 domain was identified from modelling studies, and was engineered to abrogate a putative electrostatic contact between Arg411 of the first chain of the BTB homodimer with Asp401 of the second chain of the BTB homodimer with the view that this interaction could stabilize the homodimeric complex. Since this substitution was only implemented in the last step of the BTB CH3 domain engineering, a FABxscFv BEAT antibody as described above was produced without the said D401Q substitution in the BTB CH3 domain (FAB arm with heavy chain and light chain having SEQ ID NOs: 156 and 74, respectively; scFv arm with heavy chain SEQ ID NO: 162). Upon expression and purification (as described above), it was found that this molecule bound protein A and G (FIG. 18B) but showed the presence of BTB homodimers, thus indicating that the D401Q substitution was responsible for the lack of protein A/G binding observed in the BTB homodimers, thereby making a significant contribution within a heterodimeric immunoglobulin at reducing the said BTB contaminants. Importantly, residue 401 itself is not part of the protein A/G binding site, but is located oppositely at the CH3-CH3 interface. Thus, protein A/G abrogation is not a result of directly disrupting interactions between protein A/G and the Fc region. Rather it is suggested that, unexpectedly, D401Q leads to long range conformational changes at the CH2-CH3 interface as a result of the poor pairing capabilities of BTB chains with each other. In the case of the heterodimer, the interfaces fit perfectly together and thus a proper conformation at the CH2/CH3 interface renders the protein A/G binding site functional.

This surprising result can be exploited to design a new strategy to efficiently isolate heterodimeric immunoglobulins without homodimer contaminants using the specific design that follows: the heterodimeric immunoglobulin has a first chain encompassing a Fc region of the IgG3 isotype that will include a BTA CH3 domain and a non-VH3 variable domain or a VH3 based variable domain abrogated for protein A binding (using the G65S or N82aS substitutions for example) or no variable domain and therefore has no binding to protein A, and a second chain that binds protein A encompassing a BTB D401Q CH3 domain (originating from a human IgG1 isotype for example) and either a non-VH3 variable domain or a VH3 variable domain abrogated for protein A binding (using the G65S or N82aS substitutions for example), or no variable domain. In this setting, both homodimers contain no protein A binding sites. The first homodimer is a dimer of the first chain and does not bind protein A as there is no protein A binding site while the second homodimer is a dimer of the second chain with a protein A binding site that is non-functional. The resulting heterodimer has only one protein A binding site found in the second chain (the BTB chain protein A binding site being functional only when paired with the BTA chain). Hence the heterodimer will be the only species binding to the protein A chromatography resin while unwanted homodimers of BTA and BTB chains will be washed away.

Example 7: CD3/CD38 BEAT Activity In Vivo in Cynomolgus Monkey

Cynomolgus monkeys (*Macaca fascicularis*, 1 male, 1 female per dose) were dosed by intravenous bolus injection of CD3/CD38 (comprising the CD3 heavy/light chain combination SP34 H5/L65 formatted as a scFv SEQ ID NO: 69 and the CD38 heavy chain variable region encoded by SEQ ID NO: 60 and the light chain variable region encoded by SEQ ID NO: 61 formatted as a FAB), referred to in this example as CD3/CD38 BEAT.

Immunophenotyping was performed on all animals from blood samples (EDTA) taken pre-treatment and on different time points following each administration of CD3/CD38 BEAT. Assessment of lymphocyte subsets was performed by flow cytometry using the following markers: Total T lymphocytes (CD4 and CD8), Monocytes (CD14) and CD38. The samples were acquired on a FACSCanto™ II flow cytometer. Data were analyzed using FACSDiva™ analysis software as follows: First, an electronic gate based on forward and side scatter characteristics was drawn to select the lymphocyte or monocyte populations (parent population). The absolute counts per μL of whole blood of the T lymphocyte population (CD4+ T cells and CD8+ T cells) and of the CD38 positive monocyte population (CD14+ CD38+) was calculated from their relative percentages as derived from the parent population gate and the total parent population counts from a validated hematology analyzer according to the formula: Absolute population count ($\times 10^3$/μL)=(population relative %×total parent population count)/100.

There was a clear early decrease of the T cell counts, both CD4 and CD8 positives, following the dose of 1 and 10 μg/kg (FIG. 19). Compared with cell counts obtained 1 day prior to dosing, there was a 48 and 78% decrease in CD4 T cell counts after the 1 μg/kg dose and more than 90% after the 10 μg/kg dose at the 4 hour time point. The CD8 T cell counts were even more drastically affected, with a drop of 86% after the 1 μg/kg dose. The CD4 T cell counts rebounded rapidly and were overall similar to pre dose counts after 48 hours. However the CD8 T cell counts were slower to recover and reached similar levels than pre-dose after 1 week. This transient decrease of peripheral blood T cells was expected and reflects the activation of these populations by CD3/CD38 BEAT. These observations suggest that the T lymphocytes, and in particular the cytotoxic CD8 T cells are engaged into killing activities in the tissues.

There was also a clear decrease in the circulating CD38+ monocyte population (FIG. 20). A very fast disappearance was observed, followed by a rebound between 24 and 48 h. This rebound was generally followed by a second substantial decrease in the CD38+ monocytes counts indicating that this population is likely targeted and depleted by the cytotoxic action of the T lymphocytes.

Example 8: 9G7-Based BEAT Antibodies Display Enhanced Killing Activity than an OKT10×OKT3 BEAT The potencies of two different 9G7-based BEAT antibodies vs. an OKT10-based BEAT antibody were investigated in RDL assays.

The bispecific antibody referred herein as BEAT CD38-9G7Mouse/CD3 is a BEAT CD38/CD3 antibody based on a combination of antigen binding sites described in Example 2 (OKT3 VH11/VL8 scFv for the anti-human CD3 epsilon arm and mouse-human chimeric 9G7 FAB for the anti-human CD38 arm). The anti-human CD38 arm of the bispecific antibody consisted of a BEAT heavy chain (SEQ ID NO: 177) assembled with its cognate light chain (SEQ ID NO: 178). The anti-human CD3 epsilon arm of the bispecific antibody consisted of a BEAT heavy chain (SEQ ID NO: 179) encompassing the anti-human CD3 epsilon scFv fragment. The bispecific antibody was expressed transiently and purified as described above.

The bispecific antibody referred herein as BEAT CD38-OKT10Mouse/CD3 is a BEAT CD38/CD3 antibody based on a combination of antigen binding sites described in Example 2 (OKT3 VH11/VL8 scFv for the anti-human CD3 epsilon arm and mouse-human chimeric OKT10 FAB for the anti-human CD38 arm). The anti-human CD38 arm of the bispecific antibody consisted of a BEAT heavy chain (SEQ ID NO: 180) assembled with its cognate light chain (SEQ ID NO: 181). The anti-human CD3 epsilon arm of the bispecific antibody consisted of a BEAT heavy chain (SEQ ID NO: 179) encompassing the anti-human CD3 epsilon scFv fragment. The bispecific antibody was expressed transiently and purified as described above.

The BEAT antibody referred herein as the BEAT CD38-9G7best-fit/CD3(SP34-Kappa2) antibody was described above in Example 4.

The cytotoxic potential of different BEAT antibodies based on the 9G7 or the OKT10 anti CD38 mAbs was assessed in a killing assay against the CD38+ target Daudi cells (ATCC). A flow cytometry-based readout was performed to quantify target cell death. Similar flow cytometry-based readouts were used in Moore et al. Blood. 2011 Apr. 28; 117(17):4542-51; Friedrich et al. Mol Cancer Ther 2012; 11:2664-2673; Schlereth et al. Cancer Res 2005; 65:2882-2889. Effector cells were non stimulated PBMC from healthy donors. The effector:target ratio was typically 10:1 and the incubation time was 48 h. Briefly, target cells (Daudi) were labeled with a fluorescent cytoplasmic dye such as CFSE and were distributed in 96-well plates (TPP). Antibodies serial dilutions (3× solutions) and PBMCs (50 µL/well) were distributed then distributing in corresponding wells. The Plates were incubated for 48 h in a 5% CO2 incubator at 37° C. The cells were resuspended by pipetting and were transferred into U-bottom 96-well plates (TPP). The U-bottom plates were centrifuged 3 min at 300 g, the supernatants were discarded and the cells were resuspended in 200 µL of cold FACS buffer (PBS+2% FBS+10% Versene) supplemented with 7-AAD (Becton Dickinson) at 1/40 dilution. The plates were immediately acquired on a guava easyCyte™ Flow Cytometer (Millipore). For each well, the absolute number of living target cells was determined by gating on Dye (CFSE) positive 7ADD negative population using flowjo software (Treestar). The % of specific cytotoxicity for each sample was determined using the condition in which only target cells were incubated as baseline or using the condition in which Target cells were mixed with PBMCs (no antibody condition). The EC50 values were determined using nonlinear variable slope regression method with Prism software (GraphPad software).

The data in Table 2 indicates the EC50 values obtained with the different BEAT constructs. The 9G7-based BEAT antibodies (BEAT CD38-9G7Mouse/CD3 and BEAT CD38-9G7best-fit/CD3(SP34-Kappa2) displayed a killing activity characterized by a clearly lower EC50 than the BEAT CD38-OKT10Mouse/CD3 antibody (3.2 and 1.9 pM for 9G7 based BEAT antibodies versus 125.6 pM for the OKT10 based BEAT antibody), indicating a higher cytotoxic potential of the 9G7-based anti-CD38/CD3 BEAT antibodies.

TABLE 29

G7-based BEAT antibodies display enhanced killing activity than anOKT10xOKT3 BEAT

| | BEAT CD38-9G7Mouse/CD3 | BEAT CD38-9G7best-fit/CD3(SP34-Kappa2) | BEAT CD38-OKT10Mouse/CD3 |
|---|---|---|---|
| EC50 (pM)* | 3.2 | 1.9 | 126 |

*The EC50 indicated are average values of killing assays performed with different PBMC donors. N = 8 for 9G7xOKT3, N = 2 for OKT10xOKT3 and n = 1 for 9G7xSP34(GV2)

Example 9: 9G7 and 767 Binders do not Display Agonism, in Contrast to HB7 Antibody CD38 being competent for signaling, the agonist property of 9G7 and 767 antibodies were tested, in comparison to the HB7 clone, in a calcium flux assay on Jurkat human T cell lymphoma cell line which expresses naturally CD38. The Jurkat cells were loaded with Fluo-4 Dye at 2 µM (Invitrogen) during 1 hour at 37° C. The cells were washed and resuspended in PBS PBS supplemented with 1 mM Ca2+ and 1 mM Mg2+. The samples were acquired on a FACScalibur flow cytometer (Becton Dickinson) for baseline during 40 s. Then test antibodies were added to the samples at the concentration of 10 µg/ml and the acquisition was resumed until 7 minutes. The figure G shows the mean fluorescence intensity (MFI) of the Fluo-4 dye (FL-1 channel), which is a readout of calcium mobilization into the cytoplasm of the cells, as a function of time. While the isotype control (IgG1 human antibody) did not trigger any calcium flux, the HB7 anti-CD38 antibody did induce a strong signal. Strikingly neither the 9G7 nor the 767 antibody were able to trigger a calcium mobilization signal indicating that these antibodies, in contrast to the HB7 antibody do not have CD38 agonist properties.

During the same series of experiments it was also shown for 9G7 and 767 that they specifically bind to cells expressing CD38 in a specific manner.

Example 10: Epitope Mapping h9G7 Epitope Mapping

Linear peptide mapping was used to determine the epitope of humanized 9G7 (best-fit version). The extracellular domain of human CD38 (Residues 43-300) was divided into 19 consecutive peptides, 13 amino acids in length and a final peptide of 11 amino acids in length. Peptides were fused to a human IgG1 Fc region (CH2-CH3) with a two-amino-acid linker (Ala-Ser) between Fc and peptide sequence. These constructs were termed F1-F20 (SEQ ID NOs: 182-201) and their binding analyzed by SPR. The humanized 9G7 antibody (heavy chain SEQ ID NO: 145 and light chain SEQ ID: 146) was covalently immobilized on a CM5 sensor chip (about 1800 RUs). Peptide Fc-fusions were injected at 15 nM for 240 seconds. Human CD38 extracellular domain was injected as control. Only F6 and the control gave a binding signal (FIG. 22). All fragments were re-injected at 200 nM and F6 gave a stronger signal (FIG. 23) while the remaining fragments still showed no binding (data not shown). As F6 is part of the epitope of the SAR650984 antibody disclosed in PCT publication NO: WO2008047242 (heavy chain with SEQ ID NO: 202 and light chain with SEQ ID NO: 203) their interaction was verified by SPR and confirmed (data not shown). Thus h9G7 and SAR650984 compete for binding on human CD38. Furthermore when the F6 sequence is mapped onto the 3D surface of the extracellular domain of human CD38, it overlaps with the SAR650984 epitope. However SAR650984 has been shown not to be cross-reactive with cynomolgus CD38 while humanized 9G7 binds to cynomolgus CD38 with high affinity (FIG. 24) suggesting that the two antibodies have overlapping but different epitopes.

Within the F6 sequence, residue M110 is a Valine in cynomolgus CD38. Thus in the context of the entire extracellular domain of human CD38, we mutated M110 to Valine (SEQ ID NO: 204) and compared binding of h9G7 and SAR650984. SAR650984 showed reduced binding compared to its binding on wild-type human CD38 while binding of humanized 9G7 was not impacted (data not shown). Based on the crystal structure of SAR650984 in complex with human CD38 extracellular domain (PDB accession code 4CMH, Deckert et al., 2014 Clin. Cancer Res. 20: 4574), we identified an additional residue that is potentially important for SAR650984 binding and that differs between human and cynomolgus CD38. This residue was T148 and is a methionine in cynomolgus CD38. Mutation of T148 to Methionine in the extracellular domain of human CD38 (SEQ ID NO: 205) significantly reduced the binding of SAR650984 while humanized 9G7 binding was unaffected (data not shown). A double mutant of the extracellular domain of human CD38 containing mutations M110V and T148M (SEQ ID NO: 206, see FIG. 23) abolished binding of SAR650984 while humanized 9G7 binding was not affected (FIG. 24). Thus it can be concluded that while humanized 9G7 and SAR650984 compete for binding on human CD38, the residues that are bound by these antibodies are not identical.

767 Epitope Mapping

The epitope of the 767 antibody was mapped using the same set of linear peptide-Fc fusions used for the epitope mapping experiments described above. The 767 antibody (heavy chain SEQ ID NO: 151 and light chain SEQ ID NO: 152) was covalently immobilized on a CM5 sensor chip (about 700 RUs). Peptide Fc-fusions (F1-F20, SEQ ID NO: 182-201) were injected at 1000 nM for 240 seconds. The extracellular domain of human CD38 extracellular was injected as control. Only F3 and the control gave a binding signal (FIG. 25). When the F3 sequence is mapped onto the 3D surface of the extracellular domain of human CD38 (FIG. 26), it partially overlaps with the SAR650984 epitope, more specifically with two residues: E76 and H79. However 767 is cross-reactive to cynomolgus CD38 (with lower affinity) while SAR650984 is not, suggesting that the two antibodies have overlapping but different epitopes. Furthermore SAR650984 did not bind the F3 construct by SPR (FIG. 27). Thus it can be concluded that while 767 and SAR650984 compete for binding on human CD38, the residues that are bound by these antibodies are not identical.

The invention claimed is:

1. A bispecific antibody or fragment thereof that binds to human CD38 comprising a heavy chain variable region CDR1 comprising the amino acid sequence of SEQ ID NO: 25 or SEQ ID NO: 208, a heavy chain variable region CDR2 comprising the amino acid sequence of SEQ ID NO: 26 or SEQ ID NO: 209, and a heavy chain variable region CDR3 comprising the amino acid sequence of SEQ ID NO: 27 or SEQ ID NO: 210; and comprising a light chain variable region CDR1 comprising the amino acid sequence of SEQ ID NO: 28 or SEQ ID NO: 211 or SEQ ID NO: 214, a light chain variable region CDR2 comprising the amino acid sequence of SEQ ID NO: 29 or SEQ ID NO: 212, and a light chain variable region CDR3 comprising the amino acid sequence of SEQ ID NO: 30 or SEQ ID NO: 213.

2. The bispecific antibody or fragment thereof of claim 1, wherein the bispecific antibody or fragment thereof is a murine antibody, chimeric antibody or a humanized antibody.

3. The bispecific antibody or fragment thereof of claim 1, wherein the bispecific antibody or fragment thereof comprises a heavy chain variable region sequence comprising the amino acid sequence selected from the group consisting of SEQ ID NO: 52, SEQ ID NO: 58, and SEQ ID NO: 60 or a sequence at least 80% identical to the non-CDR region of said heavy chain variable region sequences and/or wherein the bispecific antibody or fragment thereof comprises a light chain variable region sequence comprising the amino acid sequence selected from the group consisting of SEQ ID NO: 55, SEQ ID NO: 59, and SEQ ID NO: 61 or a sequence at least 80% identical to the non-CDR region of any one of said light chain variable region sequences.

4. The bispecific antibody or fragment thereof of claim 1, wherein the bispecific antibody or fragment thereof comprises a heavy chain sequence comprising the amino acid sequence selected from the group consisting of SEQ ID NO: 73, SEQ ID NO: 75, SEQ ID NO: 76, SEQ ID NO: 145, SEQ ID NO: 147, and SEQ ID NO: 149 or a sequence at least 80% identical to the non-CDR region of said heavy chain variable region sequences and/or wherein the bispecific antibody or fragment thereof comprises a light chain region sequence comprising the amino acid sequence selected from the group consisting of SEQ ID NO: 74, SEQ ID NO: 77, SEQ ID NO: 146, SEQ ID NO: 148, and SEQ ID NO: 150 or a sequence at least 80% identical to the non-CDR region of any one of said light chain variable region sequences.

5. The bispecific antibody or fragment thereof of claim 1, wherein said bispecific antibody or fragment comprises human heavy and/or light chain constant regions and wherein the human heavy constant region is selected from the group of human immunoglobulins consisting of IGHG1, non fucosylated IGHG1 and IGHG4.

6. The bispecific antibody or fragment thereof of claim 1, wherein said bispecific antibody fragment is selected from the group consisting of Fab, Fab', Fab'-SH, Fd, Fv, dAb, F(ab')2, scFv, bispecific single chain Fv dimers, diabodies, triabodies and scFv.

7. The bispecific antibody or fragment thereof of claim 1, further comprising an anti-CD3 antibody fragment selected from the group consisting of Fab, Fab', Fab'-SH, Fd, Fv, dAb, F(ab')2, scFv, bispecific single chain Fv dimers, diabodies, triabodies and scFv.

8. The bispecific antibody or fragment thereof of claim 7, wherein said anti-CD3 antibody fragment comprises a heavy chain variable region CDR1 comprising the amino acid sequence of SEQ ID NO: 3, a heavy chain variable region CDR2 comprising the amino acid sequence of SEQ ID NO: 4, and a heavy chain variable region CDR3 comprising the amino acid sequence of SEQ ID NO: 5 or SEQ ID NO: 9; and comprises a light chain variable region CDR1 comprising the amino acid sequence of SEQ ID NO: 6, a light chain variable region CDR2 comprising the amino acid sequence of SEQ ID NO: 7 or SEQ ID NO: 11, and a light chain variable region CDR3 comprising the amino acid sequence of SEQ ID NO: 8, SEQ ID NO: 10, or SEQ ID NO: 12; or wherein said anti-CD3 antibody fragment comprises a heavy chain variable region CDR1 comprising the amino acid sequence of SEQ ID NO: 163, a heavy chain variable region CDR2 comprising the amino acid sequence of SEQ ID NO: 164, and a heavy chain variable region CDR3 comprising the amino acid sequence of SEQ ID NO: 165; and comprises a light chain variable region CDR1 comprising the amino acid sequence of SEQ ID NO: 166, a light chain variable region CDR2 comprising the amino acid sequence of SEQ ID NO: 167, and a light chain variable region CDR3 comprising the amino acid sequence of SEQ ID NO: 168.

9. A composition comprising the bispecific antibody or fragment thereof of claim 1 and a pharmaceutically acceptable carrier.

10. An immunoconjugate comprising the bispecific antibody or fragment thereof of claim 1, linked to a therapeutic agent.

11. A method of treating a disease selected from the group consisting of malignant hematological diseases, including multiple myeloma, B-cell chronic lymphocytic leukaemia, B-cell acute lymphocytic leukaemia, Waldenstrom's macroglobulinemia, primary systemic amyloidosis, mantle-cell lymphoma, pro-lymphocytic/myelocytic leukaemia, acute myeloid leukaemia, chronic myeloid leukaemia, follicular lymphoma, NK-cell leukaemia, and plasma-cell leukaemia comprising administering the bispecific antibody or fragment thereof of claim 1 to a subject in need thereof.

12. The bispecific antibody or fragment thereof of claim 7, wherein said anti-CD3 antibody fragment comprises the amino acid sequence of SEQ ID NO: 67, 68, 69, or 70.

* * * * *

```
                           SEQUENCE LISTING

<160> NUMBER OF SEQ ID NOS: 214

<210> SEQ ID NO 1
<211> LENGTH: 125
<212> TYPE: PRT
<213> ORGANISM: Artificial Sequence
<220> FEATURE:
<223> OTHER INFORMATION: SEQ ID NO: 1 SP34 scFv hevay chain variable

<400> SEQUENCE: 1

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 2
<211> LENGTH: 109
<212> TYPE: PRT
<213> ORGANISM: Artificial Sequence
<220> FEATURE:
<223> OTHER INFORMATION: SEQ ID NO: 2 SP34 scfv light chain variable

<400> SEQUENCE: 2

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
```

```
                50                  55                  60
Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

Leu Trp Val Phe Gly Gly Gly Thr Lys Leu Thr Val Leu
            100                 105

<210> SEQ ID NO 3
<211> LENGTH: 8
<212> TYPE: PRT
<213> ORGANISM: Artificial Sequence
<220> FEATURE:
<223> OTHER INFORMATION: SEQ ID NO: 3 SP34 mouse CDRH1

<400> SEQUENCE: 3

Gly Phe Thr Phe Asn Thr Tyr Ala
 1               5

<210> SEQ ID NO 4
<211> LENGTH: 10
<212> TYPE: PRT
<213> ORGANISM: Artificial Sequence
<220> FEATURE:
<223> OTHER INFORMATION: SEQ ID NO: 4 SP34 mouse CDRH2

<400> SEQUENCE: 4

Ile Arg Ser Lys Tyr Asn Asn Tyr Ala Thr
 1               5                  10

<210> SEQ ID NO 5
<211> LENGTH: 16
<212> TYPE: PRT
<213> ORGANISM: Artificial Sequence
<220> FEATURE:
<223> OTHER INFORMATION: SEQ ID NO: 5 SP34 mouse CDRH3

<400> SEQUENCE: 5

Val Arg His Gly Asn Phe Gly Asn Ser Tyr Val Ser Trp Phe Ala Tyr
 1               5                  10                  15

<210> SEQ ID NO 6
<211> LENGTH: 9
<212> TYPE: PRT
<213> ORGANISM: Artificial Sequence
<220> FEATURE:
<223> OTHER INFORMATION: SEQ ID NO: 6 SP34 mouse CDRL1

<400> SEQUENCE: 6

Thr Gly Ala Val Thr Thr Ser Asn Tyr
 1               5

<210> SEQ ID NO 7
<211> LENGTH: 3
<212> TYPE: PRT
<213> ORGANISM: Artificial Sequence
<220> FEATURE:
<223> OTHER INFORMATION: SEQ ID NO: 7 SP34 mouse CDRL2

<400> SEQUENCE: 7

Gly Thr Asn
 1

<210> SEQ ID NO 8
<211> LENGTH: 9
```

```
<212> TYPE: PRT
<213> ORGANISM: Artificial Sequence
<220> FEATURE:
<223> OTHER INFORMATION: SEQ ID NO: 8 SP34 mouse CDRL3

<400> SEQUENCE: 8

Ala Leu Trp Tyr Ser Asn Leu Trp Val
1               5

<210> SEQ ID NO 9
<211> LENGTH: 16
<212> TYPE: PRT
<213> ORGANISM: Artificial Sequence
<220> FEATURE:
<223> OTHER INFORMATION: SEQ ID NO: 9 SP34 humanised CDRH3

<400> SEQUENCE: 9

Val Arg His Gly Asn Phe Gly Asn Ser Tyr Val Ser Tyr Phe Ala Tyr
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: SEQ ID NO: 10 SP34 humanised CDRL3

<400> SEQUENCE: 10

Thr Gly Ala Val Thr Ala Ala Asn Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: SEQ ID NO: 11 SP34 humanised CDRL2

<400> SEQUENCE: 11

Gly Ala Asn
1

<210> SEQ ID NO 12
<211> LENGTH: 9
<212> TYPE: PRT
<213> ORGANISM: Artificial Sequence
<220> FEATURE:
<223> OTHER INFORMATION: SEQ ID NO: 12 SP34 humanised CDRL3

<400> SEQUENCE: 12

Ala Leu Phe Tyr Ser Asn Leu Trp Val
1               5

<210> SEQ ID NO 13
<211> LENGTH: 8
<212> TYPE: PRT
<213> ORGANISM: Artificial Sequence
<220> FEATURE:
<223> OTHER INFORMATION: SEQ ID NO: 13 HB7 mouse CDRH1

<400> SEQUENCE: 13

Gly Phe Ser Leu Ile Ser Tyr Gly
1               5

<210> SEQ ID NO 14
<211> LENGTH: 7
<212> TYPE: PRT
```

<213> ORGANISM: Artificial Sequence
<220> FEATURE:
<223> OTHER INFORMATION: SEQ ID NO: 14 HB7 mouse CDRH2

<400> SEQUENCE: 14

Ile Trp Arg Gly Gly Ser Thr
1               5

<210> SEQ ID NO 15
<211> LENGTH: 13
<212> TYPE: PRT
<213> ORGANISM: Artificial Sequence
<220> FEATURE:
<223> OTHER INFORMATION: SEQ ID NO: 15 HB7 mouse CDRH3

<400> SEQUENCE: 15

Ala Lys Thr Leu Ile Thr Thr Gly Tyr Ala Met Asp Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: SEQ ID NO: 16 HB7 mouse CDRL1

<400> SEQUENCE: 16

Glu Asp Ile Tyr Asn Arg
1               5

<210> SEQ ID NO 17
<211> LENGTH: 3
<212> TYPE: PRT
<213> ORGANISM: Artificial Sequence
<220> FEATURE:
<223> OTHER INFORMATION: SEQ ID NO: 17 HB7 mouse CDRL2

<400> SEQUENCE: 17

Gly Ala Thr
1

<210> SEQ ID NO 18
<211> LENGTH: 8
<212> TYPE: PRT
<213> ORGANISM: Artificial Sequence
<220> FEATURE:
<223> OTHER INFORMATION: SEQ ID NO: 18 HB7 mouse CDRL3

<400> SEQUENCE: 18

Gln Gln Tyr Trp Ser Thr Pro Thr
1               5

<210> SEQ ID NO 19
<211> LENGTH: 8
<212> TYPE: PRT
<213> ORGANISM: Artificial Sequence
<220> FEATURE:
<223> OTHER INFORMATION: SEQ ID NO: 19 OKT10 mouse CDRH1

<400> SEQUENCE: 19

Gly Phe Asp Phe Ser Arg Ser Trp
1               5

<210> SEQ ID NO 20
<211> LENGTH: 9
<212> TYPE: PRT
<213> ORGANISM: Artificial Sequence

```
<220> FEATURE:
<223> OTHER INFORMATION: SEQ ID NO: 20 OKT10 mouse CDRH2

<400> SEQUENCE: 20

Ile Asn Pro Asp Ser Ser Thr Ile Val
1               5

<210> SEQ ID NO 21
<211> LENGTH: 9
<212> TYPE: PRT
<213> ORGANISM: Artificial Sequence
<220> FEATURE:
<223> OTHER INFORMATION: SEQ ID NO: 21 OKT10 mouse CDRH3

<400> SEQUENCE: 21

Ala Arg Tyr Gly Asn Trp Phe Pro Tyr
1               5

<210> SEQ ID NO 22
<211> LENGTH: 6
<212> TYPE: PRT
<213> ORGANISM: Artificial Sequence
<220> FEATURE:
<223> OTHER INFORMATION: SEQ ID NO: 22 OKT10 mouse CDRL1

<400> SEQUENCE: 22

Gln Asn Val Asp Thr Asn
1               5

<210> SEQ ID NO 23
<211> LENGTH: 3
<212> TYPE: PRT
<213> ORGANISM: Artificial Sequence
<220> FEATURE:
<223> OTHER INFORMATION: SEQ ID NO: 23 OKT10 mouse CDRL2

<400> SEQUENCE: 23

Ser Ala Ser
1

<210> SEQ ID NO 24
<211> LENGTH: 15
<212> TYPE: PRT
<213> ORGANISM: Artificial Sequence
<220> FEATURE:
<223> OTHER INFORMATION: SEQ ID NO: 24 OKT10 mouse CDRL3

<400> SEQUENCE: 24

Gln Gln Tyr Asp Ser Tyr Pro Leu Thr Phe Gly Ala Gly Thr Lys
1               5                   10                  15

<210> SEQ ID NO 25
<211> LENGTH: 10
<212> TYPE: PRT
<213> ORGANISM: Artificial Sequence
<220> FEATURE:
<223> OTHER INFORMATION: SEQ ID NO: 25 9G7 mouse CDRH1

<400> SEQUENCE: 25

Gly Leu Ser Leu Ser Thr Ser Gly Lys Gly
1               5                   10

<210> SEQ ID NO 26
<211> LENGTH: 7
<212> TYPE: PRT
<213> ORGANISM: Artificial Sequence
<220> FEATURE:
```

<223> OTHER INFORMATION: SEQ ID NO: 26 9G7 mouse CDRH2

<400> SEQUENCE: 26

Ile Trp Trp Asp Asp Asp Lys
1               5

<210> SEQ ID NO 27
<211> LENGTH: 13
<212> TYPE: PRT
<213> ORGANISM: Artificial Sequence
<220> FEATURE:
<223> OTHER INFORMATION: SEQ ID NO: 27 9G7 mouse CDRH3

<400> SEQUENCE: 27

Ala Arg Ile Glu Leu Gly Arg Ser Tyr Val Met Asp Tyr
1               5                   10

<210> SEQ ID NO 28
<211> LENGTH: 6
<212> TYPE: PRT
<213> ORGANISM: Artificial Sequence
<220> FEATURE:
<223> OTHER INFORMATION: SEQ ID NO: 28 9G7 mouse CDRL1

<400> SEQUENCE: 28

Gln Asp Val Ile Thr Ser
1               5

<210> SEQ ID NO 29
<211> LENGTH: 3
<212> TYPE: PRT
<213> ORGANISM: Artificial Sequence
<220> FEATURE:
<223> OTHER INFORMATION: SEQ ID NO: 29 9G7 mouse CDRL2

<400> SEQUENCE: 29

Ser Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: SEQ ID NO: 30 9G7 mouse CDRL3

<400> SEQUENCE: 30

Gln Gln His Tyr Thr Ile Pro Leu Thr
1               5

<210> SEQ ID NO 31
<211> LENGTH: 8
<212> TYPE: PRT
<213> ORGANISM: Artificial Sequence
<220> FEATURE:
<223> OTHER INFORMATION: SEQ ID NO: 31 767 mouse CDRH1

<400> SEQUENCE: 31

Gly Phe Thr Phe Ser Ser Tyr Trp
1               5

<210> SEQ ID NO 32
<211> LENGTH: 8
<212> TYPE: PRT
<213> ORGANISM: Artificial Sequence
<220> FEATURE:
<223> OTHER INFORMATION: SEQ ID NO: 32 767 mouse CDRH2

```
<400> SEQUENCE: 32

Ile Lys Gln Asp Gly Ser Glu Lys
1               5

<210> SEQ ID NO 33
<211> LENGTH: 11
<212> TYPE: PRT
<213> ORGANISM: Artificial Sequence
<220> FEATURE:
<223> OTHER INFORMATION: SEQ ID NO: 33 767 mouse CDRH3

<400> SEQUENCE: 33

Ala Arg Glu Gly Arg Thr Gly Tyr Phe Asp Tyr
1               5                   10

<210> SEQ ID NO 34
<211> LENGTH: 8
<212> TYPE: PRT
<213> ORGANISM: Artificial Sequence
<220> FEATURE:
<223> OTHER INFORMATION: SEQ ID NO: 34 767 mouse CDRL1

<400> SEQUENCE: 34

Thr Ser Asn Ile Gly Thr Asn Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: SEQ ID NO: 35 767 mouse CDRL2

<400> SEQUENCE: 35

Arg Asn Asp
1

<210> SEQ ID NO 36
<211> LENGTH: 12
<212> TYPE: PRT
<213> ORGANISM: Artificial Sequence
<220> FEATURE:
<223> OTHER INFORMATION: SEQ ID NO: 36 767 mouse CDRL3

<400> SEQUENCE: 36

Ala Ala Trp Asp Asp Ser Arg Ser Gly Val Tyr Ala
1               5                   10

<210> SEQ ID NO 37
<211> LENGTH: 98
<212> TYPE: PRT
<213> ORGANISM: Artificial Sequence
<220> FEATURE:
<223> OTHER INFORMATION: SEQ ID NO: 37 IGHV3-23*04

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 38
<211> LENGTH: 119
<212> TYPE: PRT
<213> ORGANISM: Artificial Sequence
<220> FEATURE:
<223> OTHER INFORMATION: SEQ ID NO: 38 OKT3 HC variable

<400> SEQUENCE: 38

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
 50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
                100                 105                 110

Thr Thr Leu Thr Val Ser Ser
            115

<210> SEQ ID NO 39
<211> LENGTH: 95
<212> TYPE: PRT
<213> ORGANISM: Artificial Sequence
<220> FEATURE:
<223> OTHER INFORMATION: SEQ ID NO: 39 IGKV1-39*01

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                85                  90                  95

<210> SEQ ID NO 40
<211> LENGTH: 96
<212> TYPE: PRT
<213> ORGANISM: Artificial Sequence
<220> FEATURE:
<223> OTHER INFORMATION: SEQ ID NO: 40 IGKV3-20*01
```

```
<400> SEQUENCE: 40

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 41
<211> LENGTH: 106
<212> TYPE: PRT
<213> ORGANISM: Artificial Sequence
<220> FEATURE:
<223> OTHER INFORMATION: SEQ ID NO: 41 OKT3 HC variable

<400> SEQUENCE: 41

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 42
<211> LENGTH: 125
<212> TYPE: PRT
<213> ORGANISM: Artificial Sequence
<220> FEATURE:
<223> OTHER INFORMATION: SEQ ID NO: 42 SP34 humanised VH1

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser
        115                 120                 125

<210> SEQ ID NO 43
<211> LENGTH: 125
<212> TYPE: PRT
<213> ORGANISM: Artificial Sequence
<220> FEATURE:
<223> OTHER INFORMATION: SEQ ID NO: 43 SP34 humanised VH2

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser
        115                 120                 125

<210> SEQ ID NO 44
<211> LENGTH: 125
<212> TYPE: PRT
<213> ORGANISM: Artificial Sequence
<220> FEATURE:
<223> OTHER INFORMATION: SEQ ID NO: 44 SP34 humanised VH3

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
        115                 120                 125

<210> SEQ ID NO 45
<211> LENGTH: 125
<212> TYPE: PRT
<213> ORGANISM: Artificial Sequence
```

```
<220> FEATURE:
<223> OTHER INFORMATION: SEQ ID NO: 45 SP34 humanised VH5

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
        115                 120                 125

<210> SEQ ID NO 46
<211> LENGTH: 110
<212> TYPE: PRT
<213> ORGANISM: Artificial Sequence
<220> FEATURE:
<223> OTHER INFORMATION: SEQ ID NO: 46 SP34 humanised VL21

<400> SEQUENCE: 46

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Tyr Cys Ala Leu Trp Tyr Ser
                85                  90                  95

Asn Leu Trp Val Phe Gly Gln Gly Thr Lys Leu Glu Ile Lys
            100                 105                 110

<210> SEQ ID NO 47
<211> LENGTH: 110
<212> TYPE: PRT
<213> ORGANISM: Artificial Sequence
<220> FEATURE:
<223> OTHER INFORMATION: SEQ ID NO: 47 SP34 humanised VL32

<400> SEQUENCE: 47

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Ala
            20                  25                  30

Ala Asn Tyr Ala Asn Trp Val Gln Glu Lys Pro Gly Gln Ala Phe Arg
        35                  40                  45
```

Gly Leu Ile Gly Gly Ala Asn Lys Arg Ala Pro Gly Val Pro Ala Arg
            50                  55                  60

Phe Ser Gly Ser Leu Ser Gly Asp Glu Ala Thr Leu Thr Ile Ser Ser
 65                  70                  75                  80

Leu Gln Ser Glu Asp Phe Ala Val Tyr Tyr Cys Ala Leu Phe Tyr Ser
                 85                  90                  95

Asn Leu Trp Val Phe Gly Gln Gly Thr Lys Leu Glu Ile Lys
            100                 105                 110

<210> SEQ ID NO 48
<211> LENGTH: 110
<212> TYPE: PRT
<213> ORGANISM: Artificial Sequence
<220> FEATURE:
<223> OTHER INFORMATION: SEQ ID NO: 48 SP34 humanised VL65

<400> SEQUENCE: 48

Glu Ile Val Val Thr Gln Ser Pro Ala Thr Leu Ser Val Ser Pro Gly
 1               5                  10                  15

Glu Arg Ala Thr Leu Ser Cys Arg Ser Ser Thr Gly Ala Val Thr Glu
                 20                  25                  30

Ser Asn Tyr Ala Asn Trp Val Gln Glu Lys Pro Gly Gln Ala Phe Arg
             35                  40                  45

Gly Leu Ile Gly Gly Ala Asn Lys Arg Ala Pro Gly Val Pro Ala Arg
     50                  55                  60

Phe Ser Gly Ser Leu Ser Gly Asp Glu Ala Thr Leu Thr Ile Ser Ser
 65                  70                  75                  80

Leu Gln Ser Glu Asp Phe Ala Val Tyr Tyr Cys Ala Leu Phe Tyr Ser
                 85                  90                  95

Asn Thr Trp Val Phe Gly Gln Gly Thr Lys Leu Glu Ile Lys
            100                 105                 110

<210> SEQ ID NO 49
<211> LENGTH: 110
<212> TYPE: PRT
<213> ORGANISM: Artificial Sequence
<220> FEATURE:
<223> OTHER INFORMATION: SEQ ID NO: 49 SP34 humanised VL67

<400> SEQUENCE: 49

Glu Ile Val Val Thr Gln Ser Pro Ala Thr Leu Ser Val Ser Pro Gly
 1               5                  10                  15

Glu Arg Ala Thr Leu Ser Cys Arg Ser Ser Thr Gly Ala Val Thr Ala
                 20                  25                  30

Ala Asn Tyr Ala Asn Trp Val Gln Glu Lys Pro Gly Gln Ala Phe Arg
             35                  40                  45

Gly Leu Ile Gly Gly Ala Asn Lys Arg Ala Pro Gly Val Pro Ala Arg
     50                  55                  60

Phe Ser Gly Ser Leu Ser Gly Asp Glu Ala Thr Leu Thr Ile Ser Ser
 65                  70                  75                  80

Leu Gln Ser Glu Asp Phe Ala Val Tyr Tyr Cys Ala Leu Phe Tyr Ser
                 85                  90                  95

Asn Thr Trp Val Phe Gly Gln Gly Thr Lys Leu Glu Ile Lys
            100                 105                 110

<210> SEQ ID NO 50
<211> LENGTH: 109
<212> TYPE: PRT
<213> ORGANISM: Artificial Sequence

```
<220> FEATURE:
<223> OTHER INFORMATION: SEQ ID NO: 50 OKT10 mouse VH

<400> SEQUENCE: 50

Gln Val Glu Leu Val Glu Ser Gly Gly Ser Leu Lys Leu Ser Cys Ala
1               5                   10                  15

Ala Ser Gly Phe Asp Phe Ser Arg Ser Trp Met Asn Trp Val Arg Gln
            20                  25                  30

Ala Pro Gly Lys Gly Leu Glu Trp Ile Gly Glu Ile Asn Pro Asp Ser
        35                  40                  45

Ser Thr Ile Asn Tyr Thr Thr Ser Leu Lys Asp Lys Phe Ile Ile Ser
50                  55                  60

Arg Asp Asn Ala Lys Asn Thr Leu Tyr Leu Gln Met Thr Lys Val Arg
65                  70                  75                  80

Ser Glu Asp Thr Ala Leu Tyr Tyr Cys Ala Arg Tyr Gly Asn Trp Phe
                85                  90                  95

Pro Tyr Trp Gly Gln Gly Thr Leu Val Thr Val Ser Ser
            100                 105

<210> SEQ ID NO 51
<211> LENGTH: 119
<212> TYPE: PRT
<213> ORGANISM: Artificial Sequence
<220> FEATURE:
<223> OTHER INFORMATION: SEQ ID NO: 51 HB7 mouse VH

<400> SEQUENCE: 51

Lys Val Gln Leu Gln Glu Ser Gly Pro Ser Leu Val Gln Pro Ser Gln
1               5                   10                  15

Arg Leu Ser Ile Thr Cys Thr Val Ser Gly Phe Ser Leu Ile Ser Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Phe Cys Ala
                85                  90                  95

Lys Thr Leu Ile Thr Thr Gly Tyr Ala Met Asp Tyr Trp Gly Gln Gly
            100                 105                 110

Thr Thr Val Thr Val Ser Ser
        115

<210> SEQ ID NO 52
<211> LENGTH: 121
<212> TYPE: PRT
<213> ORGANISM: Artificial Sequence
<220> FEATURE:
<223> OTHER INFORMATION: SEQ ID NO: 52 9G7 mouse VH

<400> SEQUENCE: 52

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Leu Ser Leu Ser Thr Ser
            20                  25                  30

Gly Lys Gly Val Gly Trp Ile Arg Gln Pro Ser Gly Lys Gly Leu Glu
        35                  40                  45
```

```
Trp Leu Ala His Ile Trp Trp Asp Asp Lys Arg Tyr Asn Pro Ala
         50                  55                  60

Leu Lys Ser Arg Leu Thr Ile Ser Lys Asp Thr Ser Ser Asn Gln Val
 65                  70                  75                  80

Phe Leu Lys Ile Ala Ser Val Asp Thr Ala Asp Thr Ala Thr Tyr Tyr
                     85                  90                  95

Cys Ala Arg Ile Glu Leu Gly Arg Ser Tyr Val Met Asp Tyr Trp Gly
                100                 105                 110

Gln Gly Thr Thr Val Thr Val Ser Ser
            115                 120

<210> SEQ ID NO 53
<211> LENGTH: 108
<212> TYPE: PRT
<213> ORGANISM: Artificial Sequence
<220> FEATURE:
<223> OTHER INFORMATION: SEQ ID NO: 53 OKT10 mouse VL

<400> SEQUENCE: 53

Asp Ile Leu Met Thr Gln Ser Gln Lys Ile Met Pro Thr Ser Val Gly
 1               5                  10                  15

Asp Arg Val Ser Val Thr Cys Lys Ala Ser Gln Asn Val Asp Thr Asn
                 20                  25                  30

Val Ala Trp Tyr Gln Gln Lys Pro Gly Gln Ser Pro Lys Ala Leu Ile
             35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Thr Asn Val Gln Ser
 65                  70                  75                  80

Glu Asp Leu Ala Glu Tyr Phe Cys Gln Gln Tyr Asp Ser Tyr Pro Leu
                 85                  90                  95

Thr Phe Gly Ala Gly Thr Lys Leu Asp Leu Lys Arg
            100                 105

<210> SEQ ID NO 54
<211> LENGTH: 106
<212> TYPE: PRT
<213> ORGANISM: Artificial Sequence
<220> FEATURE:
<223> OTHER INFORMATION: SEQ ID NO: 54 HB7 mouse VL

<400> SEQUENCE: 54

Asp Ile Glu Leu Thr Gln Ser Pro Ser Ser Phe Ser Val Ser Leu Gly
 1               5                  10                  15

Asp Arg Val Thr Ile Thr Cys Lys Ala Ser Glu Asp Ile Tyr Asn Arg
                 20                  25                  30

Leu Ala Trp Tyr Gln Gln Lys Pro Gly Asn Ala Pro Arg Leu Leu Ile
             35                  40                  45

Ser Gly Ala Thr Ser Leu Glu Thr Gly Val Pro Ser Arg Phe Ser Gly
 50                  55                  60

Ser Gly Ser Gly Lys Asp Tyr Thr Leu Ser Ile Thr Ser Leu Gln Thr
 65                  70                  75                  80

Glu Asp Val Ala Thr Tyr Tyr Cys Gln Gln Tyr Trp Ser Thr Pro Thr
                 85                  90                  95

Phe Gly Gly Gly Thr Lys Leu Glu Ile Lys
            100                 105

<210> SEQ ID NO 55
```

```
<211> LENGTH: 107
<212> TYPE: PRT
<213> ORGANISM: Artificial Sequence
<220> FEATURE:
<223> OTHER INFORMATION: SEQ ID NO: 55 9G7 mouse VL

<400> SEQUENCE: 55

Asp Ile Val Met Thr Gln Ser His Lys Phe Met Ser Thr Ser Val Gly
1               5                   10                  15

Asp Arg Val Ser Ile Ser Cys Lys Ala Ser Gln Asp Val Ile Thr Ser
            20                  25                  30

Val Ala Trp Phe Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Ile Pro Leu
                85                  90                  95

Thr Phe Gly Ala Gly Thr Lys Leu Glu Leu Lys
            100                 105

<210> SEQ ID NO 56
<211> LENGTH: 119
<212> TYPE: PRT
<213> ORGANISM: Artificial Sequence
<220> FEATURE:
<223> OTHER INFORMATION: SEQ ID NO: 56 HB-7 best fit VH

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Ser Tyr
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Lys Thr Leu Ile Thr Thr Gly Tyr Ala Met Asp Tyr Trp Gly Gln Gly
            100                 105                 110

Thr Leu Val Thr Val Ser Ser
        115

<210> SEQ ID NO 57
<211> LENGTH: 106
<212> TYPE: PRT
<213> ORGANISM: Artificial Sequence
<220> FEATURE:
<223> OTHER INFORMATION: SEQ ID NO: 57 HB-7 best fit VL

<400> SEQUENCE: 57

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Arg
            20                  25                  30
```

```
Leu Ala Trp Tyr Gln Gln Lys Pro Gly Lys Ala Pro Lys Leu Leu Ile
             35                  40                  45

Ser Gly Ala Thr Ser Leu Glu Thr Gly Val Pro Ser Arg Phe Ser Gly
 50                  55                  60

Ser Gly Ser Gly Lys Asp Tyr Thr Leu Thr Ile Ser Ser Leu Gln Pro
 65                  70                  75                  80

Glu Asp Phe Ala Thr Tyr Tyr Cys Gln Gln Tyr Trp Ser Thr Pro Thr
                 85                  90                  95

Phe Gly Gln Gly Thr Lys Leu Glu Ile Lys
            100                 105
```

<210> SEQ ID NO 58
<211> LENGTH: 121
<212> TYPE: PRT
<213> ORGANISM: Artificial Sequence
<220> FEATURE:
<223> OTHER INFORMATION: SEQ ID NO: 58 9G7 best fit VH

<400> SEQUENCE: 58

```
Gln Val Thr Leu Lys Glu Ser Gly Pro Thr Leu Val Lys Pro Thr Gln
 1               5                  10                  15

Thr Leu Thr Leu Thr Cys Thr Phe Ser Gly Leu Ser Leu Ser Thr Ser
             20                  25                  30

Gly Lys Gly Val Gly Trp Ile Arg Gln Pro Pro Gly Lys Ala Leu Glu
         35                  40                  45

Trp Leu Ala His Ile Trp Trp Asp Asp Lys Arg Tyr Asn Pro Ala
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Glu Leu Gly Arg Ser Tyr Val Met Asp Tyr Trp Gly
            100                 105                 110

Gln Gly Thr Leu Val Thr Val Ser Ser
            115                 120
```

<210> SEQ ID NO 59
<211> LENGTH: 107
<212> TYPE: PRT
<213> ORGANISM: Artificial Sequence
<220> FEATURE:
<223> OTHER INFORMATION: SEQ ID NO: 59 9G7 best fit VL

<400> SEQUENCE: 59

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Val Ile Thr Ser
             20                  25                  30

Val Ala Trp Phe Gln Gln Lys Pro Gly Lys Ala Pro Lys Leu Leu Ile
         35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Thr Ile Pro Leu
                 85                  90                  95

Thr Phe Gly Gln Gly Thr Lys Leu Glu Ile Lys
            100                 105
```

<210> SEQ ID NO 60
<211> LENGTH: 121
<212> TYPE: PRT
<213> ORGANISM: Artificial Sequence
<220> FEATURE:
<223> OTHER INFORMATION: SEQ ID NO: 60 9G7 best framework VH

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Phe Ser Gly Leu Ser Leu Ser Thr Ser
            20                  25                  30

Gly Lys Gly Val Gly Trp Ile Arg Gln Ala Pro Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Ile Glu Leu Gly Arg Ser Tyr Val Met Asp Tyr Trp Gly
            100                 105                 110

Gln Gly Thr Leu Val Thr Val Ser Ser
        115                 120

<210> SEQ ID NO 61
<211> LENGTH: 107
<212> TYPE: PRT
<213> ORGANISM: Artificial Sequence
<220> FEATURE:
<223> OTHER INFORMATION: SEQ ID NO: 61 9G7 best framework VL

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ile Thr Ser
            20                  25                  30

Val Ala Trp Phe Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Ile Pro Leu
                85                  90                  95

Thr Phe Gly Gln Gly Thr Lys Val Glu Ile Lys
            100                 105

<210> SEQ ID NO 62
<211> LENGTH: 118
<212> TYPE: PRT
<213> ORGANISM: Artificial Sequence
<220> FEATURE:
<223> OTHER INFORMATION: SEQ ID NO: 62 767 VH

<400> SEQUENCE: 62

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Arg Thr Gly Tyr Phe Asp Tyr Trp Gly Gln Gly Thr
                100                 105                 110

Leu Val Thr Val Ser Ser
            115

<210> SEQ ID NO 63
<211> LENGTH: 111
<212> TYPE: PRT
<213> ORGANISM: Artificial Sequence
<220> FEATURE:
<223> OTHER INFORMATION: SEQ ID NO: 63 767 VL

<400> SEQUENCE: 63

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Asn
            20                  25                  30

Tyr Val Tyr Trp Tyr Gln Gln Leu Pro Gly Thr Ala Pro Lys Leu Leu
        35                  40                  45

Ile Tyr Arg Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Arg
                85                  90                  95

Ser Gly Val Tyr Ala Phe Gly Thr Gly Thr Lys Val Thr Val Leu
                100                 105                 110

<210> SEQ ID NO 64
<211> LENGTH: 455
<212> TYPE: PRT
<213> ORGANISM: Artificial Sequence
<220> FEATURE:
<223> OTHER INFORMATION: SEQ ID NO: 64 SP34 IgG1 HC VH5

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

```
Tyr Cys Val Arg His Gly Asn Phe Gly Asn Ser Tyr Val Ser Tyr Phe
                100                 105                 110

Ala Tyr Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 65
<211> LENGTH: 448
<212> TYPE: PRT
<213> ORGANISM: Artificial Sequence
<220> FEATURE:
<223> OTHER INFORMATION: SEQ ID NO: 65 BEAT 767 HC

<400> SEQUENCE: 65
```

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Arg Thr Gly Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Lys Trp Tyr Val Asp Gly Val Glu Val His Asn Ala
        275                 280                 285

Lys Thr Lys Pro Arg Glu Glu Gln Tyr Asn Ser Thr Phe Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Thr Lys Gly Gln Pro Arg Glu Pro Ala Val Tyr Thr Leu
            340                 345                 350

Pro Pro Ser Arg Glu Glu Met Thr Lys Asn Gln Val Lys Leu Val Cys
        355                 360                 365

Leu Val Thr Gly Phe Tyr Pro Ser Asp Ile Ala Val Glu Trp Glu Ser
370                 375                 380

Ser Gly Gln Pro Glu Asn Asn Tyr Tyr Thr Thr Pro Pro Met Leu Asp
385                 390                 395                 400

Ser Asp Gly Ser Phe Ser Leu Val Ser Trp Leu Asn Val Asp Lys Ser
                405                 410                 415
```

Arg Trp Gln Gln Gly Asn Ile Phe Ser Cys Ser Val Met His Glu Ala
                420                 425                 430

Leu His Asn Arg Phe Thr Gln Lys Ser Leu Ser Leu Ser Pro Gly Lys
            435                 440                 445

<210> SEQ ID NO 66
<211> LENGTH: 218
<212> TYPE: PRT
<213> ORGANISM: Artificial Sequence
<220> FEATURE:
<223> OTHER INFORMATION: SEQ ID NO: 66 767 LC

<400> SEQUENCE: 66

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Asn
            20                  25                  30

Tyr Val Tyr Trp Tyr Gln Gln Leu Pro Gly Thr Ala Pro Lys Leu Leu
        35                  40                  45

Ile Tyr Arg Asn Asp Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Arg
                85                  90                  95

Ser Gly Val Tyr Ala Phe Gly Thr Gly Thr Lys Val Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 67
<211> LENGTH: 482
<212> TYPE: PRT
<213> ORGANISM: Artificial Sequence
<220> FEATURE:
<223> OTHER INFORMATION: SEQ ID NO: 67 SP34 VH1VL21

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

-continued

```
Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser Gly Gly Gly
        115                 120                 125

Gly Ser Gly Gly Gly Gly Ser Gly Gly Gly Gly Ser Glu Ile Val Val
    130                 135                 140

Thr Gln Ser Pro Ala Thr Leu Ser Val Ser Pro Gly Glu Arg Ala Thr
145                 150                 155                 160

Leu Ser Cys Arg Ser Ser Thr Gly Ala Val Thr Thr Ser Asn Tyr Ala
                165                 170                 175

Asn Trp Val Gln Glu Lys Pro Gly Gln Ala Phe Arg Gly Leu Ile Gly
                180                 185                 190

Gly Ala Asn Lys Arg Ala Pro Gly Val Pro Ala Arg Phe Ser Gly Ser
            195                 200                 205

Leu Ser Gly Asp Glu Ala Thr Leu Thr Ile Ser Ser Leu Gln Ser Glu
    210                 215                 220

Asp Phe Ala Val Tyr Tyr Cys Ala Leu Trp Tyr Ser Asn Leu Trp Val
225                 230                 235                 240

Phe Gly Gln Gly Thr Lys Leu Glu Ile Lys Gly Gly Gly Gly Thr Asp
                245                 250                 255

Lys Thr His Thr Cys Pro Pro Cys Pro Ala Pro Glu Leu Leu Gly Gly
                260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
    355                 360                 365

Lys Thr Ile Ser Lys Ala Lys Gly Gln Pro Arg Glu Pro Gln Val Tyr
370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480
```

Gly Lys

<210> SEQ ID NO 68
<211> LENGTH: 481
<212> TYPE: PRT
<213> ORGANISM: Artificial Sequence
<220> FEATURE:
<223> OTHER INFORMATION: SEQ ID NO: 68 SP34 VH5VL32

<400> SEQUENCE: 68

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser Gly Gly Gly
        115                 120                 125

Gly Ser Gly Gly Gly Gly Ser Gly Gly Gly Gly Ser Glu Ile Val Val
    130                 135                 140

Thr Gln Ser Pro Ala Thr Leu Ser Val Ser Pro Gly Glu Arg Ala Thr
145                 150                 155                 160

Leu Ser Cys Arg Ser Ser Thr Gly Ala Val Thr Ala Ala Asn Tyr Ala
                165                 170                 175

Asn Trp Val Gln Glu Lys Pro Gly Gln Ala Phe Arg Gly Leu Ile Gly
            180                 185                 190

Gly Ala Asn Lys Arg Ala Pro Gly Val Pro Ala Arg Phe Ser Gly Ser
        195                 200                 205

Leu Ser Gly Asp Glu Ala Thr Leu Thr Ile Ser Ser Leu Gln Ser Glu
    210                 215                 220

Asp Phe Ala Val Tyr Tyr Cys Ala Leu Phe Tyr Ser Asn Leu Trp Val
225                 230                 235                 240

Phe Gly Gln Gly Thr Lys Leu Glu Ile Lys Gly Gly Gly Gly Thr Asp
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
```

```
                355                 360                 365
Lys Thr Ile Ser Lys Ala Lys Gly Gln Pro Arg Glu Pro Glu Val Ala
        370                 375                 380

Thr Phe Pro Pro Ser Arg Asp Glu Leu Thr Lys Asn Gln Val Thr Leu
385                 390                 395                 400

Val Cys Leu Val Thr Gly Phe Tyr Pro Ser Asp Ile Ala Val Glu Trp
                405                 410                 415

Glu Ser Asn Gly Gln Pro Glu Asn Asn Tyr Lys Thr Asp Pro Pro Leu
            420                 425                 430

Leu Glu Ser Gln Gly Ser Phe Ala Leu Ser Ser Arg Leu Arg Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly

<210> SEQ ID NO 69
<211> LENGTH: 481
<212> TYPE: PRT
<213> ORGANISM: Artificial Sequence
<220> FEATURE:
<223> OTHER INFORMATION: SEQ ID NO: 69 SP34 VH5VL65

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser Gly Gly Gly
        115                 120                 125

Gly Ser Gly Gly Gly Gly Ser Gly Gly Gly Gly Ser Glu Ile Val Val
    130                 135                 140

Thr Gln Ser Pro Ala Thr Leu Ser Val Ser Pro Gly Glu Arg Ala Thr
145                 150                 155                 160

Leu Ser Cys Arg Ser Ser Thr Gly Ala Val Thr Glu Ser Asn Tyr Ala
                165                 170                 175

Asn Trp Val Gln Glu Lys Pro Gly Gln Ala Phe Arg Gly Leu Ile Gly
            180                 185                 190

Gly Ala Asn Lys Arg Ala Pro Gly Val Pro Ala Arg Phe Ser Gly Ser
        195                 200                 205

Leu Ser Gly Asp Glu Ala Thr Leu Thr Ile Ser Ser Leu Gln Ser Glu
    210                 215                 220

Asp Phe Ala Val Tyr Tyr Cys Ala Leu Phe Tyr Ser Asn Thr Trp Val
225                 230                 235                 240
```

```
Phe Gly Gln Gly Thr Lys Leu Glu Ile Lys Gly Gly Gly Thr Asp
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Glu Val Ala
    370                 375                 380

Thr Phe Pro Pro Ser Arg Asp Glu Leu Thr Lys Asn Gln Val Thr Leu
385                 390                 395                 400

Val Cys Leu Val Thr Gly Phe Tyr Pro Ser Asp Ile Ala Val Glu Trp
                405                 410                 415

Glu Ser Asn Gly Gln Pro Glu Asn Asn Tyr Lys Thr Asp Pro Pro Leu
            420                 425                 430

Leu Glu Ser Gln Gly Ser Phe Ala Leu Ser Ser Arg Leu Arg Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly

<210> SEQ ID NO 70
<211> LENGTH: 481
<212> TYPE: PRT
<213> ORGANISM: Artificial Sequence
<220> FEATURE:
<223> OTHER INFORMATION: SEQ ID NO: 70 SP34 VH5VL67

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110
```

Ala Tyr Trp Gly Gln Gly Thr Thr Val Thr Val Ser Ser Gly Gly Gly
            115                 120                 125

Gly Ser Gly Gly Gly Gly Ser Gly Gly Gly Ser Glu Ile Val Val
130                 135                 140

Thr Gln Ser Pro Ala Thr Leu Ser Val Ser Pro Gly Glu Arg Ala Thr
145                 150                 155                 160

Leu Ser Cys Arg Ser Ser Thr Gly Ala Val Thr Ala Ala Asn Tyr Ala
                165                 170                 175

Asn Trp Val Gln Glu Lys Pro Gly Gln Ala Phe Arg Gly Leu Ile Gly
            180                 185                 190

Gly Ala Asn Lys Arg Ala Pro Gly Val Pro Ala Arg Phe Ser Gly Ser
        195                 200                 205

Leu Ser Gly Asp Glu Ala Thr Leu Thr Ile Ser Ser Leu Gln Ser Glu
210                 215                 220

Asp Phe Ala Val Tyr Tyr Cys Ala Leu Phe Tyr Ser Asn Thr Trp Val
225                 230                 235                 240

Phe Gly Gln Gly Thr Lys Leu Glu Ile Lys Gly Gly Gly Gly Thr Asp
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
        290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Glu Val Ala
    370                 375                 380

Thr Phe Pro Pro Ser Arg Asp Glu Leu Thr Lys Asn Gln Val Thr Leu
385                 390                 395                 400

Val Cys Leu Val Thr Gly Phe Tyr Pro Ser Asp Ile Ala Val Glu Trp
                405                 410                 415

Glu Ser Asn Gly Gln Pro Glu Asn Asn Tyr Lys Thr Asp Pro Pro Leu
            420                 425                 430

Leu Glu Ser Gln Gly Ser Phe Ala Leu Ser Ser Arg Leu Arg Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly

<210> SEQ ID NO 71
<211> LENGTH: 449
<212> TYPE: PRT
<213> ORGANISM: Artificial Sequence
<220> FEATURE:
<223> OTHER INFORMATION: SEQ ID NO: 71 HB7 bestfit HC -continued

```
<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Ser Tyr
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Lys Thr Leu Ile Thr Thr Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Lys Trp Tyr Val Asp Gly Val Glu Val His Asn
        275                 280                 285

Ala Lys Thr Lys Pro Arg Glu Glu Gln Tyr Asn Ser Thr Phe Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Thr Lys Gly Gln Pro Arg Glu Pro Ala Val Tyr Thr
            340                 345                 350

Leu Pro Pro Ser Arg Glu Glu Met Thr Lys Asn Gln Val Lys Leu Val
        355                 360                 365

Cys Leu Val Thr Gly Phe Tyr Pro Ser Asp Ile Ala Val Glu Trp Glu
    370                 375                 380

Ser Ser Gly Gln Pro Glu Asn Asn Tyr Tyr Thr Thr Pro Pro Met Leu
385                 390                 395                 400

Asp Ser Asp Gly Ser Phe Ser Leu Val Ser Trp Leu Asn Val Asp Lys
                405                 410                 415
```

Ser Arg Trp Gln Gln Gly Asn Ile Phe Ser Cys Ser Val Met His Glu
                420                 425                 430

Ala Leu His Asn Arg Phe Thr Gln Lys Ser Leu Ser Leu Ser Pro Gly
                435                 440                 445

Lys

<210> SEQ ID NO 72
<211> LENGTH: 213
<212> TYPE: PRT
<213> ORGANISM: Artificial Sequence
<220> FEATURE:
<223> OTHER INFORMATION: SEQ ID NO: 72 HB7 bestfit LC

<400> SEQUENCE: 72

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Arg
                20                  25                  30

Leu Ala Trp Tyr Gln Gln Lys Pro Gly Lys Ala Pro Lys Leu Leu Ile
            35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 73
<211> LENGTH: 451
<212> TYPE: PRT
<213> ORGANISM: Artificial Sequence
<220> FEATURE:
<223> OTHER INFORMATION: SEQ ID NO: 73 9G7 bestfit HC

<400> SEQUENCE: 73

Gln Val Thr Leu Lys Glu Ser Gly Pro Thr Leu Val Lys Pro Thr Gln
1               5                   10                  15

Thr Leu Thr Leu Thr Cys Thr Phe Ser Gly Leu Ser Leu Ser Thr Ser
                20                  25                  30

Gly Lys Gly Val Gly Trp Ile Arg Gln Pro Pro Gly Lys Ala Leu Glu
            35                  40                  45

-continued

```
Trp Leu Ala His Ile Trp Trp Asp Asp Lys Arg Tyr Asn Pro Ala
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Glu Leu Gly Arg Ser Tyr Val Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Lys Trp Tyr Val Asp Gly Val Glu Val
        275                 280                 285

His Asn Ala Lys Thr Lys Pro Arg Glu Glu Gln Tyr Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Thr Lys Gly Gln Pro Arg Glu Pro Ala Val
            340                 345                 350

Tyr Thr Leu Pro Pro Ser Arg Glu Glu Met Thr Lys Asn Gln Val Lys
        355                 360                 365

Leu Val Cys Leu Val Thr Gly Phe Tyr Pro Ser Asp Ile Ala Val Glu
    370                 375                 380

Trp Glu Ser Ser Gly Gln Pro Glu Asn Asn Tyr Tyr Thr Thr Pro Pro
385                 390                 395                 400

Met Leu Asp Ser Asp Gly Ser Phe Ser Leu Val Ser Trp Leu Asn Val
                405                 410                 415

Asp Lys Ser Arg Trp Gln Gln Gly Asn Ile Phe Ser Cys Ser Val Met
            420                 425                 430

His Glu Ala Leu His Asn Arg Phe Thr Gln Lys Ser Leu Ser Leu Ser
        435                 440                 445

Pro Gly Lys
    450
```

<210> SEQ ID NO 74
<211> LENGTH: 214
<212> TYPE: PRT
<213> ORGANISM: Artificial Sequence
<220> FEATURE:
<223> OTHER INFORMATION: SEQ ID NO: 74 9G7 bestfit LC

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Ile Thr Ser
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Ile Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 75
<211> LENGTH: 450
<212> TYPE: PRT
<213> ORGANISM: Artificial Sequence
<220> FEATURE:
<223> OTHER INFORMATION: SEQ ID NO: 75 9G7 best framework G65S HC

<400> SEQUENCE: 75

```
Glu Val Gln Leu Val Glu Ser Gly Gly Gly Leu Val Gln Pro Gly Gly
1               5                   10                  15

Ser Leu Arg Leu Ser Cys Ala Phe Ser Gly Leu Ser Leu Ser Thr Ser
            20                  25                  30

Gly Lys Gly Val Gly Trp Ile Arg Gln Ala Pro Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95
```

```
Cys Ala Arg Ile Glu Leu Gly Arg Ser Tyr Val Met Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Gln Phe Lys Trp Tyr Val Asp Gly Val Glu Val
            275                 280                 285

His Asn Ala Lys Thr Lys Pro Arg Glu Glu Gln Tyr Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Thr Lys Gly Gln Pro Arg Glu Pro Ala Val
            340                 345                 350

Tyr Thr Leu Pro Pro Ser Arg Glu Glu Met Thr Lys Asn Gln Val Lys
                355                 360                 365

Leu Val Cys Leu Val Thr Gly Phe Tyr Pro Ser Asp Ile Ala Val Glu
370                 375                 380

Trp Glu Ser Ser Gly Gln Pro Glu Asn Asn Tyr Tyr Thr Thr Pro Pro
385                 390                 395                 400

Met Leu Asp Ser Asp Gly Ser Phe Ser Leu Val Ser Trp Leu Asn Val
                405                 410                 415

Asp Lys Ser Arg Trp Gln Gln Gly Asn Ile Phe Ser Cys Ser Val Met
            420                 425                 430

His Glu Ala Leu His Asn Arg Phe Thr Gln Lys Ser Leu Ser Leu Ser
                435                 440                 445

Pro Gly
    450

<210> SEQ ID NO 76
<211> LENGTH: 451
<212> TYPE: PRT
<213> ORGANISM: Artificial Sequence
<220> FEATURE:
<223> OTHER INFORMATION: SEQ ID NO: 76 9G7 bestfit G65S HC

<400> SEQUENCE: 76
```

-continued

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Leu Ser Leu Ser Thr Ser
            20                  25                  30

Gly Lys Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Glu Leu Gly Arg Ser Tyr Val Met Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Lys Trp Tyr Val Asp Gly Val Glu Val
            275                 280                 285

His Asn Ala Lys Thr Lys Pro Arg Glu Glu Gln Tyr Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Thr Lys Gly Gln Pro Arg Glu Pro Ala Val
            340                 345                 350

Tyr Thr Leu Pro Pro Ser Arg Glu Glu Met Thr Lys Asn Gln Val Lys
            355                 360                 365

Leu Val Cys Leu Val Thr Gly Phe Tyr Pro Ser Asp Ile Ala Val Glu
    370                 375                 380

Trp Glu Ser Ser Gly Gln Pro Glu Asn Asn Tyr Tyr Thr Thr Pro Pro
385                 390                 395                 400

Met Leu Asp Ser Asp Gly Ser Phe Ser Leu Val Ser Trp Leu Asn Val
                405                 410                 415
```

-continued

Asp Lys Ser Arg Trp Gln Gln Gly Asn Ile Phe Ser Cys Ser Val Met
            420                 425                 430

His Glu Ala Leu His Asn Arg Phe Thr Gln Lys Ser Leu Ser Leu Ser
            435                 440                 445

Pro Gly Lys
    450

<210> SEQ ID NO 77
<211> LENGTH: 214
<212> TYPE: PRT
<213> ORGANISM: Artificial Sequence
<220> FEATURE:
<223> OTHER INFORMATION: SEQ ID NO: 77 9G7 best framework LC

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ile Thr Ser
            20                  25                  30

Val Ala Trp Phe Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Ile Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 78
<211> LENGTH: 447
<212> TYPE: PRT
<213> ORGANISM: Artificial Sequence
<220> FEATURE:
<223> OTHER INFORMATION: SEQ ID NO: 78 767 G65S HC

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Ser Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Arg Thr Gly Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Lys Trp Tyr Val Asp Gly Val Glu Val His Asn Ala
        275                 280                 285

Lys Thr Lys Pro Arg Glu Glu Gln Tyr Asn Ser Thr Phe Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Thr Lys Gly Gln Pro Arg Glu Pro Ala Val Tyr Thr Leu
            340                 345                 350

Pro Pro Ser Arg Glu Glu Met Thr Lys Asn Gln Val Lys Leu Val Cys
        355                 360                 365

Leu Val Thr Gly Phe Tyr Pro Ser Asp Ile Ala Val Glu Trp Glu Ser
370                 375                 380

Ser Gly Gln Pro Glu Asn Asn Tyr Tyr Thr Thr Pro Pro Met Leu Asp
385                 390                 395                 400

Ser Asp Gly Ser Phe Ser Leu Val Ser Trp Leu Asn Val Asp Lys Ser
                405                 410                 415

Arg Trp Gln Gln Gly Asn Ile Phe Ser Cys Ser Val Met His Glu Ala
            420                 425                 430

Leu His Asn Arg Phe Thr Gln Lys Ser Leu Ser Leu Ser Pro Gly
        435                 440                 445

<210> SEQ ID NO 79
<211> LENGTH: 449

```
<212> TYPE: PRT
<213> ORGANISM: Artificial Sequence
<220> FEATURE:
<223> OTHER INFORMATION: SEQ ID NO: 79 OKT3 humanized heavy chain with
      VH domain

<400> SEQUENCE: 79
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Gly |
| Ser | Leu | Arg | Leu | Ser | Cys | Ala | Ala | Ser | Gly | Tyr | Thr | Phe | Thr | Arg |
| | | | 20 | | | | | 25 | | | | | 30 | |
| Tyr |
| Thr | Ile | His | Trp | Val | Arg | Gln | Ala | Pro | Gly | Lys | Gly | Leu | Glu | Trp |
| | | | 35 | | | | | 40 | | | | | 45 | |
| Val |
| Ala | Tyr | Ile | Asn | Pro | Ser | Arg | Gly | Tyr | Thr | Arg | Tyr | Ala | Asp | Ser |
| | 50 | | | | | 55 | | | | | 60 | | | |
| Val |
| Lys | Gly | Arg | Phe | Thr | Ile | Ser | Ala | Asp | Thr | Ser | Lys | Asn | Thr | Ala |
| 65 | | | | | 70 | | | | | 75 | | | | | 80 |
| Tyr |
| Leu | Gln | Met | Asn | Ser | Leu | Arg | Ala | Glu | Asp | Thr | Ala | Val | Tyr | Tyr |
| | | | | 85 | | | | | 90 | | | | | 95 |
| Cys |
| Ala | Arg | Tyr | Tyr | Asp | Asp | His | Tyr | Cys | Leu | Asp | Tyr | Trp | Gly | Gln |
| | | | | 100 | | | | | 105 | | | | | 110 |
| Gly |
| Thr | Leu | Val | Thr | Val | Ser | Ser | Ala | Ser | Thr | Lys | Gly | Pro | Ser | Val |
| | | | 115 | | | | | 120 | | | | | 125 | |
| Phe |
| Pro | Leu | Ala | Pro | Ser | Ser | Lys | Ser | Thr | Ser | Gly | Gly | Thr | Ala | Ala |
| | 130 | | | | | 135 | | | | | 140 | | | |
| Leu |
| Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp |
| Asn | Ser | Gly | Ala | Leu | Thr | Ser | Gly | Val | His | Thr | Phe | Pro | Ala | Val |
| | | | | 165 | | | | | 170 | | | | | 175 |
| Leu |
| Gln | Ser | Ser | Gly | Leu | Tyr | Ser | Leu | Ser | Ser | Val | Val | Thr | Val | Pro |
| | | | 180 | | | | | 185 | | | | | 190 | |
| Ser |
| Ser | Ser | Leu | Gly | Thr | Gln | Thr | Tyr | Ile | Cys | Asn | Val | Asn | His | Lys |
| | | | 195 | | | | | 200 | | | | | 205 | |
| Pro |
| Ser | Asn | Thr | Lys | Val | Asp | Lys | Lys | Val | Glu | Pro | Lys | Ser | Cys | Asp |
| | 210 | | | | | 215 | | | | | 220 | | | |
| Lys |
| Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro |
| Ser | Val | Phe | Leu | Phe | Pro | Pro | Lys | Pro | Lys | Asp | Thr | Leu | Met | Ile |
| | | | | 245 | | | | | 250 | | | | | 255 |
| Ser |
| Arg | Thr | Pro | Glu | Val | Thr | Cys | Val | Val | Val | Asp | Val | Ser | His | Glu |
| | | | 260 | | | | | 265 | | | | | 270 | |
| Asp |
| Pro | Glu | Val | Lys | Phe | Asn | Trp | Tyr | Val | Asp | Gly | Val | Glu | Val | His |
| | 275 | | | | | 280 | | | | | 285 | | | |
| Asn |
| Ala | Lys | Thr | Lys | Pro | Arg | Glu | Glu | Gln | Tyr | Asn | Ser | Thr | Tyr | Arg |
| 290 | | | | | 295 | | | | | 300 | | | | | |
| Val |
| Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu |
| Tyr | Lys | Cys | Lys | Val | Ser | Asn | Lys | Ala | Leu | Pro | Ala | Pro | Ile | Glu |
| | | | | 325 | | | | | 330 | | | | | 335 |
| Lys |
| Thr | Ile | Ser | Lys | Ala | Lys | Gly | Gln | Pro | Arg | Glu | Pro | Gln | Val | Tyr |
| | | | 340 | | | | | 345 | | | | | 350 | |
| Thr |
| Leu | Pro | Pro | Ser | Arg | Asp | Glu | Leu | Thr | Lys | Asn | Gln | Val | Ser | Leu |
| | 355 | | | | | 360 | | | | | 365 | | | |
| Thr |
| Cys | Leu | Val | Lys | Gly | Phe | Tyr | Pro | Ser | Asp | Ile | Ala | Val | Glu | Trp |
| 370 | | | | | 375 | | | | | 380 | | | | | |
| Glu |

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 80
<211> LENGTH: 449
<212> TYPE: PRT
<213> ORGANISM: Artificial Sequence
<220> FEATURE:
<223> OTHER INFORMATION: SEQ ID NO: 80 OKT3 humanized heavy chain with
      VH1 domain

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Ile His Trp Val Arg Gln Ala Pro Gly Lys Gly Leu Glu Trp Val
        35                  40                  45

Gly Tyr Ile Asn Pro Ser Arg Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Lys

<210> SEQ ID NO 81
<211> LENGTH: 449
<212> TYPE: PRT
<213> ORGANISM: Artificial Sequence
<220> FEATURE:
<223> OTHER INFORMATION: SEQ ID NO: 81 OKT3 humanized heavy chain with
      VH2 domain

<400> SEQUENCE: 81

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Arg Tyr
                20                  25                  30
Thr Met His Trp Val Arg Gln Ala Pro Gly Lys Gly Leu Glu Trp Val
            35                  40                  45
Gly Tyr Ile Asn Pro Ser Arg Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Tyr Tyr Asp Asp His Tyr Cys Leu Asp Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
```

Ser Ser Leu Gly Thr Gln Thr Tyr Ile Cys Asn Val Asn His Lys Pro
            195                 200                 205

Ser Asn Thr Lys Val Asp Lys Val Glu Pro Lys Ser Cys Asp Lys
210                 215                 220

Thr His Thr Cys Pro Pro Cys Pro Ala Pro Glu Leu Leu Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 82
<211> LENGTH: 449
<212> TYPE: PRT
<213> ORGANISM: Artificial Sequence
<220> FEATURE:
<223> OTHER INFORMATION: SEQ ID NO: 82 OKT3 humanized heavy chain with
      VH3 domain

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Ile His Trp Val Arg Gln Ala Pro Gly Lys Gly Leu Glu Trp Val
        35                  40                  45

Gly Tyr Ile Asn Pro Ser Arg Gly Tyr Thr Arg Tyr Ala Asp Ser Val
    50                  55                  60

Lys Gly Arg Phe Thr Ile Ser Thr Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 83
<211> LENGTH: 449
<212> TYPE: PRT
<213> ORGANISM: Artificial Sequence
<220> FEATURE:
<223> OTHER INFORMATION: SEQ ID NO: 83 OKT3 humanized heavy chain with
      VH4 domain

<400> SEQUENCE: 83

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Thr Phe Thr Arg Tyr
             20                  25                  30

Thr Met His Trp Val Arg Gln Ala Pro Gly Lys Gly Leu Glu Trp Val
             35                  40                  45

Gly Tyr Ile Asn Pro Ser Arg Gly Tyr Thr Arg Tyr Ala Asp Ser Val
         50                  55                  60

Lys Gly Arg Phe Thr Ile Ser Thr Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 84
<211> LENGTH: 449
<212> TYPE: PRT
<213> ORGANISM: Artificial Sequence
<220> FEATURE:
<223> OTHER INFORMATION: SEQ ID NO: 84 OKT3 humanized heavy chain with
      VH5 domain

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Val
        35                  40                  45

Gly Tyr Ile Asn Pro Ser Arg Gly Tyr Thr Arg Tyr Ala Asp Ser Val
50                  55                  60

Lys Gly Arg Phe Thr Leu Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 85
<211> LENGTH: 449
<212> TYPE: PRT
<213> ORGANISM: Artificial Sequence
<220> FEATURE:
<223> OTHER INFORMATION: SEQ ID NO: 85 OKT3 humanized heavy chain with
      VH6 domain

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Arg Tyr Ala Asp Ser Val
    50                  55                  60

Lys Gly Arg Phe Thr Leu Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
        245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 86
<211> LENGTH: 449
<212> TYPE: PRT
<213> ORGANISM: Artificial Sequence
<220> FEATURE:
<223> OTHER INFORMATION: SEQ ID NO: 86 OKT3 humanized heavy chain with
      VH7 domain

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Val
        35                  40                  45

Gly Tyr Ile Asn Pro Ser Arg Gly Tyr Thr Asn Tyr Ala Asp Ser Val
    50                  55                  60

Lys Gly Arg Phe Thr Leu Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
        180                 185                 190
Ser Ser Leu Gly Thr Gln Thr Tyr Ile Cys Asn Val Asn His Lys Pro
    195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
        260                 265                 270
Pro Glu Val Lys Phe Asn Trp Tyr Val Asp Gly Val Glu Val His Asn
    275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
        340                 345                 350
Leu Pro Pro Ser Arg Asp Glu Leu Thr Lys Asn Gln Val Ser Leu Thr
    355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
        420                 425                 430
Ala Leu His Asn His Tyr Thr Gln Lys Ser Leu Ser Leu Ser Pro Gly
    435                 440                 445
Lys

<210> SEQ ID NO 87
<211> LENGTH: 449
<212> TYPE: PRT
<213> ORGANISM: Artificial Sequence
<220> FEATURE:
<223> OTHER INFORMATION: SEQ ID NO: 87 OKT3 humanized heavy chain with
      VH8 domain

<400> SEQUENCE: 87

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Arg Tyr
            20                  25                  30
```

```
Thr Met His Trp Val Arg Gln Ala Pro Gly Lys Gly Leu Glu Trp Ile
         35                  40                  45

Gly Tyr Ile Asn Pro Ser Arg Gly Tyr Thr Tyr Tyr Ala Asp Ser Val
 50                  55                  60

Lys Gly Arg Phe Thr Leu Ser Thr Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Tyr Asp Asp His Tyr Cys Leu Asp Tyr Trp Gly Gln Gly
             100                 105                 110

Thr Leu Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
 130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Asp Lys
 210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
 290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Asp Glu Leu Thr Lys Asn Gln Val Ser Leu Thr
         355                 360                 365

Cys Leu Val Lys Gly Phe Tyr Pro Ser Asp Ile Ala Val Glu Trp Glu
 370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
         435                 440                 445

Lys
```

<210> SEQ ID NO 88
<211> LENGTH: 449
<212> TYPE: PRT
<213> ORGANISM: Artificial Sequence
<220> FEATURE:
<223> OTHER INFORMATION: SEQ ID NO: 88 OKT3 humanized heavy chain with VH9 domain

<400> SEQUENCE: 88

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Tyr Tyr Ala Asp Ser Val
    50                  55                  60

Lys Ser Arg Phe Thr Leu Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
            355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 89
<211> LENGTH: 449
<212> TYPE: PRT
<213> ORGANISM: Artificial Sequence
<220> FEATURE:
<223> OTHER INFORMATION: SEQ ID NO: 89 OKT3 humanized heavy chain with
      VH10 domain

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
                20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Tyr Tyr Ala Asp Ser Val
        50                  55                  60

Lys Ser Arg Ala Thr Leu Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
                260                 265                 270
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 90
<211> LENGTH: 449
<212> TYPE: PRT
<213> ORGANISM: Artificial Sequence
<220> FEATURE:
<223> OTHER INFORMATION: SEQ ID NO: 90 OKT3 humanized heavy chain with
      VH11 domain

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Tyr Tyr Ala Asp Ser Val
    50                  55                  60

Lys Gly Arg Phe Thr Leu Ser Thr Asp Lys Ser Lys Asn Thr Ala Tyr
65                  70                  75                  80

Leu Gln Met Ser Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 91
<211> LENGTH: 455
<212> TYPE: PRT
<213> ORGANISM: Artificial Sequence
<220> FEATURE:
<223> OTHER INFORMATION: SEQ ID NO: 91 SP34 humanized heavy chain with
    VH1 domain

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
```

```
                65                  70                  75                  80
Leu Tyr Leu Gln Met Asn Ser Leu Arg Ala Glu Asp Thr Ala Val Tyr
                    85                  90                  95

Tyr Cys Val Arg His Gly Asn Phe Gly Asn Ser Tyr Val Ser Trp Phe
                    100                 105                 110

Ala Tyr Trp Gly Gln Gly Thr Thr Val Thr Val Ser Ser Ala Ser Thr
                    115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                    180                 185                 190

Val Val Thr Val Pro Ser Ser Ser Leu Gly Thr Gln Thr Tyr Ile Cys
                    195                 200                 205

Asn Val Asn His Lys Pro Ser Asn Thr Lys Val Asp Lys Lys Val Glu
                    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                    245                 250                 255

Asp Thr Leu Met Ile Ser Arg Thr Pro Glu Val Thr Cys Val Val Val
                    260                 265                 270

Asp Val Ser His Glu Asp Pro Glu Val Lys Phe Asn Trp Tyr Val Asp
                    275                 280                 285

Gly Val Glu Val His Asn Ala Lys Thr Lys Pro Arg Glu Glu Gln Tyr
                    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                    325                 330                 335

Pro Ala Pro Ile Glu Lys Thr Ile Ser Lys Ala Lys Gly Gln Pro Arg
                    340                 345                 350

Glu Pro Gln Val Tyr Thr Leu Pro Pro Ser Arg Asp Glu Leu Thr Lys
                    355                 360                 365

Asn Gln Val Ser Leu Thr Cys Leu Val Lys Gly Phe Tyr Pro Ser Asp
                    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
                    420                 425                 430

Cys Ser Val Met His Glu Ala Leu His Asn His Tyr Thr Gln Lys Ser
                    435                 440                 445

Leu Ser Leu Ser Pro Gly Lys
            450                 455

<210> SEQ ID NO 92
<211> LENGTH: 455
<212> TYPE: PRT
<213> ORGANISM: Artificial Sequence
```

```
<220> FEATURE:
<223> OTHER INFORMATION: SEQ ID NO: 92 SP34 humanized heavy chain with
      VH2 domain

<400> SEQUENCE: 92
```

| | | | | | | | | | | | | | | |
|---|---|---|---|---|---|---|---|---|---|---|---|---|---|---|
| Glu | Val | Gln | Leu | Val | Glu | Ser | Gly | Gly | Leu | Val | Gln | Pro | Gly | Gly |
| 1 | | | | 5 | | | | | 10 | | | | | 15 |
| Ser | Leu | Arg | Leu | Ser | Cys | Ala | Ala | Ser | Gly | Phe | Thr | Phe | Asn | Thr | Tyr |
| | | 20 | | | | 25 | | | | | 30 | | | | |
| Ala | Met | Asn | Trp | Val | Arg | Gln | Ala | Pro | Gly | Lys | Gly | Leu | Glu | Trp | Val |
| | 35 | | | | | 40 | | | | | 45 | | | | |
| Ala | Arg | Ile | Arg | Ser | Lys | Tyr | Asn | Asn | Tyr | Ala | Thr | Tyr | Tyr | Ala | Asp |
| 50 | | | | | 55 | | | | | 60 | | | | | |
| Ser | Val | Lys | Ser | Arg | Phe | Thr | Ile | Ser | Arg | Asp | Asp | Ser | Lys | Asn | Thr |
| 65 | | | | | 70 | | | | | 75 | | | | | 80 |
| Leu | Tyr | Leu | Gln | Met | Asn | Ser | Leu | Arg | Ala | Glu | Asp | Thr | Ala | Val | Tyr |
| | | | | 85 | | | | | 90 | | | | | 95 | |
| Tyr | Cys | Val | Arg | His | Gly | Asn | Phe | Gly | Asn | Ser | Tyr | Val | Ser | Trp | Phe |
| | | | 100 | | | | | 105 | | | | | 110 | | |
| Ala | Tyr | Trp | Gly | Gln | Gly | Thr | Thr | Val | Thr | Val | Ser | Ser | Ala | Ser | Thr |
| | | 115 | | | | | 120 | | | | | 125 | | | |
| Lys | Gly | Pro | Ser | Val | Phe | Pro | Leu | Ala | Pro | Ser | Ser | Lys | Ser | Thr | Ser |
| 130 | | | | | 135 | | | | | 140 | | | | | |
| Gly | Gly | Thr | Ala | Ala | Leu | Gly | Cys | Leu | Val | Lys | Asp | Tyr | Phe | Pro | Glu |
| 145 | | | | | 150 | | | | | 155 | | | | | 160 |
| Pro | Val | Thr | Val | Ser | Trp | Asn | Ser | Gly | Ala | Leu | Thr | Ser | Gly | Val | His |
| | | | | 165 | | | | | 170 | | | | | 175 | |
| Thr | Phe | Pro | Ala | Val | Leu | Gln | Ser | Ser | Gly | Leu | Tyr | Ser | Leu | Ser | Ser |
| | | | 180 | | | | | 185 | | | | | 190 | | |
| Val | Val | Thr | Val | Pro | Ser | Ser | Ser | Leu | Gly | Thr | Gln | Thr | Tyr | Ile | Cys |
| | | 195 | | | | | 200 | | | | | 205 | | | |
| Asn | Val | Asn | His | Lys | Pro | Ser | Asn | Thr | Lys | Val | Asp | Lys | Lys | Val | Glu |
| | 210 | | | | | 215 | | | | | 220 | | | | |
| Pro | Lys | Ser | Cys | Asp | Lys | Thr | His | Thr | Cys | Pro | Pro | Cys | Pro | Ala | Pro |
| 225 | | | | | 230 | | | | | 235 | | | | | 240 |
| Glu | Leu | Leu | Gly | Gly | Pro | Ser | Val | Phe | Leu | Phe | Pro | Pro | Lys | Pro | Lys |
| | | | | 245 | | | | | 250 | | | | | 255 | |
| Asp | Thr | Leu | Met | Ile | Ser | Arg | Thr | Pro | Glu | Val | Thr | Cys | Val | Val | Val |
| | | | 260 | | | | | 265 | | | | | 270 | | |
| Asp | Val | Ser | His | Glu | Asp | Pro | Glu | Val | Lys | Phe | Asn | Trp | Tyr | Val | Asp |
| | | 275 | | | | | 280 | | | | | 285 | | | |
| Gly | Val | Glu | Val | His | Asn | Ala | Lys | Thr | Lys | Pro | Arg | Glu | Glu | Gln | Tyr |
| | 290 | | | | | 295 | | | | | 300 | | | | |
| Asn | Ser | Thr | Tyr | Arg | Val | Val | Ser | Val | Leu | Thr | Val | Leu | His | Gln | Asp |
| 305 | | | | | 310 | | | | | 315 | | | | | 320 |
| Trp | Leu | Asn | Gly | Lys | Glu | Tyr | Lys | Cys | Lys | Val | Ser | Asn | Lys | Ala | Leu |
| | | | | 325 | | | | | 330 | | | | | 335 | |
| Pro | Ala | Pro | Ile | Glu | Lys | Thr | Ile | Ser | Lys | Ala | Lys | Gly | Gln | Pro | Arg |
| | | | 340 | | | | | 345 | | | | | 350 | | |
| Glu | Pro | Gln | Val | Tyr | Thr | Leu | Pro | Pro | Ser | Arg | Asp | Glu | Leu | Thr | Lys |
| | | 355 | | | | | 360 | | | | | 365 | | | |
| Asn | Gln | Val | Ser | Leu | Thr | Cys | Leu | Val | Lys | Gly | Phe | Tyr | Pro | Ser | Asp |
| | 370 | | | | | 375 | | | | | 380 | | | | |
| Ile | Ala | Val | Glu | Trp | Glu | Ser | Asn | Gly | Gln | Pro | Glu | Asn | Asn | Tyr | Lys |

```
                385                 390                 395                 400
Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
                450                 455

<210> SEQ ID NO 93
<211> LENGTH: 455
<212> TYPE: PRT
<213> ORGANISM: Artificial Sequence
<220> FEATURE:
<223> OTHER INFORMATION: SEQ ID NO: 93 SP34 humanized heavy chain with
      VH3 domain

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285
```

```
Gly Val Glu Val His Asn Ala Lys Thr Lys Pro Arg Glu Glu Gln Tyr
            290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
                340                 345                 350
Glu Pro Gln Val Tyr Thr Leu Pro Pro Ser Arg Asp Glu Leu Thr Lys
            355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
                435                 440                 445
Leu Ser Leu Ser Pro Gly Lys
450                 455

<210> SEQ ID NO 94
<211> LENGTH: 455
<212> TYPE: PRT
<213> ORGANISM: Artificial Sequence
<220> FEATURE:
<223> OTHER INFORMATION: SEQ ID NO: 94 SP34 humanized heavy chain with
      VH4 domain

<400> SEQUENCE: 94

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asn Thr Tyr
                20                  25                  30
Ala Met Asn Trp Val Arg Gln Ala Pro Gly Lys Gly Leu Glu Trp Val
                35                  40                  45
Ala Arg Ile Arg Ser Lys Tyr Asn Asn Tyr Ala Thr Tyr Tyr Ala Asp
            50                  55                  60
Ser Val Lys Ser Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Val Arg His Gly Asn Phe Gly Asn Ser Tyr Val Ser Phe Phe
                100                 105                 110
Ala Tyr Trp Gly Gln Gly Thr Thr Val Thr Val Ser Ser Ala Ser Thr
            115                 120                 125
Lys Gly Pro Ser Val Phe Pro Leu Ala Pro Ser Ser Lys Ser Thr Ser
130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
                180                 185                 190
```

```
Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
            450                 455

<210> SEQ ID NO 95
<211> LENGTH: 455
<212> TYPE: PRT
<213> ORGANISM: Artificial Sequence
<220> FEATURE:
<223> OTHER INFORMATION: SEQ ID NO: 95 SP34 humanized heavy chain with
      VH5 domain

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
```

```
                85                  90                  95
Tyr Cys Val Arg His Gly Asn Phe Gly Asn Ser Tyr Val Ser Tyr Phe
                100                 105                 110
Ala Tyr Trp Gly Gln Gly Thr Thr Val Thr Val Ser Ser Ala Ser Thr
                115                 120                 125
Lys Gly Pro Ser Val Phe Pro Leu Ala Pro Ser Ser Lys Ser Thr Ser
                130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
                180                 185                 190
Val Val Thr Val Pro Ser Ser Leu Gly Thr Gln Thr Tyr Ile Cys
                195                 200                 205
Asn Val Asn His Lys Pro Ser Asn Thr Lys Val Asp Lys Lys Val Glu
                210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
                260                 265                 270
Asp Val Ser His Glu Asp Pro Glu Val Lys Phe Asn Trp Tyr Val Asp
                275                 280                 285
Gly Val Glu Val His Asn Ala Lys Thr Lys Pro Arg Glu Glu Gln Tyr
                290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
                340                 345                 350
Glu Pro Gln Val Tyr Thr Leu Pro Pro Ser Arg Asp Glu Leu Thr Lys
                355                 360                 365
Asn Gln Val Ser Leu Thr Cys Leu Val Lys Gly Phe Tyr Pro Ser Asp
                370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
                435                 440                 445
Leu Ser Leu Ser Pro Gly Lys
                450                 455

<210> SEQ ID NO 96
<211> LENGTH: 213
<212> TYPE: PRT
<213> ORGANISM: Artificial Sequence
<220> FEATURE:
<223> OTHER INFORMATION: SEQ ID NO: 96 OKT3 humanized light chain with
      VL domain
```

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Val
            20                  25                  30

Ala Trp Tyr Gln Gln Lys Pro Gly Lys Ala Pro Lys Leu Leu Ile Tyr
            35                  40                  45

Asp Thr Ser Lys Leu Tyr Ser Gly Val Pro Ser Arg Phe Ser Gly Ser
        50                  55                  60

Arg Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 97
<211> LENGTH: 213
<212> TYPE: PRT
<213> ORGANISM: Artificial Sequence
<220> FEATURE:
<223> OTHER INFORMATION: SEQ ID NO: 97 OKT3 humanized light chain with
      VL1 domain

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Val
            20                  25                  30

Ala Trp Tyr Gln Gln Lys Pro Gly Lys Ala Pro Lys Leu Leu Ile Tyr
            35                  40                  45

Asp Thr Ser Lys Leu Tyr Ser Gly Val Pro Ser Arg Phe Ser Gly Ser
        50                  55                  60

Arg Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

```
Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 98
<211> LENGTH: 213
<212> TYPE: PRT
<213> ORGANISM: Artificial Sequence
<220> FEATURE:
<223> OTHER INFORMATION: SEQ ID NO: 98 OKT3 humanized light chain with
      VL2 domain

<400> SEQUENCE: 98

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Val
            20                  25                  30

Ala Trp Tyr Gln Gln Lys Pro Gly Lys Ala Pro Lys Leu Leu Ile Tyr
        35                  40                  45

Asp Thr Ser Lys Leu Tyr Ser Gly Val Pro Ser Arg Phe Ser Gly Ser
50                  55                  60

Arg Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 99
<211> LENGTH: 213
<212> TYPE: PRT
<213> ORGANISM: Artificial Sequence
<220> FEATURE:
<223> OTHER INFORMATION: SEQ ID NO: 99 OKT3 humanized light chain with
```

VL3 domain

<400> SEQUENCE: 99

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Ser Tyr Val
            20                  25                  30

Ala Trp Tyr Gln Gln Lys Pro Gly Lys Ala Pro Lys Leu Leu Ile Tyr
        35                  40                  45

Asp Thr Ser Lys Leu Tyr Ser Gly Val Pro Ser Arg Phe Ser Gly Ser
        50                  55                  60

Arg Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 100
<211> LENGTH: 213
<212> TYPE: PRT
<213> ORGANISM: Artificial Sequence
<220> FEATURE:
<223> OTHER INFORMATION: SEQ ID NO: 100 OKT3 humanized light chain with VL4 domain

<400> SEQUENCE: 100

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Ser Tyr Val
            20                  25                  30

Ala Trp Tyr Gln Gln Lys Pro Gly Lys Ala Pro Lys Arg Trp Ile Tyr
        35                  40                  45

Asp Thr Ser Lys Leu Tyr Ser Gly Val Pro Ser Arg Phe Ser Gly Ser
        50                  55                  60

Arg Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
```

```
              115                 120                 125
Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                    165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 101
<211> LENGTH: 213
<212> TYPE: PRT
<213> ORGANISM: Artificial Sequence
<220> FEATURE:
<223> OTHER INFORMATION: SEQ ID NO: 101 OKT3 humanized light chain with
      VL5 domain

<400> SEQUENCE: 101

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

Asn Trp Tyr Gln Gln Lys Pro Gly Lys Ala Pro Lys Leu Leu Ile Tyr
        35                  40                  45

Asp Thr Ser Lys Leu Tyr Ser Gly Val Pro Ser Arg Phe Ser Gly Ser
    50                  55                  60

Arg Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                    165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 102
<211> LENGTH: 213
<212> TYPE: PRT
<213> ORGANISM: Artificial Sequence
<220> FEATURE:
```

```
<223> OTHER INFORMATION: SEQ ID NO: 102 OKT3 humanized light chain with
      VL6 domain

<400> SEQUENCE: 102

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Ser Tyr Val
            20                  25                  30

Ala Trp Tyr Gln Gln Lys Pro Gly Lys Ala Pro Lys Arg Trp Ile Tyr
        35                  40                  45

Asp Thr Ser Lys Leu Tyr Ser Gly Val Pro Ser Arg Phe Ser Gly Ser
    50                  55                  60

Arg Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 103
<211> LENGTH: 213
<212> TYPE: PRT
<213> ORGANISM: Artificial Sequence
<220> FEATURE:
<223> OTHER INFORMATION: SEQ ID NO: 103 OKT3 humanized light chain with
      VL7 domain

<400> SEQUENCE: 103

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

Asn Trp Tyr Gln Gln Lys Pro Gly Lys Ala Pro Lys Leu Leu Ile Tyr
        35                  40                  45

Asp Thr Ser Lys Leu Tyr Ser Gly Val Pro Ser Arg Phe Ser Gly Ser
    50                  55                  60

Arg Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Val Glu Ile Lys Arg Thr Val Ala Ala Pro
            100                 105                 110
```

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 104
<211> LENGTH: 213
<212> TYPE: PRT
<213> ORGANISM: Artificial Sequence
<220> FEATURE:
<223> OTHER INFORMATION: SEQ ID NO: 104 OKT3 humanized light chain with
      VL8 domain

<400> SEQUENCE: 104

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Val
            20                  25                  30

Ala Trp Tyr Gln Gln Lys Pro Gly Lys Ala Pro Lys Arg Trp Ile Tyr
        35                  40                  45

Asp Thr Ser Lys Leu Tyr Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 105
<211> LENGTH: 217
<212> TYPE: PRT
<213> ORGANISM: Artificial Sequence
<220> FEATURE:
<223> OTHER INFORMATION: SEQ ID NO: 105 SP34 humanized light chain with
     VL1 domain

<400> SEQUENCE: 105

Glu Ala Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Phe Cys Gln Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 106
<211> LENGTH: 217
<212> TYPE: PRT
<213> ORGANISM: Artificial Sequence
<220> FEATURE:
<223> OTHER INFORMATION: SEQ ID NO: 106 SP34 humanized light chain with
     VL2 domain

<400> SEQUENCE: 106

Glu Ala Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Phe Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 107
<211> LENGTH: 216
<212> TYPE: PRT
<213> ORGANISM: Artificial Sequence
<220> FEATURE:
<223> OTHER INFORMATION: SEQ ID NO: 107 SP34 humanized light chain with
      VL3 domain

<400> SEQUENCE: 107

Glu Ala Val Val Thr Gln Ser Ala Thr Leu Ser Val Ser Pro Gly Glu
1               5                   10                  15

Arg Ala Thr Leu Ser Cys Arg Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Ala Asn Lys Arg Ala Pro Gly Val Pro Ala Arg Phe
    50                  55                  60

Ser Gly Ser Leu Ser Gly Asp Glu Ala Thr Leu Thr Ile Ser Ser Leu
65                  70                  75                  80

Gln Ser Glu Asp Phe Ala Val Tyr Phe Cys Gln Leu Trp Tyr Ser Asn
                85                  90                  95

Leu Trp Val Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 108
<211> LENGTH: 216
<212> TYPE: PRT

<213> ORGANISM: Artificial Sequence
<220> FEATURE:
<223> OTHER INFORMATION: SEQ ID NO: 108 SP34 humanized light chain with VL4 domain

<400> SEQUENCE: 108

Glu Ala Val Val Thr Gln Ser Ala Thr Leu Ser Val Ser Pro Gly Glu
1               5                   10                  15

Arg Ala Thr Leu Ser Cys Arg Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Ala Asn Lys Arg Ala Pro Gly Val Pro Ala Arg Phe
    50                  55                  60

Ser Gly Ser Leu Ser Gly Asp Glu Ala Thr Leu Thr Ile Ser Ser Leu
65                  70                  75                  80

Gln Ser Glu Asp Phe Ala Val Tyr Phe Cys Ala Leu Trp Tyr Ser Asn
                85                  90                  95

Leu Trp Val Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 109
<211> LENGTH: 217
<212> TYPE: PRT
<213> ORGANISM: Artificial Sequence
<220> FEATURE:
<223> OTHER INFORMATION: SEQ ID NO: 109 SP34 humanized light chain with VL5 domain

<400> SEQUENCE: 109

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Phe Cys Ala Leu Trp Tyr Ser
                85                  90                  95

Asn Leu Trp Val Phe Gly Gln Gly Thr Lys Leu Glu Ile Lys Arg Thr

```
            100                 105                 110
Val Ala Ala Pro Ser Val Phe Ile Phe Pro Ser Asp Glu Gln Leu
            115                 120                 125
Lys Ser Gly Thr Ala Ser Val Val Cys Leu Leu Asn Asn Phe Tyr Pro
130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
        210                 215
```

<210> SEQ ID NO 110
<211> LENGTH: 217
<212> TYPE: PRT
<213> ORGANISM: Artificial Sequence
<220> FEATURE:
<223> OTHER INFORMATION: SEQ ID NO: 110 SP34 humanized light chain with VL6 domain

<400> SEQUENCE: 110

```
Glu Ala Val Val Thr Gln Ser Pro Ala Thr Leu Ser Val Ser Pro Gly
1               5                   10                  15
Glu Arg Ala Thr Leu Ser Cys Arg Ser Ser Thr Gly Ala Val Thr Thr
            20                  25                  30
Ser Asn Tyr Ala Asn Trp Val Gln Glu Lys Pro Gly Gln Ala Pro Arg
        35                  40                  45
Gly Leu Ile Gly Gly Ala Asn Lys Arg Ala Pro Gly Val Pro Ala Arg
50                  55                  60
Phe Ser Gly Ser Leu Ser Gly Asp Glu Ala Thr Leu Thr Ile Ser Ser
65                  70                  75                  80
Leu Gln Ser Glu Asp Phe Ala Val Tyr Phe Cys Ala Leu Trp Tyr Ser
                85                  90                  95
Asn Leu Trp Val Phe Gly Gln Gly Thr Lys Leu Glu Ile Lys Arg Thr
            100                 105                 110
Val Ala Ala Pro Ser Val Phe Ile Phe Pro Ser Asp Glu Gln Leu
            115                 120                 125
Lys Ser Gly Thr Ala Ser Val Val Cys Leu Leu Asn Asn Phe Tyr Pro
130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
        210                 215
```

<210> SEQ ID NO 111
<211> LENGTH: 217

```
<212> TYPE: PRT
<213> ORGANISM: Artificial Sequence
<220> FEATURE:
<223> OTHER INFORMATION: SEQ ID NO: 111 SP34 humanized light chain with
      VL7 domain

<400> SEQUENCE: 111
```

| | | | | | | | | | | | | | | | |
|---|---|---|---|---|---|---|---|---|---|---|---|---|---|---|---|
|Glu|Ile|Val|Val|Thr|Gln|Ser|Pro|Ala|Thr|Leu|Ser|Val|Ser|Pro|Gly|
|1| | | |5| | | |10| | | |15| | | |
|Glu|Arg|Ala|Thr|Leu|Ser|Cys|Arg|Ser|Ser|Thr|Gly|Ala|Val|Thr|Thr|
| | | | |20| | | |25| | | |30| | | |
|Ser|Asn|Tyr|Ala|Asn|Trp|Val|Gln|Glu|Lys|Pro|Gly|Gln|Ala|Pro|Arg|
| | | |35| | | |40| | | |45| | | | |
|Gly|Leu|Ile|Gly|Gly|Ala|Asn|Lys|Arg|Ala|Pro|Gly|Val|Pro|Ala|Arg|
| |50| | | | |55| | | | |60| | | | |
|Phe|Ser|Gly|Ser|Leu|Ser|Gly|Asp|Glu|Ala|Thr|Leu|Thr|Ile|Ser|Ser|
|65| | | | |70| | | | |75| | | | |80|
|Leu|Gln|Ser|Glu|Asp|Phe|Ala|Val|Tyr|Phe|Cys|Ala|Leu|Trp|Tyr|Ser|
| | | | |85| | | | |90| | | | |95| |
|Asn|Leu|Trp|Val|Phe|Gly|Gln|Gly|Thr|Lys|Leu|Glu|Ile|Lys|Arg|Thr|
| | | |100| | | | |105| | | | |110| | |
|Val|Ala|Ala|Pro|Ser|Val|Phe|Ile|Phe|Pro|Pro|Ser|Asp|Glu|Gln|Leu|
| | | |115| | | | |120| | | | |125| | |
|Lys|Ser|Gly|Thr|Ala|Ser|Val|Val|Cys|Leu|Leu|Asn|Asn|Phe|Tyr|Pro|
| |130| | | | |135| | | | |140| | | | |
|Arg|Glu|Ala|Lys|Val|Gln|Trp|Lys|Val|Asp|Asn|Ala|Leu|Gln|Ser|Gly|
|145| | | | |150| | | | |155| | | | |160|
|Asn|Ser|Gln|Glu|Ser|Val|Thr|Glu|Gln|Asp|Ser|Lys|Asp|Ser|Thr|Tyr|
| | | | |165| | | | |170| | | | |175| |
|Ser|Leu|Ser|Ser|Thr|Leu|Thr|Leu|Ser|Lys|Ala|Asp|Tyr|Glu|Lys|His|
| | | |180| | | | |185| | | | |190| | |
|Lys|Val|Tyr|Ala|Cys|Glu|Val|Thr|His|Gln|Gly|Leu|Ser|Ser|Pro|Val|
| | |195| | | | |200| | | | |205| | | |
|Thr|Lys|Ser|Phe|Asn|Arg|Gly|Glu|Cys| | | | | | | |
| |210| | | | |215| | | | | | | | | |

```
<210> SEQ ID NO 112
<211> LENGTH: 217
<212> TYPE: PRT
<213> ORGANISM: Artificial Sequence
<220> FEATURE:
<223> OTHER INFORMATION: SEQ ID NO: 112 SP34 humanized light chain with
      VL8 domain

<400> SEQUENCE: 112
```

| | | | | | | | | | | | | | | | |
|---|---|---|---|---|---|---|---|---|---|---|---|---|---|---|---|
|Glu|Ala|Val|Val|Thr|Gln|Ser|Pro|Ala|Thr|Leu|Ser|Val|Ser|Pro|Gly|
|1| | | |5| | | |10| | | |15| | | |
|Glu|Arg|Ala|Thr|Leu|Ser|Cys|Arg|Ser|Ser|Thr|Gly|Ala|Val|Thr|Thr|
| | | | |20| | | |25| | | |30| | | |
|Ser|Asn|Tyr|Ala|Asn|Trp|Val|Gln|Glu|Lys|Pro|Gly|Gln|Ala|Phe|Arg|
| | | |35| | | |40| | | |45| | | | |
|Gly|Leu|Ile|Gly|Gly|Ala|Asn|Lys|Arg|Ala|Pro|Gly|Val|Pro|Ala|Arg|
| |50| | | | |55| | | | |60| | | | |
|Phe|Ser|Gly|Ser|Gly|Ser|Gly|Asp|Glu|Ala|Thr|Leu|Thr|Ile|Ser|Ser|
|65| | | | |70| | | | |75| | | | |80|
|Leu|Gln|Ser|Glu|Asp|Phe|Ala|Val|Tyr|Phe|Cys|Ala|Leu|Trp|Tyr|Ser|
| | | | |85| | | | |90| | | | |95| |

```
Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
            210                 215

<210> SEQ ID NO 113
<211> LENGTH: 217
<212> TYPE: PRT
<213> ORGANISM: Artificial Sequence
<220> FEATURE:
<223> OTHER INFORMATION: SEQ ID NO: 113 SP34 humanized light chain with
      VL9 domain

<400> SEQUENCE: 113

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
            35                  40                  45

Gly Leu Ile Gly Gly Ala Asn Lys Arg Ala Pro Gly Val Pro Ala Arg
        50                  55                  60

Phe Ser Gly Ser Gly Ser Gly Asp Glu Ala Thr Leu Thr Ile Ser Ser
65                  70                  75                  80

Leu Gln Ser Glu Asp Phe Ala Val Tyr Phe Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
            210                 215

<210> SEQ ID NO 114
```

```
<211> LENGTH: 217
<212> TYPE: PRT
<213> ORGANISM: Artificial Sequence
<220> FEATURE:
<223> OTHER INFORMATION: SEQ ID NO: 114 SP34 humanized light chain with
      VL10 domain

<400> SEQUENCE: 114

Glu Ala Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Tyr Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 115
<211> LENGTH: 217
<212> TYPE: PRT
<213> ORGANISM: Artificial Sequence
<220> FEATURE:
<223> OTHER INFORMATION: SEQ ID NO: 115 SP34 humanized light chain with
      VL11 domain

<400> SEQUENCE: 115

Glu Ala Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Gly Ser Gly Thr Glu Ala Thr Leu Thr Ile Ser Ser
65                  70                  75                  80

Leu Gln Ser Glu Asp Phe Ala Val Tyr Phe Cys Ala Leu Trp Tyr Ser
                85                  90                  95
```

```
Asn Leu Trp Val Phe Gly Gln Gly Thr Lys Leu Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 116
<211> LENGTH: 217
<212> TYPE: PRT
<213> ORGANISM: Artificial Sequence
<220> FEATURE:
<223> OTHER INFORMATION: SEQ ID NO: 116 SP34 humanized light chain with
      VL12 domain

<400> SEQUENCE: 116

Glu Ala Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Thr Glu Ala Thr Leu Thr Ile Ser Ser
65                  70                  75                  80

Leu Gln Ser Glu Asp Phe Ala Val Tyr Phe Cys Ala Leu Trp Tyr Ser
                85                  90                  95

Asn Leu Trp Val Phe Gly Gln Gly Thr Lys Leu Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 117
<211> LENGTH: 217
<212> TYPE: PRT
<213> ORGANISM: Artificial Sequence
<220> FEATURE:
<223> OTHER INFORMATION: SEQ ID NO: 117 SP34 humanized light chain with VL13 domain

<400> SEQUENCE: 117

```
Glu Ala Val Val Thr Gln Ser Pro Ala Thr Leu Ser Val Ser Pro Gly
1               5                   10                  15

Glu Arg Ala Thr Leu Ser Cys Arg Ala Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Phe Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 118
<211> LENGTH: 217
<212> TYPE: PRT
<213> ORGANISM: Artificial Sequence
<220> FEATURE:
<223> OTHER INFORMATION: SEQ ID NO: 118 SP34 humanized light chain with VL14 domain

<400> SEQUENCE: 118

```
Glu Ala Val Val Thr Gln Ser Pro Ala Thr Leu Ser Val Ser Pro Gly
1               5                   10                  15

Glu Arg Ala Thr Leu Ser Cys Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Leu Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Phe Cys Ala Leu Trp Tyr Ser
```

```
                    85                  90                  95
Asn Leu Trp Val Phe Gly Gln Gly Thr Lys Leu Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 119
<211> LENGTH: 217
<212> TYPE: PRT
<213> ORGANISM: Artificial Sequence
<220> FEATURE:
<223> OTHER INFORMATION: SEQ ID NO: 119 SP34 humanized light chain with
      VL15 domain

<400> SEQUENCE: 119

Glu Ala Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Gln Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Phe Cys Ala Leu Trp Tyr Ser
                85                  90                  95

Asn Leu Trp Val Phe Gly Gln Gly Thr Lys Leu Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 120
<211> LENGTH: 217
<212> TYPE: PRT
<213> ORGANISM: Artificial Sequence
<220> FEATURE:
<223> OTHER INFORMATION: SEQ ID NO: 120 SP34 humanized light chain with VL16 domain

<400> SEQUENCE: 120

```
Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Thr Glu Ala Thr Leu Thr Ile Ser Ser
65                  70                  75                  80

Leu Gln Ser Glu Asp Phe Ala Val Tyr Phe Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 121
<211> LENGTH: 217
<212> TYPE: PRT
<213> ORGANISM: Artificial Sequence
<220> FEATURE:
<223> OTHER INFORMATION: SEQ ID NO: 121 SP34 humanized light chain with VL17 domain

<400> SEQUENCE: 121

```
Glu Ile Val Val Thr Gln Ser Pro Ala Thr Leu Ser Val Ser Pro Gly
1               5                   10                  15

Glu Arg Ala Thr Leu Ser Cys Arg Ala Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80
```

Leu Gln Ser Glu Asp Phe Ala Val Tyr Phe Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
        210                 215

<210> SEQ ID NO 122
<211> LENGTH: 217
<212> TYPE: PRT
<213> ORGANISM: Artificial Sequence
<220> FEATURE:
<223> OTHER INFORMATION: SEQ ID NO: 122 SP34 humanized light chain with
      VL18 domain

<400> SEQUENCE: 122

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Gln Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Phe Cys Ala Leu Trp Tyr Ser
                85                  90                  95

Asn Leu Trp Val Phe Gly Gly Gly Thr Lys Leu Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
        210                 215

<210> SEQ ID NO 123
<211> LENGTH: 217
<212> TYPE: PRT
<213> ORGANISM: Artificial Sequence
<220> FEATURE:
<223> OTHER INFORMATION: SEQ ID NO: 123 SP34 humanized light chain with
    VL19 domain

<400> SEQUENCE: 123

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Thr Glu Ala Thr Leu Thr Ile Ser Ser
65                  70                  75                  80

Leu Gln Ser Glu Asp Phe Ala Val Tyr Tyr Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 124
<211> LENGTH: 217
<212> TYPE: PRT
<213> ORGANISM: Artificial Sequence
<220> FEATURE:
<223> OTHER INFORMATION: SEQ ID NO: 124 SP34 humanized light chain with
    VL20 domain

<400> SEQUENCE: 124

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Gln Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Thr Glu Ala Thr Leu Thr Ile Ser Ser
65                  70                  75                  80

```
Leu Gln Ser Glu Asp Phe Ala Val Tyr Tyr Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 125
<211> LENGTH: 217
<212> TYPE: PRT
<213> ORGANISM: Artificial Sequence
<220> FEATURE:
<223> OTHER INFORMATION: SEQ ID NO: 125 SP34 humanized light chain with
      VL21 domain

<400> SEQUENCE: 125

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Tyr Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
```

210        215

<210> SEQ ID NO 126
<211> LENGTH: 217
<212> TYPE: PRT
<213> ORGANISM: Artificial Sequence
<220> FEATURE:
<223> OTHER INFORMATION: SEQ ID NO: 126 SP34 humanized light chain with
      VL22 domain

<400> SEQUENCE: 126

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Thr
            20                  25                  30

Ser Asn Tyr Ala Asn Trp Val Gln Gln Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Tyr Cys Ala Leu Trp Tyr Ser
                85                  90                  95

Asn Leu Trp Val Phe Gly Gln Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 127
<211> LENGTH: 218
<212> TYPE: PRT
<213> ORGANISM: Artificial Sequence
<220> FEATURE:
<223> OTHER INFORMATION: SEQ ID NO: 127 SP34 humanized Light chain with
      VL32

<400> SEQUENCE: 127

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Ala
            20                  25                  30

Ala Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser

```
                65                  70                  75                  80
Leu Gln Ser Glu Asp Phe Ala Val Tyr Tyr Cys Ala Leu Phe Tyr Ser
                        85                  90                  95

Asn Leu Trp Val Phe Gly Gln Gly Thr Lys Leu Glu Ile Lys Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                    165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 128
<211> LENGTH: 217
<212> TYPE: PRT
<213> ORGANISM: Artificial Sequence
<220> FEATURE:
<223> OTHER INFORMATION: SEQ ID NO: 128 SP34 humanized Light chain with
      VL65

<400> SEQUENCE: 128

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Glu
                20                  25                  30

Ser Asn Tyr Ala Asn Trp Val Gln Glu Lys Pro Gly Gln Ala Phe Arg
            35                  40                  45

Gly Leu Ile Gly Gly Ala Asn Lys Arg Ala Pro Gly Val Pro Ala Arg
        50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Tyr Cys Ala Leu Phe Tyr Ser
                        85                  90                  95

Asn Thr Trp Val Phe Gly Gln Gly Thr Lys Leu Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                    165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205
```

Thr Lys Ser Phe Asn Arg Gly Glu Cys
    210                 215

<210> SEQ ID NO 129
<211> LENGTH: 216
<212> TYPE: PRT
<213> ORGANISM: Artificial Sequence
<220> FEATURE:
<223> OTHER INFORMATION: SEQ ID NO: 129 SP34 humanized Light chain with
      VL67

<400> SEQUENCE: 129

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Ala
            20                  25                  30

Ala Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Tyr Cys Ala Leu Phe Tyr Ser
                85                  90                  95

Asn Thr Trp Val Phe Gly Gln Gly Thr Lys Leu Glu Ile Lys Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 130
<211> LENGTH: 449
<212> TYPE: PRT
<213> ORGANISM: Artificial Sequence
<220> FEATURE:
<223> OTHER INFORMATION: SEQ ID NO: 130 Chimeric OKT3 heavy chain IgG1

<400> SEQUENCE: 130

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr 65                  70                  75                  80
    Met Gln Leu Ser Ser Leu Thr Ser Glu Asp Ser Ala Val Tyr Tyr Cys
                        85                  90                  95

Ala Arg Tyr Tyr Asp Asp His Tyr Cys Leu Asp Tyr Trp Gly Gln Gly
                    100                 105                 110

Thr Thr Leu Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
    145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
    225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
    305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
    385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 131
<211> LENGTH: 213
<212> TYPE: PRT
<213> ORGANISM: Artificial Sequence
<220> FEATURE:

<223> OTHER INFORMATION: SEQ ID NO: 131 Chimeric OKT3 human kappa light
      chain

<400> SEQUENCE: 131

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 132
<211> LENGTH: 119
<212> TYPE: PRT
<213> ORGANISM: Artificial Sequence
<220> FEATURE:
<223> OTHER INFORMATION: SEQ ID NO: 132 OKT3 humanized VH8 domain

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Tyr Tyr Ala Asp Ser Val
    50                  55                  60

Lys Gly Arg Phe Thr Leu Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser

<210> SEQ ID NO 133
<211> LENGTH: 106
<212> TYPE: PRT
<213> ORGANISM: Artificial Sequence
<220> FEATURE:
<223> OTHER INFORMATION: SEQ ID NO: 133 OKT3 humanized VL8 domain

<400> SEQUENCE: 133

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Val Ser Tyr Val
            20                  25                  30

Ala Trp Tyr Gln Gln Lys Pro Gly Lys Ala Pro Lys Arg Trp Ile Tyr
        35                  40                  45

Asp Thr Ser Lys Leu Tyr Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Val Glu Ile Lys
            100                 105

<210> SEQ ID NO 134
<211> LENGTH: 119
<212> TYPE: PRT
<213> ORGANISM: Artificial Sequence
<220> FEATURE:
<223> OTHER INFORMATION: SEQ ID NO: 134 OKT3 humanized VH11 domain

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Tyr Tyr Ala Asp Ser Val
    50                  55                  60

Lys Gly Arg Phe Thr Leu Ser Thr Asp Lys Ser Lys Asn Thr Ala Tyr
65                  70                  75                  80

Leu Gln Met Ser Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser
        115

<210> SEQ ID NO 135
<211> LENGTH: 245
<212> TYPE: PRT
<213> ORGANISM: Artificial Sequence
<220> FEATURE:
<223> OTHER INFORMATION: SEQ ID NO: 135 scFv fragment humanized OKT3
      VH8-VL4

<400> SEQUENCE: 135

Glu Val Gln Leu Val Glu Ser Gly Gly Gly Leu Val Gln Pro Gly Gly

```
                  1               5                  10                 15
Ser Leu Arg Leu Ser Cys Ala Ala Ser Gly Tyr Thr Phe Thr Arg Tyr
                20                  25                 30

Thr Met His Trp Val Arg Gln Ala Pro Gly Lys Gly Leu Glu Trp Ile
                35                  40                 45

Gly Tyr Ile Asn Pro Ser Arg Gly Tyr Thr Tyr Tyr Ala Asp Ser Val
                50                  55                 60

Lys Gly Arg Phe Thr Leu Ser Thr Asp Lys Ser Lys Asn Thr Ala Tyr
65                  70                  75                 80

Leu Gln Met Asn Ser Leu Arg Ala Glu Asp Thr Ala Val Tyr Tyr Cys
                85                  90                 95

Ala Arg Tyr Tyr Asp Asp His Tyr Cys Leu Asp Tyr Trp Gly Gln Gly
                100                 105                110

Thr Leu Val Thr Val Ser Ser Gly Gly Gly Gly Ser Gly Gly Gly Gly
                115                 120                125

Ser Gly Gly Gly Gly Ser Gly Gly Gly Ala Ser Asp Ile Gln Leu Thr
                130                 135                140

Gln Ser Pro Ser Ser Leu Ser Ala Ser Val Gly Asp Arg Val Thr Ile
145                 150                 155                160

Thr Cys Arg Ala Ser Ser Ser Val Ser Tyr Val Ala Trp Tyr Gln Gln
                165                 170                175

Lys Pro Gly Lys Ala Pro Lys Arg Trp Ile Tyr Asp Thr Ser Lys Leu
                180                 185                190

Tyr Ser Gly Val Pro Ser Arg Phe Ser Gly Ser Arg Ser Gly Thr Asp
                195                 200                205

Tyr Thr Leu Thr Ile Ser Ser Leu Gln Pro Glu Asp Phe Ala Thr Tyr
                210                 215                220

Tyr Cys Gln Gln Trp Ser Ser Asn Pro Pro Thr Phe Gly Gln Gly Thr
225                 230                 235                240

Lys Val Glu Ile Lys
                245

<210> SEQ ID NO 136
<211> LENGTH: 245
<212> TYPE: PRT
<213> ORGANISM: Artificial Sequence
<220> FEATURE:
<223> OTHER INFORMATION: SEQ ID NO: 136 scFv fragment  humanized OKT3
      VH8-VL8

<400> SEQUENCE: 136

Glu Val Gln Leu Val Glu Ser Gly Gly Gly Leu Val Gln Pro Gly Gly
1               5                   10                 15

Ser Leu Arg Leu Ser Cys Ala Ala Ser Gly Tyr Thr Phe Thr Arg Tyr
                20                  25                 30

Thr Met His Trp Val Arg Gln Ala Pro Gly Lys Gly Leu Glu Trp Ile
                35                  40                 45

Gly Tyr Ile Asn Pro Ser Arg Gly Tyr Thr Tyr Tyr Ala Asp Ser Val
                50                  55                 60

Lys Gly Arg Phe Thr Leu Ser Thr Asp Lys Ser Lys Asn Thr Ala Tyr
65                  70                  75                 80

Leu Gln Met Asn Ser Leu Arg Ala Glu Asp Thr Ala Val Tyr Tyr Cys
                85                  90                 95

Ala Arg Tyr Tyr Asp Asp His Tyr Cys Leu Asp Tyr Trp Gly Gln Gly
                100                 105                110
```

```
Thr Leu Val Thr Val Ser Ser Gly Gly Gly Ser Gly Gly Gly
            115                 120                 125

Ser Gly Gly Gly Gly Ser Gly Gly Gly Ala Ser Asp Ile Gln Leu Thr
        130                 135                 140

Gln Ser Pro Ser Ser Leu Ser Ala Ser Val Gly Asp Arg Val Thr Ile
145                 150                 155                 160

Thr Cys Arg Ala Ser Ser Ser Val Ser Tyr Val Ala Trp Tyr Gln Gln
                165                 170                 175

Lys Pro Gly Lys Ala Pro Lys Arg Trp Ile Tyr Asp Thr Ser Lys Leu
            180                 185                 190

Tyr Ser Gly Val Pro Ser Arg Phe Ser Gly Ser Gly Ser Gly Thr Asp
        195                 200                 205

Tyr Thr Leu Thr Ile Ser Ser Leu Gln Pro Glu Asp Phe Ala Thr Tyr
    210                 215                 220

Tyr Cys Gln Gln Trp Ser Ser Asn Pro Pro Thr Phe Gly Gln Gly Thr
225                 230                 235                 240

Lys Val Glu Ile Lys
            245

<210> SEQ ID NO 137
<211> LENGTH: 455
<212> TYPE: PRT
<213> ORGANISM: Artificial Sequence
<220> FEATURE:
<223> OTHER INFORMATION: SEQ ID NO: 137 Chimeric SP34 heavy chain IgG1

<400> SEQUENCE: 137

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220
```

-continued

```
Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 138
<211> LENGTH: 216
<212> TYPE: PRT
<213> ORGANISM: Artificial Sequence
<220> FEATURE:
<223> OTHER INFORMATION: SEQ ID NO: 138 Chimeric SP34 light chain
      (mouse V lambda - human lambda constant domain)

<400> SEQUENCE: 138

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Arg Thr Val
            100                 105                 110

Ala Ala Pro Ser Val Phe Ile Phe Pro Pro Ser Asp Glu Gln Leu Lys
        115                 120                 125
```

```
Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 139
<211> LENGTH: 482
<212> TYPE: PRT
<213> ORGANISM: Artificial Sequence
<220> FEATURE:
<223> OTHER INFORMATION: SEQ ID NO: 139 scFv fragment  humanized SP34
      VH1-VL26 - human IgG1 Fc fusion

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser Gly Gly Gly
        115                 120                 125

Gly Ser Gly Gly Gly Gly Ser Gly Gly Gly Gly Ser Glu Ile Val Val
    130                 135                 140

Thr Gln Ser Pro Ala Thr Leu Ser Val Ser Pro Gly Glu Arg Ala Thr
145                 150                 155                 160

Leu Ser Cys Arg Ser Ser Thr Gly Ala Val Thr Ala Ala Asn Tyr Ala
                165                 170                 175

Asn Trp Val Gln Glu Lys Pro Gly Gln Ala Phe Arg Gly Leu Ile Gly
            180                 185                 190

Gly Ala Asn Lys Arg Ala Pro Gly Val Pro Ala Arg Phe Ser Gly Ser
        195                 200                 205

Leu Ser Gly Asp Glu Ala Thr Leu Thr Ile Ser Ser Leu Gln Ser Glu
    210                 215                 220

Asp Phe Ala Val Tyr Tyr Cys Ala Leu Trp Tyr Ser Asn Leu Trp Val
225                 230                 235                 240

Phe Gly Gln Gly Thr Lys Leu Glu Ile Lys Gly Gly Gly Gly Thr Asp
                245                 250                 255

Lys Thr His Thr Cys Pro Pro Cys Pro Ala Pro Glu Leu Leu Gly Gly
```

```
                260             265             270
Pro Ser Val Phe Leu Phe Pro Lys Pro Lys Asp Thr Leu Met Ile
        275             280             285
Ser Arg Thr Pro Glu Val Thr Cys Val Val Val Asp Val Ser His Glu
    290             295             300
Asp Pro Glu Val Lys Phe Asn Trp Tyr Val Asp Gly Val Glu Val His
305             310             315             320
Asn Ala Lys Thr Lys Pro Arg Glu Glu Gln Tyr Asn Ser Thr Tyr Arg
            325             330             335
Val Val Ser Val Leu Thr Val Leu His Gln Asp Trp Leu Asn Gly Lys
        340             345             350
Glu Tyr Lys Cys Lys Val Ser Asn Lys Ala Leu Pro Ala Pro Ile Glu
    355             360             365
Lys Thr Ile Ser Lys Ala Lys Gly Gln Pro Arg Glu Pro Gln Val Tyr
    370             375             380
Thr Leu Pro Pro Ser Arg Asp Glu Leu Thr Lys Asn Gln Val Ser Leu
385             390             395             400
Thr Cys Leu Val Lys Gly Phe Tyr Pro Ser Asp Ile Ala Val Glu Trp
            405             410             415
Glu Ser Asn Gly Gln Pro Glu Asn Asn Tyr Lys Thr Thr Pro Pro Val
        420             425             430
Leu Asp Ser Asp Gly Ser Phe Phe Leu Tyr Ser Lys Leu Thr Val Asp
    435             440             445
Lys Ser Arg Trp Gln Gln Gly Asn Val Phe Ser Cys Ser Val Met His
    450             455             460
Glu Ala Leu His Asn His Tyr Thr Gln Lys Ser Leu Ser Leu Ser Pro
465             470             475             480
Gly Lys

<210> SEQ ID NO 140
<211> LENGTH: 482
<212> TYPE: PRT
<213> ORGANISM: Artificial Sequence
<220> FEATURE:
<223> OTHER INFORMATION: SEQ ID NO: 140 scFv fragment  humanized SP34
      VH1-VL34 - human IgG1 Fc fusion

<400> SEQUENCE: 140

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asn Thr Tyr
            20                  25                  30
Ala Met Asn Trp Val Arg Gln Ala Pro Gly Lys Gly Leu Glu Trp Val
        35                  40                  45
Ala Arg Ile Arg Ser Lys Tyr Asn Asn Tyr Ala Thr Tyr Tyr Ala Asp
    50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
            85                  90                  95
Tyr Cys Val Arg His Gly Asn Phe Gly Asn Ser Tyr Val Ser Trp Phe
            100                 105                 110
Ala Tyr Trp Gly Gln Gly Thr Thr Val Thr Val Ser Ser Gly Gly Gly
        115                 120                 125
Gly Ser Gly Gly Gly Gly Ser Gly Gly Gly Gly Ser Glu Ile Val Val
```

```
                130             135             140
Thr Gln Ser Pro Ala Thr Leu Ser Val Ser Pro Gly Glu Arg Ala Thr
145                 150                 155                 160

Leu Ser Cys Arg Ser Ser Thr Gly Ala Val Thr Ala Ala Asn Tyr Ala
                165                 170                 175

Asn Trp Val Gln Glu Lys Pro Gly Gln Ala Phe Arg Gly Leu Ile Gly
            180                 185                 190

Gly Ala Asn Lys Arg Ala Pro Gly Val Pro Ala Arg Phe Ser Gly Ser
        195                 200                 205

Leu Ser Gly Asp Glu Ala Thr Leu Thr Ile Ser Ser Leu Gln Ser Glu
    210                 215                 220

Asp Phe Ala Val Tyr Tyr Cys Ala Leu Phe Tyr Ser Asn Ala Trp Val
225                 230                 235                 240

Phe Gly Gln Gly Thr Lys Leu Glu Ile Lys Gly Gly Gly Gly Thr Asp
                245                 250                 255

Lys Thr His Thr Cys Pro Pro Cys Pro Ala Pro Glu Leu Leu Gly Gly
                260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
        450                 455                 460

Glu Ala Leu His Asn His Tyr Thr Gln Lys Ser Leu Ser Leu Ser Pro
465                 470                 475                 480

Gly Lys

<210> SEQ ID NO 141
<211> LENGTH: 449
<212> TYPE: PRT
<213> ORGANISM: Artificial Sequence
<220> FEATURE:
<223> OTHER INFORMATION: SEQ ID NO: 141 humanized HB-7 best-fit heavy
      chain

<400> SEQUENCE: 141

Gln Val Gln Leu Gln Glu Ser Gly Pro Gly Leu Val Lys Pro Ser Glu
```

-continued

```
1               5                    10                   15
Thr Leu Ser Leu Thr Cys Thr Val Ser Gly Phe Ser Leu Ile Ser Tyr
                20                   25                   30

Gly Val His Trp Val Arg Gln Pro Gly Lys Gly Leu Glu Trp Leu
                35                   40                   45

Gly Val Ile Trp Arg Gly Gly Ser Thr Asp Tyr Asn Ala Ala Phe Met
                50                   55                   60

Ser Arg Leu Thr Ile Ser Lys Asp Asn Ser Lys Asn Gln Val Ser Leu
65                   70                   75                   80

Lys Leu Ser Ser Val Thr Ala Ala Asp Thr Ala Val Tyr Phe Cys Ala
                85                   90                   95

Lys Thr Leu Ile Thr Thr Gly Tyr Ala Met Asp Tyr Trp Gly Gln Gly
                100                  105                  110

Thr Leu Val Thr Val Ser Ala Ser Thr Lys Gly Pro Ser Val Phe
                115                  120                  125

Pro Leu Ala Pro Ser Ser Lys Ser Thr Ser Gly Gly Thr Ala Ala Leu
                130                  135                  140

Gly Cys Leu Val Lys Asp Tyr Phe Pro Glu Pro Val Thr Val Ser Trp
145                  150                  155                  160

Asn Ser Gly Ala Leu Thr Ser Gly Val His Thr Phe Pro Ala Val Leu
                165                  170                  175

Gln Ser Ser Gly Leu Tyr Ser Leu Ser Ser Val Val Thr Val Pro Ser
                180                  185                  190

Ser Ser Leu Gly Thr Gln Thr Tyr Ile Cys Asn Val Asn His Lys Pro
                195                  200                  205

Ser Asn Thr Lys Val Asp Lys Lys Val Glu Pro Lys Ser Cys Asp Lys
210                  215                  220

Thr His Thr Cys Pro Pro Cys Pro Ala Pro Glu Leu Leu Gly Gly Pro
225                  230                  235                  240

Ser Val Phe Leu Phe Pro Pro Lys Pro Lys Asp Thr Leu Met Ile Ser
                245                  250                  255

Arg Thr Pro Glu Val Thr Cys Val Val Val Asp Val Ser His Glu Asp
                260                  265                  270

Pro Glu Val Lys Phe Asn Trp Tyr Val Asp Gly Val Glu Val His Asn
                275                  280                  285

Ala Lys Thr Lys Pro Arg Glu Glu Gln Tyr Asn Ser Thr Tyr Arg Val
                290                  295                  300

Val Ser Val Leu Thr Val Leu His Gln Asp Trp Leu Asn Gly Lys Glu
305                  310                  315                  320

Tyr Lys Cys Lys Val Ser Asn Lys Ala Leu Pro Ala Pro Ile Glu Lys
                325                  330                  335

Thr Ile Ser Lys Ala Lys Gly Gln Pro Arg Glu Pro Gln Val Tyr Thr
                340                  345                  350

Leu Pro Pro Ser Arg Asp Glu Leu Thr Lys Asn Gln Val Ser Leu Thr
                355                  360                  365

Cys Leu Val Lys Gly Phe Tyr Pro Ser Asp Ile Ala Val Glu Trp Glu
                370                  375                  380

Ser Asn Gly Gln Pro Glu Asn Asn Tyr Lys Thr Thr Pro Pro Val Leu
385                  390                  395                  400

Asp Ser Asp Gly Ser Phe Phe Leu Tyr Ser Lys Leu Thr Val Asp Lys
                405                  410                  415

Ser Arg Trp Gln Gln Gly Asn Val Phe Ser Cys Ser Val Met His Glu
                420                  425                  430
```

```
Ala Leu His Asn His Tyr Thr Gln Lys Ser Leu Ser Leu Ser Pro Gly
        435                 440                 445

Lys

<210> SEQ ID NO 142
<211> LENGTH: 213
<212> TYPE: PRT
<213> ORGANISM: Artificial Sequence
<220> FEATURE:
<223> OTHER INFORMATION: SEQ ID NO: 142 Humanized HB-7 best-fit light
      chain

<400> SEQUENCE: 142

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Asp Ile Tyr Asn Arg
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
50                  55                  60

Ser Gly Ser Gly Lys Asp Tyr Thr Leu Thr Ile Ser Ser Leu Gln Pro
65                  70                  75                  80

Glu Asp Phe Ala Thr Tyr Tyr Cys Gln Gln Tyr Trp Ser Thr Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 143
<211> LENGTH: 449
<212> TYPE: PRT
<213> ORGANISM: Artificial Sequence
<220> FEATURE:
<223> OTHER INFORMATION: SEQ ID NO: 143 Chimeric HB-7 heavy chain IgG1

<400> SEQUENCE: 143

Lys Val Gln Leu Gln Glu Ser Gly Pro Ser Leu Val Gln Pro Ser Gln
1               5                   10                  15

Arg Leu Ser Ile Thr Cys Thr Val Ser Gly Phe Ser Leu Ile Ser Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
```

50                  55                  60
Ser Arg Leu Ser Ile Thr Lys Asp Asn Ser Lys Ser Gln Val Phe Phe
 65                  70                  75                  80

Lys Met Asn Ser Leu Gln Ala Asp Asp Thr Ala Ile Tyr Phe Cys Ala
                 85                  90                  95

Lys Thr Leu Ile Thr Thr Gly Tyr Ala Met Asp Tyr Trp Gly Gln Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 144
<211> LENGTH: 213

```
<212> TYPE: PRT
<213> ORGANISM: Artificial Sequence
<220> FEATURE:
<223> OTHER INFORMATION: SEQ ID NO: 144 Chimeric HB-7 human kappa light
      chain

<400> SEQUENCE: 144

Asp Ile Glu Leu Thr Gln Ser Pro Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 145
<211> LENGTH: 451
<212> TYPE: PRT
<213> ORGANISM: Artificial Sequence
<220> FEATURE:
<223> OTHER INFORMATION: SEQ ID NO: 145 Humanized 9G7 best-fit heavy
      chain

<400> SEQUENCE: 145

Gln Val Thr Leu Lys Glu Ser Gly Pro Thr Leu Val Lys Pro Thr Gln
1               5                   10                  15

Thr Leu Thr Leu Thr Cys Thr Phe Ser Gly Leu Ser Leu Ser Thr Ser
            20                  25                  30

Gly Lys Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95
```

Cys Ala Arg Ile Glu Leu Gly Arg Ser Tyr Val Met Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 146
<211> LENGTH: 214
<212> TYPE: PRT
<213> ORGANISM: Artificial Sequence
<220> FEATURE:
<223> OTHER INFORMATION: SEQ ID NO: 146 Humanized 9G7 best-fit first
      prototype light chain

<400> SEQUENCE: 146

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Ile Thr Ser
            20                  25                  30

Val Ala Trp Phe Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Ile Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 147
<211> LENGTH: 451
<212> TYPE: PRT
<213> ORGANISM: Artificial Sequence
<220> FEATURE:
<223> OTHER INFORMATION: SEQ ID NO: 147 Chimeric 9G7 heavy chain IgG1

<400> SEQUENCE: 147

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Leu Ser Leu Ser Thr Ser
            20                  25                  30

Gly Lys Gly Val Gly Trp Ile Arg Gln Pro Ser Gly Lys Gly Leu Glu
            35                  40                  45

Trp Leu Ala His Ile Trp Trp Asp Asp Lys Arg Tyr Asn Pro Ala
50                  55                  60

Leu Lys Ser Arg Leu Thr Ile Ser Lys Asp Thr Ser Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Glu Leu Gly Arg Ser Tyr Val Met Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 148
<211> LENGTH: 214
<212> TYPE: PRT
<213> ORGANISM: Artificial Sequence
<220> FEATURE:
<223> OTHER INFORMATION: SEQ ID NO: 148 Chimeric 9G7 human kappa light
      chain

<400> SEQUENCE: 148

Asp Ile Val Met Thr Gln Ser His Lys Phe Met Ser Thr Ser Val Gly
1               5                   10                  15

Asp Arg Val Ser Ile Ser Cys Lys Ala Ser Gln Asp Val Ile Thr Ser
            20                  25                  30

Val Ala Trp Phe Gln Gln Lys Pro Gly Gln Ser Pro Lys Leu Leu Ile

```
                35                  40                  45
Tyr Ser Ala Ser Tyr Arg Tyr Thr Gly Val Pro Asp Arg Phe Thr Gly
 50                  55                  60
Ser Gly Ser Gly Thr Asp Phe Thr Phe Thr Ile Ser Ser Val Gln Ala
 65                  70                  75                  80
Glu Asp Leu Ala Val Tyr Tyr Cys Gln Gln His Tyr Thr Ile Pro Leu
                 85                  90                  95
Thr Phe Gly Ala Gly Thr Lys Leu Glu Leu Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
                130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys
                210
```

<210> SEQ ID NO 149
<211> LENGTH: 451
<212> TYPE: PRT
<213> ORGANISM: Artificial Sequence
<220> FEATURE:
<223> OTHER INFORMATION: SEQ ID NO: 149 Humanized 9G7 best-framework heavy chain

<400> SEQUENCE: 149

```
Glu Val Gln Leu Val Glu Ser Gly Gly Gly Leu Val Gln Pro Gly Gly
 1                   5                  10                  15
Ser Leu Arg Leu Ser Cys Ala Phe Ser Gly Leu Ser Leu Ser Thr Ser
                 20                  25                  30
Gly Lys Gly Val Gly Trp Ile Arg Gln Ala Pro Gly Lys Gly Leu Glu
                 35                  40                  45
Trp Leu Ala His Ile Trp Trp Asp Asp Lys Arg Tyr Asn Pro Ala
 50                  55                  60
Leu Lys Ser Arg Leu Thr Ile Ser Lys Asp Thr Ser Lys Asn Thr Val
 65                  70                  75                  80
Tyr Leu Gln Met Asn Ser Leu Arg Ala Glu Asp Thr Ala Val Tyr Tyr
                 85                  90                  95
Cys Ala Arg Ile Glu Leu Gly Arg Ser Tyr Val Met Asp Tyr Trp Gly
                100                 105                 110
Gln Gly Thr Leu Val Thr Val Ser Ala Ser Thr Lys Gly Pro Ser
                115                 120                 125
Val Phe Pro Leu Ala Pro Ser Ser Lys Ser Thr Ser Gly Gly Thr Ala
                130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
```

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 150
<211> LENGTH: 214
<212> TYPE: PRT
<213> ORGANISM: Artificial Sequence
<220> FEATURE:
<223> OTHER INFORMATION: SEQ ID NO: 150 Humanized 9G7 best-framework
      light chain

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ile Thr Ser
            20                  25                  30

Val Ala Trp Phe Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln His Tyr Thr Ile Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 151
<211> LENGTH: 448
<212> TYPE: PRT
<213> ORGANISM: Artificial Sequence
<220> FEATURE:
<223> OTHER INFORMATION: SEQ ID NO: 151 Human 767 heavy chain

<400> SEQUENCE: 151

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Arg Thr Gly Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 152
<211> LENGTH: 218
<212> TYPE: PRT
<213> ORGANISM: Artificial Sequence
<220> FEATURE:
<223> OTHER INFORMATION: SEQ ID NO: 152 Human 767 light chain

<400> SEQUENCE: 152

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Thr Asn
            20                  25                  30

Tyr Val Tyr Trp Tyr Gln Gln Leu Pro Gly Thr Ala Pro Lys Leu Leu
        35                  40                  45

Ile Tyr Arg Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Arg
                85                  90                  95

Ser Gly Val Tyr Ala Phe Gly Thr Gly Thr Lys Val Thr Val Leu Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 153
<211> LENGTH: 449
<212> TYPE: PRT
<213> ORGANISM: Artificial Sequence
<220> FEATURE:
<223> OTHER INFORMATION: SEQ ID NO: 153 BEAT CD38-HB7 bestfit

<400> SEQUENCE: 153

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Ser Tyr
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Lys Thr Leu Ile Thr Thr Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Ala Val Tyr Thr
            340                 345                 350

Leu Pro Pro Ser Arg Asp Glu Leu Thr Lys Asn Gln Val Lys Leu Val
        355                 360                 365

Cys Leu Val Thr Gly Phe Tyr Pro Ser Asp Ile Ala Val Glu Trp Glu
    370                 375                 380

Ser Asn Gly Gln Pro Glu Asn Asn Tyr Tyr Thr Thr Pro Pro Val Leu
385                 390                 395                 400

Asp Ser Asp Gly Ser Phe Ser Leu Val Ser Trp Leu Asn Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 154
<211> LENGTH: 477
<212> TYPE: PRT
<213> ORGANISM: Artificial Sequence
<220> FEATURE:
<223> OTHER INFORMATION: SEQ ID NO: 154 scfv HC humanized OKT3 with
    N82aS substitution

<400> SEQUENCE: 154

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Tyr Tyr Ala Asp Ser Val
    50                  55                  60

Lys Gly Arg Phe Thr Leu Ser Thr Asp Lys Ser Lys Asn Thr Ala Tyr
65                  70                  75                  80

Leu Gln Met Ser Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Ala Ser Asp Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Ser Ser Val Ser Tyr Val Ala Trp Tyr Gln Gln
                165                 170                 175

Lys Pro Gly Lys Ala Pro Lys Arg Trp Ile Tyr Asp Thr Ser Lys Leu
            180                 185                 190
```

Tyr Ser Gly Val Pro Ser Arg Phe Ser Gly Ser Gly Ser Thr Asp
            195                 200                 205

Tyr Thr Leu Thr Ile Ser Ser Leu Gln Pro Glu Asp Phe Ala Thr Tyr
        210                 215                 220

Tyr Cys Gln Gln Trp Ser Ser Asn Pro Pro Thr Phe Gly Gln Gly Thr
225                 230                 235                 240

Lys Val Glu Ile Lys Gly Gly Gly Thr Asp Lys Thr His Thr Cys
            245                 250                 255

Pro Pro Cys Pro Ala Pro Glu Ala Ala Gly Gly Pro Ser Val Phe Leu
            260                 265                 270

Phe Pro Pro Lys Pro Lys Asp Thr Leu Met Ile Ser Arg Thr Pro Glu
            275                 280                 285

Val Thr Cys Val Val Val Asp Val Ser His Glu Asp Pro Glu Val Gln
        290                 295                 300

Phe Lys Trp Tyr Val Asp Gly Val Glu Val His Asn Ala Lys Thr Lys
305                 310                 315                 320

Pro Arg Glu Glu Gln Tyr Asn Ser Thr Phe Arg Val Val Ser Val Leu
            325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Thr Lys Gly Gln Pro Arg Glu Pro Glu Val Ala Thr Phe Pro Pro Ser
370                 375                 380

Arg Glu Glu Met Thr Lys Asn Gln Val Thr Leu Val Cys Leu Val Thr
385                 390                 395                 400

Gly Phe Tyr Pro Ser Asp Ile Ala Val Glu Trp Glu Ser Ser Gly Gln
            405                 410                 415

Pro Glu Asn Asn Tyr Asn Thr Asp Pro Pro Leu Leu Glu Ser Asp Gly
            420                 425                 430

Ser Phe Ala Leu Ser Ser Arg Leu Arg Val Asp Lys Ser Arg Trp Gln
        435                 440                 445

Gln Gly Asn Ile Phe Ser Cys Ser Val Met His Glu Ala Leu His Asn
            450                 455                 460

Arg Phe Thr Gln Lys Ser Leu Ser Leu Ser Pro Gly Lys
465                 470                 475

<210> SEQ ID NO 155
<211> LENGTH: 482
<212> TYPE: PRT
<213> ORGANISM: Artificial Sequence
<220> FEATURE:
<223> OTHER INFORMATION: SEQ ID NO: 155 scFv heavy chain(CD3 epsilon
      arm - humanized OKT3 with G65S substitution

<400> SEQUENCE: 155

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr

```
                65                  70                  75                  80
Ala Tyr Leu Gln Met Asn Asn Leu Lys Thr Glu Asp Thr Ala Val Tyr
                            85                  90                  95

Tyr Cys Val Arg His Gly Asn Phe Gly Asn Ser Tyr Ile Ser Tyr Trp
                        100                 105                 110

Ala Tyr Trp Gly Gln Gly Thr Leu Val Thr Val Ser Ser Gly Gly Gly
                    115                 120                 125

Gly Ser Gly Gly Gly Gly Ser Gly Gly Gly Ser Gln Thr Val Val
                130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                        165                 170                 175

Trp Val Gln Gln Lys Pro Gly Gln Ala Pro Arg Gly Leu Ile Gly Gly
                    180                 185                 190

Thr Lys Phe Leu Ala Pro Gly Thr Pro Ala Arg Phe Ser Gly Ser Leu
                195                 200                 205

Leu Gly Gly Lys Ala Ala Leu Thr Leu Ser Gly Val Gln Pro Glu Asp
            210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Gly Gly Gly Gly Thr Asp
                245                 250                 255

Lys Thr His Thr Cys Pro Pro Cys Pro Ala Pro Glu Ala Ala Gly Gly
                260                 265                 270

Pro Ser Val Phe Leu Phe Pro Pro Lys Pro Lys Asp Thr Leu Met Ile
                275                 280                 285

Ser Arg Thr Pro Glu Val Thr Cys Val Val Val Asp Val Ser His Glu
            290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                    325                 330                 335

Val Val Ser Val Leu Thr Val Leu His Gln Asp Trp Leu Asn Gly Lys
                340                 345                 350

Glu Tyr Lys Cys Lys Val Ser Asn Lys Ala Leu Pro Ala Pro Ile Glu
            355                 360                 365

Lys Thr Ile Ser Lys Ala Lys Gly Gln Pro Arg Glu Pro Gln Val Ala
        370                 375                 380

Thr Phe Pro Pro Ser Arg Asp Glu Leu Thr Lys Asn Gln Val Thr Leu
385                 390                 395                 400

Val Cys Leu Val Thr Gly Phe Tyr Pro Ser Asp Ile Ala Val Glu Trp
                    405                 410                 415

Glu Ser Asn Gly Gln Pro Glu Asn Asn Tyr Lys Thr Asp Pro Pro Leu
                420                 425                 430

Leu Glu Ser Gln Gly Ser Phe Ala Leu Ser Ser Arg Leu Arg Val Asp
            435                 440                 445

Lys Ser Arg Trp Gln Gln Gly Asn Val Phe Ser Cys Ser Val Met His
        450                 455                 460

Glu Ala Leu His Asn His Tyr Thr Gln Lys Ser Leu Ser Leu Ser Pro
465                 470                 475                 480

Gly Lys
```

<210> SEQ ID NO 156
<211> LENGTH: 451
<212> TYPE: PRT
<213> ORGANISM: Artificial Sequence
<220> FEATURE:
<223> OTHER INFORMATION: SEQ ID NO: 156 9G7 FAB heavy chain (anti-CD38 FAB arm with G65S substitution BTA33 FTOLALA)

<400> SEQUENCE: 156

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Leu Ser Leu Ser Thr Ser
            20                  25                  30

Gly Lys Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Glu Leu Gly Arg Ser Tyr Val Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Lys Trp Tyr Val Asp Gly Val Glu Val
        275                 280                 285

His Asn Ala Lys Thr Lys Pro Arg Glu Glu Gln Tyr Asn Ser Thr Phe
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Thr Lys Gly Gln Pro Arg Glu Pro Ala Val
            340                 345                 350

Tyr Thr Leu Pro Pro Ser Arg Glu Glu Met Thr Lys Asn Gln Val Lys
        355                 360                 365
```

```
Leu Val Cys Leu Val Thr Gly Phe Tyr Pro Ser Asp Ile Ala Val Glu
        370                 375                 380

Trp Glu Ser Ser Gly Gln Pro Glu Asn Asn Tyr Tyr Thr Thr Pro Pro
385                 390                 395                 400

Met Leu Asp Ser Asp Gly Ser Phe Ser Leu Val Ser Trp Leu Asn Val
            405                 410                 415

Asp Lys Ser Arg Trp Gln Gln Gly Asn Ile Phe Ser Cys Ser Val Met
            420                 425                 430

His Glu Ala Leu His Asn Arg Phe Thr Gln Lys Ser Leu Ser Leu Ser
            435                 440                 445

Pro Gly Lys
        450

<210> SEQ ID NO 157
<211> LENGTH: 482
<212> TYPE: PRT
<213> ORGANISM: Artificial Sequence
<220> FEATURE:
<223> OTHER INFORMATION: SEQ ID NO: 157 CD3(SP34) antibody scFv heavy
      chain (CD3 arm - humanized SP34 VH/VL domains fromWO2008/119565

<400> SEQUENCE: 157

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Gly Gly Gly Gly Thr Asp
                245                 250                 255

Lys Thr His Thr Cys Pro Pro Cys Pro Ala Pro Glu Ala Ala Gly Gly
```

```
                  260                 265                 270
Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
        290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
        340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Ala
        370                 375                 380

Thr Phe Pro Pro Ser Arg Asp Glu Leu Thr Lys Asn Gln Val Thr Leu
385                 390                 395                 400

Val Cys Leu Val Thr Gly Phe Tyr Pro Ser Asp Ile Ala Val Glu Trp
                405                 410                 415

Glu Ser Asn Gly Gln Pro Glu Asn Asn Tyr Lys Thr Asp Pro Pro Leu
                420                 425                 430

Leu Glu Ser Gln Gly Ser Phe Ala Leu Ser Ser Arg Leu Arg Val Asp
                435                 440                 445

Lys Ser Arg Trp Gln Gln Gly Asn Val Phe Ser Cys Ser Val Met His
        450                 455                 460

Glu Ala Leu His Asn His Tyr Thr Gln Lys Ser Leu Ser Leu Ser Pro
465                 470                 475                 480

Gly Lys

<210> SEQ ID NO 158
<211> LENGTH: 482
<212> TYPE: PRT
<213> ORGANISM: Artificial Sequence
<220> FEATURE:
<223> OTHER INFORMATION: SEQ ID NO: 158 scFv heavy chain (CD3 arm -
      humanized SP34 VH5/VL32)
<220> FEATURE:
<221> NAME/KEY: misc_feature
<222> LOCATION: (213)..(213)
<223> OTHER INFORMATION: Xaa can be any naturally occurring amino acid

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110
```

Ala Tyr Trp Gly Gln Gly Thr Thr Val Thr Val Ser Ser Gly Gly
            115                 120                 125

Gly Ser Gly Gly Gly Ser Gly Gly Gly Ser Glu Ile Val Val
        130                 135                 140

Thr Gln Ser Pro Ala Thr Leu Ser Val Ser Pro Gly Glu Arg Ala Thr
145                 150                 155                 160

Leu Ser Cys Arg Ser Ser Thr Gly Ala Val Thr Thr Ser Asn Tyr Ala
                165                 170                 175

Asn Trp Val Gln Glu Lys Pro Gly Gln Ala Phe Arg Gly Leu Ile Gly
            180                 185                 190

Gly Ala Asn Lys Arg Ala Pro Gly Val Pro Ala Arg Phe Ser Gly Ser
        195                 200                 205

Leu Ser Gly Asp Xaa Ala Thr Leu Thr Ile Ser Ser Leu Gln Ser Glu
210                 215                 220

Asp Phe Ala Val Tyr Tyr Cys Ala Leu Trp Tyr Ser Asn Leu Trp Val
225                 230                 235                 240

Phe Gly Gln Gly Thr Lys Leu Glu Ile Lys Gly Gly Gly Gly Thr Asp
            245                 250                 255

Lys Thr His Thr Cys Pro Pro Cys Pro Ala Pro Glu Ala Ala Gly Gly
        260                 265                 270

Pro Ser Val Phe Leu Phe Pro Pro Lys Pro Lys Asp Thr Leu Met Ile
    275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
            325                 330                 335

Val Val Ser Val Leu Thr Val Leu His Gln Asp Trp Leu Asn Gly Lys
        340                 345                 350

Glu Tyr Lys Cys Lys Val Ser Asn Lys Ala Leu Pro Ala Pro Ile Glu
    355                 360                 365

Lys Thr Ile Ser Lys Ala Lys Gly Gln Pro Arg Glu Pro Glu Val Ala
370                 375                 380

Thr Phe Pro Pro Ser Arg Asp Glu Leu Thr Lys Asn Gln Val Thr Leu
385                 390                 395                 400

Val Cys Leu Val Thr Gly Phe Tyr Pro Ser Asp Ile Ala Val Glu Trp
            405                 410                 415

Glu Ser Asn Gly Gln Pro Glu Asn Asn Tyr Lys Thr Asp Pro Pro Leu
        420                 425                 430

Leu Glu Ser Gln Gly Ser Phe Ala Leu Ser Ser Arg Leu Arg Val Asp
    435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys

<210> SEQ ID NO 159
<211> LENGTH: 482
<212> TYPE: PRT
<213> ORGANISM: Artificial Sequence
<220> FEATURE:
<223> OTHER INFORMATION: SEQ ID NO: 159 scFv heavy chain SP34 (anti-CD3
      epsilon arm BT11 LALA D401Q

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser Gly Gly Gly
        115                 120                 125

Gly Ser Gly Gly Gly Gly Ser Gly Gly Gly Gly Ser Glu Ile Val Val
130                 135                 140

Thr Gln Ser Pro Ala Thr Leu Ser Val Ser Pro Gly Glu Arg Ala Thr
145                 150                 155                 160

Leu Ser Cys Arg Ser Ser Thr Gly Ala Val Thr Glu Ser Asn Tyr Ala
            165                 170                 175

Asn Trp Val Gln Glu Lys Pro Gly Gln Ala Phe Arg Gly Leu Ile Gly
        180                 185                 190

Gly Ala Asn Lys Arg Ala Pro Gly Val Pro Ala Arg Phe Ser Gly Ser
    195                 200                 205

Leu Ser Gly Asp Glu Ala Thr Leu Thr Ile Ser Ser Leu Gln Ser Glu
210                 215                 220

Asp Phe Ala Val Tyr Tyr Cys Ala Leu Phe Tyr Ser Asn Thr Trp Val
225                 230                 235                 240

Phe Gly Gln Gly Thr Lys Leu Glu Ile Lys Gly Gly Gly Gly Thr Asp
            245                 250                 255

Lys Thr His Thr Cys Pro Pro Cys Pro Ala Pro Glu Ala Ala Gly Gly
        260                 265                 270

Pro Ser Val Phe Leu Phe Pro Pro Lys Pro Lys Asp Thr Leu Met Ile
    275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
            325                 330                 335

Val Val Ser Val Leu Thr Val Leu His Gln Asp Trp Leu Asn Gly Lys
        340                 345                 350

Glu Tyr Lys Cys Lys Val Ser Asn Lys Ala Leu Pro Ala Pro Ile Glu
    355                 360                 365

Lys Thr Ile Ser Lys Ala Lys Gly Gln Pro Arg Glu Pro Glu Val Ala
    370                 375                 380

Thr Phe Pro Pro Ser Arg Asp Glu Leu Thr Lys Asn Gln Val Thr Leu
385                 390                 395                 400

Val Cys Leu Val Thr Gly Phe Tyr Pro Ser Asp Ile Ala Val Glu Trp

```
                    405                 410                 415
Glu Ser Asn Gly Gln Pro Glu Asn Asn Tyr Lys Thr Asp Pro Pro Leu
            420                 425                 430

Leu Glu Ser Gln Gly Ser Phe Ala Leu Ser Ser Arg Leu Arg Val Asp
                435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys

<210> SEQ ID NO 160
<211> LENGTH: 227
<212> TYPE: PRT
<213> ORGANISM: Artificial Sequence
<220> FEATURE:
<223> OTHER INFORMATION: SEQ ID NO: 160 BTB IgG1_hinge-CH2-CH3: BTB11
      LALA D401Q

<400> SEQUENCE: 160

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Ala Thr Phe Pro Pro Ser Arg Asp Glu Leu Thr Lys Asn Gln Val Thr
    130                 135                 140

Leu Val Cys Leu Val Thr Gly Phe Tyr Pro Ser Asp Ile Ala Val Glu
145                 150                 155                 160

Trp Glu Ser Asn Gly Gln Pro Glu Asn Asn Tyr Lys Thr Asp Pro Pro
                165                 170                 175

Leu Leu Glu Ser Gln Gly Ser Phe Ala Leu Ser Ser Arg Leu Arg Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 161
<211> LENGTH: 482
<212> TYPE: PRT
<213> ORGANISM: Artificial Sequence
<220> FEATURE:
<223> OTHER INFORMATION: SEQ ID NO: 161 scFv heavy chain SP34(anti-CD3
``` epsilon arm - with G65S substitution BTB11 LALA D401Q)

<400> SEQUENCE: 161

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser Gly Gly Gly
        115                 120                 125

Gly Ser Gly Gly Gly Gly Ser Gly Gly Gly Gly Ser Glu Ile Val Val
    130                 135                 140

Thr Gln Ser Pro Ala Thr Leu Ser Val Ser Pro Gly Glu Arg Ala Thr
145                 150                 155                 160

Leu Ser Cys Arg Ser Ser Thr Gly Ala Val Thr Glu Ser Asn Tyr Ala
                165                 170                 175

Asn Trp Val Gln Glu Lys Pro Gly Gln Ala Phe Arg Gly Leu Ile Gly
            180                 185                 190

Gly Ala Asn Lys Arg Ala Pro Gly Val Pro Ala Arg Phe Ser Gly Ser
        195                 200                 205

Leu Ser Gly Asp Glu Ala Thr Leu Thr Ile Ser Ser Leu Gln Ser Glu
    210                 215                 220

Asp Phe Ala Val Tyr Tyr Cys Ala Leu Phe Tyr Ser Asn Thr Trp Val
225                 230                 235                 240

Phe Gly Gln Gly Thr Lys Leu Glu Ile Lys Gly Gly Gly Gly Thr Asp
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Glu Val Ala
    370                 375                 380

Thr Phe Pro Pro Ser Arg Asp Glu Leu Thr Lys Asn Gln Val Thr Leu
385                 390                 395                 400

-continued

```
Val Cys Leu Val Thr Gly Phe Tyr Pro Ser Asp Ile Ala Val Glu Trp
                405                 410                 415

Glu Ser Asn Gly Gln Pro Glu Asn Asn Tyr Lys Thr Asp Pro Pro Leu
            420                 425                 430

Leu Glu Ser Gln Gly Ser Phe Ala Leu Ser Ser Arg Leu Arg Val Asp
        435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys

<210> SEQ ID NO 162
<211> LENGTH: 482
<212> TYPE: PRT
<213> ORGANISM: Artificial Sequence
<220> FEATURE:
<223> OTHER INFORMATION: SEQ ID NO: 162 scFv heavy chain SP34 (anti-CD3
      epsilon arm - with G65S substitution BTB11 LALA no D401Q)

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser Gly Gly Gly
        115                 120                 125

Gly Ser Gly Gly Gly Gly Ser Gly Gly Gly Gly Ser Glu Ile Val Val
    130                 135                 140

Thr Gln Ser Pro Ala Thr Leu Ser Val Ser Pro Gly Glu Arg Ala Thr
145                 150                 155                 160

Leu Ser Cys Arg Ser Ser Thr Gly Ala Val Thr Glu Ser Asn Tyr Ala
                165                 170                 175

Asn Trp Val Gln Glu Lys Pro Gly Gln Ala Phe Arg Gly Leu Ile Gly
            180                 185                 190

Gly Ala Asn Lys Arg Ala Pro Gly Val Pro Ala Arg Phe Ser Gly Ser
        195                 200                 205

Leu Ser Gly Asp Glu Ala Thr Leu Thr Ile Ser Ser Leu Gln Ser Glu
    210                 215                 220

Asp Phe Ala Val Tyr Tyr Cys Ala Leu Phe Tyr Ser Asn Thr Trp Val
225                 230                 235                 240

Phe Gly Gln Gly Thr Lys Leu Glu Ile Lys Gly Gly Gly Gly Thr Asp
                245                 250                 255

Lys Thr His Thr Cys Pro Pro Cys Pro Ala Pro Glu Ala Ala Gly Gly
            260                 265                 270
```

-continued

```
Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
        290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Ala
    370                 375                 380

Thr Phe Pro Pro Ser Arg Asp Glu Leu Thr Lys Asn Gln Val Thr Leu
385                 390                 395                 400

Val Cys Leu Val Thr Gly Phe Tyr Pro Ser Asp Ile Ala Val Glu Trp
                405                 410                 415

Glu Ser Asn Gly Gln Pro Glu Asn Asn Tyr Lys Thr Asp Pro Pro Leu
            420                 425                 430

Leu Glu Ser Asp Gly Ser Phe Ala Leu Ser Ser Arg Leu Arg Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys

<210> SEQ ID NO 163
<211> LENGTH: 8
<212> TYPE: PRT
<213> ORGANISM: Artificial Sequence
<220> FEATURE:
<223> OTHER INFORMATION: SEQ ID NO: 163 OKT3 mouse hCDR1

<400> SEQUENCE: 163

Gly Tyr Thr Phe Thr Arg Tyr Thr
1               5

<210> SEQ ID NO 164
<211> LENGTH: 8
<212> TYPE: PRT
<213> ORGANISM: Artificial Sequence
<220> FEATURE:
<223> OTHER INFORMATION: SEQ ID NO: 164 OKT3 mouse hCDR2

<400> SEQUENCE: 164

Ile Asn Pro Ser Arg Gly Tyr Thr
1               5

<210> SEQ ID NO 165
<211> LENGTH: 12
<212> TYPE: PRT
<213> ORGANISM: Artificial Sequence
<220> FEATURE:
<223> OTHER INFORMATION: SEQ ID NO: 165 OKT3 mouse hCDR3

<400> SEQUENCE: 165

Ala Arg Tyr Tyr Asp Asp His Tyr Cys Leu Asp Tyr
1               5                   10
```

<210> SEQ ID NO 166
<211> LENGTH: 5
<212> TYPE: PRT
<213> ORGANISM: Artificial Sequence
<220> FEATURE:
<223> OTHER INFORMATION: SEQ ID NO: 166 OKT3 mouse lCDR1

<400> SEQUENCE: 166

Ser Ser Val Ser Tyr
1               5

<210> SEQ ID NO 167
<211> LENGTH: 3
<212> TYPE: PRT
<213> ORGANISM: Artificial Sequence
<220> FEATURE:
<223> OTHER INFORMATION: SEQ ID NO: 167 OKT3 mouse lCDR2

<400> SEQUENCE: 167

Asp Thr Ser
1

<210> SEQ ID NO 168
<211> LENGTH: 9
<212> TYPE: PRT
<213> ORGANISM: Artificial Sequence
<220> FEATURE:
<223> OTHER INFORMATION: SEQ ID NO: 168 OKT3 mouse lCDR3

<400> SEQUENCE: 168

Gln Gln Trp Ser Ser Asn Pro Pro Thr
1               5

<210> SEQ ID NO 169
<211> LENGTH: 26
<212> TYPE: PRT
<213> ORGANISM: Artificial Sequence
<220> FEATURE:
<223> OTHER INFORMATION: SEQ ID NO: 169 26 residue linker

<400> SEQUENCE: 169

Gly Ser Ala Asp Asp Ala Lys Lys Asp Ala Ala Lys Lys Asp Asp Ala
1               5                   10                  15

Lys Lys Asp Asp Ala Lys Lys Asp Gly Ser
            20                  25

<210> SEQ ID NO 170
<211> LENGTH: 435
<212> TYPE: PRT
<213> ORGANISM: Artificial Sequence
<220> FEATURE:
<223> OTHER INFORMATION: SEQ ID NO: 170 CD3 gamma-epsilon-Fc protein

<400> SEQUENCE: 170

Gln Ser Ile Lys Gly Asn His Leu Val Lys Val Tyr Asp Tyr Gln Glu
1               5                   10                  15

Asp Gly Ser Val Leu Leu Thr Cys Asp Ala Glu Ala Lys Asn Ile Thr
            20                  25                  30

Trp Phe Lys Asp Gly Lys Met Ile Gly Phe Leu Thr Glu Asp Lys Lys
        35                  40                  45

Lys Trp Asn Leu Gly Ser Asn Ala Lys Asp Pro Arg Gly Met Tyr Gln
    50                  55                  60

Cys Lys Gly Ser Gln Asn Lys Ser Lys Pro Leu Gln Val Tyr Tyr Arg

```
                65                  70                  75                  80
        Met Gly Ser Ala Asp Asp Ala Lys Lys Asp Ala Lys Lys Asp Asp
                        85                  90                  95

Ala Lys Lys Asp Asp Ala Lys Lys Asp Gly Ser Gln Asp Gly Asn Glu
                        100                 105                 110

Glu Met Gly Gly Ile Thr Gln Thr Pro Tyr Lys Val Ser Ile Ser Gly
                        115                 120                 125

Thr Thr Val Ile Leu Thr Cys Pro Gln Tyr Pro Gly Ser Glu Ile Leu
                        130                 135                 140

Trp Gln His Asn Asp Lys Asn Ile Gly Gly Asp Glu Asp Asp Lys Asn
        145                 150                 155                 160

Ile Gly Ser Asp Glu Asp His Leu Ser Leu Lys Glu Phe Ser Glu Leu
                        165                 170                 175

Glu Gln Ser Gly Tyr Tyr Val Cys Tyr Pro Arg Gly Ser Lys Pro Glu
                        180                 185                 190

Asp Ala Asn Phe Tyr Leu Tyr Leu Arg Ala Arg Val Gly Gly Gly Gly
                        195                 200                 205

Thr Asp Lys Thr His Thr Cys Pro Pro Cys Pro Ala Pro Glu Leu Leu
                        210                 215                 220

Gly Gly Pro Ser Val Phe Leu Phe Pro Pro Lys Pro Lys Asp Thr Leu
        225                 230                 235                 240

Met Ile Ser Arg Thr Pro Glu Val Thr Cys Val Val Val Asp Val Ser
                        245                 250                 255

His Glu Asp Pro Glu Val Lys Phe Asn Trp Tyr Val Asp Gly Val Glu
                        260                 265                 270

Val His Asn Ala Lys Thr Lys Pro Arg Glu Glu Gln Tyr Asn Ser Thr
                        275                 280                 285

Tyr Arg Val Val Ser Val Leu Thr Val Leu His Gln Asp Trp Leu Asn
                        290                 295                 300

Gly Lys Glu Tyr Lys Cys Lys Val Ser Asn Lys Ala Leu Pro Ala Pro
        305                 310                 315                 320

Ile Glu Lys Thr Ile Ser Lys Ala Lys Gly Gln Pro Arg Glu Pro Gln
                        325                 330                 335

Val Tyr Thr Leu Pro Pro Ser Arg Asp Glu Leu Thr Lys Asn Gln Val
                        340                 345                 350

Ser Leu Thr Cys Leu Val Lys Gly Phe Tyr Pro Ser Asp Ile Ala Val
                        355                 360                 365

Glu Trp Glu Ser Asn Gly Gln Pro Glu Asn Asn Tyr Lys Thr Thr Pro
                        370                 375                 380

Pro Val Leu Asp Ser Asp Gly Ser Phe Phe Leu Tyr Ser Lys Leu Thr
        385                 390                 395                 400

Val Asp Lys Ser Arg Trp Gln Gln Gly Asn Val Phe Ser Cys Ser Val
                        405                 410                 415

Met His Glu Ala Leu His Asn His Tyr Thr Gln Lys Ser Leu Ser Leu
                        420                 425                 430

Ser Pro Gly
                435

<210> SEQ ID NO 171
<211> LENGTH: 26
<212> TYPE: PRT
<213> ORGANISM: Artificial Sequence
<220> FEATURE:
<223> OTHER INFORMATION: SEQ ID NO: 171 Human CD3 epsilon 1-26
```

<400> SEQUENCE: 171

| Gln | Asp | Gly | Asn | Glu | Glu | Met | Gly | Gly | Ile | Thr | Gln | Thr | Pro | Tyr | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Ser | Ile | Ser | Gly | Thr | Thr | Val | Ile | Leu |
|-----|-----|-----|-----|-----|-----|-----|-----|-----|-----|
|     |     |     | 20  |     |     |     |     | 25  |     |

<210> SEQ ID NO 172
<211> LENGTH: 26
<212> TYPE: PRT
<213> ORGANISM: Artificial Sequence
<220> FEATURE:
<223> OTHER INFORMATION: SEQ ID NO: 172 Cynomolgus CD3 epsilon 1-26

<400> SEQUENCE: 172

| Gln | Asp | Gly | Asn | Glu | Glu | Met | Gly | Ser | Ile | Thr | Gln | Thr | Pro | Tyr | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Ser | Ile | Ser | Gly | Thr | Thr | Val | Ile | Leu |
|-----|-----|-----|-----|-----|-----|-----|-----|-----|-----|
|     |     |     | 20  |     |     |     |     | 25  |     |

<210> SEQ ID NO 173
<211> LENGTH: 258
<212> TYPE: PRT
<213> ORGANISM: Artificial Sequence
<220> FEATURE:
<223> OTHER INFORMATION: SEQ ID NO: 173 Human CD3 epsilon 1-26 fc fusion

<400> SEQUENCE: 173

| Gln | Asp | Gly | Asn | Glu | Glu | Met | Gly | Gly | Ile | Thr | Gln | Thr | Pro | Tyr | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Ser | Ile | Ser | Gly | Thr | Thr | Val | Ile | Leu | Gly | Gly | Gly | Gly | Thr | Asp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Lys | Thr | His | Thr | Cys | Pro | Pro | Cys | Pro | Ala | Pro | Glu | Leu | Leu | Gly | Gly |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Pro | Ser | Val | Phe | Leu | Phe | Pro | Pro | Lys | Pro | Lys | Asp | Thr | Leu | Met | Ile |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Ser | Arg | Thr | Pro | Glu | Val | Thr | Cys | Val | Val | Val | Asp | Val | Ser | His | Glu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Asp | Pro | Glu | Val | Lys | Phe | Asn | Trp | Tyr | Val | Asp | Gly | Val | Glu | Val | His |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asn | Ala | Lys | Thr | Lys | Pro | Arg | Glu | Glu | Gln | Tyr | Asn | Ser | Thr | Tyr | Arg |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Val | Val | Ser | Val | Leu | Thr | Val | Leu | His | Gln | Asp | Trp | Leu | Asn | Gly | Lys |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Glu | Tyr | Lys | Cys | Lys | Val | Ser | Asn | Lys | Ala | Leu | Pro | Ala | Pro | Ile | Glu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Lys | Thr | Ile | Ser | Lys | Ala | Lys | Gly | Gln | Pro | Arg | Glu | Pro | Gln | Val | Tyr |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Thr | Leu | Pro | Pro | Ser | Arg | Asp | Glu | Leu | Thr | Lys | Asn | Gln | Val | Ser | Leu |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Thr | Cys | Leu | Val | Lys | Gly | Phe | Tyr | Pro | Ser | Asp | Ile | Ala | Val | Glu | Trp |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Glu | Ser | Asn | Gly | Gln | Pro | Glu | Asn | Asn | Tyr | Lys | Thr | Thr | Pro | Pro | Val |
|-----|-----|-----|-----|-----|-----|-----|-----|-----|-----|-----|-----|-----|-----|-----|-----|
|     | 195 |     |     |     |     | 200 |     |     |     |     | 205 |     |     |     |     |

| Leu | Asp | Ser | Asp | Gly | Ser | Phe | Phe | Leu | Tyr | Ser | Lys | Leu | Thr | Val | Asp |
|-----|-----|-----|-----|-----|-----|-----|-----|-----|-----|-----|-----|-----|-----|-----|-----|
| 210 |     |     |     |     | 215 |     |     |     |     | 220 |     |     |     |     |     |

| Lys | Ser | Arg | Trp | Gln | Gln | Gly | Asn | Val | Phe | Ser | Cys | Ser | Val | Met | His |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

```
Glu Ala Leu His Asn His Tyr Thr Gln Lys Ser Leu Ser Leu Ser Pro
            245                 250                 255

Gly Lys

<210> SEQ ID NO 174
<211> LENGTH: 258
<212> TYPE: PRT
<213> ORGANISM: Artificial Sequence
<220> FEATURE:
<223> OTHER INFORMATION: SEQ ID NO: 174 Cynomolgus CD3 epsilon 1-26 fc
      fusion

<400> SEQUENCE: 174

Gln Asp Gly Asn Glu Glu Met Gly Ser Ile Thr Gln Thr Pro Tyr Gln
1               5                   10                  15

Val Ser Ile Ser Gly Thr Thr Val Ile Leu Gly Gly Gly Gly Thr Asp
            20                  25                  30

Lys Thr His Thr Cys Pro Pro Cys Pro Ala Pro Glu Leu Leu Gly Gly
        35                  40                  45

Pro Ser Val Phe Leu Phe Pro Pro Lys Pro Lys Asp Thr Leu Met Ile
    50                  55                  60

Ser Arg Thr Pro Glu Val Thr Cys Val Val Val Asp Val Ser His Glu
65                  70                  75                  80

Asp Pro Glu Val Lys Phe Asn Trp Tyr Val Asp Gly Val Glu Val His
                85                  90                  95

Asn Ala Lys Thr Lys Pro Arg Glu Glu Gln Tyr Asn Ser Thr Tyr Arg
            100                 105                 110

Val Val Ser Val Leu Thr Val Leu His Gln Asp Trp Leu Asn Gly Lys
        115                 120                 125

Glu Tyr Lys Cys Lys Val Ser Asn Lys Ala Leu Pro Ala Pro Ile Glu
    130                 135                 140

Lys Thr Ile Ser Lys Ala Lys Gly Gln Pro Arg Glu Pro Gln Val Tyr
145                 150                 155                 160

Thr Leu Pro Pro Ser Arg Asp Glu Leu Thr Lys Asn Gln Val Ser Leu
                165                 170                 175

Thr Cys Leu Val Lys Gly Phe Tyr Pro Ser Asp Ile Ala Val Glu Trp
            180                 185                 190

Glu Ser Asn Gly Gln Pro Glu Asn Asn Tyr Lys Thr Thr Pro Pro Val
        195                 200                 205

Leu Asp Ser Asp Gly Ser Phe Phe Leu Tyr Ser Lys Leu Thr Val Asp
    210                 215                 220

Lys Ser Arg Trp Gln Gln Gly Asn Val Phe Ser Cys Ser Val Met His
225                 230                 235                 240

Glu Ala Leu His Asn His Tyr Thr Gln Lys Ser Leu Ser Leu Ser Pro
                245                 250                 255

Gly Lys

<210> SEQ ID NO 175
<211> LENGTH: 264
<212> TYPE: PRT
<213> ORGANISM: Artificial Sequence
<220> FEATURE:
<223> OTHER INFORMATION: SEQ ID NO: 175 human CD38 6-His fusion

<400> SEQUENCE: 175

Val Pro Arg Trp Arg Gln Gln Trp Ser Gly Pro Gly Thr Thr Lys Arg
1               5                   10                  15
```

Phe Pro Glu Thr Val Leu Ala Arg Cys Val Lys Tyr Thr Glu Ile His
                20                  25                  30

Pro Glu Met Arg His Val Asp Cys Gln Ser Val Trp Asp Ala Phe Lys
            35                  40                  45

Gly Ala Phe Ile Ser Lys His Pro Cys Asn Ile Thr Glu Glu Asp Tyr
        50                  55                  60

Gln Pro Leu Met Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
        115                 120                 125

Gln Ser Cys Pro Asp Trp Arg Lys Asp Cys Ser Asn Asn Pro Val Ser
        130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
        210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile His His His His His His
            260

<210> SEQ ID NO 176
<211> LENGTH: 264
<212> TYPE: PRT
<213> ORGANISM: Artificial Sequence
<220> FEATURE:
<223> OTHER INFORMATION: SEQ ID NO: 176 cynomolgus CD38 6-His fusion

<400> SEQUENCE: 176

Val Pro Arg Trp Arg Gln Gln Trp Ser Gly Ser Gly Thr Thr Ser Arg
1               5                   10                  15

Phe Pro Glu Thr Val Leu Ala Arg Cys Val Lys Tyr Thr Glu Val His
                20                  25                  30

Pro Glu Met Arg His Val Asp Cys Gln Ser Val Trp Asp Ala Phe Lys
            35                  40                  45

Gly Ala Phe Ile Ser Lys Tyr Pro Cys Asn Ile Thr Glu Glu Asp Tyr
        50                  55                  60

Gln Pro Leu Val Lys Leu Gly Thr Gln Thr Val Pro Cys Asn Lys Thr
65                  70                  75                  80

Leu Leu Trp Ser Arg Ile Lys Asp Leu Ala His Gln Phe Thr Gln Val
                85                  90                  95

Gln Arg Asp Met Phe Thr Leu Glu Asp Met Leu Leu Gly Tyr Leu Ala
            100                 105                 110

```
Asp Asp Leu Thr Trp Cys Gly Glu Phe Asn Thr Phe Glu Ile Asn Tyr
            115                 120                 125

Gln Ser Cys Pro Asp Trp Arg Lys Asp Cys Ser Asn Asn Pro Val Ser
        130                 135                 140

Val Phe Trp Lys Thr Val Ser Arg Arg Phe Ala Glu Thr Ala Cys Gly
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Ala Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
210                 215                 220

Ser Lys Arg Asn Ile Arg Phe Phe Cys Lys Asn Ile Tyr Arg Pro Asp
225                 230                 235                 240

Lys Phe Leu Gln Cys Val Lys Asn Pro Glu Asp Ser Ser Cys Leu Ser
                245                 250                 255

Gly Ile His His His His His His
            260

<210> SEQ ID NO 177
<211> LENGTH: 451
<212> TYPE: PRT
<213> ORGANISM: Artificial Sequence
<220> FEATURE:
<223> OTHER INFORMATION: SEQ ID NO: 177 Mouse-human 9G7 chimeric BEAT
      heavy chain

<400> SEQUENCE: 177

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Leu Ser Leu Ser Thr Ser
            20                  25                  30

Gly Lys Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Ala Arg Ile Glu Leu Gly Arg Ser Tyr Val Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Ala Val
            340                 345                 350
Tyr Thr Leu Pro Pro Ser Arg Asp Glu Leu Thr Lys Asn Gln Val Lys
        355                 360                 365
Leu Val Cys Leu Val Thr Gly Phe Tyr Pro Ser Asp Ile Ala Val Glu
370                 375                 380
Trp Glu Ser Asn Gly Gln Pro Glu Asn Asn Tyr Tyr Thr Thr Pro Pro
385                 390                 395                 400
Val Leu Asp Ser Asp Gly Ser Phe Ser Leu Val Ser Trp Leu Asn Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 178
<211> LENGTH: 214
<212> TYPE: PRT
<213> ORGANISM: Artificial Sequence
<220> FEATURE:
<223> OTHER INFORMATION: SEQ ID NO: 178 Mouse-human 9G7 chimeric light
      chain

<400> SEQUENCE: 178

Asp Ile Val Met Thr Gln Ser His Lys Phe Met Ser Thr Ser Val Gly
1               5                   10                  15
Asp Arg Val Ser Ile Ser Cys Lys Ala Ser Gln Asp Val Ile Thr Ser
            20                  25                  30
Val Ala Trp Phe Gln Gln Lys Pro Gly Gln Ser Pro Lys Leu Leu Ile
        35                  40                  45
Tyr Ser Ala Ser Tyr Arg Tyr Thr Gly Val Pro Asp Arg Phe Thr Gly
    50                  55                  60
Ser Gly Ser Gly Thr Asp Phe Thr Phe Thr Ile Ser Ser Val Gln Ala
65                  70                  75                  80
Glu Asp Leu Ala Val Tyr Tyr Cys Gln Gln His Tyr Thr Ile Pro Leu
                85                  90                  95
Thr Phe Gly Ala Gly Thr Lys Leu Glu Leu Lys Arg Thr Val Ala Ala
```

```
            100                 105                 110
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 179
<211> LENGTH: 472
<212> TYPE: PRT
<213> ORGANISM: Artificial Sequence
<220> FEATURE:
<223> OTHER INFORMATION: SEQ ID NO: 179 Humanized OKT3 VH11/VL8 scFv
      BEAT heavy chain

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Tyr Ala Asp Ser Val
    50                  55                  60

Lys Gly Arg Phe Thr Leu Ser Thr Asp Lys Ser Lys Asn Thr Ala Tyr
65                  70                  75                  80

Leu Gln Met Ser Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Gln Leu Thr Gln Ser Pro Ser Ser
    130                 135                 140

Leu Ser Ala Ser Val Gly Asp Arg Val Thr Ile Thr Cys Arg Ala Ser
145                 150                 155                 160

Ser Ser Val Ser Tyr Val Ala Trp Tyr Gln Gln Lys Pro Gly Lys Ala
                165                 170                 175

Pro Lys Arg Trp Ile Tyr Asp Thr Ser Lys Leu Tyr Ser Gly Val Pro
            180                 185                 190

Ser Arg Phe Ser Gly Ser Gly Ser Gly Thr Asp Tyr Thr Leu Thr Ile
        195                 200                 205

Ser Ser Leu Gln Pro Glu Asp Phe Ala Thr Tyr Tyr Cys Gln Gln Trp
    210                 215                 220

Ser Ser Asn Pro Pro Thr Phe Gly Gln Gly Thr Lys Val Glu Ile Lys
225                 230                 235                 240
```

```
Gly Gly Gly Gly Thr Asp Lys Thr His Thr Cys Pro Pro Cys Pro Ala
                245                 250                 255

Pro Glu Ala Ala Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Lys Trp Tyr Val
    290                 295                 300

Asp Gly Val Glu Val His Asn Ala Lys Thr Lys Pro Arg Glu Glu Gln
305                 310                 315                 320

Tyr Asn Ser Thr Phe Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Thr Lys Gly Gln Pro
        355                 360                 365

Arg Glu Pro Glu Val Ala Thr Phe Pro Pro Ser Arg Glu Glu Met Thr
    370                 375                 380

Lys Asn Gln Val Thr Leu Val Cys Leu Val Thr Gly Phe Tyr Pro Ser
385                 390                 395                 400

Asp Ile Ala Val Glu Trp Glu Ser Ser Gly Gln Pro Glu Asn Asn Tyr
                405                 410                 415

Asn Thr Asp Pro Pro Leu Leu Glu Ser Asp Gly Ser Phe Ala Leu Ser
            420                 425                 430

Ser Arg Leu Arg Val Asp Lys Ser Arg Trp Gln Gln Gly Asn Ile Phe
        435                 440                 445

Ser Cys Ser Val Met His Glu Ala Leu His Asn Arg Phe Thr Gln Lys
    450                 455                 460

Ser Leu Ser Leu Ser Pro Gly Lys
465                 470

<210> SEQ ID NO 180
<211> LENGTH: 439
<212> TYPE: PRT
<213> ORGANISM: Artificial Sequence
<220> FEATURE:
<223> OTHER INFORMATION: SEQ ID NO: 180 Mouse-human OKT10 chimeric BEAT
      heavy chain

<400> SEQUENCE: 180

Gln Val Glu Leu Val Glu Ser Gly Gly Ser Leu Lys Leu Ser Cys Ala
1               5                   10                  15

Ala Ser Gly Phe Asp Phe Ser Arg Ser Trp Met Asn Trp Val Arg Gln
            20                  25                  30

Ala Pro Gly Lys Gly Leu Glu Trp Ile Gly Glu Ile Asn Pro Asp Ser
        35                  40                  45

Ser Thr Ile Asn Tyr Thr Thr Ser Leu Lys Asp Lys Phe Ile Ile Ser
    50                  55                  60

Arg Asp Asn Ala Lys Asn Thr Leu Tyr Leu Gln Met Thr Lys Val Arg
65                  70                  75                  80

Ser Glu Asp Thr Ala Leu Tyr Tyr Cys Ala Arg Tyr Gly Asn Trp Phe
                85                  90                  95

Pro Tyr Trp Gly Gln Gly Thr Leu Val Thr Val Ser Ser Ala Ser Thr
            100                 105                 110

Lys Gly Pro Ser Val Phe Pro Leu Ala Pro Ser Ser Lys Ser Thr Ser
        115                 120                 125
```

```
Gly Gly Thr Ala Ala Leu Gly Cys Leu Val Lys Asp Tyr Phe Pro Glu
        130             135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
            275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Ala Val Tyr Thr Leu Pro Pro Ser Arg Asp Glu Leu Thr Lys
            340                 345                 350

Asn Gln Val Lys Leu Val Cys Leu Val Thr Gly Phe Tyr Pro Ser Asp
            355                 360                 365

Ile Ala Val Glu Trp Glu Ser Asn Gly Gln Pro Glu Asn Asn Tyr Tyr
            370                 375                 380

Thr Thr Pro Pro Val Leu Asp Ser Asp Gly Ser Phe Ser Leu Val Ser
385                 390                 395                 400

Trp Leu Asn Val Asp Lys Ser Arg Trp Gln Gln Gly Asn Val Phe Ser
                405                 410                 415

Cys Ser Val Met His Glu Ala Leu His Asn His Tyr Thr Gln Lys Ser
                420                 425                 430

Leu Ser Leu Ser Pro Gly Lys
            435

<210> SEQ ID NO 181
<211> LENGTH: 213
<212> TYPE: PRT
<213> ORGANISM: Artificial Sequence
<220> FEATURE:
<223> OTHER INFORMATION: SEQ ID NO: 181 Mouse-human OKT10 chimeric
      light chain

<400> SEQUENCE: 181

Asp Ile Leu Met Thr Gln Ser Gln Lys Ile Met Pro Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
```

```
            35                  40                  45
Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Thr Asn Val Gln Ser
 65                  70                  75                  80

Glu Asp Leu Ala Glu Tyr Phe Cys Gln Gln Tyr Asp Ser Tyr Pro Leu
                 85                  90                  95

Thr Phe Gly Ala Gly Thr Lys Leu Asp Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
    210

<210> SEQ ID NO 182
<211> LENGTH: 242
<212> TYPE: PRT
<213> ORGANISM: Artificial Sequence
<220> FEATURE:
<223> OTHER INFORMATION: SEQ ID NO: 182 F1-Fc fusion

<400> SEQUENCE: 182

Val Pro Arg Trp Arg Gln Gln Trp Ser Gly Pro Gly Thr Ala Ser Asp
 1               5                  10                  15

Lys Thr His Thr Cys Pro Pro Cys Pro Ala Pro Glu Leu Leu Gly Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
 50                  55                  60

Asp Pro Glu Val Lys Phe Asn Trp Tyr Val Asp Gly Val Glu Val His
 65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
```

```
                    180                 185                 190
Leu Asp Ser Asp Gly Ser Phe Phe Leu Tyr Ser Lys Leu Thr Val Asp
            195                 200                 205

Lys Ser Arg Trp Gln Gln Gly Asn Val Phe Ser Cys Val Met His
        210                 215                 220

Glu Ala Leu His Asn His Tyr Thr Gln Lys Ser Leu Ser Leu Ser Pro
225                 230                 235                 240

Gly Lys

<210> SEQ ID NO 183
<211> LENGTH: 242
<212> TYPE: PRT
<213> ORGANISM: Artificial Sequence
<220> FEATURE:
<223> OTHER INFORMATION: SEQ ID NO: 183 F2-Fc fusion

<400> SEQUENCE: 183

Thr Lys Arg Phe Pro Glu Thr Val Leu Ala Arg Cys Val Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 184
<211> LENGTH: 242
<212> TYPE: PRT
<213> ORGANISM: Artificial Sequence
<220> FEATURE:
<223> OTHER INFORMATION: SEQ ID NO: 184 F3-Fc fusion

<400> SEQUENCE: 184
```

```
Lys Tyr Thr Glu Ile His Pro Glu Met Arg His Val Asp Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 185
<211> LENGTH: 242
<212> TYPE: PRT
<213> ORGANISM: Artificial Sequence
<220> FEATURE:
<223> OTHER INFORMATION: SEQ ID NO: 185 F4-Fc fusion

<400> SEQUENCE: 185

Cys Gln Ser Val Trp Asp Ala Phe Lys Gly Ala Phe Ile Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110
```

```
Glu Tyr Lys Cys Lys Val Ser Asn Lys Ala Leu Pro Ala Pro Ile Glu
            115                 120                 125

Lys Thr Ile Ser Lys Ala Lys Gly Gln Pro Arg Glu Pro Gln Val Tyr
        130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 186
<211> LENGTH: 242
<212> TYPE: PRT
<213> ORGANISM: Artificial Sequence
<220> FEATURE:
<223> OTHER INFORMATION: SEQ ID NO: 186 F5-Fc fusion

<400> SEQUENCE: 186

Ser Lys His Pro Cys Asn Ile Thr Glu Glu Asp Tyr Gln Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
```

```
                225                 230                 235                 240

Gly Lys

<210> SEQ ID NO 187
<211> LENGTH: 242
<212> TYPE: PRT
<213> ORGANISM: Artificial Sequence
<220> FEATURE:
<223> OTHER INFORMATION: SEQ ID NO: 187 F6-Fc fusion

<400> SEQUENCE: 187

Pro Leu Met Lys Leu Gly Thr Gln Thr Val Pro Cys Asn Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
210                 215                 220

Glu Ala Leu His Asn His Tyr Thr Gln Lys Ser Leu Ser Leu Ser Pro
225                 230                 235                 240

Gly Lys

<210> SEQ ID NO 188
<211> LENGTH: 242
<212> TYPE: PRT
<213> ORGANISM: Artificial Sequence
<220> FEATURE:
<223> OTHER INFORMATION: SEQ ID NO: 188 F7-Fc fusion

<400> SEQUENCE: 188

Lys Ile Leu Leu Trp Ser Arg Ile Lys Asp Leu Ala His Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45
```

Ser Arg Thr Pro Glu Val Thr Cys Val Val Val Asp Val Ser His Glu
 50                  55                  60

Asp Pro Glu Val Lys Phe Asn Trp Tyr Val Asp Gly Val Glu Val His
 65                  70                  75                  80

Asn Ala Lys Thr Lys Pro Arg Glu Glu Gln Tyr Asn Ser Thr Tyr Arg
                 85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 189
<211> LENGTH: 242
<212> TYPE: PRT
<213> ORGANISM: Artificial Sequence
<220> FEATURE:
<223> OTHER INFORMATION: SEQ ID NO: 189 F8-Fc fusion

<400> SEQUENCE: 189

Gln Phe Thr Gln Val Gln Arg Asp Met Phe Thr Leu Glu Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
 50                  55                  60

Asp Pro Glu Val Lys Phe Asn Trp Tyr Val Asp Gly Val Glu Val His
 65                  70                  75                  80

Asn Ala Lys Thr Lys Pro Arg Glu Glu Gln Tyr Asn Ser Thr Tyr Arg
                 85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
210                 215                 220

Glu Ala Leu His Asn His Tyr Thr Gln Lys Ser Leu Ser Leu Ser Pro
225                 230                 235                 240

Gly Lys

<210> SEQ ID NO 190
<211> LENGTH: 242
<212> TYPE: PRT
<213> ORGANISM: Artificial Sequence
<220> FEATURE:
<223> OTHER INFORMATION: SEQ ID NO: 190 F9-Fc fusion

<400> SEQUENCE: 190

Asp Thr Leu Leu Gly Tyr Leu Ala Asp Asp Leu Thr Trp Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
210                 215                 220

Glu Ala Leu His Asn His Tyr Thr Gln Lys Ser Leu Ser Leu Ser Pro
225                 230                 235                 240

Gly Lys

<210> SEQ ID NO 191
<211> LENGTH: 242
<212> TYPE: PRT
<213> ORGANISM: Artificial Sequence

```
<220> FEATURE:
<223> OTHER INFORMATION: SEQ ID NO: 191 F10-Fc fusion

<400> SEQUENCE: 191

Cys Gly Glu Phe Asn Thr Ser Lys Ile Asn Tyr Gln Ser Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 192
<211> LENGTH: 242
<212> TYPE: PRT
<213> ORGANISM: Artificial Sequence
<220> FEATURE:
<223> OTHER INFORMATION: SEQ ID NO: 192 F11-Fc fusion

<400> SEQUENCE: 192

Cys Pro Asp Trp Arg Lys Asp Cys Ser Asn Asn Pro Val Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95
```

```
Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 193
<211> LENGTH: 242
<212> TYPE: PRT
<213> ORGANISM: Artificial Sequence
<220> FEATURE:
<223> OTHER INFORMATION: SEQ ID NO: 193 F12-Fc fusion

<400> SEQUENCE: 193

Ser Val Phe Trp Lys Thr Val Ser Arg Arg Phe Ala Glu Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205
```

```
Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 194
<211> LENGTH: 242
<212> TYPE: PRT
<213> ORGANISM: Artificial Sequence
<220> FEATURE:
<223> OTHER INFORMATION: SEQ ID NO: 194 F13-Fc fusion

<400> SEQUENCE: 194

Ala Ala Cys Asp Val Val His Val Met Leu Asn Gly Ser Ala Ser Asp
1               5                  10                  15

Lys Thr His Thr Cys Pro Pro Cys Pro Ala Pro Glu Leu Leu Gly Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 195
<211> LENGTH: 242
<212> TYPE: PRT
<213> ORGANISM: Artificial Sequence
<220> FEATURE:
<223> OTHER INFORMATION: SEQ ID NO: 195 F14-Fc fusion

<400> SEQUENCE: 195

Arg Ser Lys Ile Phe Asp Lys Asn Ser Thr Phe Gly Ser Ala Ser Asp
1               5                  10                  15

Lys Thr His Thr Cys Pro Pro Cys Pro Ala Pro Glu Leu Leu Gly Gly
```

-continued

```
                20                  25                  30
Pro Ser Val Phe Leu Phe Pro Pro Lys Pro Lys Asp Thr Leu Met Ile
        35                  40                  45
Ser Arg Thr Pro Glu Val Thr Cys Val Val Val Asp Val Ser His Glu
    50                  55                  60
Asp Pro Glu Val Lys Phe Asn Trp Tyr Val Asp Gly Val Glu Val His
65                  70                  75                  80
Asn Ala Lys Thr Lys Pro Arg Glu Glu Gln Tyr Asn Ser Thr Tyr Arg
                85                  90                  95
Val Val Ser Val Leu Thr Val Leu His Gln Asp Trp Leu Asn Gly Lys
            100                 105                 110
Glu Tyr Lys Cys Lys Val Ser Asn Lys Ala Leu Pro Ala Pro Ile Glu
        115                 120                 125
Lys Thr Ile Ser Lys Ala Lys Gly Gln Pro Arg Glu Pro Gln Val Tyr
    130                 135                 140
Thr Leu Pro Pro Ser Arg Asp Glu Leu Thr Lys Asn Gln Val Ser Leu
145                 150                 155                 160
Thr Cys Leu Val Lys Gly Phe Tyr Pro Ser Asp Ile Ala Val Glu Trp
                165                 170                 175
Glu Ser Asn Gly Gln Pro Glu Asn Asn Tyr Lys Thr Thr Pro Pro Val
            180                 185                 190
Leu Asp Ser Asp Gly Ser Phe Phe Leu Tyr Ser Lys Leu Thr Val Asp
        195                 200                 205
Lys Ser Arg Trp Gln Gln Gly Asn Val Phe Ser Cys Ser Val Met His
    210                 215                 220
Glu Ala Leu His Asn His Tyr Thr Gln Lys Ser Leu Ser Leu Ser Pro
225                 230                 235                 240

Gly Lys

<210> SEQ ID NO 196
<211> LENGTH: 242
<212> TYPE: PRT
<213> ORGANISM: Artificial Sequence
<220> FEATURE:
<223> OTHER INFORMATION: SEQ ID NO: 196 F15-Fc fusion

<400> SEQUENCE: 196

Val Glu Val His Asn Leu Gln Pro Glu Lys Val Gln Thr Ala Ser Asp
1               5                   10                  15
Lys Thr His Thr Cys Pro Pro Cys Pro Ala Pro Glu Leu Leu Gly Gly
                20                  25                  30
Pro Ser Val Phe Leu Phe Pro Pro Lys Pro Lys Asp Thr Leu Met Ile
        35                  40                  45
Ser Arg Thr Pro Glu Val Thr Cys Val Val Val Asp Val Ser His Glu
    50                  55                  60
Asp Pro Glu Val Lys Phe Asn Trp Tyr Val Asp Gly Val Glu Val His
65                  70                  75                  80
Asn Ala Lys Thr Lys Pro Arg Glu Glu Gln Tyr Asn Ser Thr Tyr Arg
                85                  90                  95
Val Val Ser Val Leu Thr Val Leu His Gln Asp Trp Leu Asn Gly Lys
            100                 105                 110
Glu Tyr Lys Cys Lys Val Ser Asn Lys Ala Leu Pro Ala Pro Ile Glu
        115                 120                 125
Lys Thr Ile Ser Lys Ala Lys Gly Gln Pro Arg Glu Pro Gln Val Tyr
    130                 135                 140
```

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
        210                 215                 220

Glu Ala Leu His Asn His Tyr Thr Gln Lys Ser Leu Ser Leu Ser Pro
225                 230                 235                 240

Gly Lys

<210> SEQ ID NO 197
<211> LENGTH: 242
<212> TYPE: PRT
<213> ORGANISM: Artificial Sequence
<220> FEATURE:
<223> OTHER INFORMATION: SEQ ID NO: 197 F16-Fc fusion

<400> SEQUENCE: 197

Leu Glu Ala Trp Val Ile His Gly Gly Arg Glu Asp Ser Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
        210                 215                 220

Glu Ala Leu His Asn His Tyr Thr Gln Lys Ser Leu Ser Leu Ser Pro
225                 230                 235                 240

Gly Lys

<210> SEQ ID NO 198
<211> LENGTH: 242
<212> TYPE: PRT
<213> ORGANISM: Artificial Sequence
<220> FEATURE:
<223> OTHER INFORMATION: SEQ ID NO: 198 F17-Fc fusion

<400> SEQUENCE: 198

```
Arg Asp Leu Cys Gln Asp Pro Thr Ile Lys Glu Leu Glu Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
210                 215                 220

Glu Ala Leu His Asn His Tyr Thr Gln Lys Ser Leu Ser Leu Ser Pro
225                 230                 235                 240

Gly Lys
```

<210> SEQ ID NO 199
<211> LENGTH: 242
<212> TYPE: PRT
<213> ORGANISM: Artificial Sequence
<220> FEATURE:
<223> OTHER INFORMATION: SEQ ID NO: 199 F18-Fc fusion

<400> SEQUENCE: 199

```
Ser Ile Ile Ser Lys Arg Asn Ile Gln Phe Ser Cys Lys Ala Ser Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
50                  55                  60

Asp Pro Glu Val Lys Phe Asn Trp Tyr Val Asp Gly Val Glu Val His
```

```
                65                  70                  75                  80
Asn Ala Lys Thr Lys Pro Arg Glu Glu Gln Tyr Asn Ser Thr Tyr Arg
                    85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
            115                 120                 125

Lys Thr Ile Ser Lys Ala Lys Gly Gln Pro Arg Glu Pro Gln Val Tyr
        130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 200
<211> LENGTH: 242
<212> TYPE: PRT
<213> ORGANISM: Artificial Sequence
<220> FEATURE:
<223> OTHER INFORMATION: SEQ ID NO: 200 F19-Fc fusion

<400> SEQUENCE: 200

Asn Ile Tyr Arg Pro Asp Lys Phe Leu Gln Cys Val Lys Ala Ser Asp
1               5                   10                  15

Lys Thr His Thr Cys Pro Pro Cys Pro Ala Pro Glu Leu Leu Gly Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
        50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                    85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
            115                 120                 125

Lys Thr Ile Ser Lys Ala Lys Gly Gln Pro Arg Glu Pro Gln Val Tyr
        130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190
```

```
Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
210                 215                 220

Glu Ala Leu His Asn His Tyr Thr Gln Lys Ser Leu Ser Leu Ser Pro
225                 230                 235                 240

Gly Lys

<210> SEQ ID NO 201
<211> LENGTH: 240
<212> TYPE: PRT
<213> ORGANISM: Artificial Sequence
<220> FEATURE:
<223> OTHER INFORMATION: SEQ ID NO: 201 F20-Fc fusion

<400> SEQUENCE: 201

Asn Pro Glu Asp Ser Ser Cys Thr Ser Glu Ile Ala Ser Asp Lys Thr
1               5                   10                  15

His Thr Cys Pro Pro Cys Pro Ala Pro Glu Leu Leu Gly Gly Pro Ser
            20                  25                  30

Val Phe Leu Phe Pro Pro Lys Pro Lys Asp Thr Leu Met Ile Ser Arg
        35                  40                  45

Thr Pro Glu Val Thr Cys Val Val Val Asp Val Ser His Glu Asp Pro
50                  55                  60

Glu Val Lys Phe Asn Trp Tyr Val Asp Gly Val Glu Val His Asn Ala
65                  70                  75                  80

Lys Thr Lys Pro Arg Glu Glu Gln Tyr Asn Ser Thr Tyr Arg Val Val
                85                  90                  95

Ser Val Leu Thr Val Leu His Gln Asp Trp Leu Asn Gly Lys Glu Tyr
            100                 105                 110

Lys Cys Lys Val Ser Asn Lys Ala Leu Pro Ala Pro Ile Glu Lys Thr
        115                 120                 125

Ile Ser Lys Ala Lys Gly Gln Pro Arg Glu Pro Gln Val Tyr Thr Leu
    130                 135                 140

Pro Pro Ser Arg Asp Glu Leu Thr Lys Asn Gln Val Ser Leu Thr Cys
145                 150                 155                 160

Leu Val Lys Gly Phe Tyr Pro Ser Asp Ile Ala Val Glu Trp Glu Ser
                165                 170                 175

Asn Gly Gln Pro Glu Asn Asn Tyr Lys Thr Thr Pro Pro Val Leu Asp
            180                 185                 190

Ser Asp Gly Ser Phe Phe Leu Tyr Ser Lys Leu Thr Val Asp Lys Ser
        195                 200                 205

Arg Trp Gln Gln Gly Asn Val Phe Ser Cys Ser Val Met His Glu Ala
    210                 215                 220

Leu His Asn His Tyr Thr Gln Lys Ser Leu Ser Leu Ser Pro Gly Lys
225                 230                 235                 240

<210> SEQ ID NO 202
<211> LENGTH: 450
<212> TYPE: PRT
<213> ORGANISM: Artificial Sequence
<220> FEATURE:
<223> OTHER INFORMATION: SEQ ID NO: 202 SAR650984 HC

<400> SEQUENCE: 202

Gln Val Gln Leu Val Gln Ser Gly Ala Glu Val Ala Lys Pro Gly Thr
1               5                   10                  15
```

```
Ser Val Lys Leu Ser Cys Lys Ala Ser Gly Tyr Thr Phe Thr Asp Tyr
         20                  25                  30

Trp Met Gln Trp Val Lys Gln Arg Pro Gly Gln Gly Leu Glu Trp Ile
         35                  40                  45

Gly Thr Ile Tyr Pro Gly Asp Gly Asp Thr Gly Tyr Ala Gln Lys Phe
 50                  55                  60

Gln Gly Lys Ala Thr Leu Thr Ala Asp Lys Ser Ser Lys Thr Val Tyr
 65                  70                  75                  80

Met His Leu Ser Ser Leu Ala Ser Glu Asp Ser Ala Val Tyr Tyr Cys
             85                  90                  95

Ala Arg Gly Asp Tyr Tyr Gly Ser Asn Ser Leu Asp Tyr Trp Gly Gln
             100                 105                 110

Gly Thr Ser Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
                 180                 185                 190

Ser Ser Ser Leu Gly Thr Gln Thr Tyr Ile Cys Asn Val Asn His Lys
             195                 200                 205

Pro Ser Asn Thr Lys Val Asp Lys Lys Val Glu Pro Lys Ser Cys Asp
         210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
                 260                 265                 270

Asp Pro Glu Val Lys Phe Asn Trp Tyr Val Asp Gly Val Glu Val His
             275                 280                 285

Asn Ala Lys Thr Lys Pro Arg Glu Glu Gln Tyr Asn Ser Thr Tyr Arg
         290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
                 340                 345                 350

Thr Leu Pro Pro Ser Arg Asp Glu Leu Thr Lys Asn Gln Val Ser Leu
             355                 360                 365

Thr Cys Leu Val Lys Gly Phe Tyr Pro Ser Asp Ile Ala Val Glu Trp
         370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430
```

Glu Ala Leu His Asn His Tyr Thr Gln Lys Ser Leu Ser Leu Ser Pro
            435                 440                 445

Gly Lys
    450

<210> SEQ ID NO 203
<211> LENGTH: 214
<212> TYPE: PRT
<213> ORGANISM: Artificial Sequence
<220> FEATURE:
<223> OTHER INFORMATION: SEQ ID NO: 203 SAR650984 LC

<400> SEQUENCE: 203

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 204
<211> LENGTH: 264
<212> TYPE: PRT
<213> ORGANISM: Artificial Sequence
<220> FEATURE:
<223> OTHER INFORMATION: SEQ ID NO: 204 Human CD38 extracellular domain
      with M110V substitution

<400> SEQUENCE: 204

Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
            20                  25                  30

Pro Glu Met Arg His Val Asp Cys Gln Ser Val Trp Asp Ala Phe Lys
        35                  40                  45

Gly Ala Phe Ile Ser Lys His Pro Cys Asn Ile Thr Glu Glu Asp Tyr

```
                    50                  55                  60
Gln Pro Leu Val Lys Leu Gly Thr Gln Thr Val Pro Cys Asn Lys Ile
 65                  70                  75                  80

Leu Leu Trp Ser Arg Ile Lys Asp Leu Ala His Gln Phe Thr Gln Val
                     85                  90                  95

Gln Arg Asp Met Phe Thr Leu Glu Asp Thr Leu Leu Gly Tyr Leu Ala
                100                 105                 110

Asp Asp Leu Thr Trp Cys Gly Glu Phe Asn Thr Ser Lys Ile Asn Tyr
                115                 120                 125

Gln Ser Cys Pro Asp Trp Arg Lys Asp Cys Ser Asn Asn Pro Val Ser
            130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
                180                 185                 190

Val Gln Thr Leu Glu Ala Trp Val Ile His Gly Gly Arg Glu Asp Ser
            195                 200                 205

Arg Asp Leu Cys Gln Asp Pro Thr Ile Lys Glu Leu Glu Ser Ile Ile
210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile His His His His His His
            260

<210> SEQ ID NO 205
<211> LENGTH: 264
<212> TYPE: PRT
<213> ORGANISM: Artificial Sequence
<220> FEATURE:
<223> OTHER INFORMATION: SEQ ID NO: 205 Human CD38 extracellular domain
      with T148M substitution

<400> SEQUENCE: 205

Val Pro Arg Trp Arg Gln Gln Trp Ser Gly Pro Gly Thr Thr Lys Arg
  1               5                  10                  15

Phe Pro Glu Thr Val Leu Ala Arg Cys Val Lys Tyr Thr Glu Ile His
                 20                  25                  30

Pro Glu Met Arg His Val Asp Cys Gln Ser Val Trp Asp Ala Phe Lys
             35                  40                  45

Gly Ala Phe Ile Ser Lys His Pro Cys Asn Ile Thr Glu Glu Asp Tyr
         50                  55                  60

Gln Pro Leu Met Lys Leu Gly Thr Gln Thr Val Pro Cys Asn Lys Ile
 65                  70                  75                  80

Leu Leu Trp Ser Arg Ile Lys Asp Leu Ala His Gln Phe Thr Gln Val
                     85                  90                  95

Gln Arg Asp Met Phe Thr Leu Glu Asp Met Leu Leu Gly Tyr Leu Ala
                100                 105                 110

Asp Asp Leu Thr Trp Cys Gly Glu Phe Asn Thr Ser Lys Ile Asn Tyr
                115                 120                 125

Gln Ser Cys Pro Asp Trp Arg Lys Asp Cys Ser Asn Asn Pro Val Ser
            130                 135                 140
```

```
Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
            165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
            195                 200                 205

Arg Asp Leu Cys Gln Asp Pro Thr Ile Lys Glu Leu Glu Ser Ile Ile
            210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
            245                 250                 255

Glu Ile His His His His His His
            260

<210> SEQ ID NO 206
<211> LENGTH: 264
<212> TYPE: PRT
<213> ORGANISM: Artificial Sequence
<220> FEATURE:
<223> OTHER INFORMATION: SEQ ID NO: 206 Human CD38 extracellular domain
      with M110V and T148M substitutions

<400> SEQUENCE: 206

Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
            20                  25                  30

Pro Glu Met Arg His Val Asp Cys Gln Ser Val Trp Asp Ala Phe Lys
            35                  40                  45

Gly Ala Phe Ile Ser Lys His Pro Cys Asn Ile Thr Glu Glu Asp Tyr
50                  55                  60

Gln Pro Leu Val Lys Leu Gly Thr Gln Thr Val Pro Cys Asn Lys Ile
65                  70                  75                  80

Leu Leu Trp Ser Arg Ile Lys Asp Leu Ala His Gln Phe Thr Gln Val
            85                  90                  95

Gln Arg Asp Met Phe Thr Leu Glu Asp Met Leu Leu Gly Tyr Leu Ala
            100                 105                 110

Asp Asp Leu Thr Trp Cys Gly Glu Phe Asn Thr Ser Lys Ile Asn Tyr
            115                 120                 125

Gln Ser Cys Pro Asp Trp Arg Lys Asp Cys Ser Asn Asn Pro Val Ser
            130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
            165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
            195                 200                 205

Arg Asp Leu Cys Gln Asp Pro Thr Ile Lys Glu Leu Glu Ser Ile Ile
            210                 215                 220

Ser Lys Arg Asn Ile Gln Phe Ser Cys Lys Asn Ile Tyr Arg Pro Asp
225                 230                 235                 240
```

```
Lys Phe Leu Gln Cys Val Lys Asn Pro Glu Asp Ser Ser Cys Thr Ser
                245                 250                 255

Glu Ile His His His His His His
            260

<210> SEQ ID NO 207
<211> LENGTH: 481
<212> TYPE: PRT
<213> ORGANISM: Artificial Sequence
<220> FEATURE:
<223> OTHER INFORMATION: SEQ ID NO: 207 mouse SP34 reformatted as an
      scFv

<400> SEQUENCE: 207

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala Gly Gly Gly
        115                 120                 125

Gly Ser Gly Gly Gly Gly Ser Gly Gly Gly Gly Ser Gln Ala Val Val
    130                 135                 140

Thr Gln Glu Ser Ala Leu Thr Thr Ser Pro Gly Glu Thr Val Thr Leu
145                 150                 155                 160

Thr Cys Arg Ser Ser Thr Gly Ala Val Thr Thr Ser Asn Tyr Ala Asn
                165                 170                 175

Trp Val Gln Glu Lys Pro Asp His Leu Phe Thr Gly Leu Ile Gly Gly
            180                 185                 190

Thr Asn Lys Arg Ala Pro Gly Val Pro Ala Arg Phe Ser Gly Ser Leu
        195                 200                 205

Ile Gly Asp Lys Ala Ala Leu Thr Ile Thr Gly Ala Gln Thr Glu Asp
    210                 215                 220

Glu Ala Ile Tyr Phe Cys Ala Leu Trp Tyr Ser Asn Leu Trp Val Phe
225                 230                 235                 240

Gly Gly Gly Thr Lys Leu Thr Val Leu Gly Gly Gly Thr Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
```

```
                325                 330                 335
Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys

<210> SEQ ID NO 208
<211> LENGTH: 12
<212> TYPE: PRT
<213> ORGANISM: Artificial Sequence
<220> FEATURE:
<223> OTHER INFORMATION: SEQ ID NO: 208 Extended Kabat 9G7 mouse CDRH1

<400> SEQUENCE: 208

Gly Leu Ser Leu Ser Thr Ser Gly Lys Gly Val Gly
1               5                   10

<210> SEQ ID NO 209
<211> LENGTH: 19
<212> TYPE: PRT
<213> ORGANISM: Artificial Sequence
<220> FEATURE:
<223> OTHER INFORMATION: SEQ ID NO: 209 Extended Kabat 9G7 mouse CDRH2

<400> SEQUENCE: 209

Trp Leu Ala His Ile Trp Trp Asp Asp Lys Arg Tyr Asn Pro Ala
1               5                   10                  15

Leu Lys Ser

<210> SEQ ID NO 210
<211> LENGTH: 13
<212> TYPE: PRT
<213> ORGANISM: Artificial Sequence
<220> FEATURE:
<223> OTHER INFORMATION: SEQ ID NO: 210 Extended Kabat 9G7 mouse CDRH3

<400> SEQUENCE: 210

Ala Arg Ile Glu Leu Gly Arg Ser Tyr Val Met Asp Tyr
1               5                   10

<210> SEQ ID NO 211
<211> LENGTH: 13
<212> TYPE: PRT
<213> ORGANISM: Artificial Sequence
<220> FEATURE:
<223> OTHER INFORMATION: SEQ ID NO: 211 Extended Kabat 9G7 mouse CDRL1
```

```
<400> SEQUENCE: 211

Lys Ala Ser Gln Asp Val Ile Thr Ser Val Ala Trp Phe
1               5                   10

<210> SEQ ID NO 212
<211> LENGTH: 11
<212> TYPE: PRT
<213> ORGANISM: Artificial Sequence
<220> FEATURE:
<223> OTHER INFORMATION: SEQ ID NO: 212 Extended Kabat 9G7 mouse CDRL2

<400> SEQUENCE: 212

Leu Leu Ile Tyr Ser Ala Ser Tyr Arg Tyr Thr
1               5                   10

<210> SEQ ID NO 213
<211> LENGTH: 9
<212> TYPE: PRT
<213> ORGANISM: Artificial Sequence
<220> FEATURE:
<223> OTHER INFORMATION: SEQ ID NO: 213 Extended Kabat 9G7 mouse CDRL3

<400> SEQUENCE: 213

Gln Gln His Tyr Thr Ile Pro Leu Thr
1               5

<210> SEQ ID NO 214
<211> LENGTH: 13
<212> TYPE: PRT
<213> ORGANISM: Artificial Sequence
<220> FEATURE:
<223> OTHER INFORMATION: SEQ ID NO: 214 Extended Kabat 9G7 best fit
      CDRL1

<400> SEQUENCE: 214

Gln Ala Ser Gln Asp Val Ile Thr Ser Val Ala Trp Phe
1               5                   10
```